(12) United States Patent
Wiltzius et al.

(10) Patent No.: US 10,597,456 B2
(45) Date of Patent: Mar. 24, 2020

(54) CHIMERIC RECEPTORS AND METHODS OF USE THEREOF

(71) Applicants: KITE PHARMA, Inc., Santa Monica, CA (US); AMGEN INC., Thousand Oaks, CA (US)

(72) Inventors: Jed Wiltzius, Woodland Hills, CA (US); Ruben Alvarez Rodriguez, Los Angeles, CA (US); Alice Bakker, Thousand Oaks, CA (US); Lawren Wu, Thousand Oaks, CA (US); Tara Arvedson, Thousand Oaks, CA (US)

(73) Assignees: AMGEN INC., Thousand Oaks, CA (US); KITE PHARMA, INC., Santa Monica, CA (US)

( * ) Notice: Subject to any disclaimer, the term of this patent is extended or adjusted under 35 U.S.C. 154(b) by 0 days.

(21) Appl. No.: 15/476,699

(22) Filed: Mar. 31, 2017

(65) Prior Publication Data
US 2017/0283500 A1  Oct. 5, 2017

Related U.S. Application Data

(60) Provisional application No. 62/317,068, filed on Apr. 1, 2016.

(51) Int. Cl.
| | | |
|---|---|---|
| *C07K 16/28* | (2006.01) | |
| *C07K 14/725* | (2006.01) | |
| *C07K 14/705* | (2006.01) | |
| *A61K 39/00* | (2006.01) | |
| *C07K 14/435* | (2006.01) | |
| *C12N 15/86* | (2006.01) | |

(52) U.S. Cl.
CPC ........ *C07K 16/2851* (2013.01); *C07K 14/435* (2013.01); *C07K 14/7051* (2013.01); *C07K 14/70517* (2013.01); *C07K 14/70521* (2013.01); *C12N 15/86* (2013.01); *A61K 2039/505* (2013.01); *C07K 2317/565* (2013.01); *C07K 2317/622* (2013.01); *C07K 2319/02* (2013.01); *C07K 2319/03* (2013.01); *C07K 2319/30* (2013.01); *C07K 2319/33* (2013.01); *C12N 2740/15043* (2013.01)

(58) Field of Classification Search
CPC .......... C07K 14/7051; C07K 14/70517; C07K 14/70521; C07K 16/2851
See application file for complete search history.

(56) References Cited

U.S. PATENT DOCUMENTS

| | | | |
|---|---|---|---|
| 4,946,778 A | 8/1990 | Ladner et al. | |
| 5,260,203 A | 11/1993 | Ladner et al. | |
| 5,728,388 A | 3/1998 | Terman | |
| 5,827,642 A | 10/1998 | Riddell et al. | |
| 5,830,462 A | 11/1998 | Crabtree et al. | |
| 5,834,266 A | 11/1998 | Crabtree et al. | |
| 5,869,337 A | 2/1999 | Crabtree et al. | |
| 6,040,177 A | 3/2000 | Riddell et al. | |
| 6,165,787 A | 12/2000 | Crabtree et al. | |
| 6,319,494 B1 | 11/2001 | Capon et al. | |
| 6,797,514 B2 | 9/2004 | Berenson et al. | |
| 6,867,041 B2 | 3/2005 | Berenson et al. | |
| 6,905,874 B2 | 6/2005 | Berenson et al. | |
| 7,709,226 B2 | 5/2010 | Foote | |
| 7,741,465 B1 | 6/2010 | Eshhar et al. | |
| 8,465,743 B2 | 6/2013 | Rosenberg et al. | |
| 8,486,693 B2 | 7/2013 | Park et al. | |
| 8,536,310 B2 | 9/2013 | Abo et al. | |
| 9,034,324 B2 | 5/2015 | Kalled et al. | |
| 9,163,090 B2 | 10/2015 | Jiang et al. | |
| 9,845,362 B2 | 12/2017 | Mukherjee | |
| 2002/0006409 A1 | 1/2002 | Wood | |
| 2002/0164588 A1 | 11/2002 | Eisenberg et al. | |
| 2004/0014194 A1 | 1/2004 | Beyer et al. | |
| 2004/0197328 A1 | 10/2004 | Young et al. | |
| 2006/0051651 A1 | 3/2006 | Rock et al. | |
| 2010/0285037 A1 | 11/2010 | Abo | |
| 2011/0280889 A1 | 11/2011 | Schendel et al. | |
| 2011/0286980 A1 | 11/2011 | Brenner | |
| 2012/0130076 A1 | 5/2012 | Holt et al. | |
| 2012/0213783 A1 | 8/2012 | Rosenberg | |
| 2012/0227134 A1 | 9/2012 | Schon et al. | |
| 2013/0079246 A1 | 3/2013 | De Smedt et al. | |
| 2013/0287748 A1 | 10/2013 | June et al. | |
| 2013/0295118 A1* | 11/2013 | Jiang ................. | C07K 16/3061 424/174.1 |
| 2014/0010861 A1 | 1/2014 | Bancel et al. | |

(Continued)

FOREIGN PATENT DOCUMENTS

| | | |
|---|---|---|
| JP | 6262724 B2 | 1/2018 |
| WO | WO-88/01649 A1 | 3/1988 |

(Continued)

OTHER PUBLICATIONS

Devereux et al., "A comprehensive set of sequence analysis programs for the VAX," Nucl. Acid Res., 12:387-395 (1984).
Hombach et al., "OX40 costimulation by a chimeric antigen receptor abrogates CD28 and IL-2 induced IL-10 secretion by redirected CD4(+) T cells," Oncoimmunology, 1(4): 458-466 (2012).
Martin and Thornton, "Structural families in loops of homologous proteins: automatic classification, modelling and application to antibodies," J. Mol. Biol, 263:800-815 (1996).

(Continued)

*Primary Examiner* — Jessica H Roark
(74) *Attorney, Agent, or Firm* — Arrigo, Lee, Guttman & Mouta-Bellum LLP

(57) ABSTRACT

Antigen binding molecules, chimeric receptors, and engineered immune cells are disclosed in accordance with the invention. The invention further relates to vectors, compositions, and methods of treatment and/or detection using the antigen binding molecules and engineered immune cells.

46 Claims, 12 Drawing Sheets
Specification includes a Sequence Listing.

(56) References Cited

U.S. PATENT DOCUMENTS

| | | |
|---|---|---|
| 2014/0050708 A1 | 2/2014 | Powell, Jr. et al. |
| 2014/0099309 A1 | 4/2014 | Powell, Jr. et al. |
| 2014/0154228 A1 | 6/2014 | Volk et al. |
| 2014/0171649 A1 | 6/2014 | Li et al. |
| 2014/0227237 A1 | 8/2014 | June et al. |
| 2014/0286987 A1 | 9/2014 | Spencer et al. |
| 2014/0328812 A1 | 11/2014 | Campana |
| 2015/0051266 A1 | 2/2015 | Kochenderfer |
| 2015/0225480 A1 | 8/2015 | Powell, Jr. |
| 2015/0266973 A1 | 9/2015 | Jarjour et al. |
| 2015/0368360 A1 | 12/2015 | Liang et al. |
| 2016/0046700 A1 | 2/2016 | Foster et al. |
| 2016/0046724 A1 | 2/2016 | Brogdon et al. |
| 2016/0051651 A1 | 2/2016 | Brogdon et al. |
| 2016/0297884 A1 | 10/2016 | Kuo et al. |
| 2016/0297885 A1 | 10/2016 | Kuo et al. |
| 2016/0311907 A1 | 10/2016 | Brogdon et al. |
| 2016/0340649 A1 | 11/2016 | Brown et al. |
| 2017/0183418 A1 | 7/2017 | Cellectis |
| 2017/0281766 A1 | 10/2017 | Wiltzius et al. |
| 2017/0283500 A1 | 10/2017 | Wiltzius |
| 2017/0283504 A1 | 10/2017 | Wiltzius |

FOREIGN PATENT DOCUMENTS

| | | |
|---|---|---|
| WO | 2005/000894 A2 | 1/2005 |
| WO | WO-2008/081035 A1 | 7/2008 |
| WO | 2012031744 | 3/2012 |
| WO | 2012033885 | 3/2012 |
| WO | 2012/163805 A1 | 5/2012 |
| WO | WO-2012/079000 A1 | 6/2012 |
| WO | WO-2012/129514 A1 | 9/2012 |
| WO | 2013/154760 A1 | 3/2013 |
| WO | 2013/0139625 A1 | 11/2013 |
| WO | 2014/122143 A1 | 8/2014 |
| WO | 2014127261 | 8/2014 |
| WO | WO-2014/127261 A1 | 8/2014 |
| WO | 2014186469 | 11/2014 |
| WO | 2015077789 | 5/2015 |
| WO | 2015080981 | 6/2015 |
| WO | WO-2015/090229 A1 | 6/2015 |
| WO | WO-2015/120096 A2 | 8/2015 |
| WO | 2015/142675 A2 | 9/2015 |
| WO | 2015142675 | 9/2015 |
| WO | 2015158671 | 10/2015 |
| WO | 2016/014535 A1 | 1/2016 |
| WO | 2016/014789 A2 | 1/2016 |
| WO | 2016014565 | 1/2016 |
| WO | 2016044745 | 3/2016 |
| WO | 2016090369 | 6/2016 |
| WO | 2016094304 | 6/2016 |
| WO | 2013/142034 A1 | 10/2017 |
| WO | 2017173256 | 10/2017 |
| WO | 2017173349 | 10/2017 |
| WO | 2017173384 | 10/2017 |
| WO | 2017173410 | 10/2017 |

OTHER PUBLICATIONS

Song et al., "CD27 costimulation augments the survival and antitumor activity of redirected human T cells in vivo," Blood, 119:696-706 (2012).
Wu et al., "Remote control of therapeutic T Cells through a small molecule-gated chimeric receptor," Science, 350 (6258):293 (2015).
International Search Report for PCT/2017/025573 dated Aug. 11, 2017 (6 pages).
Non-Final Office Action for U.S. Appl. No. 15/476,309 dated Mar. 1, 2019 (35 pages).
Restriction Requirement for U.S. Appl. No. 15/476,309 dated Sep. 4, 2018 (12 pages).
Written Opinion for PCT/US2017/025573 dated Aug. 11, 2017 (8 pages).
Written Opinion for PCT/US2017/025351 dated Aug. 22, 2017 (6 pages).
Written Opinion for PCT/US2017/025516 dated Aug. 25, 2017 (8 pages).
Rudikoff et al., "Single amino acid substitution altering antigen-binding specificity," Proc. Natl. Acad. Sci. USA, 79:1979-1983 (1982).
Colman, "Effects of amino acid sequence changes on antibody-antigen interactions," A Structural View of Immune Recognition by Antibodies, pp. 33-36 (1994).
Ibragimova et al., "Stability of the β-Sheet of the WW Domain: A Molecular Dynamics Simulation Study," Biophysical Journal 77:2191-2198 (1999).
Prazma et al., "Dendritic cell CD83: A therapeutic target or innocent bystander?" Immunology Letters, 115:1-8 (2008).
Non-Final Office Action for U.S. Appl. No. 15/475,681 dated Dec. 5, 2018 (28 pages).
Office Action for Cuban application No. 2018-0121 dated Jan. 8, 2019 (2 pages).
International Search Report for PCT/US2017/025351 dated Aug. 22, 2017 (6 pages).
Hipp et al., "A Novel BCMA/CD3 Bispecific T-cell Engager for the Treatment of Multiple Myeloma Induces Selective Lysis in Vitro and in Vivo," Leukemia (2017), p. 1743-1751, 31, www.nature.com/leu, doi:10.1038/eu.2016.388.
Hymowitz et al., "Structures of APRIL-Receptor Complexes," J. Biol. Chem. (2005), 280, pp. 7218-7227, doi: 10.1074/ibc.M411714200 originally published online Nov. 12, 2004.
Kochenderfer et al., "Construction and preclinical evaluation of an anti-CD19 chimeric antigen receptor," Journal of Immunotherapty, 32(7):689-702 (2009).
Kochenderfer et al., "A Phase 1 Clinical Trial of Treatment of B-Cell Malignancies with Autologous Anti-CD19-CAR-Transduced T Cell," Blood, 116(1):1179-1180 (2010).
Yu et al., "APRIL and TALL-1 and receptors BCMA and TACI: system for regulating humoral immunity," Nature Immunology, 1(3):252-256 (2000).
International Search Report for PCT/US2017/025516 dated Jul. 21, 2017 (6 pages).
Office Action for Cuban application No. 2018-0120 dated Jan. 8, 2019 (2 pages).
International Search Report for PCT/US2017/025613 dated Jun. 27, 2017 (13 pages).
Kowolik, Claudia M., "CD28 Costimulation Provided through a CD19-Specific ChimericAntigen Receptor EnhancesInvivoPersistence and AntitumorEfficacy of Adoptively Transferred T Cells", Cancer Res 2006; 66: (22). Nov. 15, 2006.
Sadelain, M., et al., "The Basic Principles of Chimeric Antigen Receptor Design", Cancer Discovery, Apr. 2, 2013, pp. 388-398.
Evans, E., et al., "Crystal Structure of a Soluble CD28-Fab Complex", Nature Immunology, vol. 6, No. 3 Mar. 2005, pp. 271-279.
Dotti et al., "Design and Development of Therapies using Chimeric Antigen Receptor-Expressing T Cells," Immunol. Rev., 257(1):1-35 (2014).
Geldres et al., "Chimeric antigen receptor-redirected T cells return to the bench," Seminars in Immunology, 28:3-9 (2016).
Fesnak et al., "Engineered T cells: the promise and challenges of cancer immunotherapy," Nature, 16:566-581 (2016).
De Oliveira et al., "Modification of Hematopoietic Stem/Progenitor Cells with CD19-Specific Chimeric Antigen Receptors as a Novel Approach for Cancer Immunotherapy," Human Gene Therapy, 24:824-839 (2013).
Kariv et al., "Analysis of the site of interaction of CD28 with its counter-receptors CD80 and CD86 and correlation with function," Journal of Immunol., 157:29-38 (1996).
Australian examination report for application No. 2017240788 dated May 24, 2019 (3 pages).
Moroccan examination report for application No. 43603 dated Mar. 14, 2018 (8 pages).
Al-Lazikani et al., "Standard conformations for the canonical structures of immunoglobulins" J Mol Biol, 1997, 273: 927-948.
Bricogne, "Direct phase determination by entropy maximization and likelihood ranking: status report and perspectives", Acta Crystallogr D Biol Crystallogr, 1993, 49(Pt 1): 37-60.

(56) References Cited

OTHER PUBLICATIONS

Bricogne, "[23] Bayesian statistical viewpoint on structure determination: Basic concepts and examples", Meth Enzymol, 1997, 276A: 361-423.
Champe et al., "Monoclonal Antibodies That Block the Activity of Leukocyte Function-associated Antigen 1 Recognize Three Discrete Epitopes in the Inserted Domain of CD11a", J Biol Chem, 1995, 270(3): 1388-94.
Chayen, "The role of oil in macromolecular crystallization", Structure, 1997, 5(10): 1269-1274.
Chothia et al., "Canonical structures for the hypervariable regions of immunoglobulins", J Mol Biol, 1987, 196: 901-917.
Chothia et al., "Structural repertoire of the human VH segments" J Mol Biol, 1992, 227: 799-817.
Cunningham et al., "High-resolution epitope mapping of hGH-receptor interactions by alanine-scanning mutagenesis", Science 244(4908): 1081-85 (1989).
Giege et al., "Crystallogenesis of biological macromolecules: facts and perspectives", Acta Crystallogr D Biol Crystallogr, 1994, 50(Pt 4): 339-350.
McPherson, "Current approaches to macromolecular crystallization", Eur J Biochem, 1990, 189: 1-23.
McPherson, "Crystallization of Proteins from Polyethylene Glycol", J Biol Chem, 1976, 251(20): 6300-6303.
Roversi et al., "Modeling prior distributions of atoms for macromolecular refinement and completion", Acta Crystallogr D Biol Crystallogr, 2000, 56 (Pt 10): 1316-1323.
Eshhar E., "Tumor-specific T-bodies: towards clinical application" Cancer Immunol Immunother (1997) 45: 131-136.
Tramontano et al., "Framework residue 71 is a major determinant of the position and conformation of the second hypervariable region in the VH domains of immunoglobulins" J Mol Biol, 1990, 215(1): 175-82.
Gautier et al. "Site-Specific Protein Labeling, Methods and Protocols", Springer 2015, pp. 1-267.
Fauchere, "Elements for the Rational Design of Peptide Drugs", Advances in Drug Research, vol. 15, 1986, 41 pages.
Chothia et al., "Conformations of immunoglobulin hypervariable regions", Nature, 1989, 342(6252):877-883.
Golub, et al., "Immunology—A Synthesis (2nd Edition)", Sinauer Assoc., Sunderland, Mass. (1991), table of contents only, 13 pages.
Kabat et al. "Sequences of Proteins of Immunological Interest", 1991, 5th Ed., NIH Publication 91-3242, Bethesda MD title page, publication page, and table of contents only, 10 pages.
Verber, et al., "The design of metabolically-stable peptide analogs,". Trends in Neurosciences, Sep. 1985, pp. 392-396.
Evans et al. "Design of nonpeptidal ligands for a peptide receptor: cholecystokinin antagonists" J. Med. Chem, 1987 30:1229-39.
Dayhoff et al. A model of evolutionary change in proteins, in Dayhoff, M.O. Edition, Atlas of Protein Sequence and Structure, 1978, Natl. Biomed. Res. Found., Washington DC, 5(3), 345-352.
Henilkoff et al. "Amino acid substitution matrices from protein blocks", Proc Natl Acad Sci U S A., 89(22): 10915-10919, Nov. 15, 1992.
Wyckoff et al., eds., Methods in Enzymology vol. 114—Diffraction Methods for Biological Macromolecules, Academic Press, Orlando, FL; title page, publication page, and table of contents only, 5 pages (1985).
Wyckoff et al., eds., Methods in Enzymology vol. 115. Diffraction Methods for Biological Macromolecules, Academic Press, Orlando, FL; title page, publication page, and table of contents only, 4 pages (1985).
Krause, A. et al., "Antigen-dependent CD28 Signaling Selectively Enhances Survival and Proliferation in Genetically Modified Activated Human Primary T Lymphocytes", J. Exp. Med., vol. 188, No. 4, Aug. 17, 1998, 619-626.
Finney H., et al., "Chimeric Receptors Providing Both Primary and Costimulatory Signaling in T Cells from a Single Gene Product", J Immunol 1998; 161:2791-2797.
Kalos M., et al., "T Cells with Chimeric Antigen Receptors Have Potent Antitumor Effects and Can Establish Memory in Patients with Advanced Leukemia", Aug. 10, 2011 vol. 3 Issue 95 95ra73, Science Translational Medicine.
Porter D., et al., "Chimeric Antigen Receptor-Modified T Cells in Chronic Lymphoid Leukemia", The new England Journal of Medicine, 2011;365:725-33.
Hombach, A., et al., "Tumor-Specific T Cell Activation by Recombinant Immunoreceptors: CD3z Signaling and CD28 Costimulation Are Simultaneously Required for Efficient IL-2 Secretion and Can Be Integrated Into One Combined CD28/CD3z Signaling Receptor Molecule". J Immunol 2001; 167:6123-6131.
Fegan, A. et al., "Chemically Controlled Protein Assembly: Techniques and Applications", Chem. Rev. 2010, 110, 3315-3336.
Graham, F., et al., "A New Technique for the Assay of Infectivity of Human Adenovirus 5 DNA", Virology 52, 1973, 456-467.
Guedan, S., et al., "ICOS-based chimeric antigen receptors program bipolar TH17/TH1 cells", Blood 2014 124:1070-1080; doi: https://doi.org/10.1182/blood-2013-10-535245.
Shen, C., et al., "Chimeric antigen receptor containing ICOS signaling domain mediates specific and efficient antitumor effect of T cells against EGFRvIII expressing glioma", Journal of Hematology Oncology 2013, 6:33.
Song, D., et al., "Pro-survival signaling via CD27 costimulation drives effective CAR T-cell therapy", OncoImmunology 1:4, 547-549; Jul. 2012.
Hartl et al., "Genetics: Principles and Analysis", 1997, Jones and Bartlett Publishers.
van Rhenen, et al., "The novelAMLstem cell-associated antigen CLL-1 aids in discrimination between normal and leukemic stem cells", Blood, Oct. 1, 2007 , vol. 110, No. 7.
Bakker, A., et al, "C-Type Lectin-Like Molecule-1: A Novel Myeloid Cell Surface Marker Associated with Acute Myeloid Leukemia", Cancer Research 64, 8443-8450, Nov. 15, 2004.
Gross et al., "Therapeutic Potential of T Cell Chimeric Antigen Receptors (CARs) in Cancer Treatment: Counteracting Off-Tumor Toxicities for Safe CAR T Cell Therapy", Annu. Rev. Pharmacol. Toxicol. 56:59-83 (2016).
Kabat EA, et al., "Attempts to locate complementarity-determining residues in the variable positions of light and heavy chains.". Ann N Y Acad Sci. Dec. 31, 1971;190:382-93. PMID: 5290024.
Lovelock, J.E. et al., "Prevention of freezing damage to living cells by dimethyl sulphoxide.", Nature. May 16, 1959;183(4672):1394-5. PMID: 13657132.
Ashwood-Smith, "Preservation of mouse bone marrow at −79 degrees C. with dimethyl sulphoxide.", Nature, 1961; 190, 1204-1205.
Rinfret, A. P., "Factors affecting the erythrocyte during rapid freezing and thawing", Ann N Y Acad Sci. Apr. 13, 1960;85:576-9.
Stahli C., "Distinction of epitopes by monoclonal antibodies". Methods Enzymol. 1983;92:242-53.
Kirkland T.N., et al., "Analysis of the fine specificity and cross-reactivity of monoclonal anti-lipid A antibodies."J Immunol. Dec. 1, 1986;137(11):3614-9.
Morel G.A., et al., "Monoclonal antibodies to bovine serum albumin: affinity and specificity determinations.", Mol Immunol. Jan. 1988;25(1):7-15.
Cheung R.C., "Epitope-specific antibody response to the surface antigen of duck hepatitis B virus in infected ducks", Virology. Jun. 1990;176(2):546-52.
Moldenhauer, G., "Identity of HML-1 antigen on intestinal intraepithelial T cells and of B-ly7 antigen on hairy cell leukaemia.", Scand J Immunol. Aug. 1990;32(2):77-82.
Davis, et. al, "Basic Methods in Molegular Biology", 1986, Elsevier, Table of Contents Only.
Sambrook, J., et al., "Molecular Cloning A Laboratory Manual", 2001, Third Edition, Cold Spring Harbor Laboratory Press, Table of contents only.
Rinfret, AP, "Factors Affecting the Erythrocyte During Rapid Freezing" Ann N Y Acad Sci. 1960;85:576-94.
Sloviter Ha, et al., "Recovery and transfusion of human erythrocytes after freezing in polyglycol solutions.", Nature. Dec. 1, 1962;196:899-900. PMID: 13989282 Publisher: Nature.

(56) References Cited

OTHER PUBLICATIONS

Graham FL, et al, "A new technique for the assay of infectivity of human adenovirus 5 DNA", Virology. Apr. 1973;52(2):456-67.
Chu G, "SV40 DNA transfection of cells in suspension: analysis of the efficiency of transcription and translation of T-antigen", Gene. Mar. 1981;13(2):197-202.
Harlow, et al., Antibodies: A Laboratory Manual, Cold Spring Harbor Laboratory, eds., 1988.
Hua Lu, et al.; "Tragett ing Human C-Type Lectin-Like Molecule-1 (CLL-1) with a Bispecific Antibody for Acute Myeloid Leukemia Immunotherapy", Angew Chen Int.Engl. Sep. 8, 2014, 53 (37); pp. 9841-9845.
Xiaoxian Zhao, et al.; "Trageting C-Type Lectin-Like Molecule-1 for Antibody-Mediated Immunotherapy in Acute Myeloid Leukemia", Maematologica, Jul. 31, 2009, vol.
Haruko Tashiro, et al.; Treatment of Acute Myeloid Leukemia with T Cells Expressing Chimeric Antigen Receptors Directed to C-Type Lectin-Like Molecule 1; Molecular Therapy, Sep. 2017; vol. 25, No. 9.
Van Rhenen, Anna et. al. The novel AML stem cell-associated antigen CLL-1 aids in discrimination between normal and leukemic stem cells, Blood 2007 110:2659-2666; doi: https://doi.org/10.1182/blood-2007-03-083048.
Bakker, A.B.H., et al., C-Type Lectin-Like Molecule-1: A Novel Myeloid Cell Surface Marker Associated with Acute Myeloid LeukemiaCancer Res. 64:8443-8450 (2004).
Marshall et al., Identification and Characterization of a Novel Human Myeloid Inhibitory C-type Lectin-like Receptor (MICL) That Is Predominantly Expressed on Granulocytes and Monocytes, J. Biol. Chem. 279:14792-14802 (2004).
C-type lectin domain family 12 member A isoform 1 [*Homo sapiens*], NCBI Reference Sequence: NP_612210.4, ://www.ncbi.nlm.nih.gov/protein/NP_612210.4, retrieved on Oct. 2, 2017.
UniProtKB—Q5QGZ9 (CL12A_HUMAN), (2008), ://www.uniprot.org/uniprot/Q5QGZ9, retrieved on Oct. 2, 2017.
First Examination Report for New Zealand Patent Application No. 747172, which was dated Aug. 29, 2019 and is related to this subject application.
English translation of Office Action and Search Report for Taiwanese Patent Application No. 106111224, which was dated Sep. 20, 2019 and is related to this subject application.
Original version of Office Action for Taiwanese Patent Application No. 106111224, which was dated Sep. 10, 2019 and is related to this subject application.
Original version of Search Report for Taiwanese Patent Application No. 106111224, which was dated Sep. 10, 2019 and is related to this subject application.
First Examination Report for Canadian Application No. 3019650, dated Sep. 19, 2019, which is related to this subject application.
Supplementary European Search Report for EP Application No. EP 17 77 6859, which was dated Oct. 7, 2019, and is related to this subject application.
Leong S.R. et al.: "An anti-CD3/anti-CLL-1 bispecific antibody for the treatment of acute myeloid leukemia", Blood, Feb. 2, 2017, vol. 129, No. 5, pp. 609-618.
First Office Action in Primary Examination for Taiwanese Patent Application No. 106111228; 883738, dated Sep. 23, 2019, and is related to this subject application.
Search Report in Primary Examination for Taiwanese Patent Application No. 106111228; 883738, dated Sep. 23, 2019, and is related to this subject application.
English Translation of First Office Action and Search Report in Primary Examination for Taiwanese Patent Application No. 106111228; 883738, dated Sep. 23, 2019, and is related to this subject application.
Office Action dated Oct. 2, 2019 for Taiwan Patent Application No. 106111226, which is related to this subject application.
Search Report dated Oct. 2, 2019 for Taiwan Patent Application No. 106111226, which is related to this subject application.

English Translation of Office Action dated Oct. 2, 2019 for Taiwan Patent Application No. 106111226, which is related to this subject application.
Supplementary Partial European Search Report, dated Sep. 19, 2019 for European Patent Application No. 17776833, which is related to this subject application.
Final Office Action for U.S. Appl. No. 15/476,309, dated Sep. 10, 2019, which is related to this subject application.
Jena et al., "Redirecting T-cell specificity by introducing a tumor-specific chimeric antigen receptor", Blood Aug. 19, 2010, vol. 116, No. 7, pp. 1035-1044.
Bonini et al., "Adoptive T-cell therapy for cancer. The era of engineered T cells", European Journal of Immunology; 2015, vol. 45: pp. 2457-2469.
Chames et al., "Therapeutic antibodies: successes, limitations and hopes for the future", British Journal of Pharmacology; 2009, vol. 157, pp. 220-233.
Gura et al., "Systems for Identifying New Drugs Are Often Faulty", Science, Nov. 7, 1997, vol. 278, pp. 1041-1042.
Kaiser et al., "First Pass at Cancer Genome Reveals Complex Landscape", Science; 2006, vol. 313, p. 1370.
Original version of Office Action for Japanese Patent Application No. 2018-551953, dated Oct. 29, 2019, which is related to this subject application.
English translation of Office Action for Japanese Patent Application No. 2018-551953, dated Oct. 29, 2019, which is related to this subject application.
Original version of Official Action for Panamanian Patent Application No. PI/2018/92399-01, dated Mar. 14, 2019, which is related to this subject application.
English translation of Official Action for Panamanian Patent Application No. PI/2018/92399-01, dated Mar. 14, 2019, which is related to this subject application.
Guest Ryan D et al: The Role of Extracellular Spacer Regions in the Optimal Design of Chimeric Immune Receptors—Evaluation of Four Different SCFVS and ANTIGENS11, Journal of Immunotherapy, Lippincott Williams & Wilkins, US, vol. 28, No. 3, pp. 203-211, Jan. 1, 2005 (Jan. 1, 2005).
English translation First Official Action—dated Nov. 7, 2019 (EA Application No. 201891992), related to this subject application.
Examiner Initiated Interview Summary (U.S. Appl. No. 15/476,699) dated Jun. 14, 2019.
Notice of Acceptance of request to add inventor in U.S. Appl. No. 15/476,309, dated Jun. 18, 2019.
Final Office Action (U.S. Appl. No. 15/475,681) dated Apr. 23, 2019, related to this subject application.
Notice of Allowance for U.S. Appl. No. 15/475,681, dated Jun. 24, 2019 (37 Pages).
Orignal First Official Action—dated Nov. 7, 2019 (EA Application No. 201891992), related to this subject application.
Communication 70a and 70a(2)(EP Application No. 17776859.5)(dated Oct. 24, 2019), related to this subject application.
MA Examination Report (English translation (MA Application No. MA 43603), dated Mar. 3, 2018, related to this subject application.
Original Office Action PE Patent Application No. 001934-2018/DIN)(dated Oct. 18, 2019), related to this subject application.
English translation of Office Action in PE Patent Application No. 001934-2018/DIN)(dated Oct. 19, 2019), related to this subject application.
Communication Pursuant to Rule 164(1) EPC, Application No. EP17776833.0—1116 / 3436036 PCT/US2017025516related to this subject application, dated Oct. 2, 2019.
International Search Report for PCT/US2017/025613 dated Jul. 12, 2017.
Communication 70a and 70a(2)(EP Application No. 17776766.2)(dated Nov. 22, 2019), related to this subject application.
Granting Resolution Colombian Patent Application National Phase No. NC2018/0010547, dated Nov. 25, 2019.
European search Report for Application No. 17776766.2, PCT/US2017025351 dated Nov. 5, 2019.
Addition of Inventor (Jonathan Bellk added as an inventor to the application)(SG Patent Application No. 11201808403S)—dated Nov. 6, 2019.

(56) References Cited

OTHER PUBLICATIONS

Amendment Notification—Request for Correction of Error Accepted Accepted (Jonathan Bellk added as an inventor to the application)(NZ Patent Application No. 746700)—dated Oct. 4, 2019.
Second Notice of Allowance (U.S. Appl. No. 15/475,681) dated Oct. 24, 2019.
Restriction Requirement (U.S. Appl. No. 15/475,681) dated Aug. 7, 2018.
Notice to File Missing Parts (U.S. Appl. No. 16/570,645) dated Sep. 24, 2019.
Notice to File Corrected Application Papers (U.S. Appl. No. 16/569,341) dated Sep. 25, 2019.
Notice to File Corrected Application Papers (U.S. Appl. No. 16/658,480) dated Oct. 29, 2019.
Notice to Comply With Requirements for Sequence Disclosure (U.S. Appl. No. 15/476,699) dated Aug. 14, 2018.
Supplementary European Search Report for EP Application No. EP 17776859, which was dated Oct. 7, 2019, and is related to this subject matter.
Notification Prior to Examination of Patent Application No. 261941 According to Section 18 of the Law and Regulation 36 of the Regulations dated Nov. 17, 2019.
English Translation notification Prior to Examination of Patent Application No. 261941 According to Section 18 of the Law and Regulation 36 of the Regulations dated Nov. 17, 2019.
Notification Prior to Examination of Patent Application No. 262041 According to Section 18 of the Law and Regulation 36 of the Regulations dated Nov. 17, 2019.
English Translation Notification Prior to Examination of Patent Application No. 262041 According to Section 18 of the Law and Regulation 36 of the Regulations dated Nov. 17, 2019.
Notification Prior to Examination of Patent Application No. 261942 According to Section 18 of the Law and Regulation 36 of the Regulation dated Nov. 17, 2019.
English Translation Notification Prior to Examination of Patent Application No. 261942 According to Section 18 of the Law and Regulation 36 of the Regulations dated Nov. 17, 2019.
Official Office Action in Colombia Patent Application No.—NC2019/0008646, dated Dec. 6, 2019.
English Translation Official Office Action in Colombia Patent Application No.—NC2019/0008646, dated Dec. 6, 2019.
English Translation of Granting Resolution Colombian Patent Application National Phase No. NC2018/0010547, dated Nov. 25, 2019.
Grant of Request to add Co-Inventor (Jonathan Bellk added as an inventor to the application)(TH Patent Application No. 1801006120)—dated Oct. 29, 2019 (receipt serves as grantt).
English Translation of Grant of Request to add Co-Inventor (Jonathan Bellk added as an inventor to the application) (TH Patent Application No. 1801006120)—dated Oct. 29, 2019.
First Office Action for Ukrainian Patent Application No. a 2018 09953, which was dated Oct. 31, 2019 and is related to this subject application.
English Translatlation of First Office Action for Ukrainian Patent Application No. a 2018 09953, which was dated Oct. 31, 2019 and is related to this subject application.
Original and English Translation of Office Action dated Jan. 6, 2020 in Korean Patent Application No. 10-2018-7031572.

* cited by examiner

CLL1 CAR expression determined by protein L at day 12 after transduction

Protein L →

FIGURE 9A – Anti-CLL-1 Binding Molecules

```
                        FR1                      CDR1              FR2              CDR2
24C1_VH      QVQLQESGPGLVKPSETLSLTCTVS GGSISS--Y YWSWIRQPPGKGLEWIGYI YYSGS-T
24C8_VH      QVQLQESGPGLVKPSQTLSLTCTVS GGSISSGGY YWSWIRQHPGKGLEWIGYI HHSGS-T
20C5.1_VH    QVQLVQSGAEVKKPGASVKVSCKVS GYTLT--EI SMHWVRQAPGKGLEWMGGI DPEDGET
20C5.2_VH    QVQLVESGGGVVQPGRSLRLSCAAS GFTFSS--Y GMHWVRQAPGKGLEWVAVI SYDGSNK
             ****:**  : :*. :: ::.  *  :::       *:** *******:. :  ...:
                         FR3                     CDR3               FR4
24C1_VH      NYNPSLKSRVTISVDTSKNQFSLKLSSVTAADTAVYYCVS LVYCGGDCYSGFDY WGQGTL
24C8_VH      HYNPSLKSRVTISIDTSKNLFSLRLSSVTAADTAVYYCAS LVYCGGDCYSGFDY WGQGTL
20C5.1_VH    IYAQKFQGRVTVTEDTSTDTAYMELSSLRSEDTAVYYCAT ESRGIG--WPYFDY WGQGTL
20C5.2_VH    YYVDSVKGRFTISRDNSKNRLYLQMNSLRAEDTAVYYCAR ERYSG------PDY WGQGTL
             *  ...:.*:.*:: *.*.:    :.:.*:  : ******. ******
               FR4
24C1_VH      VTVSS
24C8_VH      VTVSS
20C5.1_VH    VTVSS
20C5.2_VH    VTVSS
             *****
```

FIGURE 9B

|           | SEQ ID NO: | | | |
|-----------|------|------|------|------|
|           | VH   | CDR1 | CDR2 | CDR3 |
| 24C1_VH   | 16   | 17   | 18   | 19   |
| 24C8_VH   | 50   | 51   | 52   | 53   |
| 20C5.1_VH | 72   | 73   | 74   | 75   |
| 20C5.2_VH | 94   | 95   | 96   | 97   |

FIGURE 9C – Anti-CLL-1 Binding Molecules

```
              FR1                         CDR1             FR2              CDR2      FR3
24C1_VL    DIQLTQSPSSLSASVGDRVSFTC QASQDINNFLN WYQQKPGKAPKLLIY DASNLET GVPS
24C8_VL    DIQLTQSPSSLSASVGDRVSFTC QASQDINNFLN WYQQKPGKAPKLLIY DASNLET GVPS
20C5.1_VL  DIQMTQSPSSLSASVGDRVTITC RASQSISSYLN WYQQKPGKAPKLLIS GASSLKS GVPS
20C5.2_VL  EIVMTQSPATLSVSPGERATLSC RASQSVSSLLT WYQQKPGQAPRLLIF GASTRAT GIPA
           :* :****;;**.* *;*.:::*;***.... *.******;**;***  .**.  :*;*;

FR3                                CDR3            FR4
24C1_VL    RFSGSGSGTDFTFTISSLQPEDIATYYC QQYGNLPFT FGGGTKVEIKR
24C8_VL    RFSGSGSGTDFTFTISSLQPEDIATYYC QQYGNLPFT FGGGTKVEIKR
20C5.1_VL  RFSGSGSGTDFTLTISSLPPEDFATYYC QQSYSTPIT FGQGTRLEIKR
20C5.2_VL  RFSGSGSGTGFTLTISSLQSEDFAVYYC QQYDTWPFT FGPGTKVDFKR
           ********.**;***** ,**;*.**** , *;*;**  **::::;**
```

FIGURE 9D

|  | SEQ ID NO: | | | |
|---|---|---|---|---|
|  | VL | CDR1 | CDR2 | CDR3 |
| 24C1_VL | 21 | 22 | 23 | 24 |
| 24C8_VL | 55 | 56 | 57 | 58 |
| 20C5.1_VL | 77 | 78 | 79 | 80 |
| 20C5.2_VL | 99 | 100 | 101 | 102 |

SEQUENCE LISTING

<160> NUMBER OF SEQ ID NOS: 147

<210> SEQ ID NO 1
<211> LENGTH: 294
<212> TYPE: DNA
<213> ORGANISM: Homo sapiens

<400> SEQUENCE: 1

```
cttgataatg aaaagtcaaa cggaacaatc attcacgtga agggcaagca cctctgtccg      60
tcacccttgt ccctggtcc atccaagcca ttctgggtgt tggtcgtagt gggtggagtc     120
ctcgcttgtt actctctgct cgtcaccgtg gcttttataa tcttctgggt tagatccaaa    180
agaagccgcc tgctccatag cgattacatg aatatgactc cacgccgccc tggccccaca    240
aggaaacact accagcctta cgcaccacct agagatttcg ctgcctatcg gagc           294
```

<210> SEQ ID NO 2
<211> LENGTH: 98
<212> TYPE: PRT
<213> ORGANISM: Homo sapiens

<400> SEQUENCE: 2

```
Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro Phe Trp
            20                  25                  30

Val Leu Val Val Val Gly Gly Val Leu Ala Cys Tyr Ser Leu Leu Val
        35                  40                  45

Thr Val Ala Phe Ile Ile Phe Trp Val Arg Ser Lys Arg Ser Arg Leu
    50                  55                  60

Leu His Ser Asp Tyr Met Asn Met Thr Pro Arg Arg Pro Gly Pro Thr
65                  70                  75                  80

Arg Lys His Tyr Gln Pro Tyr Ala Pro Pro Arg Asp Phe Ala Ala Tyr
                85                  90                  95

Arg Ser
```

<210> SEQ ID NO 3
<211> LENGTH: 90
<212> TYPE: DNA
<213> ORGANISM: Homo sapiens

<400> SEQUENCE: 3

```
cttgataatg aaaagtcaaa cggaacaatc attcacgtga agggcaagca cctctgtccg      60
tcacccttgt ccctggtcc atccaagcca                                         90
```

<210> SEQ ID NO 4
<211> LENGTH: 30
<212> TYPE: PRT
<213> ORGANISM: Homo sapiens

<400> SEQUENCE: 4

Leu Asp Asn Glu Lys Ser Asn Gly Thr Ile Ile His Val Lys Gly Lys

```
                1               5                  10                  15

His Leu Cys Pro Ser Pro Leu Phe Pro Gly Pro Ser Lys Pro
            20                  25                  30

<210> SEQ ID NO 5
<211> LENGTH: 81
<212> TYPE: DNA
<213> ORGANISM: Homo sapiens

<400> SEQUENCE: 5
ttctgggtgt tggtcgtagt gggtggagtc ctcgcttgtt actctctgct cgtcaccgtg      60
gcttttataa tcttctgggt t                                                81

<210> SEQ ID NO 6
<211> LENGTH: 27
<212> TYPE: PRT
<213> ORGANISM: Homo sapiens

<400> SEQUENCE: 6

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 7
<211> LENGTH: 123
<212> TYPE: DNA
<213> ORGANISM: Homo sapiens

<400> SEQUENCE: 7
agatccaaaa gaagccgcct gctccatagc gattacatga atatgactcc acgccgccct      60
ggccccacaa ggaaacacta ccagccttac gcaccaccta gagatttcgc tgcctatcgg     120
agc                                                                   123

<210> SEQ ID NO 8
<211> LENGTH: 41
<212> TYPE: PRT
<213> ORGANISM: Homo sapiens

<400> SEQUENCE: 8

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 9
<211> LENGTH: 336
<212> TYPE: DNA
<213> ORGANISM: Homo sapiens

<400> SEQUENCE: 9
agggtgaagt tttccagatc tgcagatgca ccagcgtatc agcagggcca gaaccaactg      60
tataacgagc tcaacctggg acgcagggaa gagtatgacg ttttggacaa gcgcagagga     120
cgggaccctg agatgggtgg caaaccaaga cgaaaaaacc cccaggaggg tctctataat     180
gagctgcaga aggataagat ggctgaagcc tattctgaaa taggcatgaa aggagagcgg     240
agaaggggaa aagggcacga cggtttgtac caggggactca gcactgctac gaaggatact     300
```

```
tatgacgctc tccacatgca agccctgcca cctagg                                    336
```

<210> SEQ ID NO 10
<211> LENGTH: 112
<212> TYPE: PRT
<213> ORGANISM: Homo sapiens

<400> SEQUENCE: 10

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 11
<211> LENGTH: 117
<212> TYPE: DNA
<213> ORGANISM: Homo sapiens

<400> SEQUENCE: 11

```
attgaggtga tgtatccacc gccttacctg gataacgaaa agagtaacgg taccatcatt        60
cacgtgaaag gtaaacacct gtgtccttct cccctcttcc ccgggccatc aaagccc          117
```

<210> SEQ ID NO 12
<211> LENGTH: 39
<212> TYPE: PRT
<213> ORGANISM: Homo sapiens

<400> SEQUENCE: 12

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35
```

<210> SEQ ID NO 13
<211> LENGTH: 288
<212> TYPE: DNA
<213> ORGANISM: Homo sapiens

<400> SEQUENCE: 13

```
gctgcagcat tgagcaactc aataatgtat tttagtcact ttgtaccagt gttcttgccg        60
gctaagccta ctaccacacc cgctccacgg ccacctaccc cagctcctac catcgcttca       120
cagcctctgt ccctgcgccc agaggcttgc cgaccggccg caggggcgc tgttcatacc        180 agaggactgg atttcgcctg cgatatctat atctgggcac cctggccgg aacctgcggc        240 gtactcctgc tgtccctggt catcacgctc tattgtaatc acaggaac                    288
```

<210> SEQ ID NO 14
<211> LENGTH: 96
<212> TYPE: PRT
<213> ORGANISM: Homo sapiens

<400> SEQUENCE: 14

Ala Ala Ala Leu Ser Asn Ser Ile Met Tyr Phe Ser His Phe Val Pro
1               5                   10                  15

Val Phe Leu Pro Ala Lys Pro Thr Thr Thr Pro Ala Pro Arg Pro Pro
            20                  25                  30

Thr Pro Ala Pro Thr Ile Ala Ser Gln Pro Leu Ser Leu Arg Pro Glu
        35                  40                  45

Ala Cys Arg Pro Ala Ala Gly Gly Ala Val His Thr Arg Gly Leu Asp
    50                  55                  60

Phe Ala Cys Asp Ile Tyr Ile Trp Ala Pro Leu Ala Gly Thr Cys Gly
65                  70                  75                  80

Val Leu Leu Leu Ser Leu Val Ile Thr Leu Tyr Cys Asn His Arg Asn
                85                  90                  95

<210> SEQ ID NO 15
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
caggtgcagc tgcaggaatc cggaccgggg ctggtgaagc ccagcgagac tctgagtctc      60
acgtgtacag tttctggagg tagcattagc tcctactatt ggtcatggat aaggcagccc     120
cccgggaagg gattggaatg gatcggctat atttactaca gtgggagcac caattacaac     180
ccctcactga agtctagagt tacaatcagc gttgacacct caaagaatca gttcagtttg     240
aaattgtcta gcgtcacagc agctgataca gccgtctatt attgtgtttc tctggtctat     300
tgcggtgggg attgttacag tggctttgac tattgggggc agggtactct ggttacagtt     360
tcttcc                                                                 366

<210> SEQ ID NO 16
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Ser Leu Val Tyr Cys Gly Gly Asp Cys Tyr Ser Gly Phe Asp Tyr Trp
            100                 105                 110

Gly Gln Gly Thr Leu Val Thr Val Ser Ser
        115                 120

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Ser Ile Ser Ser Tyr
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Tyr Ser Gly Ser
1               5

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Val Tyr Cys Gly Gly Asp Cys Tyr Ser Gly Phe Asp Tyr
1               5                   10

<210> SEQ ID NO 20
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
gacatccagt tgacacagag cccgagttcc ttgtccgcct ccgtcgggga tagagtgtca      60
tttacctgtc aggcctctca ggatattaat aactttctga attggtatca gcaaaagccc    120
ggaaaggcac ccaagctgtt gatttacgac gccagtaacc tggagacagg cgtgccctcc    180
cggtttagtg gtagcggaag cggtacggat tttaccttta ctatcagctc tctccaaccc    240
gaagacattg caacctacta ttgtcaacaa tatggaaacc tgccttttac atttggcggc    300
ggcaccaagg tggagattaa gcgg                                           324

<210> SEQ ID NO 21
<211> LENGTH: 108
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 21

Asp Ile Gln Leu Thr Gln Ser Pro Ser Ser Leu Ser Ala Ser Val Gly
1               5                   10                  15

Asp Arg Val Ser Phe Thr Cys Gln Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gly Asn Leu Pro Phe
                85                  90                  95

Thr Phe Gly Gly Gly Thr Lys Val Glu Ile Lys Arg
            100                 105

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ala Ser Gln Asp Ile Asn Asn Phe Leu Asn
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asp Ala Ser Asn Leu Glu Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gln Tyr Gly Asn Leu Pro Phe Thr
1               5

<210> SEQ ID NO 25
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggcactcc ccgtaactgc tctgctgctg ccgttggcat tgctcctgca cgccgcacgc    60

-continued

```
ccgcaggtcc aactgcaaga aagcggaccc ggactggtga agccttctga gacacttagt    120
ctgacgtgca cggtcagtgg cggctccatc tcctcctatt attggtcatg gatacgacaa    180
cccccaggta agggcctgga atggattggc tatatctact attcaggaag cacgaactac    240
aatcccagcc tgaagtcccg agtgacaatt tcagtagata ccagtaaaaa ccagttcagt    300
cttaaactgt caagcgtgac agctgccgac accgctgtgt attactgcgt ctcactggtg    360
tattgtggag gggattgtta tagcgggttc gattattggg acagggaac cctggtgact    420
gtatcttccg gcggcggcgg ctcaggggt ggcggtagtg gcggtggggg ttccgatatt    480
caactgacac aatcccccag ctcactcagc gccagcgtgg gggacagggt tagctttacc    540
tgtcaagcct ctcaggatat aaataacttt ctgaactggt atcaacagaa gcctgggaag    600
gcgcccaaac tcctgatcta tgatgcgtcc aacctggaaa ctggcgtgcc ttcacgcttt    660
agcggctctg gcagtggtac agacttcact tttaccatct cttcacttca gccggaggac    720
atcgccacat attactgtca acagtacgga aacttgccct tacttttgg aggcggcacc    780
aaagttgaaa tcaaaagggc cgctgccctg ataacgaaa agagcaatgg gactataata    840
catgttaaag gaaaacacct gtgtccatct cccctgttcc ctggaccgtc aaagccattt    900
tgggtgctcg tggttgtcgg tggcgttctc gcctgttata gcttgctggt gacagtagcc    960
ttcattatct tttgggtgag atccaaaaga agccgcctgc tccatagcga ttacatgaat   1020
atgactccac gccgccctgg ccccacaagg aaacactacc agccttacgc accacctaga   1080
gatttcgctg cctatcggag cagggtgaag ttttccagat ctgcagatgc accagcgtat   1140
cagcagggcc agaaccaact gtataacgag ctcaacctgg gacgcaggga gagtatgac    1200
gttttggaca gcgcagagg acgggaccct gagatgggtg gcaaaccaag acgaaaaaac   1260
ccccaggagg gtctctataa tgagctgcag aaggataaga tggctgaagc ctattctgaa   1320
ataggcatga aggagagcg gagaagggga aagggcacg acggtttgta ccagggactc   1380
agcactgcta cgaaggatac ttatgacgct ctccacatgc aagccctgcc acctaggtaa   1440
```

<210> SEQ ID NO 26
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Thr Val Ser Gly Gly
            35                  40                  45

Ser Ile Ser Ser Tyr Tyr Trp Ser Trp Ile Arg Gln Pro Pro Gly Lys
        50                  55                  60

Gly Leu Glu Trp Ile Gly Tyr Ile Tyr Tyr Ser Gly Ser Thr Asn Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Val Ser Leu Val Tyr Cys Gly Asp Cys Tyr Ser
            115                 120                 125

Gly Phe Asp Tyr Trp Gly Gln Gly Thr Leu Val Thr Val Ser Ser Gly
130                 135                 140

Gly Gly Gly Ser Gly Gly Gly Ser Gly Gly Gly Ser Asp Ile
145                 150                 155                 160

Gln Leu Thr Gln Ser Pro Ser Leu Ser Ala Ser Val Gly Asp Arg
                165                 170                 175

Val Ser Phe Thr Cys Gln Ala Ser Gln Asp Ile Asn Asn Phe Leu Asn
            180                 185                 190

Trp Tyr Gln Gln Lys Pro Gly Lys Ala Pro Lys Leu Leu Ile Tyr Asp
            195                 200                 205

Ala Ser Asn Leu Glu Thr Gly Val Pro Ser Arg Phe Ser Gly Ser Gly
            210                 215                 220

Ser Gly Thr Asp Phe Thr Phe Thr Ile Ser Ser Leu Gln Pro Glu Asp
225                 230                 235                 240

Ile Ala Thr Tyr Tyr Cys Gln Gln Tyr Gly Asn Leu Pro Phe Thr Phe
                245                 250                 255

Gly Gly Gly Thr Lys Val Glu Ile Lys Arg Ala Ala Ala Leu Asp Asn
            260                 265                 270

Glu Lys Ser Asn Gly Thr Ile Ile His Val Lys Gly Lys His Leu Cys
            275                 280                 285

Pro Ser Pro Leu Phe Pro Gly Pro Ser Lys Pro Phe Trp Val Leu Val
            290                 295                 300

Val Val Gly Gly Val Leu Ala Cys Tyr Ser Leu Leu Val Thr Val Ala
305                 310                 315                 320

Phe Ile Ile Phe Trp Val Arg Ser Lys Arg Ser Arg Leu Leu His Ser
                325                 330                 335

Asp Tyr Met Asn Met Thr Pro Arg Arg Pro Gly Pro Thr Arg Lys His
            340                 345                 350

Tyr Gln Pro Tyr Ala Pro Pro Arg Asp Phe Ala Ala Tyr Arg Ser Arg
            355                 360                 365

Val Lys Phe Ser Arg Ser Ala Asp Ala Pro Ala Tyr Gln Gln Gly Gln
            370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
            435                 440                 445

Arg Gly Lys Gly His Asp Gly Leu Tyr Gln Gly Leu Ser Thr Ala Thr
            450                 455                 460

Lys Asp Thr Tyr Asp Ala Leu His Met Gln Ala Leu Pro Pro Arg
465                 470                 475

<210> SEQ ID NO 27
<211> LENGTH: 1374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
caggtccaac tgcaagaaag cggacccgga ctggtgaagc cttctgagac acttagtctg      60
acgtgcacgg tcagtggcgg ctccatctcc tcctattatt ggtcatggat acgacaaccc     120
ccaggtaagg gcctggaatg gattggctat atctactatt caggaagcac gaactacaat     180
cccagcctga agtcccgagt gacaatttca gtagatacca gtaaaaacca gttcagtctt     240
aaactgtcaa gcgtgacagc tgccgacacc gctgtgtatt actgcgtctc actggtgtat     300
tgtggagggg attgttatag cgggttcgat tattggggac agggaaccct ggtgactgta     360
tcttccggcg gcggcggctc agggggtggc ggtagtggcg gtggggttc cgatattcaa      420
ctgacacaat cccccagctc actcagcgcc agcgtggggg acagggttag ctttacctgt     480
caagcctctc aggatataaa taactttctg aactggtatc aacagaagcc tgggaaggcg     540
cccaaactcc tgatctatga tgcgtccaac ctggaaactg gcgtgccttc acgctttagc     600
ggctctggca gtggtacaga cttcactttt accatctctt cacttcagcc ggaggacatc     660
gccacatatt actgtcaaca gtacggaaac ttgccctta cttttggagg cggcaccaaa      720
gttgaaatca aagggccgc tgccctggat aacgaaaaga gcaatgggac tataatacat      780
gttaaaggaa acacctgtg tccatctccc ctgttccctg accgtcaaa gccattttgg       840
gtgctcgtgg ttgtcggtgg cgttctcgcc tgttatagct tgctggtgac agtagccttc     900
attatctttt gggtgagatc caaaagaagc cgcctgctcc atagcgatta catgaatatg     960
actccacgcc gccctggccc cacaaggaaa cactaccagc cttacgcacc acctagagat    1020
ttcgctgcct atcggagcag ggtgaagttt tccagatctg cagatgcacc agcgtatcag    1080
cagggccaga accaactgta taacgagctc aacctgggac gcagggaaga gtatgacgtt    1140
ttggacaagc gcagaggacg ggaccctgag atgggtggca aaccaagacg aaaaaacccc    1200
caggagggtc tctataatga gctgcagaag gataagatgg ctgaagccta ttctgaaata    1260
ggcatgaaag gagagcggag aaggggaaaa gggcacgacg gtttgtacca gggactcagc    1320
actgctacga aggatactta tgacgctctc cacatgcaag ccctgccacc tagg          1374
```

<210> SEQ ID NO 28
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Ser Leu Val Tyr Cys Gly Gly Asp Cys Tyr Ser Gly Phe Asp Tyr Trp
            100                 105                 110

Gly Gln Gly Thr Leu Val Thr Val Ser Ser Gly Gly Gly Ser Gly
            115                 120                 125

Gly Gly Gly Ser Gly Gly Gly Ser Asp Ile Gln Leu Thr Gln Ser
130                 135                 140

Pro Ser Ser Leu Ser Ala Ser Val Gly Asp Arg Val Ser Phe Thr Cys
145                 150                 155                 160

Gln Ala Ser Gln Asp Ile Asn Asn Phe Leu Asn Trp Tyr Gln Gln Lys
                165                 170                 175

Pro Gly Lys Ala Pro Lys Leu Leu Ile Tyr Asp Ala Ser Asn Leu Glu
            180                 185                 190

Thr Gly Val Pro Ser Arg Phe Ser Gly Ser Gly Ser Gly Thr Asp Phe
        195                 200                 205

Thr Phe Thr Ile Ser Ser Leu Gln Pro Glu Asp Ile Ala Thr Tyr Tyr
    210                 215                 220

Cys Gln Gln Tyr Gly Asn Leu Pro Phe Thr Phe Gly Gly Gly Thr Lys
225                 230                 235                 240

Val Glu Ile Lys Arg Ala Ala Ala Leu Asp Asn Glu Lys Ser Asn Gly
                245                 250                 255

Thr Ile Ile His Val Lys Gly Lys His Leu Cys Pro Ser Pro Leu Phe
            260                 265                 270

Pro Gly Pro Ser Lys Pro Phe Trp Val Leu Val Val Val Gly Gly Val
        275                 280                 285

Leu Ala Cys Tyr Ser Leu Leu Val Thr Val Ala Phe Ile Ile Phe Trp
    290                 295                 300

Val Arg Ser Lys Arg Ser Arg Leu Leu His Ser Asp Tyr Met Asn Met
305                 310                 315                 320

Thr Pro Arg Arg Pro Gly Pro Thr Arg Lys His Tyr Gln Pro Tyr Ala
                325                 330                 335

Pro Pro Arg Asp Phe Ala Ala Tyr Arg Ser Arg Val Lys Phe Ser Arg
            340                 345                 350

Ser Ala Asp Ala Pro Ala Tyr Gln Gln Gly Gln Asn Gln Leu Tyr Asn
        355                 360                 365

Glu Leu Asn Leu Gly Arg Arg Glu Glu Tyr Asp Val Leu Asp Lys Arg
    370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
        435                 440                 445

Ala Leu His Met Gln Ala Leu Pro Pro Arg
    450                 455

<210> SEQ ID NO 29
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
atggcactcc ccgtaactgc tctgctgctg ccgttggcat tgctcctgca cgccgcacgc     60

```
ccgcaggtgc agctgcagga atccggaccg gggctggtga agcccagcga gactctgagt    120
ctcacgtgta cagtttctgg aggtagcatt agctcctact attggtcatg gataaggcag    180
cccccgggaa agggattgga atggatcggc tatatttact acagtgggag caccaattac    240
aaccctcac  tgaagtctag agttacaatc agcgttgaca cctcaaagaa tcagttcagt    300
ttgaaattgt ctagcgtcac agcagctgat acagccgtct attattgtgt ttctctggtc    360
tattgcggtg gggattgtta cagtggcttt gactattggg gcagggtac  tctggttaca    420
gtttcttccg ggggggagg  ctctgggggc ggaggctcag gtggtggagg cagcgacatc    480
cagttgacac agagcccgag ttccttgtcc gcctccgtcg gggatagagt gtcatttacc    540
tgtcaggcct ctcaggatat taataacttt ctgaattggt atcagcaaaa gcccggaaag    600
gcacccaagc tgttgattta cgacgccagt aacctggaga caggcgtgcc ctcccggttt    660
agtggtagcg gaagcggtac ggatttttacc tttactatca gctctctcca acccgaagac    720
attgcaacct actattgtca acaatatgga aacctgcctt ttacatttgg cggcggcacc    780
aaggtggaga ttaagcgggc ggcagctatt gaggtgatgt atccaccgcc ttacctggat    840
aacgaaaaga gtaacggtac catcattcac gtgaaggta  aacacctgtg tccttctccc    900
ctcttccccg ggccatcaaa gcccttctgg gttcttgtgg tcgtgggagg cgtgcttgct    960
tgttattctc tgctcgttac cgtggcgttt atcattttt  gggttagatc caaaagaagc   1020
cgcctgctcc atagcgatta catgaatatg actccacgcc gcctggccc  cacaaggaaa   1080
cactaccagc cttacgcacc acctagagat ttcgctgcct atcggagcag ggtgaagttt   1140
tccagatctg cagatgcacc agcgtatcag cagggccaga accaactgta taacgagctc   1200
aacctgggac gcagggaaga gtatgacgtt ttggacaagc gcagaggacg ggaccctgag   1260
atgggtggca aaccaagacg aaaaaacccc caggagggtc tctataatga gctgcagaag   1320
gataagatgg ctgaagccta ttctgaaata ggcatgaaag gagagcggag aaggggaaaa   1380
gggcacgacg gtttgtacca gggactcagc actgctacga aggatactta tgacgctctc   1440
cacatgcaag ccctgccacc taggtaa                                       1467
```

<210> SEQ ID NO 30
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Ser Tyr Tyr Trp Ser Trp Ile Arg Gln Pro Pro Gly Lys
    50                  55                  60

Gly Leu Glu Trp Ile Gly Tyr Ile Tyr Tyr Ser Gly Ser Thr Asn Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110
```

-continued

Val Tyr Tyr Cys Val Ser Leu Val Cys Gly Gly Asp Cys Tyr Ser
            115                 120                 125

Gly Phe Asp Tyr Trp Gly Gln Gly Thr Leu Val Thr Val Ser Ser Gly
    130                 135                 140

Gly Gly Gly Ser Gly Gly Gly Ser Gly Gly Gly Ser Asp Ile
145                 150                 155                 160

Gln Leu Thr Gln Ser Pro Ser Ser Leu Ser Ala Ser Val Gly Asp Arg
            165                 170                 175

Val Ser Phe Thr Cys Gln Ala Ser Gln Asp Ile Asn Asn Phe Leu Asn
            180                 185                 190

Trp Tyr Gln Gln Lys Pro Gly Lys Ala Pro Lys Leu Leu Ile Tyr Asp
            195                 200                 205

Ala Ser Asn Leu Glu Thr Gly Val Pro Ser Arg Phe Ser Gly Ser Gly
            210                 215                 220

Ser Gly Thr Asp Phe Thr Phe Thr Ile Ser Ser Leu Gln Pro Glu Asp
225                 230                 235                 240

Ile Ala Thr Tyr Tyr Cys Gln Gln Tyr Gly Asn Leu Pro Phe Thr Phe
            245                 250                 255

Gly Gly Gly Thr Lys Val Glu Ile Lys Arg Ala Ala Ile Glu Val
            260                 265                 270

Met Tyr Pro Pro Pro Tyr Leu Asp Asn Glu Lys Ser Asn Gly Thr Ile
            275                 280                 285

Ile His Val Lys Gly Lys His Leu Cys Pro Ser Pro Leu Phe Pro Gly
            290                 295                 300

Pro Ser Lys Pro Phe Trp Val Leu Val Val Val Gly Gly Val Leu Ala
305                 310                 315                 320

Cys Tyr Ser Leu Leu Val Thr Val Ala Phe Ile Ile Phe Trp Val Arg
            325                 330                 335

Ser Lys Arg Ser Arg Leu Leu His Ser Asp Tyr Met Asn Met Thr Pro
            340                 345                 350

Arg Arg Pro Gly Pro Thr Arg Lys His Tyr Gln Pro Tyr Ala Pro Pro
            355                 360                 365

Arg Asp Phe Ala Ala Tyr Arg Ser Arg Val Lys Phe Ser Arg Ser Ala
            370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
            405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
            485

<210> SEQ ID NO 31
<211> LENGTH: 1401
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 31

```
caggtgcagc tgcaggaatc cggaccgggg ctggtgaagc ccagcgagac tctgagtctc      60
acgtgtacag tttctggagg tagcattagc tcctactatt ggtcatggat aaggcagccc     120
cccgggaagg gattggaatg gatcggctat atttactaca gtgggagcac caattacaac     180
ccctcactga agtctagagt tacaatcagc gttgacacct caaagaatca gttcagtttg     240
aaattgtcta gcgtcacagc agctgataca gccgtctatt attgtgtttc tctggtctat     300
tgcggtgggg attgttacag tggctttgac tattgggggc agggtactct ggttacagtt     360
tcttccgggg ggggaggctc tggggcggaa ggctcaggtg gtggaggcag cgacatccag     420
ttgacacaga gcccgagttc cttgtccgcc tccgtcgggg atagagtgtc atttacctgt     480
caggcctctc aggatattaa taactttctg aattggtatc agcaaaagcc cggaaaggca     540
cccaagctgt tgatttacga cgccagtaac ctggagacag gcgtgccctc ccggtttagt     600
ggtagcggaa gcggtacgga ttttacccttt actatcagct ctctccaacc cgaagacatt     660
gcaacctact attgtcaaca atatggaaac ctgccttttta catttggcgg cggcaccaag     720
gtggagatta agcgggcggc agctattgag gtgatgtatc caccgcctta cctggataac     780
gaaaagagta acgtaccat cattcacgtg aaaggtaaac acctgtgtcc ttctcccctc     840
ttccccgggc catcaaagcc cttctgggtt cttgtggtcg tgggaggcgt gcttgcttgt     900
tattctctgc tcgttaccgt ggcgtttatc attttttggg ttagatccaa aagaagccgc     960
ctgctccata gcgattacat gaatatgact ccacgccgcc ctggccccac aaggaaacac    1020
taccagcctt acgcaccacc tagagatttc gctgcctatc ggagcagggt gaagttttcc    1080
agatctgcag atgcaccagc gtatcagcag ggccagaacc aactgtataa cgagctcaac    1140
ctgggacgca gggaagagta tgacgttttg gacaagcgca gaggacggga ccctgagatg    1200
ggtggcaaac caagacgaaa aaaccccag gagggtctct ataatgagct gcagaaggat    1260
aagatggctg aagcctattc tgaaataggc atgaaaggag agcggagaag gggaaagggg    1320
cacgacggtt tgtaccaggg actcagcact gctacgaagg atacttatga cgctctccac    1380
atgcaagccc tgccacctag g                                              1401
```

<210> SEQ ID NO 32
<211> LENGTH: 467
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 32

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80
```

-continued

```
Lys Leu Ser Ser Val Thr Ala Ala Asp Thr Ala Val Tyr Tyr Cys Val
                 85                  90                  95
Ser Leu Val Tyr Cys Gly Gly Asp Cys Tyr Ser Gly Phe Asp Tyr Trp
            100                 105                 110
Gly Gln Gly Thr Leu Val Thr Val Ser Ser Gly Gly Gly Gly Ser Gly
        115                 120                 125
Gly Gly Ser Gly Gly Gly Ser Asp Ile Gln Leu Thr Gln Ser
    130                 135                 140
Pro Ser Ser Leu Ser Ala Ser Val Gly Asp Arg Val Ser Phe Thr Cys
145                 150                 155                 160
Gln Ala Ser Gln Asp Ile Asn Asn Phe Leu Asn Trp Tyr Gln Gln Lys
                165                 170                 175
Pro Gly Lys Ala Pro Lys Leu Leu Ile Tyr Asp Ala Ser Asn Leu Glu
            180                 185                 190
Thr Gly Val Pro Ser Arg Phe Ser Gly Ser Gly Ser Gly Thr Asp Phe
        195                 200                 205
Thr Phe Thr Ile Ser Ser Leu Gln Pro Glu Asp Ile Ala Thr Tyr Tyr
    210                 215                 220
Cys Gln Gln Tyr Gly Asn Leu Pro Phe Thr Phe Gly Gly Gly Thr Lys
225                 230                 235                 240
Val Glu Ile Lys Arg Ala Ala Ala Ile Glu Val Met Tyr Pro Pro Pro
                245                 250                 255
Tyr Leu Asp Asn Glu Lys Ser Asn Gly Thr Ile Ile His Val Lys Gly
            260                 265                 270
Lys His Leu Cys Pro Ser Pro Leu Phe Pro Gly Pro Ser Lys Pro Phe
        275                 280                 285
Trp Val Leu Val Val Val Gly Gly Val Leu Ala Cys Tyr Ser Leu Leu
    290                 295                 300
Val Thr Val Ala Phe Ile Ile Phe Trp Val Arg Ser Lys Arg Ser Arg
305                 310                 315                 320
Leu Leu His Ser Asp Tyr Met Asn Met Thr Pro Arg Arg Pro Gly Pro
                325                 330                 335
Thr Arg Lys His Tyr Gln Pro Tyr Ala Pro Pro Arg Asp Phe Ala Ala
            340                 345                 350
Tyr Arg Ser Arg Val Lys Phe Ser Arg Ser Ala Asp Ala Pro Ala Tyr
        355                 360                 365
Gln Gln Gly Gln Asn Gln Leu Tyr Asn Glu Leu Asn Leu Gly Arg Arg
    370                 375                 380
Glu Glu Tyr Asp Val Leu Asp Lys Arg Gly Arg Asp Pro Glu Met
385                 390                 395                 400
Gly Gly Lys Pro Arg Arg Lys Asn Pro Gln Glu Gly Leu Tyr Asn Glu
                405                 410                 415
Leu Gln Lys Asp Lys Met Ala Glu Ala Tyr Ser Glu Ile Gly Met Lys
            420                 425                 430
Gly Glu Arg Arg Arg Gly Lys Gly His Asp Gly Leu Tyr Gln Gly Leu
        435                 440                 445
Ser Thr Ala Thr Lys Asp Thr Tyr Asp Ala Leu His Met Gln Ala Leu
    450                 455                 460
Pro Pro Arg
465

<210> SEQ ID NO 33
<211> LENGTH: 1548
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 33

```
atggcactcc ccgtaactgc tctgctgctg ccgttggcat tgctcctgca cgccgcacgc      60
ccgcaggtgc aattgcaaga gtccggcccc ggactcgtta aacccagtga gacgcttagc     120
ctgacctgta ccgtctcagg gggcagcatc tcctcttatt actggagctg gatcaggcag     180
cctccaggaa aaggccttga atggattggg tacatctact actctggctc aacaaattat     240
aatccatccc tgaagtcccg cgtgactatc tctgtggaca ccagcaagaa tcagttttca     300
ctgaagttgt ctagtgttac cgcggccgac accgccgtat actactgtgt gtctcttgtg     360
tactgtggcg gcgactgcta ttccgggttc gactactggg gccaagggac tctggtaacc     420
gtgtcctcag gcggcggcgg gtcaggagga ggcggcagtg gaggtggcgg ctccgacatc     480
cagctgacac aatcaccatc ttccctttca gcttcagtcg gggacagagt gtccttcaca     540
tgccaggcca gccaggatat caataacttc ctgaactggt accaacagaa acccggaaag     600
gctccaaagc tcctgatcta tgatgcttcc aacctggaga ccggcgtgcc ctccaggttc     660
agtggttcag gatcaggcac tgactttacg ttcaccatat ccagtcttca gcccgaagac     720
attgcaacct attactgcca acaatacggg aaccttccct ttacattcgg aggcggcacc     780
aaggtggaaa tcaaaagggc tgcagcattg agcaactcaa taatgtattt tagtcacttt     840
gtaccagtgt tcttgccggc taagcctact accacacccg ctccacggcc acctacccca     900
gctcctacca tcgcttcaca gcctctgtcc ctgcgcccag aggcttgccg accggccgca     960
gggggcgctg ttcataccag aggactggat ttcgcctgcg atatctatat ctgggcaccc    1020
ctggccggaa cctgcggcgt actcctgctg tccctggtca tcacgctcta ttgtaatcac    1080
aggaacagat ccaaaagaag ccgcctgctc catagcgatt acatgaatat gactccacgc    1140
cgccctggcc ccacaaggaa acactaccag ccttacgcac acctagaga tttcgctgcc    1200
tatcggagca gggtgaagtt ttccagatct gcagatgcac cagcgtatca gcagggccag    1260
aaccaactgt ataacgagct caacctggga cgcaggaag agtatgacgt tttggacaag    1320
cgcagaggac gggaccctga gatgggtggc aaaccaagac gaaaaaaccc ccaggagggt    1380
ctctataatg agctgcagaa ggataagatg gctgaagcct attctgaaat aggcatgaaa    1440
ggagagcgga gaggggaaa agggcacgac ggtttgtacc agggactcag cactgctacg    1500
aaggatactt atgacgctct ccacatgcaa gccctgccac ctaggtaa               1548
```

<210> SEQ ID NO 34
<211> LENGTH: 515
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
                20                  25                  30

Val Lys Pro Ser Glu Thr Leu Ser Leu Thr Cys Thr Val Ser Gly Gly
            35                  40                  45
```

```
Ser Ile Ser Ser Tyr Tyr Trp Ser Trp Ile Arg Gln Pro Pro Gly Lys
    50              55                  60
Gly Leu Glu Trp Ile Gly Tyr Ile Tyr Tyr Ser Gly Ser Thr Asn Tyr
65              70                  75                  80
Asn Pro Ser Leu Lys Ser Arg Val Thr Ile Ser Val Asp Thr Ser Lys
                85                  90                  95
Asn Gln Phe Ser Leu Lys Leu Ser Ser Val Thr Ala Ala Asp Thr Ala
                100                 105                 110
Val Tyr Tyr Cys Val Ser Leu Val Tyr Cys Gly Gly Asp Cys Tyr Ser
            115                 120                 125
Gly Phe Asp Tyr Trp Gly Gln Gly Thr Leu Val Thr Val Ser Ser Gly
    130                 135                 140
Gly Gly Ser Gly Gly Gly Gly Ser Gly Gly Gly Ser Asp Ile
145                 150                 155                 160
Gln Leu Thr Gln Ser Pro Ser Ser Leu Ser Ala Ser Val Gly Asp Arg
                165                 170                 175
Val Ser Phe Thr Cys Gln Ala Ser Gln Asp Ile Asn Asn Phe Leu Asn
            180                 185                 190
Trp Tyr Gln Gln Lys Pro Gly Lys Ala Pro Lys Leu Leu Ile Tyr Asp
        195                 200                 205
Ala Ser Asn Leu Glu Thr Gly Val Pro Ser Arg Phe Ser Gly Ser Gly
    210                 215                 220
Ser Gly Thr Asp Phe Thr Phe Thr Ile Ser Ser Leu Gln Pro Glu Asp
225                 230                 235                 240
Ile Ala Thr Tyr Tyr Cys Gln Gln Tyr Gly Asn Leu Pro Phe Thr Phe
                245                 250                 255
Gly Gly Gly Thr Lys Val Glu Ile Lys Arg Ala Ala Ala Leu Ser Asn
            260                 265                 270
Ser Ile Met Tyr Phe Ser His Phe Val Pro Val Phe Leu Pro Ala Lys
        275                 280                 285
Pro Thr Thr Thr Pro Ala Pro Arg Pro Pro Thr Pro Ala Pro Thr Ile
    290                 295                 300
Ala Ser Gln Pro Leu Ser Leu Arg Pro Glu Ala Cys Arg Pro Ala Ala
305                 310                 315                 320
Gly Gly Ala Val His Thr Arg Gly Leu Asp Phe Ala Cys Asp Ile Tyr
                325                 330                 335
Ile Trp Ala Pro Leu Ala Gly Thr Cys Gly Val Leu Leu Leu Ser Leu
            340                 345                 350
Val Ile Thr Leu Tyr Cys Asn His Arg Asn Arg Ser Lys Arg Ser Arg
        355                 360                 365
Leu Leu His Ser Asp Tyr Met Asn Met Thr Pro Arg Arg Pro Gly Pro
    370                 375                 380
Thr Arg Lys His Tyr Gln Pro Tyr Ala Pro Pro Arg Asp Phe Ala Ala
385                 390                 395                 400
Tyr Arg Ser Arg Val Lys Phe Ser Arg Ser Ala Asp Ala Pro Ala Tyr
                405                 410                 415
Gln Gln Gly Gln Asn Gln Leu Tyr Asn Glu Leu Asn Leu Gly Arg Arg
            420                 425                 430
Glu Glu Tyr Asp Val Leu Asp Lys Arg Arg Gly Arg Asp Pro Glu Met
        435                 440                 445
Gly Gly Lys Pro Arg Arg Lys Asn Pro Gln Glu Gly Leu Tyr Asn Glu
450                 455                 460
Leu Gln Lys Asp Lys Met Ala Glu Ala Tyr Ser Glu Ile Gly Met Lys
```

```
                465                 470                 475                 480
Gly Glu Arg Arg Arg Gly Lys Gly His Asp Gly Leu Tyr Gln Gly Leu
                    485                 490                 495

Ser Thr Ala Thr Lys Asp Thr Tyr Asp Ala Leu His Met Gln Ala Leu
                500                 505                 510

Pro Pro Arg
        515

<210> SEQ ID NO 35
<211> LENGTH: 1482
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
caggtgcaat tgcaagagtc cggccccgga ctcgttaaac ccagtgagac gcttagcctg      60
acctgtaccg tctcaggggg cagcatctcc tcttattact ggagctggat caggcagcct    120
ccaggaaaag gccttgaatg gattgggtac atctactact ctggctcaac aaattataat    180
ccatccctga gtcccgcgt gactatctct gtggacacca gcaagaatca gttttcactg     240
aagttgtcta gtgttaccgc ggccgacacc gccgtatact actgtgtgtc tcttgtgtac    300
tgtggcggcg actgctattc cgggttcgac tactggggcc aagggactct ggtaaccgtg    360
tcctcaggcg gcggcgggtc aggaggaggc ggcagtggag gtggcggctc cgacatccag    420
ctgacacaat caccatcttc cctttcagct tcagtcgggg acagagtgtc cttcacatgc    480
caggccagcc aggatatcaa taacttcctg aactggtacc aacagaaacc cggaaaggct    540
ccaaagctcc tgatctatga tgcttccaac ctggagaccg gcgtgccctc aggttcagt    600 ggttcaggat caggcactga ctttacgttc accatatcca gtcttcagcc cgaagacatt    660
gcaacctatt actgccaaca atacgggaac cttcccttta cattcggagg cggcaccaag    720
gtggaaatca aagggctgc agcattgagc aactcaataa tgtattttag tcactttgta    780
ccagtgttct tgccggctaa gcctactacc acacccgctc cacggccacc taccccagct    840
cctaccatcg cttcacagcc tctgtccctg cgcccagagg cttgccgacc ggccgcaggg    900
ggcgctgttc ataccagagg actggatttc gcctgcgata tctatatctg gcacccctg    960 gccggaacct gcggcgtact cctgctgtcc ctggtcatca cgctctattg taatcacagg   1020
aacagatcca aagaagccg cctgctccat agcgattaca tgaatatgac tccacgccgc   1080
cctggcccca aaggaaaaca ctaccagcct tacgcaccac ctagagattt cgctgcctat   1140
cggagcaggg tgaagttttc cagatctgca gatgcaccag cgtatcagca gggccagaac   1200
caactgtata cgagctcaa cctgggacgc agggaagagt atgacgtttt ggacaagcgc   1260
agaggacggg accctgagat gggtggcaaa ccaagacgaa aaacccccca ggagggtctc   1320
tataatgagc tgcagaagga taagatggct gaagcctatt ctgaaatagg catgaaagga   1380
gagcggagaa ggggaaaagg gcacgacggt ttgtaccagg gactcagcac tgctacgaag   1440
gatacttatg acgctctcca catgcaagcc ctgccaccta gg                      1482

<210> SEQ ID NO 36
<211> LENGTH: 494
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 36

```
Gln Val Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Ser Ser Tyr
            20                  25                  30
Tyr Trp Ser Trp Ile Arg Gln Pro Pro Gly Lys Gly Leu Glu Trp Ile
        35                  40                  45
Gly Tyr Ile Tyr Tyr Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Val
                85                  90                  95
Ser Leu Val Tyr Cys Gly Gly Asp Cys Tyr Ser Gly Phe Asp Tyr Trp
            100                 105                 110
Gly Gln Gly Thr Leu Val Thr Val Ser Ser Gly Gly Gly Ser Gly
        115                 120                 125
Gly Gly Gly Ser Gly Gly Gly Ser Asp Ile Gln Leu Thr Gln Ser
    130                 135                 140
Pro Ser Ser Leu Ser Ala Ser Val Gly Asp Arg Val Ser Phe Thr Cys
145                 150                 155                 160
Gln Ala Ser Gln Asp Ile Asn Asn Phe Leu Asn Trp Tyr Gln Lys
                165                 170                 175
Pro Gly Lys Ala Pro Lys Leu Leu Ile Tyr Asp Ala Ser Asn Leu Glu
            180                 185                 190
Thr Gly Val Pro Ser Arg Phe Ser Gly Ser Gly Ser Gly Thr Asp Phe
        195                 200                 205
Thr Phe Thr Ile Ser Ser Leu Gln Pro Glu Asp Ile Ala Thr Tyr Tyr
    210                 215                 220
Cys Gln Gln Tyr Gly Asn Leu Pro Phe Thr Phe Gly Gly Gly Thr Lys
225                 230                 235                 240
Val Glu Ile Lys Arg Ala Ala Ala Leu Ser Asn Ser Ile Met Tyr Phe
                245                 250                 255
Ser His Phe Val Pro Val Phe Leu Pro Ala Lys Pro Thr Thr Thr Pro
            260                 265                 270
Ala Pro Arg Pro Pro Thr Pro Ala Pro Thr Ile Ala Ser Gln Pro Leu
        275                 280                 285
Ser Leu Arg Pro Glu Ala Cys Arg Pro Ala Ala Gly Gly Ala Val His
    290                 295                 300
Thr Arg Gly Leu Asp Phe Ala Cys Asp Ile Tyr Ile Trp Ala Pro Leu
305                 310                 315                 320
Ala Gly Thr Cys Gly Val Leu Leu Leu Ser Leu Val Ile Thr Leu Tyr
                325                 330                 335
Cys Asn His Arg Asn Arg Ser Lys Arg Ser Arg Leu Leu His Ser Asp
            340                 345                 350
Tyr Met Asn Met Thr Pro Arg Arg Pro Gly Pro Thr Arg Lys His Tyr
        355                 360                 365
Gln Pro Tyr Ala Pro Pro Arg Asp Phe Ala Ala Tyr Arg Ser Arg Val
    370                 375                 380
Lys Phe Ser Arg Ser Ala Asp Ala Pro Ala Tyr Gln Gln Gly Gln Asn
385                 390                 395                 400
```

```
Gln Leu Tyr Asn Glu Leu Asn Leu Gly Arg Arg Glu Glu Tyr Asp Val
            405                 410                 415

Leu Asp Lys Arg Arg Gly Arg Asp Pro Glu Met Gly Gly Lys Pro Arg
        420                 425                 430

Arg Lys Asn Pro Gln Glu Gly Leu Tyr Asn Glu Leu Gln Lys Asp Lys
    435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

<210> SEQ ID NO 37
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37

```
atggcactcc ccgtaactgc tctgctgctg ccgttggcat tgctcctgca cgccgcacgc      60
ccggatatcc agctcacgca atccccctca agcttgagtg cctccgtggg cgaccgggtg     120
tccttcacat gtcaggcaag ccaagacata ataatttcc tgaattggta ccaacaaaaa      180
cccggcaagg ctcccaaact cctgatttat gatgcctcca atctggagac cggggtccct     240
tctagattca gcggaagtgg cagcggcaca gactttacat ttactatctc ttctctgcaa     300
ccagaggaca tcgccacata ctattgccag caatacggca atctgccctt caccttcgga     360
ggcggaacca aggtagaaat taaaggggc ggtggaggct ccggagggg gggctctggc       420
ggagggggct cccaagtaca attgcaggag tcaggcctg gactcgtgaa gccttcagaa      480
actttgtcac tgacatgtac agtgtccggc ggaagcattt ccagttacta ttggtcctgg    540
attagacagc cacccggcaa aggactggaa tggattggat atatctacta ctctggatct     600
acaaactata atcccagcct caatccagg gtcactatta gtgtggatac atcaaagaat      660
cagttctcct tgaagctgag ctcagtcact gctgccgaca ccgcagtgta ctattgtgtg     720
agcctggtct actgcggcgg agattgctac agcggtttcg attactgggg ccagggcacc     780
ctggttaccg ttagttccgc ggctgctctt gataacgaga gtccaacgg tacgattatc     840
cacgttaagg taagcacct tgccctagc ccgctgttcc caggcccag taagccctt       900
tgggtcctcg ttgtggtagg tggggtactc gcctgctact ccctgctcgt cactgtcgca     960
ttcatcatct ctgggtcag atccaaaaga agccgcctgc tccatagcga ttacatgaat     1020
atgactccac gccgccctgg ccccacaagg aaacactacc agccttacgc accacctaga    1080
gatttcgctg cctatcggag cagggtgaag ttttccagat ctgcagatgc caagcgtat     1140
cagcagggcc agaaccaact gtataacgag ctcaacctgg gacgcaggga gagtatgac     1200
gttttggaca gcgcagagg acgggaccct gagatgggtg gcaaaccaag acgaaaaaac     1260
ccccaggagg gtctctataa tgagctgcag aaggataaga tggctgaagc ctattctgaa    1320
ataggcatga aggagagcg gagaagggga aagggcacg acggtttgta ccagggactc     1380
agcactgcta cgaaggatac ttatgacgct ctccacatgc aagccctgcc acctaggtaa    1440
```

<210> SEQ ID NO 38

```
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Leu Thr Gln Ser Pro Ser Ser Leu Ser Ala Ser Val Gly
1               5                   10                  15

Asp Arg Val Ser Phe Thr Cys Gln Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gly Asn Leu Pro Phe
                85                  90                  95

Thr Phe Gly Gly Gly Thr Lys Val Glu Ile Lys Arg Gly Gly Gly Gly
            100                 105                 110

Ser Gly Gly Gly Gly Ser Gly Gly Gly Ser Gln Val Gln Leu Gln
        115                 120                 125

Glu Ser Gly Pro Gly Leu Val Lys Pro Ser Glu Thr Leu Ser Leu Thr
130                 135                 140

Cys Thr Val Ser Gly Gly Ser Ile Ser Ser Tyr Tyr Trp Ser Trp Ile
145                 150                 155                 160

Arg Gln Pro Pro Gly Lys Gly Leu Glu Trp Ile Gly Tyr Ile Tyr Tyr
                165                 170                 175

Ser Gly Ser Thr Asn Tyr Asn Pro Ser Leu Lys Ser Arg Val Thr Ile
            180                 185                 190

Ser Val Asp Thr Ser Lys Asn Gln Phe Ser Leu Lys Leu Ser Ser Val
        195                 200                 205

Thr Ala Ala Asp Thr Ala Val Tyr Tyr Cys Val Ser Leu Val Tyr Cys
210                 215                 220

Gly Gly Asp Cys Tyr Ser Gly Phe Asp Tyr Trp Gly Gln Gly Thr Leu
225                 230                 235                 240

Val Thr Val Ser Ser Ala Ala Ala Leu Asp Asn Glu Lys Ser Asn Gly
                245                 250                 255

Thr Ile Ile His Val Lys Gly Lys His Leu Cys Pro Ser Pro Leu Phe
            260                 265                 270

Pro Gly Pro Ser Lys Pro Phe Trp Val Leu Val Val Val Gly Gly Val
        275                 280                 285

Leu Ala Cys Tyr Ser Leu Leu Val Thr Val Ala Phe Ile Ile Phe Trp
290                 295                 300

Val Arg Ser Lys Arg Ser Arg Leu Leu His Ser Asp Tyr Met Asn Met
305                 310                 315                 320

Thr Pro Arg Arg Pro Gly Pro Thr Arg Lys His Tyr Gln Pro Tyr Ala
                325                 330                 335

Pro Pro Arg Asp Phe Ala Ala Tyr Arg Ser Arg Val Lys Phe Ser Arg
            340                 345                 350

Ser Ala Asp Ala Pro Ala Tyr Gln Gln Gly Gln Asn Gln Leu Tyr Asn
        355                 360                 365

Glu Leu Asn Leu Gly Arg Arg Glu Glu Tyr Asp Val Leu Asp Lys Arg
```

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
        435                 440                 445

Ala Leu His Met Gln Ala Leu Pro Pro Arg
    450                 455

<210> SEQ ID NO 39
<211> LENGTH: 1374
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gatatccagc tcacgcaatc cccctcaagc ttgagtgcct ccgtgggcga ccgggtgtcc      60
ttcacatgtc aggcaagcca agacataaat aatttcctga attggtacca acaaaaaccc     120
ggcaaggctc ccaaactcct gatttatgat gcctccaatc tggagaccgg ggtcccttct     180
agattcagcg gaagtggcag cggcacagac tttacattta ctatctcttc tctgcaacca     240
gaggacatcg ccacatacta ttgccagcaa tacggcaatc tgccccttca cttcggaggc     300
ggaaccaagg tagaaattaa aggggcggt ggaggctccg gagggggggg ctctggcgga     360
gggggctccc aagtacaatt gcaggagtca gggcctggac tcgtgaagcc ttcagaaact     420
ttgtcactga catgtacagt gtccggcgga agcatttcca gttactattg gtcctggatt     480
agacagccac ccggcaaagg actggaatgg attggatata tctactactc tggatctaca     540
aactataatc ccagcctcaa atccagggtc actattagtg tggatacatc aaagaatcag     600
ttctccttga agctgagctc agtcactgct gccgacaccg cagtgtacta ttgtgtgagc     660
ctggtctact gcggcggaga ttgctacagc ggtttcgatt actggggcca gggcacccctg    720 gttaccgtta gttccgcggc tgctcttgat aacgagaagt ccaacggtac gattatccac     780
gttaagggta agcacctttg ccctagcccg ctgttcccag ccccagtaa gccctttgg      840 gtcctcgttg tggtaggtgg ggtactcgcc tgctactccc tgctcgtcac tgtcgcattc     900
atcatcttct gggtcagatc caaaagaagc cgcctgctcc atagcgatta catgaatatg     960
actccacgcc gccctggccc cacaaggaaa cactaccagc cttacgcacc acctagagat    1020
ttcgctgcct atcggagcag ggtgaagttt tccagatctg cagatgcacc agcgtatcag    1080
cagggccaga accaactgta taacgagctc aacctgggac gcaggaaga gtatgacgtt    1140 ttggacaagc gcagaggacg ggaccctgag atgggtggca aaccaagacg aaaaaaccc    1200 caggagggtc tctataatga gctgcagaag ataagatgg ctgaagccta ttctgaaata    1260
ggcatgaaag gagagcggag aaggggaaaa gggcacgacg gtttgtacca gggactcagc    1320
actgctacga aggatactta tgacgctctc cacatgcaag ccctgccacc tagg         1374

<210> SEQ ID NO 40
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Asp Ile Gln Leu Thr Gln Ser Pro Ser Ser Leu Ser Ala Ser Val Gly
1               5                   10                  15

Asp Arg Val Ser Phe Thr Cys Gln Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gly Asn Leu Pro Phe
                85                  90                  95

Thr Phe Gly Gly Gly Thr Lys Val Glu Ile Lys Arg Gly Gly Gly Gly
            100                 105                 110

Ser Gly Gly Gly Gly Ser Gly Gly Gly Ser Gln Val Gln Leu Gln
            115                 120                 125

Glu Ser Gly Pro Gly Leu Val Lys Pro Ser Glu Thr Leu Ser Leu Thr
            130                 135                 140

Cys Thr Val Ser Gly Gly Ser Ile Ser Ser Tyr Tyr Trp Ser Trp Ile
145                 150                 155                 160

Arg Gln Pro Pro Gly Lys Gly Leu Glu Trp Ile Gly Tyr Ile Tyr Tyr
                165                 170                 175

Ser Gly Ser Thr Asn Tyr Asn Pro Ser Leu Lys Ser Arg Val Thr Ile
            180                 185                 190

Ser Val Asp Thr Ser Lys Asn Gln Phe Ser Leu Lys Leu Ser Ser Val
        195                 200                 205

Thr Ala Ala Asp Thr Ala Val Tyr Tyr Cys Val Ser Leu Val Tyr Cys
    210                 215                 220

Gly Gly Asp Cys Tyr Ser Gly Phe Asp Tyr Trp Gly Gln Gly Thr Leu
225                 230                 235                 240

Val Thr Val Ser Ser Ala Ala Ala Leu Asp Asn Glu Lys Ser Asn Gly
            245                 250                 255

Thr Ile Ile His Val Lys Gly Lys His Leu Cys Pro Ser Pro Leu Phe
            260                 265                 270

Pro Gly Pro Ser Lys Pro Phe Trp Val Leu Val Val Val Gly Gly Val
            275                 280                 285

Leu Ala Cys Tyr Ser Leu Leu Val Thr Val Ala Phe Ile Ile Phe Trp
        290                 295                 300

Val Arg Ser Lys Arg Ser Arg Leu Leu His Ser Asp Tyr Met Asn Met
305                 310                 315                 320

Thr Pro Arg Arg Pro Gly Pro Thr Arg Lys His Tyr Gln Pro Tyr Ala
                325                 330                 335

Pro Pro Arg Asp Phe Ala Ala Tyr Arg Ser Arg Val Lys Phe Ser Arg
            340                 345                 350

Ser Ala Asp Ala Pro Ala Tyr Gln Gln Gly Gln Asn Gln Leu Tyr Asn
            355                 360                 365

Glu Leu Asn Leu Gly Arg Arg Glu Glu Tyr Asp Val Leu Asp Lys Arg
            370                 375                 380

Arg Gly Arg Asp Pro Glu Met Gly Gly Lys Pro Arg Arg Lys Asn Pro

Gln Glu Gly Leu Tyr Asn Glu Leu Gln Lys Asp Lys Met Ala Glu Ala
385                 390                 395                 400

Tyr Ser Glu Ile Gly Met Lys Gly Arg Arg Gly Lys Gly His
            405                 410                 415

Asp Gly Leu Tyr Gln Gly Leu Ser Thr Ala Thr Lys Asp Thr Tyr Asp
            420                 425                 430

Ala Leu His Met Gln Ala Leu Pro Pro Arg
        435                 440                 445

450                 455

<210> SEQ ID NO 41
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
atggcactcc ccgtaactgc tctgctgctg ccgttggcat tgctcctgca cgccgcacgc    60
ccggatatcc agctgaccca gtctccatcc tctttgagtg cctccgtggg tgaccgcgtc   120
tctttcactt gccaagccag ccaagacatc aacaactttc tgaattggta ccagcagaaa   180
ccaggcaaag caccaaagct cctcatctac gacgcctcca acctggaaac cggggtgccc   240
agcaggttta gcgggagcgg ttctggcacg gattttacgt tcaccatctc ctctctgcag   300
cccgaggata tagctactta ttactgtcag cagtacggga atctgccatt tacttttggg   360
ggtggaacta aggtggaaat caaaaggggc ggcggggaa gcggggcgg gggctcaggt    420 ggcgagggaa ccaggtgca actccaggaa agtggcccag gattggtgaa gcccagcgag   480 acccttttccc ttacttgtac tgttagcgga ggcagcataa gcagctacta ttggtcctgg   540
atcagacagc caccagggaa agggcttgaa tggattggct acatttacta ttccgggtcc   600
accaactaca acccatccct caagtcccgc gtgacaattt ccgtcgacac aagcaagaac   660 cagttctctcc tgaaacttag tagcgtcact gctgcagata cagcagtgta ctattgtgtc   720
agccttgtct actgtggcgg cgactgctac agtggctttg attactgggg acagggcacg   780
ctcgtgacag tgtccagcgc tgcggctatc gaggtaatgt atccgccacc gtatctggac   840
aacgagaagt ctaatgggac aatcattcac gtgaagggga agcacctgtg tccatccccc   900
ctgtttccgg tcccagtaa acccttctgg gtgcttgttg tcgttggcgg ggtgctggcc   960
tgctattccc tgctggtgac cgtcgcgttt attattttct gggttagatc caaaagaagc  1020
cgcctgctcc atagcgatta catgaatatg actccacgcc gcctggccc cacaaggaaa  1080 cactaccagc cttacgcacc cctagagat tcgctgcct atcggagcag ggtgaagttt  1140
tccagatctg cagatgcacc agcgtatcag cagggccaga accaactgta taacgagctc  1200
aacctgggac gcagggaaga gtatgacgtt ttggacaagc gcagaggacg ggaccctgag  1260
atgggtggca aaccaagacg aaaaaacccc caggagggtc tctataatga gctgcagaag  1320
gataagatgg ctgaagccta ttctgaaata ggcatgaaag gagagcggag aaggggaaaa  1380
gggcacgacg gtttgtacca gggactcagc actgctacga ggatacttga tgacgctctc  1440
cacatgcaag ccctgccacc taggtaa                                     1467

<210> SEQ ID NO 42
<211> LENGTH: 488
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 42

```
Met Ala Leu Pro Val Thr Ala Leu Leu Leu Pro Leu Ala Leu Leu Leu
1               5                  10                  15

His Ala Ala Arg Pro Asp Ile Gln Leu Thr Gln Ser Pro Ser Ser Leu
            20                  25                  30

Ser Ala Ser Val Gly Asp Arg Val Ser Phe Thr Cys Gln Ala Ser Gln
        35                  40                  45

Asp Ile Asn Asn Phe Leu Asn Trp Tyr Gln Gln Lys Pro Gly Lys Ala
    50                  55                  60

Pro Lys Leu Leu Ile Tyr Asp Ala Ser Asn Leu Glu Thr Gly Val Pro
65                  70                  75                  80

Ser Arg Phe Ser Gly Ser Gly Ser Gly Thr Asp Phe Thr Phe Thr Ile
                85                  90                  95

Ser Ser Leu Gln Pro Glu Asp Ile Ala Thr Tyr Tyr Cys Gln Gln Tyr
            100                 105                 110

Gly Asn Leu Pro Phe Thr Phe Gly Gly Gly Thr Lys Val Glu Ile Lys
        115                 120                 125

Arg Gly Gly Gly Gly Ser Gly Gly Gly Gly Ser Gly Gly Gly Gly Ser
    130                 135                 140

Gln Val Gln Leu Gln Glu Ser Gly Pro Gly Leu Val Lys Pro Ser Glu
145                 150                 155                 160

Thr Leu Ser Leu Thr Cys Thr Val Ser Gly Gly Ser Ile Ser Ser Tyr
                165                 170                 175

Tyr Trp Ser Trp Ile Arg Gln Pro Pro Gly Lys Gly Leu Glu Trp Ile
            180                 185                 190

Gly Tyr Ile Tyr Tyr Ser Gly Ser Thr Asn Tyr Asn Pro Ser Leu Lys
        195                 200                 205

Ser Arg Val Thr Ile Ser Val Asp Thr Ser Lys Asn Gln Phe Ser Leu
    210                 215                 220

Lys Leu Ser Ser Val Thr Ala Ala Asp Thr Ala Val Tyr Tyr Cys Val
225                 230                 235                 240

Ser Leu Val Tyr Cys Gly Gly Asp Cys Tyr Ser Gly Phe Asp Tyr Trp
                245                 250                 255

Gly Gln Gly Thr Leu Val Thr Val Ser Ser Ala Ala Ala Ile Glu Val
            260                 265                 270

Met Tyr Pro Pro Pro Tyr Leu Asp Asn Glu Lys Ser Asn Gly Thr Ile
        275                 280                 285

Ile His Val Lys Gly Lys His Leu Cys Pro Ser Pro Leu Phe Pro Gly
    290                 295                 300

Pro Ser Lys Pro Phe Trp Val Leu Val Val Val Gly Gly Val Leu Ala
305                 310                 315                 320

Cys Tyr Ser Leu Leu Val Thr Val Ala Phe Ile Ile Phe Trp Val Arg
                325                 330                 335

Ser Lys Arg Ser Arg Leu Leu His Ser Asp Tyr Met Asn Met Thr Pro
            340                 345                 350

Arg Arg Pro Gly Pro Thr Arg Lys His Tyr Gln Pro Tyr Ala Pro Pro
        355                 360                 365

Arg Asp Phe Ala Ala Tyr Arg Ser Arg Val Lys Phe Ser Arg Ser Ala
    370                 375                 380
```

```
Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
            405                 410                 415

Arg Asp Pro Glu Met Gly Gly Lys Pro Arg Arg Lys Asn Pro Gln Glu
        420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
        450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
            485

<210> SEQ ID NO 43
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
gatatccagc tgacccagtc tccatcctct ttgagtgcct ccgtgggtga ccgcgtctct        60
ttcacttgcc aagccagcca agacatcaac aactttctga attggtacca gcagaaacca       120
ggcaaagcac caaagctcct catctacgac gcctccaacc tggaaaccgg ggtgcccagc       180
aggtttagcg ggagcggttc tggcacggat tttacgttca ccatctcctc tctgcagccc       240
gaggatatag ctacttatta ctgtcagcag tacgggaatc tgccatttac ttttgggggt       300
ggaactaagg tggaaatcaa aaggggcggc gggggaagcg ggggcggggg ctcaggtggc       360
ggagggagca aggtgcaact ccaggaaagt ggcccaggat tggtgaagcc agcgagacc       420 ctttccctta cttgtactgt tagcggaggc agcataagca gctactattg gtcctggatc       480
agacagccac cagggaaagg gcttgaatgg attggctaca tttactattc cgggtccacc       540
aactacaacc catccctcaa gtcccgcgtg acaatttccg tcgacacaag caagaaccag       600
ttctccctga acttagtagc cgtcactgct gcagatacag cagtgtacta ttgtgtcagc       660
cttgtctact gtggcggcga ctgctacagt ggctttgatt actggggaca gggcacgctc       720
gtgacagtgt ccagcgctgc ggctatcgag gtaatgtatc cgccaccgta tctggacaac       780
gagaagtcta atgggacaat cattcacgtg aaggggaagc acctgtgtcc atccccctg       840 tttccgggtc ccagtaaacc cttctgggtg cttgttgtcg ttggcggggt gctggcctgc       900
tattccctgc tggtgaccgt cgcgtttatt attttctggg ttagatccaa aagaagccgc       960
ctgctccata gcgattacat gaatatgact ccacgccgcc ctggccccac aaggaaacac      1020
taccagcctt acgcaccacc tagagatttc gctgcctatc ggagcagggt gaagttttcc      1080
agatctgcag atgcaccagc gtatcagcag ggccagaacc aactgtataa cgagctcaac      1140
ctgggacgca gggaagagta tgacgttttg gacaagcgca gaggacggga ccctgagatg      1200
ggtggcaaac caagacgaaa aaaccccag gagggtctct ataatgagct gcagaaggat      1260
aagatggctg aagcctattc tgaaataggc atgaaggag gcggagaag ggaaaaggg       1320 cacgacggtt tgtaccaggg actcagcact gctacgaagg atacttatga cgctctccac      1380
atgcaagccc tgccacctag g                                                1401
```

<210> SEQ ID NO 44
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Leu Thr Gln Ser Pro Ser Ser Leu Ser Ala Ser Val Gly
1               5                   10                  15

Asp Arg Val Ser Phe Thr Cys Gln Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gly Asn Leu Pro Phe
                85                  90                  95

Thr Phe Gly Gly Gly Thr Lys Val Glu Ile Lys Arg Gly Gly Gly Gly
            100                 105                 110

Ser Gly Gly Gly Gly Ser Gly Gly Gly Ser Gln Val Gln Leu Gln
        115                 120                 125

Glu Ser Gly Pro Gly Leu Val Lys Pro Ser Glu Thr Leu Ser Leu Thr
    130                 135                 140

Cys Thr Val Ser Gly Gly Ser Ile Ser Ser Tyr Tyr Trp Ser Trp Ile
145                 150                 155                 160

Arg Gln Pro Pro Gly Lys Gly Leu Glu Trp Ile Gly Tyr Ile Tyr Tyr
                165                 170                 175

Ser Gly Ser Thr Asn Tyr Asn Pro Ser Leu Lys Ser Arg Val Thr Ile
            180                 185                 190

Ser Val Asp Thr Ser Lys Asn Gln Phe Ser Leu Lys Leu Ser Ser Val
        195                 200                 205

Thr Ala Ala Asp Thr Ala Val Tyr Tyr Cys Val Ser Leu Val Tyr Cys
    210                 215                 220

Gly Gly Asp Cys Tyr Ser Gly Phe Asp Tyr Trp Gly Gln Gly Thr Leu
225                 230                 235                 240

Val Thr Val Ser Ser Ala Ala Ile Glu Val Met Tyr Pro Pro
                245                 250                 255

Tyr Leu Asp Asn Glu Lys Ser Asn Gly Thr Ile Ile His Val Lys Gly
            260                 265                 270

Lys His Leu Cys Pro Ser Pro Leu Phe Pro Gly Pro Ser Lys Pro Phe
        275                 280                 285

Trp Val Leu Val Val Val Gly Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Arg Val Lys Phe Ser Arg Ser Ala Asp Ala Pro Ala Tyr

|     | 355 |     |     |     | 360 |     |     |     |     | 365 |     |
| --- | --- | --- | --- | --- | --- | --- | --- | --- | --- | --- | --- |

Gln Gln Gly Gln Asn Gln Leu Tyr Asn Glu Leu Asn Leu Gly Arg Arg
    370                    375                    380

Glu Glu Tyr Asp Val Leu Asp Lys Arg Arg Gly Arg Asp Pro Glu Met
385                    390                    395                400

Gly Gly Lys Pro Arg Arg Lys Asn Pro Gln Glu Gly Leu Tyr Asn Glu
                405                    410                    415

Leu Gln Lys Asp Lys Met Ala Glu Ala Tyr Ser Glu Ile Gly Met Lys
            420                    425                    430

Gly Glu Arg Arg Arg Gly Lys Gly His Asp Gly Leu Tyr Gln Gly Leu
                435                    440                    445

Ser Thr Ala Thr Lys Asp Thr Tyr Asp Ala Leu His Met Gln Ala Leu
      450                    455                    460

Pro Pro Arg
465

<210> SEQ ID NO 45
<211> LENGTH: 1548
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 45

```
atggcactcc ccgtaactgc tctgctgctg ccgttggcat tgctcctgca cgccgcacgc      60
ccggacattc aattgaccca gtccctagc agtctctcag caagtgtggg agatagggtg     120
tcattcacct gtcaggcttc acaggacatc aacaacttcc tcaattggta tcagcagaag     180
ccagggaagg caccaaagct gctcatatat gacgcttcaa accttgaaac cggagtacct     240
agccgcttca gcggaagcgg atcagggact gacttcactt ttaccatctc ttcactgcag     300
cccgaagaca tcgccacata ctactgccag cagtacggaa acttgccttt tacatttggg     360
ggcggcacca agtggagat taagcgaggg ggaggcggct caggaggcgg tggctccgga     420
ggcgggggtt cccaggtcca gctccaggaa tccggcccag gtctggttaa gcccagtgaa     480
actttgtccc tcacgtgtac tgtgagcggt ggttcaatct cctcatacta ttggtcttgg     540
atacggcaac tcctggaaa gggcctcgag tggatcggct atatctacta tagtggctcc     600
actaattaca acccttccct caagtccaga gtcaccattt ccgtggacac atctaagaac     660
cagttcagtc tgaagttgtc cagcgttaca gccgcagaca cagccgttta ttactgtgtg     720
tctcttgttt actgcgggg gagactgttat agcggcttcg attactgggg ccagggcacc     780
ttggtcacag tctcttccgc ggccgcccte tctaacagta ttatgtactt ttctcatttt     840 gtaccgtgt tccttcccgc taagccaact actacccegg ccccacggcc gcctacccct     900
gcacccacaa tagccagtca gcctttgagc ctgagacctg aggcttgtcg gccggctgct     960
gggggtgcag tgcacacacg aggtcttgat tttgcttgcg acatatacat ctgggcccct    1020
ctggccggga cctgtggggt gctgcttctg agcttggtca tcacgctcta ttgcaaccat    1080
cgcaacagat ccaaaagaag ccgcctgctc catagcgatt acatgaatat gactccacgc    1140
cgccctggcc ccacaaggaa acactaccag ccttacgcac acctagaga tttcgctgcc    1200 tatcggagca gggtgaagtt ttccagatct gcagatgcac cagcgtatca gcagggccag    1260
aaccaactgt ataacgagct caacctggga cgcagggaag agtatgacgt tttggacaag    1320
cgcagaggac gggaccctga gatgggtggc aaaccaagac gaaaaaaccc ccaggaggtt    1380
```

```
ctctataatg agctgcagaa ggataagatg gctgaagcct attctgaaat aggcatgaaa   1440
ggagagcgga gaaggggaaa agggcacgac ggtttgtacc agggactcag cactgctacg   1500
aaggatactt atgacgctct ccacatgcaa gccctgccac ctaggtaa                1548
```

<210> SEQ ID NO 46
<211> LENGTH: 515
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 46

```
Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Leu
            20                  25                  30

Ser Ala Ser Val Gly Asp Arg Val Ser Phe Thr Cys Gln Ala Ser Gln
        35                  40                  45

Asp Ile Asn Asn Phe Leu Asn Trp Tyr Gln Gln Lys Pro Gly Lys Ala
    50                  55                  60

Pro Lys Leu Leu Ile Tyr Asp Ala Ser Asn Leu Glu Thr Gly Val Pro
65                  70                  75                  80

Ser Arg Phe Ser Gly Ser Gly Ser Gly Thr Asp Phe Thr Phe Thr Ile
                85                  90                  95

Ser Ser Leu Gln Pro Glu Asp Ile Ala Thr Tyr Tyr Cys Gln Gln Tyr
            100                 105                 110

Gly Asn Leu Pro Phe Thr Phe Gly Gly Gly Thr Lys Val Glu Ile Lys
        115                 120                 125

Arg Gly Gly Gly Gly Ser Gly Gly Gly Ser Gly Gly Gly Gly Ser
    130                 135                 140

Gln Val Gln Leu Gln Glu Ser Gly Pro Gly Leu Val Lys Pro Ser Glu
145                 150                 155                 160

Thr Leu Ser Leu Thr Cys Thr Val Ser Gly Gly Ser Ile Ser Ser Tyr
                165                 170                 175

Tyr Trp Ser Trp Ile Arg Gln Pro Pro Gly Lys Gly Leu Glu Trp Ile
            180                 185                 190

Gly Tyr Ile Tyr Tyr Ser Gly Ser Thr Asn Tyr Asn Pro Ser Leu Lys
        195                 200                 205

Ser Arg Val Thr Ile Ser Val Asp Thr Ser Lys Asn Gln Phe Ser Leu
    210                 215                 220

Lys Leu Ser Ser Val Thr Ala Ala Asp Thr Ala Val Tyr Tyr Cys Val
225                 230                 235                 240

Ser Leu Val Tyr Cys Gly Gly Asp Cys Tyr Ser Gly Phe Asp Tyr Trp
                245                 250                 255

Gly Gln Gly Thr Leu Val Thr Val Ser Ser Ala Ala Ala Leu Ser Asn
            260                 265                 270

Ser Ile Met Tyr Phe Ser His Phe Val Pro Val Phe Leu Pro Ala Lys
        275                 280                 285

Pro Thr Thr Thr Pro Ala Pro Arg Pro Pro Thr Pro Ala Pro Thr Ile
    290                 295                 300

Ala Ser Gln Pro Leu Ser Leu Arg Pro Glu Ala Cys Arg Pro Ala Ala
305                 310                 315                 320

Gly Gly Ala Val His Thr Arg Gly Leu Asp Phe Ala Cys Asp Ile Tyr
```

```
                    325                 330                 335
Ile Trp Ala Pro Leu Ala Gly Thr Cys Gly Val Leu Leu Ser Leu
                340                 345                 350

Val Ile Thr Leu Tyr Cys Asn His Arg Asn Arg Ser Lys Arg Ser Arg
                355                 360                 365

Leu Leu His Ser Asp Tyr Met Asn Met Thr Pro Arg Arg Pro Gly Pro
            370                 375                 380

Thr Arg Lys His Tyr Gln Pro Tyr Ala Pro Pro Arg Asp Phe Ala Ala
385                 390                 395                 400

Tyr Arg Ser Arg Val Lys Phe Ser Arg Ser Ala Asp Ala Pro Ala Tyr
                405                 410                 415

Gln Gln Gly Gln Asn Gln Leu Tyr Asn Glu Leu Asn Leu Gly Arg Arg
            420                 425                 430

Glu Glu Tyr Asp Val Leu Asp Lys Arg Arg Gly Arg Asp Pro Glu Met
        435                 440                 445

Gly Gly Lys Pro Arg Arg Lys Asn Pro Gln Glu Gly Leu Tyr Asn Glu
    450                 455                 460

Leu Gln Lys Asp Lys Met Ala Glu Ala Tyr Ser Glu Ile Gly Met Lys
465                 470                 475                 480

Gly Glu Arg Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
        515

<210> SEQ ID NO 47
<211> LENGTH: 1482
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
gacattcaat tgacccagtc ccctagcagt ctctcagcaa gtgtgggaga tagggtgtca      60
ttcacctgtc aggcttcaca ggacatcaac aacttcctca attggtatca gcagaagcca    120
gggaaggcac caaagctgct catatatgac gcttcaaacc ttgaaaccgg agtacctagc    180
cgcttcagcg gaagcggatc agggactgac ttcactttta ccatctcttc actgcagccc    240
gaagacatcg ccacatacta ctgccagcag tacggaaact tgcctttrac atttgggggc    300
ggcaccaaag tggagattaa gcagggggga ggcggctcag gaggcggtgg ctccggaggc    360 ggggggttccc aggtccagct ccaggaatcc ggcccaggtc tggttaagcc cagtgaaact    420
ttgtccctca cgtgtactgt gagcggtggt tcaatctcct catactattg gtcttggata    480
cggcaacctc ctggaaaggg cctcgagtgg atcggctata tctactatag tggctccact    540
aattacaacc cttccctcaa gtccagagtc accatttccg tggacacatc taagaaccag    600
ttcagtctga gttgtccag cgttacagcc gcagacacag ccgttttatta ctgtgtgtct    660 cttgttact gcgggggaga ctgttatagc ggcttcgatt actggggcca gggcaccttg    720
gtcacagtct cttccgcggc cgccctctct aacagtatta tgtactttc tcattttgta    780 cccgtgttcc ttcccgctaa gccaactact accccggccc cacggccgcc taccccctgca    840 cccacaatag ccagtcagcc tttgagcctg agacctgagg cttgtcggcc ggctgctggg    900
```

```
ggtgcagtgc acacacgagg tcttgatttt gcttgcgaca tatacatctg ggcccctctg    960
gccgggacct gtggggtgct gcttctgagc ttggtcatca cgctctattg caaccatcgc   1020
aacagatcca aagaagccg cctgctccat agcgattaca tgaatatgac tccacgccgc   1080
cctggcccca aaggaaaaca ctaccagcct tacgcaccac ctagagattt cgctgcctat   1140
cggagcaggg tgaagttttc cagatctgca gatgcaccag cgtatcagca gggccagaac   1200
caactgtata cgagctcaa cctgggacgc agggaagagt atgacgtttt ggacaagcgc   1260
agaggacggg accctgagat gggtggcaaa ccaagacgaa aaaccccca ggagggtctc   1320 tataatgagc tgcagaagga taagatggct gaagcctatt ctgaaatagg catgaaagga   1380
gagcggagaa ggggaaaagg gcacgacggt ttgtaccagg gactcagcac tgctacgaag   1440
gatacttatg acgctctcca catgcaagcc ctgccaccta gg                     1482
```

<210> SEQ ID NO 48
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Asp Ile Gln Leu Thr Gln Ser Pro Ser Ser Leu Ser Ala Ser Val Gly
1               5                   10                  15

Asp Arg Val Ser Phe Thr Cys Gln Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gly Asn Leu Pro Phe
                85                  90                  95

Thr Phe Gly Gly Gly Thr Lys Val Glu Ile Lys Arg Gly Gly Gly Gly
            100                 105                 110

Ser Gly Gly Gly Gly Ser Gly Gly Gly Ser Gln Val Gln Leu Gln
        115                 120                 125

Glu Ser Gly Pro Gly Leu Val Lys Pro Ser Glu Thr Leu Ser Leu Thr
130                 135                 140

Cys Thr Val Ser Gly Gly Ser Ile Ser Ser Tyr Tyr Trp Ser Trp Ile
145                 150                 155                 160

Arg Gln Pro Pro Gly Lys Gly Leu Glu Trp Ile Gly Tyr Ile Tyr Tyr
                165                 170                 175

Ser Gly Ser Thr Asn Tyr Asn Pro Ser Leu Lys Ser Arg Val Thr Ile
            180                 185                 190

Ser Val Asp Thr Ser Lys Asn Gln Phe Ser Leu Lys Leu Ser Ser Val
        195                 200                 205

Thr Ala Ala Asp Thr Ala Val Tyr Tyr Cys Val Ser Leu Val Tyr Cys
    210                 215                 220

Gly Gly Asp Cys Tyr Ser Gly Phe Asp Tyr Trp Gly Gln Gly Thr Leu
225                 230                 235                 240

Val Thr Val Ser Ser Ala Ala Ala Leu Ser Asn Ser Ile Met Tyr Phe
                245                 250                 255
```

Ser His Phe Val Pro Val Phe Leu Pro Ala Lys Pro Thr Thr Thr Pro
                260                 265                 270

Ala Pro Arg Pro Pro Thr Pro Ala Pro Thr Ile Ala Ser Gln Pro Leu
            275                 280                 285

Ser Leu Arg Pro Glu Ala Cys Arg Pro Ala Ala Gly Gly Ala Val His
        290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Asn His Arg Asn Arg Ser Lys Arg Ser Arg Leu Leu His Ser Asp
                340                 345                 350

Tyr Met Asn Met Thr Pro Arg Arg Pro Gly Pro Thr Arg Lys His Tyr
                355                 360                 365

Gln Pro Tyr Ala Pro Pro Arg Asp Phe Ala Ala Tyr Arg Ser Arg Val
            370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
                435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490

<210> SEQ ID NO 49
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
caggtacagc tgcaggaatc tgggcccgga cttgtcaagc caagtcagac actttctctt      60
acatgtaccg tgagcggcgg aagtataagc agtggaggct tttactggtc ttggatacgg     120
cagcacccag gcaaaggctt ggagtggatt ggatacattc atcattcagg atctacacac     180
tataatccat cccttaagtc ccgggtcacc attagcattg atacgtctaa gaatctgttc     240
agtctcaggc tgtcctccgt cactgctgcc gacacagccg tgtactactg cgcctccttg     300
gtttactgcg gaggcgactg ttatagcggc tttgattatt gggggcaggg gaccctcgta     360
accgtgagct ct                                                          372

<210> SEQ ID NO 50
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 50

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Phe Tyr Trp Ser Trp Ile Arg Gln His Pro Gly Lys Gly Leu Glu
        35                  40                  45

Trp Ile Gly Tyr Ile His His Ser Gly Ser Thr His Tyr Asn Pro Ser
    50                  55                  60

Leu Lys Ser Arg Val Thr Ile Ser Ile Asp Thr Ser Lys Asn Leu Phe
65                  70                  75                  80

Ser Leu Arg Leu Ser Ser Val Thr Ala Ala Asp Thr Ala Val Tyr Tyr
                85                  90                  95

Cys Ala Ser Leu Val Tyr Cys Gly Gly Asp Cys Tyr Ser Gly Phe Asp
            100                 105                 110

Tyr Trp Gly Gln Gly Thr Leu Val Thr Val Ser Ser
        115                 120

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Gly Ser Ile Ser Ser Gly Gly Phe
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His His Ser Gly Ser
1               5

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Leu Val Tyr Cys Gly Gly Asp Cys Tyr Ser Gly Phe Asp Tyr
1               5                   10

<210> SEQ ID NO 54
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
```

```
gatatccagc tcactcaaag cccctctagt ctctctgcct cagtggggga tcgggtcagt        60
tttacttgtc aagcttcaca ggatatcaac aacttcctta attggtatca gcagaagcca       120
ggaaaagcac ccaagctgct catctatgat gcctcaaatt tggagacggg tgttcccagt       180
cgattctctg gtcagggtc cgggaccgac tttacgttta cgatctcctc tctgcagccc        240
gaagacatcg ccacatacta ttgtcaacag tacggcaact tgccttttac atttgggggc      300
gggactaagg ttgaaatcaa gagg                                              324
```

```
<210> SEQ ID NO 55
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Gln Leu Thr Gln Ser Pro Ser Ser Leu Ser Ala Ser Val Gly
1               5                   10                  15

Asp Arg Val Ser Phe Thr Cys Gln Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gly Asn Leu Pro Phe
                85                  90                  95

Thr Phe Gly Gly Gly Thr Lys Val Glu Ile Lys Arg
            100                 105
```

```
<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gln Ala Ser Gln Asp Ile Asn Asn Phe Leu Asn
1               5                   10
```

```
<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Asp Ala Ser Asn Leu Glu Thr
1               5
```

```
<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 58

Gln Gln Tyr Gly Asn Leu Pro Phe Thr
1               5

<210> SEQ ID NO 59
<211> LENGTH: 1446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

```
atggcactcc ccgtaactgc tctgctgctg ccgttggcat tgctcctgca cgccgcacgc    60
ccgcaggtac agctgcagga atctgggccc ggacttgtca agccaagtca gacactttct   120
cttacatgta ccgtgagcgg cggaagtata agcagtggag cttttactg gtcttggata    180
cggcagcacc caggcaaagg cttggagtgg attggataca ttcatcattc aggatctaca   240
cactataatc catcccttaa gtcccgggtc accattagca ttgatacgtc taagaatctg   300
ttcagtctca ggctgtcctc cgtcactgct gccgacacag ccgtgtacta ctgcgcctcc   360
ttggtttact gcggaggcga ctgttatagc ggctttgatt attgggggca ggggaccctc   420
gtaaccgtga gctctggagg gggtgggagc ggggaggag gttcagggggg gggcggctcc   480
gatatccagc tcactcaaag cccctctagt ctctctgcct cagtggggga tcgggtcagt   540
tttacttgtc aagcttcaca ggatatcaac aacttcctta attggtatca gcagaagcca   600
ggaaaagcac ccaagctgct catctatgat gcctcaaatt ggagacgggg tgttcccagt   660
cgattctctg gctcagggtc cgggaccgac tttacgttta cgatctcctc tctgcagccc   720
gaagacatcg ccacatacta ttgtcaacag tacggcaact gcctttcac atttggggc    780
gggactaagg ttgaaatcaa gagggccgct gcactggaca tgagaagtc caacggcacc   840
atcatccacg tgaagggcaa gcacctgtgc cctagtcctc tgttcccagg cccatccaaa   900
cctttttggg ttcttgttgt ggtcgggggg gtgctggcct gctattctct gctggtcacg   960
gtggccttca taattttctg ggttagatcc aaaagaagcc gcctgctcca tagcgattac  1020
atgaatatga ctccacgccg ccctggcccc acaaggaaac actaccagcc ttacgcacca  1080
cctagagatt cgctgccta tcggagcagg gtgaagtttt ccagatctgc agatgcacca  1140
gcgtatcagc agggccagaa ccaactgtat aacgagctca acctgggacg cagggaagag  1200
tatgacgttt tggacaagcg cagaggacgg gaccctgaga tgggtggcaa accaagacga  1260
aaaaaccccc aggagggtct ctataatgag ctgcagaagg ataagatggc tgaagcctat  1320
tctgaaatag gcatgaaagg agagcggaga aggggaaaag ggcacgacgg tttgtaccag  1380
ggactcagca ctgctacgaa ggatacttat gacgctctcc acatgcaagc cctgccacct  1440
aggtaa                                                              1446
```

<210> SEQ ID NO 60
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Gln Thr Leu Ser Leu Thr Cys Thr Val Ser Gly Gly
        35                  40                  45

Ser Ile Ser Ser Gly Gly Phe Tyr Trp Ser Trp Ile Arg Gln His Pro
    50                  55                  60

Gly Lys Gly Leu Glu Trp Ile Gly Tyr Ile His Ser Gly Ser Thr
65                  70                  75                  80

His Tyr Asn Pro Ser Leu Lys Ser Arg Val Thr Ile Ser Ile Asp Thr
            85                  90                  95

Ser Lys Asn Leu Phe Ser Leu Arg Leu Ser Ser Val Thr Ala Ala Asp
            100                 105                 110

Thr Ala Val Tyr Tyr Cys Ala Ser Leu Val Tyr Cys Gly Gly Asp Cys
        115                 120                 125

Tyr Ser Gly Phe Asp Tyr Trp Gly Gln Gly Thr Leu Val Thr Val Ser
    130                 135                 140

Ser Gly Gly Gly Gly Ser Gly Gly Gly Ser Gly Gly Gly Gly Ser
145                 150                 155                 160

Asp Ile Gln Leu Thr Gln Ser Pro Ser Ser Leu Ser Ala Ser Val Gly
            165                 170                 175

Asp Arg Val Ser Phe Thr Cys Gln Ala Ser Gln Asp Ile Asn Asn Phe
            180                 185                 190

Leu Asn Trp Tyr Gln Gln Lys Pro Gly Lys Ala Pro Lys Leu Leu Ile
    195                 200                 205

Tyr Asp Ala Ser Asn Leu Glu Thr Gly Val Pro Ser Arg Phe Ser Gly
    210                 215                 220

Ser Gly Ser Gly Thr Asp Phe Thr Phe Thr Ile Ser Ser Leu Gln Pro
225                 230                 235                 240

Glu Asp Ile Ala Thr Tyr Tyr Cys Gln Gln Tyr Gly Asn Leu Pro Phe
            245                 250                 255

Thr Phe Gly Gly Gly Thr Lys Val Glu Ile Lys Arg Ala Ala Ala Leu
            260                 265                 270

Asp Asn Glu Lys Ser Asn Gly Thr Ile Ile His Val Lys Gly Lys His
            275                 280                 285

Leu Cys Pro Ser Pro Leu Phe Pro Gly Pro Ser Lys Pro Phe Trp Val
    290                 295                 300

Leu Val Val Val Gly Gly Val Leu Ala Cys Tyr Ser Leu Leu Val Thr
305                 310                 315                 320

Val Ala Phe Ile Ile Phe Trp Val Arg Ser Lys Arg Ser Arg Leu Leu
            325                 330                 335

His Ser Asp Tyr Met Asn Met Thr Pro Arg Arg Pro Gly Pro Thr Arg
            340                 345                 350

Lys His Tyr Gln Pro Tyr Ala Pro Pro Arg Asp Phe Ala Ala Tyr Arg
    355                 360                 365

Ser Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
            405                 410                 415

Lys Pro Arg Arg Lys Asn Pro Gln Glu Gly Leu Tyr Asn Glu Leu Gln
```

```
            420                 425                 430
Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg
```

<210> SEQ ID NO 61
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

| | |
|---|---|
| caggtacagc tgcaggaatc tgggcccgga cttgtcaagc caagtcagac actttctctt | 60 |
| acatgtaccg tgagcggcgg aagtataagc agtggaggct tttactggtc ttggatacgg | 120 |
| cagcacccag gcaaaggctt ggagtggatt ggatacattc atcattcagg atctacacac | 180 |
| tataatccat cccttaagtc ccgggtcacc attagcattg atacgtctaa gaatctgttc | 240 |
| agtctcaggc tgtcctccgt cactgctgcc gacacagccg tgtactactg cgcctccttg | 300 |
| gtttactgcg gaggcgactg ttatagcggc tttgattatt gggggcaggg gaccctcgta | 360 |
| accgtgagct ctggaggggg tgggagcggg ggaggaggtt caggggggggg cggctccgat | 420 |
| atccagctca ctcaaagccc ctctagtctc tctgcctcag tgggggatcg ggtcagtttt | 480 |
| acttgtcaag cttcacagga tatcaacaac ttccttaatt ggtatcagca gaagccagga | 540 |
| aaagcaccca agctgctcat ctatgatgcc tcaaatttgg agacgggtgt tcccagtcga | 600 |
| ttctctgggt cagggtccgg gaccgacttt acgtttacga tctcctctct gcagcccgaa | 660 |
| gacatcgcca catactattg tcaacagtac ggcaacttgc cttcacatt tggggcggg | 720 |
| actaaggttg aaatcaagag gccgctgca ctggacaatg agaagtccaa cggcaccatc | 780 |
| atccacgtga agggcaagca cctgtgccct agtcctctgt tcccaggccc atccaaacct | 840 |
| tttggttc ttgttgtggt cgggggggtg ctggcctgct attctctgct ggtcacggtg | 900 |
| gccttcataa ttttctgggt tagatccaaa agaagccgcc tgctccatag cgattacatg | 960 |
| aatatgactc cacgccgccc tggccccaca aggaaacact accagcctta cgcaccacct | 1020 |
| agagatttcg ctgcctatcg gagcagggtg aagttttcca gatctgcaga tgcaccagcg | 1080 |
| tatcagcagg gccagaacca actgtataac gagctcaacc tgggacgcag gaagagtat | 1140 |
| gacgttttgg acaagcgcag aggacgggac cctgagatgg gtggcaaacc aagacgaaaa | 1200 |
| aacccccagg agggtctcta taatgagctg cagaaggata agatggctga agcctattct | 1260 |
| gaaataggca tgaaaggaga gcggagaagg ggaaaagggc acgacggttt gtaccaggga | 1320 |
| ctcagcactg ctacgaagga tacttatgac gctctccaca tgcaagccct gccacctagg | 1380 |

<210> SEQ ID NO 62
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Gly
            20                  25                  30

Gly Phe Tyr Trp Ser Trp Ile Arg Gln His Pro Gly Lys Gly Leu Glu
            35                  40                  45

Trp Ile Gly Tyr Ile His His Ser Gly Ser Thr His Tyr Asn Pro Ser
    50                  55                  60

Leu Lys Ser Arg Val Thr Ile Ser Ile Asp Thr Ser Lys Asn Leu Phe
65                  70                  75                  80

Ser Leu Arg Leu Ser Ser Val Thr Ala Ala Asp Thr Ala Val Tyr Tyr
                85                  90                  95

Cys Ala Ser Leu Val Tyr Cys Gly Gly Asp Cys Tyr Ser Gly Phe Asp
            100                 105                 110

Tyr Trp Gly Gln Gly Thr Leu Val Thr Val Ser Ser Gly Gly Gly
            115                 120                 125

Ser Gly Gly Gly Gly Ser Gly Gly Gly Ser Asp Ile Gln Leu Thr
130                 135                 140

Gln Ser Pro Ser Ser Leu Ser Ala Ser Val Gly Asp Arg Val Ser Phe
145                 150                 155                 160

Thr Cys Gln Ala Ser Gln Asp Ile Asn Asn Phe Leu Asn Trp Tyr Gln
            165                 170                 175

Gln Lys Pro Gly Lys Ala Pro Lys Leu Leu Ile Tyr Asp Ala Ser Asn
            180                 185                 190

Leu Glu Thr Gly Val Pro Ser Arg Phe Ser Gly Ser Gly Ser Gly Thr
            195                 200                 205

Asp Phe Thr Phe Thr Ile Ser Ser Leu Gln Pro Glu Asp Ile Ala Thr
210                 215                 220

Tyr Tyr Cys Gln Gln Tyr Gly Asn Leu Pro Phe Thr Phe Gly Gly Gly
225                 230                 235                 240

Thr Lys Val Glu Ile Lys Arg Ala Ala Ala Leu Asp Asn Glu Lys Ser
            245                 250                 255

Asn Gly Thr Ile Ile His Val Lys Gly Lys His Leu Cys Pro Ser Pro
            260                 265                 270

Leu Phe Pro Gly Pro Ser Lys Pro Phe Trp Val Leu Val Val Val Gly
            275                 280                 285

Gly Val Leu Ala Cys Tyr Ser Leu Leu Val Thr Val Ala Phe Ile Ile
            290                 295                 300

Phe Trp Val Arg Ser Lys Arg Ser Arg Leu Leu His Ser Asp Tyr Met
305                 310                 315                 320

Asn Met Thr Pro Arg Arg Pro Gly Pro Thr Arg Lys His Tyr Gln Pro
            325                 330                 335

Tyr Ala Pro Pro Arg Asp Phe Ala Ala Tyr Arg Ser Arg Val Lys Phe
            340                 345                 350

Ser Arg Ser Ala Asp Ala Pro Ala Tyr Gln Gln Gly Gln Asn Gln Leu
            355                 360                 365

Tyr Asn Glu Leu Asn Leu Gly Arg Arg Glu Glu Tyr Asp Val Leu Asp
370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
            405                 410                 415

Glu Ala Tyr Ser Glu Ile Gly Met Lys Gly Glu Arg Arg Gly Lys
       420                 425                 430

Gly His Asp Gly Leu Tyr Gln Gly Leu Ser Thr Ala Thr Lys Asp Thr
       435                 440                 445

Tyr Asp Ala Leu His Met Gln Ala Leu Pro Pro Arg
       450                 455                 460

<210> SEQ ID NO 63
<211> LENGTH: 1473
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
atggcactcc ccgtaactgc tctgctgctg ccgttggcat tgctcctgca cgccgcacgc      60
ccgcaggtgc agctgcagga aagcggtccg ggacttgtca agccgtccca aacgctgagt     120
ctgacgtgta ctgtctctgg tggctctatt tcttccgggg gcttttattg gtcttggatc     180
agacaacacc ctggcaaagg ctggagtgg atagggtata ttcaccactc tgggtccact     240
cactacaacc catcattgaa atccagagtg actatctcaa tcgacacatc aagaaccttt    300
ttcagcctga ggttgtcatc agttaccgcc gctgacaccg cggtgtatta ttgcgcctct    360
ctcgtgtact gcggtggcga ttgttatagt ggctttgact actgggggca ggggacattg    420
gttaccgttt caagtggagg cggtgggtct ggcgggggcg gtagcggagg tgggggagc     480
gacatacagc ttacgcagag ccctccagc ctttcagcct ccgtggggga tagggtgtcc     540
tttacctgcc aggcttccca ggacataaac aacttcctca attggtatca gcaaaagccc     600
gggaaagcac caaagctgct catctacgat gccagcaacc tggaaaccgg agtgccgtct    660
cgcttctctg gaagtggcag tgggaccgat ttcactttta caatctcaag tttgcagcca    720
gaagacattg caacatacta ctgtcaacag tacggcaatc tccccttta catttggggg    780
ggaactaaag tggagattaa gcgcgctgca gccattgaag ttatgtatcc gccccgtat    840
ctggataacg agaaatctaa tggtaccata atacatgtga aggggaagca cctctgtcca     900
tcaccgctgt tccccggccc ttcaaaacct ttctgggtac tcgttgtcgt gggtggagtt    960
ctggcctgct atagtctgct ggtgaccgtg gcgtttatca tcttctgggt aagatccaaa    1020
agaagccgcc tgctccatag cgattacatg aatatgactc cacgccgccc tggccccaca    1080
aggaaacact accagcctta cgcaccacct agagattcg ctgcctatcg gagcagggtg    1140
aagtttttcca gatctgcaga tgcaccagcg tatcagcagg gccagaacca actgtataac    1200
gagctcaacc tgggacgcag ggaagagtat gacgttttgg acaagcgcag aggacgggac    1260
cctgagatgg gtggcaaacc aagacgaaaa aacccccagg agggtctcta taatgagctg    1320
cagaaggata agatggctga agcctattct gaaataggca tgaaggaga gcggagaagg    1380
ggaaaagggc acgacggttt gtaccaggga ctcagcactg ctacgaagga tacttatgac    1440
gctctccaca tgcaagccct gccacctagg taa                                1473
```

<210> SEQ ID NO 64
<211> LENGTH: 490
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Met Ala Leu Pro Val Thr Ala Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Gln Thr Leu Ser Leu Thr Cys Thr Val Ser Gly Gly
        35                  40                  45

Ser Ile Ser Ser Gly Gly Phe Tyr Trp Ser Trp Ile Arg Gln His Pro
    50                  55                  60

Gly Lys Gly Leu Glu Trp Ile Gly Tyr Ile His His Ser Gly Ser Thr
65                  70                  75                  80

His Tyr Asn Pro Ser Leu Lys Ser Arg Val Thr Ile Ser Ile Asp Thr
                85                  90                  95

Ser Lys Asn Leu Phe Ser Leu Arg Leu Ser Ser Val Thr Ala Ala Asp
            100                 105                 110

Thr Ala Val Tyr Tyr Cys Ala Ser Leu Val Tyr Cys Gly Gly Asp Cys
        115                 120                 125

Tyr Ser Gly Phe Asp Tyr Trp Gly Gln Gly Thr Leu Val Thr Val Ser
    130                 135                 140

Ser Gly Gly Gly Gly Ser Gly Gly Gly Ser Gly Gly Gly Gly Ser
145                 150                 155                 160

Asp Ile Gln Leu Thr Gln Ser Pro Ser Ser Leu Ser Ala Ser Val Gly
                165                 170                 175

Asp Arg Val Ser Phe Thr Cys Gln Ala Ser Gln Asp Ile Asn Asn Phe
            180                 185                 190

Leu Asn Trp Tyr Gln Gln Lys Pro Gly Lys Ala Pro Lys Leu Leu Ile
        195                 200                 205

Tyr Asp Ala Ser Asn Leu Glu Thr Gly Val Pro Ser Arg Phe Ser Gly
    210                 215                 220

Ser Gly Ser Gly Thr Asp Phe Thr Phe Thr Ile Ser Ser Leu Gln Pro
225                 230                 235                 240

Glu Asp Ile Ala Thr Tyr Tyr Cys Gln Gln Tyr Gly Asn Leu Pro Phe
                245                 250                 255

Thr Phe Gly Gly Gly Thr Lys Val Glu Ile Lys Arg Ala Ala Ala Ile
            260                 265                 270

Glu Val Met Tyr Pro Pro Pro Tyr Leu Asp Asn Glu Lys Ser Asn Gly
        275                 280                 285

Thr Ile Ile His Val Lys Gly Lys His Leu Cys Pro Ser Pro Leu Phe
    290                 295                 300

Pro Gly Pro Ser Lys Pro Phe Trp Val Leu Val Val Val Gly Gly Val
305                 310                 315                 320

Leu Ala Cys Tyr Ser Leu Leu Val Thr Val Ala Phe Ile Ile Phe Trp
                325                 330                 335

Val Arg Ser Lys Arg Ser Arg Leu Leu His Ser Asp Tyr Met Asn Met
            340                 345                 350

Thr Pro Arg Arg Pro Gly Pro Thr Arg Lys His Tyr Gln Pro Tyr Ala
        355                 360                 365

Pro Pro Arg Asp Phe Ala Ala Tyr Arg Ser Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
```

```
                    405                 410                 415
Arg Gly Arg Asp Pro Glu Met Gly Gly Lys Pro Arg Lys Asn Pro
                420                 425                 430

Gln Glu Gly Leu Tyr Asn Glu Leu Gln Lys Asp Lys Met Ala Glu Ala
        435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 65
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
caggtgcagc tgcaggaaag cggtccggga cttgtcaagc cgtcccaaac gctgagtctg      60
acgtgtactg tctctggtgg ctctatttct tccgggggct tttattggtc ttggatcaga     120
caacaccctg gcaaagggct ggagtggata gggtatattc accactctgg gtccactcac     180
tacaacccat cattgaaatc cagagtgact atctcaatcg acacatccaa gaacctttc      240 agcctgaggt tgtcatcagt taccgccgct gacaccgcgg tgtattattg cgcctctctc     300
gtgtactgcg gtggcgattg ttatagtggc tttgactact ggggccaggg gacattggtt     360
accgtttcaa gtgaggcggt gggtctggc gggccggta gcggaggtgg ggggagcgac      420
atacagctta cgcagagccc ctccagcctt tcagcctccg tggggggatag ggtgtcctt      480 acctgccagg cttcccagga cataaacaac ttcctcaatt ggtatcagca aaagcccggg     540
aaagcaccaa agctgctcat ctacgatgcc agcaacctgg aaaccggagt gccgtctcgc     600
ttctctggaa gtggcagtgg gaccgatttc acttttacaa tctcaagttt gcagccagaa     660
gacattgcaa catactactg tcaacagtac ggcaatctcc cctttacatt tgggggggga     720
actaaagtgg agattaagcg cgctgcagcc attgaagtta tgtatccgcc ccgtatctg      780 gataacgaga atctaatgg taccataata catgtgaagg ggaagcacct ctgtccatca      840
ccgctgttcc ccggcccttc aaaacctttc tgggtactcg ttgtcgtggg tggagttctg     900
gcctgctata gtctgctggt gaccgtggcg tttatcatct tctgggtaag atccaaaaga     960
agccgcctgc tccatagcga ttacatgaat atgactccac gccgccctgg ccccacaagg    1020
aaacactacc agccttacgc accacctaga gatttcgctg cctatcggag cagggtgaag    1080
ttttccagat ctgcagatgc accagcgtat cagcagggcc agaaccaact gtataacgag    1140
ctcaacctgg gacgcaggga gagtatgac gttttggaca gcgcagagg acgggaccct     1200 gagatgggtg gcaaaccaag acgaaaaaac ccccaggagg gtctctataa tgagctgcag    1260
aaggataaga tggctgaagc ctattctgaa ataggcatga aggagagcg gagaagggga    1320 aaagggcacg acggtttgta ccagggactc agcactgcta cgaaggatac ttatgacgct    1380
ctccacatgc aagccctgcc acctagg                                       1407

<210> SEQ ID NO 66
<211> LENGTH: 469
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Phe Tyr Trp Ser Trp Ile Arg Gln His Pro Gly Lys Gly Leu Glu
        35                  40                  45

Trp Ile Gly Tyr Ile His His Ser Gly Ser Thr His Tyr Asn Pro Ser
    50                  55                  60

Leu Lys Ser Arg Val Thr Ile Ser Ile Asp Thr Ser Lys Asn Leu Phe
65                  70                  75                  80

Ser Leu Arg Leu Ser Ser Val Thr Ala Ala Asp Thr Ala Val Tyr Tyr
                85                  90                  95

Cys Ala Ser Leu Val Tyr Cys Gly Gly Asp Cys Tyr Ser Gly Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Asp Ile Gln Leu Thr
    130                 135                 140

Gln Ser Pro Ser Ser Leu Ser Ala Ser Val Gly Asp Arg Val Ser Phe
145                 150                 155                 160

Thr Cys Gln Ala Ser Gln Asp Ile Asn Asn Phe Leu Asn Trp Tyr Gln
                165                 170                 175

Gln Lys Pro Gly Lys Ala Pro Lys Leu Leu Ile Tyr Asp Ala Ser Asn
            180                 185                 190

Leu Glu Thr Gly Val Pro Ser Arg Phe Ser Gly Ser Gly Ser Gly Thr
        195                 200                 205

Asp Phe Thr Phe Thr Ile Ser Ser Leu Gln Pro Glu Asp Ile Ala Thr
    210                 215                 220

Tyr Tyr Cys Gln Gln Tyr Gly Asn Leu Pro Phe Thr Phe Gly Gly Gly
225                 230                 235                 240

Thr Lys Val Glu Ile Lys Arg Ala Ala Ala Ile Glu Val Met Tyr Pro
                245                 250                 255

Pro Pro Tyr Leu Asp Asn Glu Lys Ser Asn Gly Thr Ile Ile His Val
            260                 265                 270

Lys Gly Lys His Leu Cys Pro Ser Pro Leu Phe Pro Gly Pro Ser Lys
        275                 280                 285

Pro Phe Trp Val Leu Val Val Val Gly Gly Val Leu Ala Cys Tyr Ser
    290                 295                 300

Leu Leu Val Thr Val Ala Phe Ile Ile Phe Trp Val Arg Ser Lys Arg
305                 310                 315                 320

Ser Arg Leu Leu His Ser Asp Tyr Met Asn Met Thr Pro Arg Arg Pro
                325                 330                 335

Gly Pro Thr Arg Lys His Tyr Gln Pro Tyr Ala Pro Pro Arg Asp Phe
            340                 345                 350

Ala Ala Tyr Arg Ser Arg Val Lys Phe Ser Arg Ser Ala Asp Ala Pro
        355                 360                 365

Ala Tyr Gln Gln Gly Gln Asn Gln Leu Tyr Asn Glu Leu Asn Leu Gly
    370                 375                 380
```

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
            405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
        435                 440                 445

Gly Leu Ser Thr Ala Thr Lys Asp Thr Tyr Asp Ala Leu His Met Gln
    450                 455                 460

Ala Leu Pro Pro Arg
465

<210> SEQ ID NO 67
<211> LENGTH: 1554
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
atggcactcc ccgtaactgc tctgctgctg ccgttggcat tgctcctgca cgccgcacgc      60
ccgcaggtgc agttgcagga aagcgggcct ggccttgtga aaccaagcca gactactgagc     120
ctgacatgca ctgtgtccgg cgggtccata tcttccgggg ttttttattg gtcctggata     180
cgccagcatc ccgggaaagg acttgaatgg attggatata tccaccattc cggaagcacc     240
cactacaatc caagccttaa atcccgggtg acaatctcca tcgacacctc aaagaatctt     300
ttttcccctgc ggttgtcttc agtaactgcc gccgataccg ctgtgtacta ctgtgccagc     360
ctcgtctatt gcggcggaga ttgttattct gggttcgatt attggggtca aggcacactg     420
gtaactgtca gcagcggagg cggcggttcc gggggcgggg cagtggaggg ggcggatct     480
gacattcagc ttacgcagtc cccatcttca cttagcgcca gcgttggcga tcgggtcagc     540
ttcacgtgtc aagcaagtca ggatatcaac aactttctta actggtacca gcagaagcca     600
ggcaaggcac ccaagttgct gatttacgat gcttctaacc tcgagacggg agtgcctagc     660
cgcttctccg ggagcggcag cggcacagac tttacctta cgatttccag tctgcagcca     720
gaggatatag caacttatta ctgtcagcag tatggcaacc tccctttac cttcggtggt     780
ggcacaaagg tcgagattaa aagagccgca gcgttgtcca actccataat gtatttttct     840
cattttgtgc ccgtctttct gcctgccaaa cctaccacca ccccgcccc acgaccacct     900
actccagccc ccaccatcgc ctcccagccc tcagcctga ggccagaggc ttgtcgccct     960
gctgcggggg gcgctgtcca taccagagga ctcgacttcg cctgcgatat ttatatatgg    1020
gccccctcg ccggcacctg cggagtcttg ctcctgagcc ttgtgatcac gctttattgt    1080
aaccatcgga atagatccaa aagaagccgc ctgctccata cgattacat gaatatgact    1140
ccacgccgcc ctggccccac aaggaaacac taccagcctt acgcaccacc tagagattc    1200
gctgcctatc ggagcagggt gaagttttcc agatctgcag atgcaccagc gtatcagcag    1260
ggccagaacc aactgtataa cgagctcaac ctgggacgca gggaagagta tgacgttttg    1320
gacaagcgca gaggacggga ccctgagatg ggtggcaaac caagacgaaa aaaccccag    1380
gagggtctct ataatgagct gcagaaggat aagatggctg aagcctattc tgaaataggc    1440
atgaaaggag agcggagaag gggaaaaggg cacgacggtt tgtaccaggg actcagcact    1500
gctacgaagg atacttatga cgctctccac atgcaagccc tgccacctag gtaa     1554

<210> SEQ ID NO 68
<211> LENGTH: 517
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Gln Thr Leu Ser Leu Thr Cys Thr Val Ser Gly Gly
        35                  40                  45

Ser Ile Ser Ser Gly Gly Phe Tyr Trp Ser Trp Ile Arg Gln His Pro
    50                  55                  60

Gly Lys Gly Leu Glu Trp Ile Gly Tyr Ile His His Ser Gly Ser Thr
65                  70                  75                  80

His Tyr Asn Pro Ser Leu Lys Ser Arg Val Thr Ile Ser Ile Asp Thr
                85                  90                  95

Ser Lys Asn Leu Phe Ser Leu Arg Leu Ser Ser Val Thr Ala Ala Asp
            100                 105                 110

Thr Ala Val Tyr Tyr Cys Ala Ser Leu Val Tyr Cys Gly Gly Asp Cys
        115                 120                 125

Tyr Ser Gly Phe Asp Tyr Trp Gly Gln Gly Thr Leu Val Thr Val Ser
    130                 135                 140

Ser Gly Gly Gly Gly Ser Gly Gly Gly Ser Gly Gly Gly Gly Ser
145                 150                 155                 160

Asp Ile Gln Leu Thr Gln Ser Pro Ser Ser Leu Ser Ala Ser Val Gly
                165                 170                 175

Asp Arg Val Ser Phe Thr Cys Gln Ala Ser Gln Asp Ile Asn Asn Phe
            180                 185                 190

Leu Asn Trp Tyr Gln Gln Lys Pro Gly Lys Ala Pro Lys Leu Leu Ile
        195                 200                 205

Tyr Asp Ala Ser Asn Leu Glu Thr Gly Val Pro Ser Arg Phe Ser Gly
    210                 215                 220

Ser Gly Ser Gly Thr Asp Phe Thr Phe Thr Ile Ser Ser Leu Gln Pro
225                 230                 235                 240

Glu Asp Ile Ala Thr Tyr Tyr Cys Gln Gln Tyr Gly Asn Leu Pro Phe
                245                 250                 255

Thr Phe Gly Gly Gly Thr Lys Val Glu Ile Lys Arg Ala Ala Ala Leu
            260                 265                 270

Ser Asn Ser Ile Met Tyr Phe Ser His Phe Val Pro Val Phe Leu Pro
        275                 280                 285

Ala Lys Pro Thr Thr Thr Pro Ala Pro Arg Pro Pro Thr Pro Ala Pro
    290                 295                 300

Thr Ile Ala Ser Gln Pro Leu Ser Leu Arg Pro Glu Ala Cys Arg Pro
305                 310                 315                 320

Ala Ala Gly Gly Ala Val His Thr Arg Gly Leu Asp Phe Ala Cys Asp
                325                 330                 335

Ile Tyr Ile Trp Ala Pro Leu Ala Gly Thr Cys Gly Val Leu Leu Leu
            340                 345                 350
```

```
Ser Leu Val Ile Thr Leu Tyr Cys Asn His Arg Asn Arg Ser Lys Arg
        355                 360                 365

Ser Arg Leu Leu His Ser Asp Tyr Met Asn Met Thr Pro Arg Arg Pro
    370                 375                 380

Gly Pro Thr Arg Lys His Tyr Gln Pro Tyr Ala Pro Pro Arg Asp Phe
385                 390                 395                 400

Ala Ala Tyr Arg Ser Arg Val Lys Phe Ser Arg Ser Ala Asp Ala Pro
                405                 410                 415

Ala Tyr Gln Gln Gly Gln Asn Gln Leu Tyr Asn Glu Leu Asn Leu Gly
            420                 425                 430

Arg Arg Glu Glu Tyr Asp Val Leu Asp Lys Arg Gly Arg Asp Pro
        435                 440                 445

Glu Met Gly Gly Lys Pro Arg Arg Lys Asn Pro Gln Glu Gly Leu Tyr
    450                 455                 460

Asn Glu Leu Gln Lys Asp Lys Met Ala Glu Ala Tyr Ser Glu Ile Gly
465                 470                 475                 480

Met Lys Gly Glu Arg Arg Gly Lys Gly His Asp Gly Leu Tyr Gln
                485                 490                 495

Gly Leu Ser Thr Ala Thr Lys Asp Thr Tyr Asp Ala Leu His Met Gln
            500                 505                 510

Ala Leu Pro Pro Arg
        515

<210> SEQ ID NO 69
<211> LENGTH: 1488
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
caggtgcagt tgcaggaaag cgggcctggc cttgtgaaac caagccagac actgagcctg      60
acatgcactg tgtccggcgg gtccatatct tccgggggtt tttattggtc ctggatacgc     120
cagcatcccg ggaaaggact tgaatggatt ggatatatcc accattccgg aagcacccac     180
tacaatccaa gccttaaatc ccgggtgaca atctccatcg acacctcaaa gaatcttttt     240
tccctgcggt tgtcttcagt aactgccgcc gataccgctg tgtactactg tgccagcctc     300
gtctattgcg gcggagattg ttattctggg ttcgattatt ggggtcaagg cacactggta     360
actgtcagca gcggaggcgg cggttccggg ggcgggggca gtggaggggg cggatctgac     420
attcagctta cgcagtcccc atcttcactt agcgccagcg ttggcgatcg ggtcagcttc     480
acgtgtcaag caagtcagga tatcaacaac tttcttaact ggtaccagca gaagccaggc     540
aaggcaccca gttgctgat ttacgatgct tctaacctcg agacgggagt gcctagccgc     600
ttctccggga gcggcagcgg cacagacttt acctttacga tttccagtct gcagccagag     660
gatatagcaa cttattactg tcagcagtat ggcaacctcc cttttacctt cggtggtggc     720
acaaaggtcg agattaaaag agccgcagcg ttgtccaact ccataatgta tttttctcat     780
tttgtgcccg tctttctgcc tgccaaacct accaccaccc ccgccccacg accacctact     840
ccagccccca ccatcgcctc ccagcccctc agcctgaggc cagaggcttg tcgccctgct     900
gcggggggcg ctgtccatac cagaggactc gacttcgcct gcgatattta tatgggcc     960 cccctcgccg gcacctgcgg agtcttgctc ctgagccttg tgatcacgct ttattgtaac    1020
```

```
catcggaata gatccaaaag aagccgcctg ctccatagcg attacatgaa tatgactcca   1080
cgccgccctg gccccacaag gaaacactac cagccttacg caccacctag agatttcgct   1140
gcctatcgga gcagggtgaa gttttccaga tctgcagatg caccagcgta tcagcagggc   1200
cagaaccaac tgtataacga gctcaacctg gacgcaggg  aagagtatga cgttttggac   1260
aagcgcagag gacgggaccc tgagatgggt ggcaaaccaa gacgaaaaaa ccccaggag    1320 ggtctctata atgagctgca gaaggataag atggctgaag cctattctga aataggcatg   1380
aaaggagagc ggagaagggg aaaagggcac gacggtttgt accagggact cagcactgct   1440
acgaaggata cttatgacgc tctccacatg caagccctgc cacctagg              1488
```

<210> SEQ ID NO 70
<211> LENGTH: 496
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Phe Tyr Trp Ser Trp Ile Arg Gln His Pro Gly Lys Gly Leu Glu
        35                  40                  45

Trp Ile Gly Tyr Ile His His Ser Gly Ser Thr His Tyr Asn Pro Ser
    50                  55                  60

Leu Lys Ser Arg Val Thr Ile Ser Ile Asp Thr Ser Lys Asn Leu Phe
65                  70                  75                  80

Ser Leu Arg Leu Ser Ser Val Thr Ala Ala Asp Thr Ala Val Tyr Tyr
                85                  90                  95

Cys Ala Ser Leu Val Tyr Cys Gly Gly Asp Cys Tyr Ser Gly Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Asp Ile Gln Leu Thr
    130                 135                 140

Gln Ser Pro Ser Ser Leu Ser Ala Ser Val Gly Asp Arg Val Ser Phe
145                 150                 155                 160

Thr Cys Gln Ala Ser Gln Asp Ile Asn Asn Phe Leu Asn Trp Tyr Gln
                165                 170                 175

Gln Lys Pro Gly Lys Ala Pro Lys Leu Leu Ile Tyr Asp Ala Ser Asn
            180                 185                 190

Leu Glu Thr Gly Val Pro Ser Arg Phe Ser Gly Ser Gly Ser Gly Thr
        195                 200                 205

Asp Phe Thr Phe Thr Ile Ser Ser Leu Gln Pro Glu Asp Ile Ala Thr
    210                 215                 220

Tyr Tyr Cys Gln Gln Tyr Gly Asn Leu Pro Phe Thr Phe Gly Gly Gly
225                 230                 235                 240

Thr Lys Val Glu Ile Lys Arg Ala Ala Ala Leu Ser Asn Ser Ile Met
                245                 250                 255

Tyr Phe Ser His Phe Val Pro Val Phe Leu Pro Ala Lys Pro Thr Thr
            260                 265                 270

Thr Pro Ala Pro Arg Pro Pro Thr Pro Ala Pro Thr Ile Ala Ser Gln
```

```
                275                 280                 285
Pro Leu Ser Leu Arg Pro Glu Ala Cys Arg Pro Ala Ala Gly Gly Ala
        290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Ser Leu Val Ile Thr
                325                 330                 335

Leu Tyr Cys Asn His Arg Asn Arg Ser Lys Arg Ser Arg Leu Leu His
                340                 345                 350

Ser Asp Tyr Met Asn Met Thr Pro Arg Arg Pro Gly Pro Thr Arg Lys
                355                 360                 365

His Tyr Gln Pro Tyr Ala Pro Pro Arg Asp Phe Ala Ala Tyr Arg Ser
        370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
                420                 425                 430

Pro Arg Arg Lys Asn Pro Gln Glu Gly Leu Tyr Asn Glu Leu Gln Lys
                435                 440                 445

Asp Lys Met Ala Glu Ala Tyr Ser Glu Ile Gly Met Lys Gly Glu Arg
        450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

<210> SEQ ID NO 71
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
caggtccaac tggtgcagtc cggagccgaa gtcaagaaac caggtgcctc cgttaaagtg      60
agttgcaaag tctctggata cactctgacc gagctctcta tgcactgggt ccggcaggcc     120
cccggcaagg gattggaatg gatgggcggg ttcgatcctg aggacggaga gactatctac     180
gctcaaaaat tccagggacg agtgactgtg accgaagaca ctagtaccga cactgcctac     240
atggaacttt cctctctgcg atcagaagat accgcagtgt actactgtgc tactgaatct     300
aggggcattg gatggcccta cttcgattac tggggtcagg gaactctggt gactgtctcc     360
agc                                                                   363

<210> SEQ ID NO 72
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Gln Val Gln Leu Val Gln Ser Gly Ala Glu Val Lys Lys Pro Gly Ala
1               5                   10                  15
```

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Val Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Ser Arg Gly Ile Gly Trp Pro Tyr Phe Asp Tyr Trp Gly
            100                 105                 110

Gln Gly Thr Leu Val Thr Val Ser Ser
        115                 120

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Tyr Thr Leu Thr Glu Leu
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asp Pro Glu Asp Gly Glu
1               5

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Ser Arg Gly Ile Gly Trp Pro Tyr Phe Asp Tyr
1               5                   10

<210> SEQ ID NO 76
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
gatattcaga tgactcaatc tccttcttct ctgtccgctt ccgtgggcga tagagtgacc      60
attacttgta gggcgtccca gtcaatctcc agttatttga attggtatca gcagaagccc     120

```
gggaaagcac ctaagctgtt gatcagcggg gcttctagcc tgaagagtgg ggtaccttca      180
cggttcagcg gaagcggaag cggaaccgat ttcaccctga ctatcagcag cctgccacct      240
gaggactttg caacttacta ctgccaacag tcatacagca ctccgatcac tttcggccag      300
ggcacccggc tcgaaatcaa gcgc                                             324
```

```
<210> SEQ ID NO 77
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Ser Gly Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Pro Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg
            100                 105

```
<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78
```

Arg Ala Ser Gln Ser Ile Ser Ser Tyr Leu Asn
1               5                   10

```
<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79
```

Gly Ala Ser Ser Leu Lys Ser
1               5

```
<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80
```

Gln Gln Ser Tyr Ser Thr Pro Ile Thr
1               5

<210> SEQ ID NO 81
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

| | | | | |
|---|---|---|---|---|
| atggcactcc | ccgtaactgc | tctgctgctg | ccgttggcat | tgctcctgca cgccgcacgc | 60 |
| ccgcaggtcc | aactggtgca | gtccggagcc | gaagtcaaga | aaccaggtgc ctccgttaaa | 120 |
| gtgagttgca | aagtctctgg | atacactctg | accgagctct | ctatgcactg gtccggcag | 180 |
| gcccccggca | agggattgga | atggatgggc | gggttcgatc | ctgaggacgg agagactatc | 240 |
| tacgctcaaa | aattccaggg | acgagtgact | gtgaccgaag | acactagtac cgacactgcc | 300 |
| tacatggaac | tttcctctct | gcgatcagaa | gataccgcag | tgtactactg tgctactgaa | 360 |
| tctaggggca | ttggatggcc | ctacttcgat | tactggggtc | agggaactct ggtgactgtc | 420 |
| tccagcggtg | gaggtggcag | cggtggtggc | ggaagcgggg | gggcggctc tgatattcag | 480 |
| atgactcaat | ctccttcttc | tctgtccgct | tccgtgggcg | atagagtgac cattacttgt | 540 |
| agggcgtccc | agtcaatctc | cagttatttg | aattggtatc | agcagaagcc cgggaaagca | 600 |
| cctaagctgt | tgatcagcgg | ggcttctagc | ctgaagagtg | ggtaccttc acggttcagc | 660 |
| ggaagcggaa | gcgaaccga | tttcaccctg | actatcagca | gcctgccacc tgaggacttt | 720 |
| gcaacttact | actgccaaca | gtcatacagc | actccgatca | ctttcggcca gggcacccgg | 780 |
| ctcgaaatca | agcgcgctgc | tgctttggac | aatgagaagt | caaacggcac catcatacat | 840 |
| gttaaaggta | acatctgtg | tccctccccg | ctgttccccg | gccttccaa accgttctgg | 900 |
| gttctggtgg | tggtcggagg | cgtactcgct | tgctatagtc | tgctggtaac tgtcgccttc | 960 |
| atcatctttt | gggtgagatc | caaaagaagc | cgcctgctcc | atagcgatta catgaatatg | 1020 |
| actccacgcc | gccctggccc | cacaaggaaa | cactaccagc | cttacgcacc acctagagat | 1080 |
| ttcgctgcct | atcggagcag | ggtgaagttt | tccagatctg | cagatgcacc agcgtatcag | 1140 |
| cagggccaga | accaactgta | taacgagctc | aacctgggac | gcaggaaga gtatgacgtt | 1200 |
| ttggacaagc | gcagaggacg | ggaccctgag | atgggtggca | aaccaagacg aaaaaacccc | 1260 |
| caggagggtc | tctataatga | gctgcagaag | gataagatgg | ctgaagccta ttctgaaata | 1320 |
| ggcatgaaag | gagagcggag | aaggggaaaa | gggcacgacg | gtttgtacca gggactcagc | 1380 |
| actgctacga | aggatactta | tgacgctctc | cacatgcaag | ccctgccacc taggtaa | 1437 |

<210> SEQ ID NO 82
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

-continued

```
Lys Lys Pro Gly Ala Ser Val Lys Val Ser Cys Lys Val Ser Gly Tyr
             35                  40                  45

Thr Leu Thr Glu Leu Ser Met His Trp Val Arg Gln Ala Pro Gly Lys
 50                  55                  60

Gly Leu Glu Trp Met Gly Gly Phe Asp Pro Glu Asp Gly Glu Thr Ile
 65                  70                  75                  80

Tyr Ala Gln Lys Phe Gln Gly Arg Val Thr Val Thr Glu Asp Thr Ser
                 85                  90                  95

Thr Asp Thr Ala Tyr Met Glu Leu Ser Ser Leu Arg Ser Glu Asp Thr
                100                 105                 110

Ala Val Tyr Tyr Cys Ala Thr Glu Ser Arg Gly Ile Gly Trp Pro Tyr
            115                 120                 125

Phe Asp Tyr Trp Gly Gln Gly Thr Leu Val Thr Val Ser Ser Gly Gly
130                 135                 140

Gly Gly Ser Gly Gly Gly Ser Gly Gly Gly Ser Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Ser Ile Ser Ser Tyr Leu Asn Trp
            180                 185                 190

Tyr Gln Gln Lys Pro Gly Lys Ala Pro Lys Leu Leu Ile Ser Gly Ala
                195                 200                 205

Ser Ser Leu Lys Ser Gly Val Pro Ser Arg Phe Ser Gly Ser Gly Ser
            210                 215                 220

Gly Thr Asp Phe Thr Leu Thr Ile Ser Ser Leu Pro Pro Glu Asp Phe
225                 230                 235                 240

Ala Thr Tyr Tyr Cys Gln Gln Ser Tyr Ser Thr Pro Ile Thr Phe Gly
                245                 250                 255

Gln Gly Thr Arg Leu Glu Ile Lys Arg Ala Ala Ala Leu Asp Asn Glu
            260                 265                 270

Lys Ser Asn Gly Thr Ile Ile His Val Lys Gly Lys His Leu Cys Pro
            275                 280                 285

Ser Pro Leu Phe Pro Gly Pro Ser Lys Pro Phe Trp Val Leu Val Val
        290                 295                 300

Val Gly Gly Val Leu Ala Cys Tyr Ser Leu Leu Val Thr Val Ala Phe
305                 310                 315                 320

Ile Ile Phe Trp Val Arg Ser Lys Arg Ser Arg Leu Leu His Ser Asp
                325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Arg Val
                355                 360                 365

Lys Phe Ser Arg Ser Ala Asp Ala Pro Ala Tyr Gln Gln Gly Gln Asn
            370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
            420                 425                 430

Met Ala Glu Ala Tyr Ser Glu Ile Gly Met Lys Gly Glu Arg Arg Arg
435                 440                 445

Gly Lys Gly His Asp Gly Leu Tyr Gln Gly Leu Ser Thr Ala Thr Lys
```

Asp Thr Tyr Asp Ala Leu His Met Gln Ala Leu Pro Pro Arg
465                 470                 475

<210> SEQ ID NO 83
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
caggtccaac tggtgcagtc cggagccgaa gtcaagaaac caggtgcctc cgttaaagtg      60
agttgcaaag tctctggata cactctgacc gagctctcta tgcactgggt ccggcaggcc     120
cccggcaagg gattggaatg gatgggcggg ttcgatcctg aggacggaga gactatctac     180
gctcaaaaat tccagggacg agtgactgtg accgaagaca ctagtaccga cactgcctac     240
atggaacttt cctctctgcg atcagaagat accgcagtgt actactgtgc tactgaatct     300
aggggcattg gatggcccta cttcgattac tggggtcagg gaactctggt gactgtctcc     360
agcggtggag gtggcagcgg tggtggcgga agcgggggg gcggctctga tattcagatg     420
actcaatctc cttcttctct gtccgcttcc gtgggcgata gagtgaccat tacttgtagg     480
gcgtcccagt caatctccag ttatttgaat tggtatcagc agaagcccgg aaagcaccct     540
aagctgttga tcagcggggc ttctagcctg aagagtgggg taccttcacg gttcagcgga     600
agcggaagcg gaaccgattt caccctgact atcagcagcc tgccacctga ggactttgca     660
acttactact gccaacagtc atacagcact ccgatcactt tcggccaggg cacccggctc     720
gaaatcaagc gcgctgctgc tttggacaat gagaagtcaa acggcaccat catacatgtt     780
aaaggtaaac atctgtgtcc ctccccgctg ttccccggcc cttccaaacc gttctgggtt     840
ctggtggtgg tcggaggcgt actcgcttgc tatagtctgc tggtaactgt cgccttcatc     900
atcttttggg tgagatccaa aagaagccgc ctgctccata gcgattacat gaatatgact     960
ccacgccgcc ctggccccac aaggaaacac taccagcctt acgcaccacc tagagatttc    1020
gctgcctatc ggagcagggt gaagttttcc agatctgcag atgcaccagc gtatcagcag    1080
ggccagaacc aactgtataa cgagctcaac ctgggacgca gggaagagta tgacgttttg    1140
gacaagcgca gaggacggga ccctgagatg ggtggcaaac caagacgaaa aaaccccag     1200
gagggtctct ataatgagct gcagaaggat aagatggctg aagcctattc tgaaataggc    1260
atgaaaggag agcggagaag gggaaaaggg cacgacggtt tgtaccaggg actcagcact    1320
gctacgaagg atacttatga cgctctccac atgcaagccc tgccacctag g             1371

<210> SEQ ID NO 84
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

-continued

```
Ser Met His Trp Val Arg Gln Ala Pro Gly Lys Gly Leu Glu Trp Met
         35                  40                  45
Gly Gly Phe Asp Pro Glu Asp Gly Glu Thr Ile Tyr Ala Gln Lys Phe
 50                  55                  60
Gln Gly Arg Val Thr Val Thr Glu Asp Thr Ser Thr Asp Thr Ala Tyr
 65                  70                  75                  80
Met Glu Leu Ser Ser Leu Arg Ser Glu Asp Thr Ala Val Tyr Tyr Cys
                 85                  90                  95
Ala Thr Glu Ser Arg Gly Ile Gly Trp Pro Tyr Phe Asp Tyr Trp Gly
                100                 105                 110
Gln Gly Thr Leu Val Thr Val Ser Ser Gly Gly Gly Ser Gly Gly
            115                 120                 125
Gly Gly Ser Gly Gly Gly Ser Asp Ile Gln Met Thr Gln Ser Pro
130                 135                 140
Ser Ser Leu Ser Ala Ser Val Gly Asp Arg Val Thr Ile Thr Cys Arg
145                 150                 155                 160
Ala Ser Gln Ser Ile Ser Ser Tyr Leu Asn Trp Tyr Gln Gln Lys Pro
                165                 170                 175
Gly Lys Ala Pro Lys Leu Leu Ile Ser Gly Ala Ser Ser Leu Lys Ser
                180                 185                 190
Gly Val Pro Ser Arg Phe Ser Gly Ser Gly Ser Gly Thr Asp Phe Thr
            195                 200                 205
Leu Thr Ile Ser Ser Leu Pro Pro Glu Asp Phe Ala Thr Tyr Tyr Cys
            210                 215                 220
Gln Gln Ser Tyr Ser Thr Pro Ile Thr Phe Gly Gln Gly Thr Arg Leu
225                 230                 235                 240
Glu Ile Lys Arg Ala Ala Ala Leu Asp Asn Glu Lys Ser Asn Gly Thr
                245                 250                 255
Ile Ile His Val Lys Gly Lys His Leu Cys Pro Ser Pro Leu Phe Pro
                260                 265                 270
Gly Pro Ser Lys Pro Phe Trp Val Leu Val Val Val Gly Gly Val Leu
            275                 280                 285
Ala Cys Tyr Ser Leu Leu Val Thr Val Ala Phe Ile Ile Phe Trp Val
290                 295                 300
Arg Ser Lys Arg Ser Arg Leu Leu His Ser Asp Tyr Met Asn Met Thr
305                 310                 315                 320
Pro Arg Arg Pro Gly Pro Thr Arg Lys His Tyr Gln Pro Tyr Ala Pro
                325                 330                 335
Pro Arg Asp Phe Ala Ala Tyr Arg Ser Arg Val Lys Phe Ser Arg Ser
            340                 345                 350
Ala Asp Ala Pro Ala Tyr Gln Gln Gly Gln Asn Gln Leu Tyr Asn Glu
            355                 360                 365
Leu Asn Leu Gly Arg Arg Glu Glu Tyr Asp Val Leu Asp Lys Arg Arg
            370                 375                 380
Gly Arg Asp Pro Glu Met Gly Gly Lys Pro Arg Arg Lys Asn Pro Gln
385                 390                 395                 400
Glu Gly Leu Tyr Asn Glu Leu Gln Lys Asp Lys Met Ala Glu Ala Tyr
                405                 410                 415
Ser Glu Ile Gly Met Lys Gly Glu Arg Arg Arg Gly Lys Gly His Asp
                420                 425                 430
Gly Leu Tyr Gln Gly Leu Ser Thr Ala Thr Lys Asp Thr Tyr Asp Ala
            435                 440                 445
Leu His Met Gln Ala Leu Pro Pro Arg
```

450             455

<210> SEQ ID NO 85
<211> LENGTH: 1464
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
atggcactcc ccgtaactgc tctgctgctg ccgttggcat tgctcctgca cgccgcacgc      60
ccgcaggtgc agcttgtgca gagcggggcc gaggtgaaga gcccggggc cagcgtcaaa      120
gtgtcctgta aggtcagcgg ttacaccctc accgagctga gcatgcactg ggtacggcag     180
gctcccggca aggtcttga gtggatgggt ggatttgatc agaagatgg agagactatc       240
tacgcccaga gttccaggg ccgggtcacc gtaacagaag acacctcaac tgacaccgct      300
tacatggagc tgagttcact gcggtccgag gacacggccg tgtattattg tgccaccgag     360
agccgcggaa tcggatggcc ttacttcgac tactggggac agggtacact tgttacagta    420
tcatccgggg gtggcggctc tggtgggggc ggctccggag ggggtggatc agatatccaa    480
atgactcaaa gtccaagttc cctgtctgcc tcagtcggag atagagtcac cataacctgc    540
agggcaagtc agtccatctc ctcctatctg aactggtacc aacagaaacc tggaaaggcg    600
cctaagctcc tgatctccgg agcctcatct ttgaaatccg gtgtcccatc tcgcttcagt    660
ggctctggaa gcggtacaga ttttactttg accattagca gcctcccacc ggaagacttt    720
gctacatatt actgccagca gtcttactca accccaatca ccttcgggca aggcaccaga    780
ctcgaaataa aaagagcagc tgctatcgag gttatgtacc caccgccgta cttggataac    840
gaaaaaagca atgggaccat cattcatgtg aagggtaagc cctttgccc tagcccactg    900
tttcctggcc cgagtaaacc ctttggga cttgtggtcg tcggcggcgt gctggcctgc    960
tactcactcc tggttaccgt cgcattcatc atcttttggg tgagatccaa aagaagccgc    1020
ctgctcccata gcgattacat gaatatgact ccacgccgcc ctggccccac aaggaaacac    1080
taccagcctt acgcaccacc tagagatttc gctgcctatc ggagcagggt gaagttttcc    1140
agatctgcag atgcaccagc gtatcagcag ggccagaacc aactgtataa cgagctcaac    1200
ctgggacgca gggaagagta tgacgttttg acaagcgca gaggacggga ccctgagatg    1260
ggtggcaaac caagacgaaa aaaccccag gagggtctct ataatgagct gcagaaggat    1320
aagatggctg aagcctattc tgaaataggc atgaaggag agcggagaag gggaaaaggg    1380
cacgacggtt tgtaccaggg actcagcact gctacgaagg atacttatga cgctctccac    1440
atgcaagccc tgccacctag gtaa                                             1464
```

<210> SEQ ID NO 86
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

```
Lys Lys Pro Gly Ala Ser Val Lys Val Ser Cys Lys Val Ser Gly Tyr
            35                  40                  45

Thr Leu Thr Glu Leu Ser Met His Trp Val Arg Gln Ala Pro Gly Lys
     50                  55                  60

Gly Leu Glu Trp Met Gly Gly Phe Asp Pro Glu Asp Gly Glu Thr Ile
 65                  70                  75                  80

Tyr Ala Gln Lys Phe Gln Gly Arg Val Thr Val Thr Glu Asp Thr Ser
                 85                  90                  95

Thr Asp Thr Ala Tyr Met Glu Leu Ser Ser Leu Arg Ser Glu Asp Thr
                100                 105                 110

Ala Val Tyr Tyr Cys Ala Thr Glu Ser Arg Gly Ile Gly Trp Pro Tyr
            115                 120                 125

Phe Asp Tyr Trp Gly Gln Gly Thr Leu Val Thr Val Ser Ser Gly Gly
130                 135                 140

Gly Gly Ser Gly Gly Gly Gly Ser Gly Gly Gly Gly Ser Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Ser Ile Ser Ser Tyr Leu Asn Trp
            180                 185                 190

Tyr Gln Gln Lys Pro Gly Lys Ala Pro Lys Leu Leu Ile Ser Gly Ala
            195                 200                 205

Ser Ser Leu Lys Ser Gly Val Pro Ser Arg Phe Ser Gly Ser Gly Ser
            210                 215                 220

Gly Thr Asp Phe Thr Leu Thr Ile Ser Ser Leu Pro Pro Glu Asp Phe
225                 230                 235                 240

Ala Thr Tyr Tyr Cys Gln Gln Ser Tyr Ser Thr Pro Ile Thr Phe Gly
                245                 250                 255

Gln Gly Thr Arg Leu Glu Ile Lys Arg Ala Ala Ala Ile Glu Val Met
            260                 265                 270

Tyr Pro Pro Pro Tyr Leu Asp Asn Glu Lys Ser Asn Gly Thr Ile Ile
            275                 280                 285

His Val Lys Gly Lys His Leu Cys Pro Ser Pro Leu Phe Pro Gly Pro
            290                 295                 300

Ser Lys Pro Phe Trp Val Leu Val Val Val Gly Gly Val Leu Ala Cys
305                 310                 315                 320

Tyr Ser Leu Leu Val Thr Val Ala Phe Ile Ile Phe Trp Val Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
            355                 360                 365

Asp Phe Ala Ala Tyr Arg Ser Arg Val Lys Phe Ser Arg Ser Ala Asp
370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
            435                 440                 445
```

Ile Gly Met Lys Gly Glu Arg Arg Arg Gly Lys Gly His Asp Gly Leu
450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 87
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
caggtgcagc ttgtgcagag cggggccgag gtgaagaagc ccggggccag cgtcaaagtg    60
tcctgtaagg tcagcggtta caccctcacc gagctgagca tgcactgggt acggcaggct   120
cccggcaaag gtcttgagtg gatgggtgga tttgatccag aagatggaga gactatctac   180
gcccagaagt tccagggccg ggtcaccgta acagaagaca cctcaactga caccgcttac   240
atggagctga gttcactgcg gtccgaggac acggccgtgt attattgtgc caccgagagc   300
cgcggaatcg gatggcctta cttcgactac tggggacagg gtacacttgt tacagtatca   360
tccgggggtg gcggctctgg tggggcggc tccgagggg gtggatcaga tatccaaatg   420
actcaaagtc caagttccct gtctgcctca gtcggagata gagtcaccat aacctgcagg   480
gcaagtcagt ccatctcctc ctatctgaac tggtaccaac agaaacctgg aaaggcgcct   540
aagctcctga tctccggagc ctcatctttg aaatccggtg tcccatctcg cttcagtggc   600
tctggaagcg gtacagattt tactttgacc attagcagcc tccaccggga agactttgct   660
acatattact gccagcagtc ttactcaacc ccaatcacct cgggcaagg caccagactc   720 gaaatdaaaa gagcagctgc tatcgaggtt atgtacccac cgccgtactt ggataacgaa   780
aaaagcaatg gaccatcat tcatgtgaag ggtaagcacc tttgccctag cccactgttt   840
cctggcccga gtaaaccctt tgggtactt gtggtcgtcg gcggcgtgct ggcctgctac   900
tcactcctgg ttaccgtcgc attcatcatc ttttgggtga gatccaaaag aagccgcctg   960
ctccatagcg attacatgaa tatgactcca cgccgccctg gccccacaag gaaacactac  1020
cagccttacg caccacctag agatttcgct gcctatcgga gcagggtgaa gttttccaga  1080
tctgcagatg caccagcgta tcagcagggc cagaaccaac tgtataacga gctcaacctg  1140
ggacgcaggg aagagtatga cgttttggac aagcgcagag acgggaccc tgagatgggt  1200 ggcaaaccaa gacgaaaaaa cccccaggag ggtctctata tgagctgca gaaggataag  1260 atggctgaag cctattctga aataggcatg aaaggagagc ggagaagggg aaaagggcac  1320
gacggtttgt accagggact cagcactgct acgaaggata cttatgacgc tctccacatg  1380
caagccctgc cacctagg                                                1398

<210> SEQ ID NO 88
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

-continued

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Val Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Ser Arg Gly Ile Gly Trp Pro Tyr Phe Asp Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
            165                 170                 175

Gly Lys Ala Pro Lys Leu Leu Ile Ser Gly Ala Ser Ser Leu Lys Ser
            180                 185                 190

Gly Val Pro Ser Arg Phe Ser Gly Ser Gly Ser Gly Thr Asp Phe Thr
        195                 200                 205

Leu Thr Ile Ser Ser Leu Pro Pro Glu Asp Phe Ala Thr Tyr Tyr Cys
    210                 215                 220

Gln Gln Ser Tyr Ser Thr Pro Ile Thr Phe Gly Gln Gly Thr Arg Leu
225                 230                 235                 240

Glu Ile Lys Arg Ala Ala Ala Ile Glu Val Met Tyr Pro Pro Pro Tyr
            245                 250                 255

Leu Asp Asn Glu Lys Ser Asn Gly Thr Ile Ile His Val Lys Gly Lys
        260                 265                 270

His Leu Cys Pro Ser Pro Leu Phe Pro Gly Pro Ser Lys Pro Phe Trp
    275                 280                 285

Val Leu Val Val Val Gly Gly Val Leu Ala Cys Tyr Ser Leu Leu Val
        290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
            325                 330                 335

Arg Lys His Tyr Gln Pro Tyr Ala Pro Pro Arg Asp Phe Ala Ala Tyr
        340                 345                 350

Arg Ser Arg Val Lys Phe Ser Arg Ser Ala Asp Ala Pro Ala Tyr Gln
    355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
            405                 410                 415

Gln Lys Asp Lys Met Ala Glu Ala Tyr Ser Glu Ile Gly Met Lys Gly
```

420             425                 430
Glu Arg Arg Arg Gly Lys Gly His Asp Gly Leu Tyr Gln Gly Leu Ser
            435                 440                 445
Thr Ala Thr Lys Asp Thr Tyr Asp Ala Leu His Met Gln Ala Leu Pro
        450                 455                 460
Pro Arg
465

<210> SEQ ID NO 89
<211> LENGTH: 1545
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89

```
atggcactcc cgtaactgc tctgctgctg ccgttggcat tgctcctgca cgccgcacgc      60
ccgcaggtgc agttggtgca aagcggcgca gaagttaaga aacctggggc gtcagttaag    120
gtgtcttgca aagtatctgg ctataccctc actgagctgt ccatgcattg ggtaaggcag    180
gctcctggaa aggggctcga atggatggga ggatttgacc ctgaagacgg agagaccatc    240
tacgcccaga attccaggg tagagtaaca gtgactgagg acactagcac tgacacagcg    300
tacatggagc tgagttctct gagaagtgag gacacagccg tttactactg cgctaccgag    360
tccagaggta ttggctggcc atacttcgac tattggggtc agggcaccct ggttacagtg    420
agttcaggag gcggggggctc tggggggggc ggttccggag ggggggggctc agatatacag    480
atgacgcaga gtccatcaag tctctcagcc agcgtgggag atcgcgtgac tattacttgc    540
cgcgccagcc agagtattag ctcctatctg aattggtacc agcaaaagcc cgggaaggcc    600
cctaagcttc tgatttctgg cgcctcctct ttgaagtcag gtgtgccaag cagatttagc    660
gggtctggaa gtggcactga ctttacactt actatctcca gcctgccccc agaggatttt    720
gccacatatt actgtcagca aagctactct actccaatca ctttcggcca gggcacaaga    780
ttggagatta gagggctgc cgcactttca aattccatca tgtatttcag ccattttgtg    840
cctgtttttc ttccggccaa acctacaacc actcccgccc acgcccacc tactcccgcc    900
cctaccattg cctcccagcc tctgtctctt agacctgagg cttgtagacc tgctgccggc    960
ggagccgtgc acactcgcgg tctggacttc gcctgcgaca tctatatctg gcccctctg   1020
gccggcacct gcggcgttct ccttctctca ctcgtaatca cactctattg caatcacagg   1080
aacagatcca aagaagccg cctgctccat agcgattaca tgaatatgac tccacgccgc   1140
cctggccca aaggaaaca ctaccagcct tacgcaccac ctagagattt cgctgcctat   1200
cggagcaggg tgaagttttc cagatctgca gatgcaccag cgtatcagca gggccagaac   1260
caactgtata cgagctcaa cctgggacgc agggaagagt atgacgtttt ggacaagcgc   1320
agaggacggg accctgagat gggtggcaaa ccaagacgaa aaaccccca ggagggtctc   1380
tataatgagc tgcagaagga taagatggct gaagcctatt ctgaaatagg catgaaagga   1440
gagcggagaa ggggaaaagg gcacgacggt ttgtaccagg gactcagcac tgctacgaag   1500
gatacttatg acgctctcca catgcaagcc ctgccaccta ggtaa                 1545
```

<210> SEQ ID NO 90
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Val Ser Gly Tyr
        35                  40                  45

Thr Leu Thr Glu Leu Ser Met His Trp Val Arg Gln Ala Pro Gly Lys
    50                  55                  60

Gly Leu Glu Trp Met Gly Gly Phe Asp Pro Glu Asp Gly Glu Thr Ile
65                  70                  75                  80

Tyr Ala Gln Lys Phe Gln Gly Arg Val Thr Val Thr Glu Asp Thr Ser
                85                  90                  95

Thr Asp Thr Ala Tyr Met Glu Leu Ser Ser Leu Arg Ser Glu Asp Thr
            100                 105                 110

Ala Val Tyr Tyr Cys Ala Thr Glu Ser Arg Gly Ile Gly Trp Pro Tyr
        115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Ser Ile Ser Ser Tyr Leu Asn Trp
            180                 185                 190

Tyr Gln Gln Lys Pro Gly Lys Ala Pro Lys Leu Leu Ile Ser Gly Ala
        195                 200                 205

Ser Ser Leu Lys Ser Gly Val Pro Ser Arg Phe Ser Gly Ser Gly Ser
    210                 215                 220

Gly Thr Asp Phe Thr Leu Thr Ile Ser Ser Leu Pro Pro Glu Asp Phe
225                 230                 235                 240

Ala Thr Tyr Tyr Cys Gln Gln Ser Tyr Ser Thr Pro Ile Thr Phe Gly
                245                 250                 255

Gln Gly Thr Arg Leu Glu Ile Lys Arg Ala Ala Ala Leu Ser Asn Ser
            260                 265                 270

Ile Met Tyr Phe Ser His Phe Val Pro Val Phe Leu Pro Ala Lys Pro
        275                 280                 285

Thr Thr Thr Pro Ala Pro Arg Pro Pro Thr Pro Ala Pro Thr Ile Ala
    290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Phe Ala Cys Asp Ile Tyr Ile
                325                 330                 335

Trp Ala Pro Leu Ala Gly Thr Cys Gly Val Leu Leu Leu Ser Leu Val
            340                 345                 350

Ile Thr Leu Tyr Cys Asn His Arg Asn Arg Ser Lys Arg Ser Arg Leu
        355                 360                 365

Leu His Ser Asp Tyr Met Asn Met Thr Pro Arg Arg Pro Gly Pro Thr
    370                 375                 380

Arg Lys His Tyr Gln Pro Tyr Ala Pro Pro Arg Asp Phe Ala Ala Tyr

```
              385                 390                 395                 400
Arg Ser Arg Val Lys Phe Ser Arg Ser Ala Asp Ala Pro Ala Tyr Gln
                    405                 410                 415

Gln Gly Gln Asn Gln Leu Tyr Asn Glu Leu Asn Leu Gly Arg Arg Glu
                420                 425                 430

Glu Tyr Asp Val Leu Asp Lys Arg Arg Gly Arg Asp Pro Glu Met Gly
            435                 440                 445

Gly Lys Pro Arg Arg Lys Asn Pro Gln Glu Gly Leu Tyr Asn Glu Leu
450                 455                 460

Gln Lys Asp Lys Met Ala Glu Ala Tyr Ser Glu Ile Gly Met Lys Gly
465                 470                 475                 480

Glu Arg Arg Arg Gly Lys Gly His Asp Gly Leu Tyr Gln Gly Leu Ser
                485                 490                 495

Thr Ala Thr Lys Asp Thr Tyr Asp Ala Leu His Met Gln Ala Leu Pro
                500                 505                 510

Pro Arg

<210> SEQ ID NO 91
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
caggtgcagt tggtgcaaag cggcgcagaa gttaagaaac tggggcgtc  agttaaggtg        60 tcttgcaaag tatctggcta taccctcact gagctgtcca tgcattgggt aaggcaggct       120
cctggaaagg ggctcgaatg gatgggagga tttgaccctg aagacggaga gaccatctac       180
gcccagaaat tccagggtag agtaacagtg actgaggaca ctagcactga cacagcgtac       240
atggagctga gttctctgag aagtgaggac acagccgttt actactgcgc taccgagtcc       300
agaggtattg gctggccata cttcgactat tggggtcagg gcaccctggt tacagtgagt       360
tcaggaggcg ggggctctgg ggggggcggt tccgagggg ggggctcaga tatacagatg       420
acgcagagtc catcaagtct ctcagccagc gtgggagatc gcgtgactat tacttgccgc       480
gccagccaga gtattagctc ctatctgaat tggtaccagc aaaagcccgg gaaggcccct       540
aagcttctga tttctggcgc ctcctctttg aagtcaggtg tgccaagcag atttagcggg       600
tctggaagtg gcactgactt tacacttact atctccagcc tgcccccaga ggattttgcc       660
acatattact gtcagcaaag ctactctact ccaatcactt tcggccaggg cacaagattg       720
gagattaaga gggctgccgc actttcaaat tccatcatgt atttcagcca ttttgtgcct       780 gttttcttc cggccaaacc tacaaccact cccgccccac gcccacctac tcccgcccct       840
accattgcct cccagcctct gtctcttaga cctgaggctt gtagacctgc tgccggcgga       900
gccgtgcaca ctcgcggtct ggacttcgcc tgcgacatct atatctgggc ccctctggcc       960
ggcacctgcg gcgttctcct tctctcactc gtaatcacac tctattgcaa tcacaggaac      1020
agatccaaaa gaagccgcct gctccatagc gattacatga atatgactcc acgccgccct      1080
ggccccacaa ggaaacacta ccagccttac gcaccaccta gagatttcgc tgcctatcgg      1140
agcagggtga gttttccag  atctgcagat gcaccagcgt atcagcaggg ccagaaccaa      1200
ctgtataacg agctcaacct gggacgcagg gaagagtatg acgttttgga caagcgcaga      1260
ggacgggacc ctgagatggg tggcaaacca agacgaaaaa accccagga  gggtctctat      1320
```

```
aatgagctgc agaaggataa gatggctgaa gcctattctg aaataggcat gaaaggagag    1380
cggagaaggg gaaaagggca cgacggtttg taccagggac tcagcactgc tacgaaggat    1440
acttatgacg ctctccacat gcaagccctg ccacctagg                           1479
```

<210> SEQ ID NO 92
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Val Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Ser Arg Gly Ile Gly Trp Pro Tyr Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Ser Gly Ala Ser Ser Leu Lys Ser
            180                 185                 190

Gly Val Pro Ser Arg Phe Ser Gly Ser Gly Ser Gly Thr Asp Phe Thr
        195                 200                 205

Leu Thr Ile Ser Ser Leu Pro Pro Glu Asp Phe Ala Thr Tyr Tyr Cys
    210                 215                 220

Gln Gln Ser Tyr Ser Thr Pro Ile Thr Phe Gly Gln Gly Thr Arg Leu
225                 230                 235                 240

Glu Ile Lys Arg Ala Ala Ala Leu Ser Asn Ser Ile Met Tyr Phe Ser
                245                 250                 255

His Phe Val Pro Val Phe Leu Pro Ala Lys Pro Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
```

```
                          325                 330                 335
Asn His Arg Asn Arg Ser Lys Arg Ser Arg Leu Leu His Ser Asp Tyr
                340                 345                 350

Met Asn Met Thr Pro Arg Arg Pro Gly Pro Thr Arg Lys His Tyr Gln
            355                 360                 365

Pro Tyr Ala Pro Pro Arg Asp Phe Ala Ala Tyr Arg Ser Arg Val Lys
        370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 93
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
caggtccagt tggtcgaaag tggcggtggt gtagtgcagc cgggccgcag tttgaggctt    60
tcctgtgcgg cttcaggctt tactttttcc agctatggaa tgcactgggt gcggcaggcc   120
cccggcaaag gacttgagtg gtggccgtc  atttcttatg acggatcaga taagtactac   180
gtggacagcg tcaagggcag attcaccatc tctaggcaca cagtaaaaa  tagactctac   240 ctccagatga atagcctcag agctgaagac acggccgtct actattgtgc tcgggagcgg   300
tatagtggca gagactactg ggggcagggc acactcgtta cagtgagtag c            351
```

<210> SEQ ID NO 94
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Val Asp Ser Val
    50                  55                  60

Lys Gly Arg Phe Thr Ile Ser Arg Asp Asn Ser Lys Asn Arg Leu Tyr
```

```
                65                  70                  75                  80
Leu Gln Met Asn Ser Leu Arg Ala Glu Asp Thr Ala Val Tyr Tyr Cys
                        85                  90                  95

Ala Arg Glu Arg Tyr Ser Gly Arg Asp Tyr Trp Gly Gln Gly Thr Leu
                100                 105                 110

Val Thr Val Ser Ser
            115

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Phe Thr Phe Ser Ser Tyr
1               5

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ser Tyr Asp Gly Ser Asp
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Glu Arg Tyr Ser Gly Arg Asp Tyr
1               5

<210> SEQ ID NO 98
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 98
gagattgtta tgacccagag tcctgcgacc ctctcagtca gccccgggga gcgcgcaact      60
ttgtcttgca gagctagtca gtccgtgtcc tctcttctga catggtacca gcaaaagccc     120
gggcaggctc cgcgcctttt gatctttggg gcttcaacaa gagccactgg gattcccgca     180
cgattctctg gctccgggag cggtactggt tcaccctga cgattagcag tctccagagc      240
gaggacttcg ccgtatacta ctgccagcag tacgatacgt ggccattcac ttttggacca     300
gggactaaag tggattttaa gcgc                                            324

<210> SEQ ID NO 99
<211> LENGTH: 108
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Leu
            20                  25                  30

Leu Thr Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Gly Ser Gly Thr Gly Phe Thr Leu Thr Ile Ser Ser Leu Gln Ser
65                  70                  75                  80

Glu Asp Phe Ala Val Tyr Tyr Cys Gln Gln Tyr Asp Thr Trp Pro Phe
                85                  90                  95

Thr Phe Gly Pro Gly Thr Lys Val Asp Phe Lys Arg
            100                 105

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Ala Ser Gln Ser Val Ser Ser Leu Leu Thr
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Ala Ser Thr Arg Ala Thr
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gln Gln Tyr Asp Thr Trp Pro Phe Thr
1               5

<210> SEQ ID NO 103
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 103

```
atggcactcc ccgtaactgc tctgctgctg ccgttggcat tgctcctgca cgccgcacgc      60
ccgcaggtcc agttggtcga aagtggcggt ggtgtagtgc agccgggccg cagtttgagg     120
ctttcctgtg cggcttcagg ctttactttt tccagctatg gaatgcactg ggtgcggcag     180
gccccccggca aaggacttga gtgggtggcc gtcatttctt atgacggatc agataagtac    240
tacgtggaca gcgtcaaggg cagattcacc atctctaggg acaacagtaa aaatagactc    300
tacctccaga tgaatagcct cagagctgaa gacacggccg tctactattg tgctcgggag    360
cggtatagtg gcagagacta ctgggggcag ggcacactcg ttacagtgag tagcggcgga    420
ggagggagtg ggggcggtgg ctccggtgga ggaggttctg agattgttat gacccagagt    480
cctgcgaccc tctcagtcag ccccggggag gcgcaacttt gtcttgcag agctagtcag    540
tccgtgtcct ctcttctgac atggtaccag caaaagcccg ggcaggctcc cgccttttg    600
atctttgggg cttcaacaag agccactggg attcccgcac gattctctgg ctccgggagc    660
ggtactggtt tcaccctgac gattagcagt ctccagagcg aggacttcgc cgtatactac    720
tgccagcagt acgatacgtg gccattcact tttggaccag ggactaaagt ggattttaag    780
cgcgccgccg ctctcgataa cgaaaagtca aatggcacca taatccacgt caaaggcaag    840
cacctgtgcc cttccccgct cttccccgga cccagtaaac catttttggg gctggttgtt    900
gtgggggggcg tgctggcctg ctatagcctt ttggtcactg tagccttcat tattttttgg    960
gtcagatcca aaagaagccg cctgctccat agcgattaca tgaatatgac tccacgccgc   1020
cctggccccca aaggaaaaca ctaccagcct tacgcaccac ctagagattt cgctgcctat   1080
cggagcaggg tgaagttttc cagatctgca gatgcaccag cgtatcagca gggccagaac   1140
caactgtata acgagctcaa cctgggacgc agggaagagt atgacgtttt ggacaagcgc   1200
agaggacggg accctgagat gggtggcaaa ccaagacgaa aaaccccca ggagggtctc   1260
tataatgagc tgcagaagga taagatggct gaagcctatt ctgaaatagg catgaaagga   1320
gagcggagaa ggggaaaagg gcacgacggt ttgtaccagg gactcagcac tgctacgaag   1380
gatacttatg acgctctcca catgcaagcc ctgccaccta ggtaa                   1425
```

<210> SEQ ID NO 104
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

```
Met Ala Leu Pro Val Thr Ala Leu Leu Leu Pro Leu Ala Leu Leu Leu
1               5                  10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asp Lys Tyr
65                  70                  75                  80

Tyr Val Asp Ser Val Lys Gly Arg Phe Thr Ile Ser Arg Asp Asn Ser
                85                  90                  95
```

Lys Asn Arg Leu Tyr Leu Gln Met Asn Ser Leu Arg Ala Glu Asp Thr
            100                 105                 110

Ala Val Tyr Tyr Cys Ala Arg Glu Arg Tyr Ser Gly Arg Asp Tyr Trp
        115                 120                 125

Gly Gln Gly Thr Leu Val Thr Val Ser Ser Gly Gly Gly Gly Ser Gly
    130                 135                 140

Gly Gly Ser Gly Gly Gly Gly Ser Glu Ile Val Met Thr Gln Ser
145                 150                 155                 160

Pro Ala Thr Leu Ser Val Ser Pro Gly Glu Arg Ala Thr Leu Ser Cys
                165                 170                 175

Arg Ala Ser Gln Ser Val Ser Ser Leu Leu Thr Trp Tyr Gln Gln Lys
            180                 185                 190

Pro Gly Gln Ala Pro Arg Leu Leu Ile Phe Gly Ala Ser Thr Arg Ala
        195                 200                 205

Thr Gly Ile Pro Ala Arg Phe Ser Gly Ser Gly Ser Gly Thr Gly Phe
    210                 215                 220

Thr Leu Thr Ile Ser Ser Leu Gln Ser Glu Asp Phe Ala Val Tyr Tyr
225                 230                 235                 240

Cys Gln Gln Tyr Asp Thr Trp Pro Phe Thr Phe Gly Pro Gly Thr Lys
                245                 250                 255

Val Asp Phe Lys Arg Ala Ala Ala Leu Asp Asn Glu Lys Ser Asn Gly
            260                 265                 270

Thr Ile Ile His Val Lys Gly Lys His Leu Cys Pro Ser Pro Leu Phe
        275                 280                 285

Pro Gly Pro Ser Lys Pro Phe Trp Val Leu Val Val Val Gly Gly Val
    290                 295                 300

Leu Ala Cys Tyr Ser Leu Leu Val Thr Val Ala Phe Ile Ile Phe Trp
305                 310                 315                 320

Val Arg Ser Lys Arg Ser Arg Leu Leu His Ser Asp Tyr Met Asn Met
                325                 330                 335

Thr Pro Arg Arg Pro Gly Pro Thr Arg Lys His Tyr Gln Pro Tyr Ala
            340                 345                 350

Pro Pro Arg Asp Phe Ala Ala Tyr Arg Ser Arg Val Lys Phe Ser Arg
        355                 360                 365

Ser Ala Asp Ala Pro Ala Tyr Gln Gln Gly Gln Asn Gln Leu Tyr Asn
    370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
        435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro Arg
465                 470

<210> SEQ ID NO 105
<211> LENGTH: 1359
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 105

```
caggtccagt tggtcgaaag tggcggtggt gtagtgcagc cgggccgcag tttgaggctt     60
tcctgtgcgg cttcaggctt tacttttttcc agctatggaa tgcactgggt gcggcaggcc    120
cccggcaaag gacttgagtg ggtggccgtc atttcttatg acggatcaga taagtactac    180
gtggacagcg tcaagggcag attcaccatc tctaggaca acagtaaaaa tagactctac     240
ctccagatga atagcctcag agctgaagac acggccgtct actattgtgc tcgggagcgg    300
tatagtggca gagactactg ggggcagggc acactcgtta cagtgagtag cggcggagga    360
gggagtgggg gcggtggctc cggtggagga ggttctgaga ttgttatgac ccagagtcct    420
gcgaccctct cagtcagccc cggggagcgc gcaactttgt cttgcagagc tagtcagtcc    480
gtgtcctctc ttctgacatg gtaccagcaa aagcccgggc aggctccgcg cctttttgatc   540
tttgggctt caacaagagc cactgggatt cccgcacgat tctctggctc cgggagcggt     600
actggtttca ccctgacgat tagcagtctc cagagcgagg acttcgccgt atactactgc    660
cagcagtacg atacgtggcc attcactttt ggaccaggc ctaaagtgga tttaagcgc     720
gccgccgctc tcgataacga aaagtcaaat ggcaccataa tccacgtcaa aggcaagcac    780
ctgtgccctt ccccgctctt ccccggaccc agtaaaccat tttgggtgct ggttgttgtg    840
gggggcgtgc tggcctgcta tagccttttg gtcactgtag ccttcattat tttttgggtc    900
agatccaaaa gaagccgcct gctccatagc gattacatga aatgactcc acgccgccct    960
ggccccacaa ggaaacacta ccagccttac gcaccaccta gagatttcgc tgcctatcgg   1020
agcagggtga gttttccag atctgcagat gcaccagcgt atcagcaggg ccagaaccaa    1080
ctgtataacg agctcaacct gggacgcagg gaagagtatg acgttttgga caagcgcaga   1140
ggacgggacc ctgagatggg tgcaaaacca agacgaaaaa accccagga gggtctctat    1200
aatgagctgc agaaggataa gatggctgaa gcctattctg aaataggcat gaaaggagag   1260
cggagaaggg gaaagggca cgacggtttg taccagggac tcagcactgc tacgaaggat   1320
acttatgacg ctctccacat gcaagccctg ccacctagg                          1359
```

<210> SEQ ID NO 106
<211> LENGTH: 453
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 106

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Val Asp Ser Val
    50                  55                  60

Lys Gly Arg Phe Thr Ile Ser Arg Asp Asn Ser Lys Asn Arg Leu Tyr
65                  70                  75                  80

Leu Gln Met Asn Ser Leu Arg Ala Glu Asp Thr Ala Val Tyr Tyr Cys
                85                  90                  95
```

Ala Arg Glu Arg Tyr Ser Gly Arg Asp Tyr Trp Gln Gly Thr Leu
            100                 105                 110

Val Thr Val Ser Ser Gly Gly Gly Ser Gly Gly Gly Ser Gly
        115                 120                 125

Gly Gly Gly Ser Glu Ile Val Met Thr Gln Ser Pro Ala Thr Leu Ser
130                 135                 140

Val Ser Pro Gly Glu Arg Ala Thr Leu Ser Cys Arg Ala Ser Gln Ser
145                 150                 155                 160

Val Ser Ser Leu Leu Thr Trp Tyr Gln Gln Lys Pro Gly Gln Ala Pro
                165                 170                 175

Arg Leu Leu Ile Phe Gly Ala Ser Thr Arg Ala Thr Gly Ile Pro Ala
                180                 185                 190

Arg Phe Ser Gly Ser Gly Ser Gly Thr Gly Phe Thr Leu Thr Ile Ser
                195                 200                 205

Ser Leu Gln Ser Glu Asp Phe Ala Val Tyr Tyr Cys Gln Gln Tyr Asp
                210                 215                 220

Thr Trp Pro Phe Thr Phe Gly Pro Gly Thr Lys Val Asp Phe Lys Arg
225                 230                 235                 240

Ala Ala Ala Leu Asp Asn Glu Lys Ser Asn Gly Thr Ile Ile His Val
                245                 250                 255

Lys Gly Lys His Leu Cys Pro Ser Pro Leu Phe Pro Gly Pro Ser Lys
                260                 265                 270

Pro Phe Trp Val Leu Val Val Gly Gly Val Leu Ala Cys Tyr Ser
                275                 280                 285

Leu Leu Val Thr Val Ala Phe Ile Ile Phe Trp Val Arg Ser Lys Arg
                290                 295                 300

Ser Arg Leu Leu His Ser Asp Tyr Met Asn Met Thr Pro Arg Arg Pro
305                 310                 315                 320

Gly Pro Thr Arg Lys His Tyr Gln Pro Tyr Ala Pro Pro Arg Asp Phe
                325                 330                 335

Ala Ala Tyr Arg Ser Arg Val Lys Phe Ser Arg Ser Ala Asp Ala Pro
                340                 345                 350

Ala Tyr Gln Gln Gly Gln Asn Gln Leu Tyr Asn Glu Leu Asn Leu Gly
                355                 360                 365

Arg Arg Glu Glu Tyr Asp Val Leu Asp Lys Arg Arg Gly Arg Asp Pro
                370                 375                 380

Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly
                405                 410                 415

Met Lys Gly Glu Arg Arg Arg Gly Lys Gly His Asp Gly Leu Tyr Gln
                420                 425                 430

Gly Leu Ser Thr Ala Thr Lys Asp Thr Tyr Asp Ala Leu His Met Gln
                435                 440                 445

Ala Leu Pro Pro Arg
    450

<210> SEQ ID NO 107
<211> LENGTH: 1452
<212> TYPE: DNA
<213> ORGANISM: Artificial Sequence
<220> FEATURE:
<223> OTHER INFORMATION: Description of Artificial Sequence: Synthetic
      polynucleotide -continued

<400> SEQUENCE: 107

```
atggcactcc ccgtaactgc tctgctgctg ccgttggcat tgctcctgca cgccgcacgc      60
ccgcaggtgc agctcgtgga gtctggcggc ggcgtggtcc agcccggccg gtccctgcgc     120
ctgtcctgcg ccgccagcgg gtttactttt cctcctacg gcatgcactg ggtgcgccag     180
gctcccggca agggcctcga gtgggtcgcc gtgatctcat acgatgggtc agacaaatac     240
tatgtcgatt ctgttaaagg gcggtttacc atttcaagag ataactctaa gaataggctg     300
tatttgcaga tgaacagcct gagggctgaa gataccgcag tgtactattg cgctagggag     360
cggtatagtg gccgcgatta ctggggacag ggtacactgg tgaccgtgag ctctggggggt    420
ggcggaagcg ggggtggcgg aagcggcgga ggggggtagtg aaattgtgat gacccagtct    480
ccggctacac tttcagtctc ccctggggag agagctacac tgtcatgcag agcgtcccag    540
tccgtctctt ctctccttac ctggtatcag cagaagcccg gccaggctcc tcgactgctg    600
atcttcggtg cctccacaag ggcgaccggg attccagccc gcttctcagg ttctgggagc    660
ggaactggtt tcactttgac aatcagttca ctgcagtcag aggatttcgc cgtgtactac    720
tgccagcaat acgacacatg gccattcact ttcggacccg gtaccaaagt cgatttcaag    780
agagccgcgg ccatcgaggt tatgtaccca ccaccatatc tggacaatga aaaagcaat     840
ggaaccatta tccatgtgaa gggtaaaacc ctctgcccta gcccacttttt ccctggccca    900
tcaaagccct tctgggtctt ggtggtcgtg ggggtgtgc tggcctgtta cagccttctg    960
gtgacggttg ctttcattat cttctgggtt agatccaaaa gaagccgcct gctccatagc   1020
gattacatga atatgactcc acgccgccct ggccccacaa ggaaacacta ccagccttac   1080
gcaccaccta gagatttcgc tgcctatcgg agcagggtga agttttccag atctgcagat   1140
gcaccagcgt atcagcaggg ccagaaccaa ctgtataacg agctcaacct gggacgcagg   1200
gaagagtatg acgttttgga caagcgcaga ggacgggacc ctgagatggg tggcaaacca   1260
agacgaaaaa accccagga gggtctctat aatgagctgc agaaggataa gatggctgaa   1320
gcctattctg aaataggcat gaaaggagag cggagaaggg gaaaagggca cgacggtttg   1380
taccagggac tcagcactgc tacgaaggat acttatgacg ctctccacat gcaagccctg   1440
ccacctaggt aa                                                       1452
```

<210> SEQ ID NO 108
<211> LENGTH: 483
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asp Lys Tyr
65                  70                  75                  80

Tyr Val Asp Ser Val Lys Gly Arg Phe Thr Ile Ser Arg Asp Asn Ser
```

```
                    85                  90                  95
Lys Asn Arg Leu Tyr Leu Gln Met Asn Ser Leu Arg Ala Glu Asp Thr
                100                 105                 110

Ala Val Tyr Tyr Cys Ala Arg Glu Arg Tyr Ser Gly Arg Asp Tyr Trp
            115                 120                 125

Gly Gln Gly Thr Leu Val Thr Val Ser Ser Gly Gly Gly Gly Ser Gly
        130                 135                 140

Gly Gly Gly Ser Gly Gly Gly Ser Glu Ile Val Met Thr Gln Ser
145                 150                 155                 160

Pro Ala Thr Leu Ser Val Ser Pro Gly Glu Arg Ala Thr Leu Ser Cys
                165                 170                 175

Arg Ala Ser Gln Ser Val Ser Ser Leu Leu Thr Trp Tyr Gln Gln Lys
            180                 185                 190

Pro Gly Gln Ala Pro Arg Leu Leu Ile Phe Gly Ala Ser Thr Arg Ala
        195                 200                 205

Thr Gly Ile Pro Ala Arg Phe Ser Gly Ser Gly Ser Gly Thr Gly Phe
    210                 215                 220

Thr Leu Thr Ile Ser Ser Leu Gln Ser Glu Asp Phe Ala Val Tyr Tyr
225                 230                 235                 240

Cys Gln Gln Tyr Asp Thr Trp Pro Phe Thr Phe Gly Pro Gly Thr Lys
                245                 250                 255

Val Asp Phe Lys Arg Ala Ala Ile Glu Val Met Tyr Pro Pro Pro
            260                 265                 270

Tyr Leu Asp Asn Glu Lys Ser Asn Gly Thr Ile Ile His Val Lys Gly
        275                 280                 285

Lys His Leu Cys Pro Ser Pro Leu Phe Pro Gly Pro Ser Lys Pro Phe
    290                 295                 300

Trp Val Leu Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg

<210> SEQ ID NO 109
<211> LENGTH: 1386
```

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
caggtgcagc tcgtggagtc tggcggcggc gtggtccagc ccggccggtc cctgcgcctg     60
tcctgcgccg ccagcgggtt tacttttttcc tcctacggca tgcactgggt gcgccaggct   120
cccggcaagg gcctcgagtg gtcgccgtg atctcatacg atgggtcaga caaatactat    180
gtcgattctg ttaaagggcg gtttaccatt tcaagagata actctaagaa taggctgtat    240
ttgcagatga acagcctgag ggctgaagat accgcagtgt actattgcgc tagggagcgg    300
tatagtggcc gcgattactg gggacagggt acactggtga ccgtgagctc tgggggtggc    360
ggaagcgggg gtggcggaag cggcggaggg ggtagtgaaa ttgtgatgac ccagtctccg    420
gctacacttt cagtctcccc tggggagaga gctacactgt catgcagagc gtcccagtcc    480
gtctcttctc tccttacctg gtatcagcag aagcccggcc aggctcctcg actgctgatc    540
ttcggtgcct ccacaagggc gaccgggatt ccagcccgct ctcaggttc tgggagcgga     600 actggtttca ctttgacaat cagttcactg cagtcagagg atttcgccgt gtactactgc    660
cagcaatacg acacatggcc attcactttc ggacccggta ccaaagtcga tttcaagaga    720
gccgcggcca tcgaggttat gtacccacca ccatatctgg acaatgaaaa agcaatgga    780 accattatcc atgtgaaggg taaacacctc tgccctagcc cacttttccc tggcccatca    840 aagccccttct gggtcttggt ggtcgtgggg ggtgtgctgg cctgttacag ccttctggtg    900
acggttgctt tcattatctt ctgggttaga tccaaaagaa gccgcctgct ccatagcgat    960
tacatgaata tgactccacg ccgccctggc ccacaaggaa acactacca gccttacgca    1020 ccacctagag atttcgctgc ctatcggagc agggtgaagt tttccagatc tgcagatgca    1080
ccagcgtatc agcagggcca gaaccaactg tataacgagc tcaacctggg acgcaggaa    1140 gagtatgacg ttttggacaa gcgcagagga cgggaccctg agatgggtgg caaaccaaga    1200
cgaaaaaacc cccaggaggg tctctataat gagctgcaga aggataagat ggctgaagcc    1260
tattctgaaa taggcatgaa aggagagcgg agaagggaa aagggcacga cggtttgtac    1320
cagggactca gcactgctac gaaggatact tatgacgctc tccacatgca agccctgcca    1380
cctagg                                                              1386

<210> SEQ ID NO 110
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Val Asp Ser Val
    50                  55                  60
```

```
Lys Gly Arg Phe Thr Ile Ser Arg Asp Asn Ser Lys Asn Arg Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Tyr Ser Gly Arg Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Met Thr Gln Ser Pro Ala Thr Leu Ser
    130                 135                 140

Val Ser Pro Gly Glu Arg Ala Thr Leu Ser Cys Arg Ala Ser Gln Ser
145                 150                 155                 160

Val Ser Ser Leu Leu Thr Trp Tyr Gln Gln Lys Pro Gly Gln Ala Pro
                165                 170                 175

Arg Leu Leu Ile Phe Gly Ala Ser Thr Arg Ala Thr Gly Ile Pro Ala
            180                 185                 190

Arg Phe Ser Gly Ser Gly Ser Gly Thr Gly Phe Thr Leu Thr Ile Ser
        195                 200                 205

Ser Leu Gln Ser Glu Asp Phe Ala Val Tyr Tyr Cys Gln Gln Tyr Asp
    210                 215                 220

Thr Trp Pro Phe Thr Phe Gly Pro Gly Thr Lys Val Asp Phe Lys Arg
225                 230                 235                 240

Ala Ala Ala Ile Glu Val Met Tyr Pro Pro Pro Tyr Leu Asp Asn Glu
                245                 250                 255

Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
    290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460

<210> SEQ ID NO 111
<211> LENGTH: 1533
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 111

```
atggcactcc ccgtaactgc tctgctgctg ccgttggcat tgctcctgca cgccgcacgc     60
ccgcaggtgc agttggttga atcaggaggg ggtgtggtgc aacccggtcg gtcactgcgc    120
ctcagttgtg ctgcttccgg gtttactttc agctcatatg ggatgcactg ggtacgcag    180
gctccaggta aaggcttgga atgggtggcg gtgatcagct atgacggctc tgacaaatat    240
tatgtggact ccgtgaaagg cagattcacc atcagtcgag acaactcaaa gaatagactc    300
tacttgcaga tgaatagcct ccgggccgaa gatactgcag tctattattg cgcccgggag    360
cgctacagtg aaagagacta ttgggggcaa ggaactcttg tcacagtctc atctggcggc    420
ggcggcagcg gtggggggcgg atctggcggg ggcggcagcg aaatcgttat gactcagagt    480
cctgccacac tgagcgttag ccctggtgag agagcaacac ttagctgcag agctagtcag    540
agtgtttcca gtcttttgac atggtaccaa cagaagcccg gtcaagctcc acgactgctc    600
atcttcggtg catccacccg cgcaaccggg atacccgccc ggttttccgg ttctggaagt    660
ggcacaggat tcacgctcac catttcttct ctgcagtctg aagactttgc cgtgtattac    720
tgccagcagt acgatacctg gccctttacc tttggcccag gtactaaagt ggattttaaa    780
cgagctgctg cactttccaa tagtattatg tacttttcac attttgtgcc cgtgttcctg    840
cctgcgaagc ctacgacaac cccagcccct aggccgccca ccggccccca aactattgcc    900
tcccagccat tgtctctgag acccgaagct gcagacctg ctgctggagg cgccgttcac    960
acccgaggat tggattcgc atgtgacatt tacatctggg cccctttggc cggaacctgc   1020
ggtgtgctgc tgctgtcact cgtgattaca ctttactgca ccaccgaaa cagatccaaa    1080
agaagccgcc tgctccatag cgattacatg aatatgactc cacgccgccc tggcccccaca   1140
aggaaacact accagcctta cgcaccacct agagatttcg ctgcctatcg gagcagggtg   1200
aagttttcca gatctgcaga tgcaccagcg tatcagcagg gccagaacca actgtataac   1260
gagctcaacc tgggacgcag ggaagagtat gacgttttgg acaagcgcag aggacgggac   1320
cctgagatgg gtggcaaacc aagacgaaaa aaccccagg agggtctcta taatgagctg   1380
cagaaggata gatgctga agcctattct gaaataggca tgaaggaga gcggagaagg   1440
ggaaaagggc acgacggttt gtaccaggga ctcagcactg ctacgaagga tacttatgac   1500
gctctccaca tgcaagccct gccacctagg taa                                1533
```

<210> SEQ ID NO 112
<211> LENGTH: 509
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 112

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45
```

-continued

```
Thr Phe Ser Ser Tyr Gly Met His Trp Val Arg Gln Ala Pro Gly Lys
     50                  55                  60

Gly Leu Glu Trp Val Ala Val Ile Ser Tyr Asp Gly Ser Asp Lys Tyr
 65                  70                  75                  80

Tyr Val Asp Ser Val Lys Gly Arg Phe Thr Ile Ser Arg Asp Asn Ser
                 85                  90                  95

Lys Asn Arg Leu Tyr Leu Gln Met Asn Ser Leu Arg Ala Glu Asp Thr
            100                 105                 110

Ala Val Tyr Tyr Cys Ala Arg Glu Arg Tyr Ser Gly Arg Asp Tyr Trp
        115                 120                 125

Gly Gly Thr Leu Val Thr Val Ser Ser Gly Gly Gly Ser Gly Gly
    130                 135                 140

Gly Gly Ser Gly Gly Gly Ser Glu Ile Val Met Thr Gln Ser Pro
145                 150                 155                 160

Ala Thr Leu Ser Val Ser Pro Gly Glu Arg Ala Thr Leu Ser Cys Arg
                165                 170                 175

Ala Ser Gln Ser Val Ser Ser Leu Leu Thr Trp Tyr Gln Gln Lys Pro
            180                 185                 190

Gly Gln Ala Pro Arg Leu Leu Ile Phe Gly Ala Ser Thr Arg Ala Thr
        195                 200                 205

Gly Ile Pro Ala Arg Phe Ser Gly Ser Gly Ser Gly Thr Gly Phe Thr
    210                 215                 220

Leu Thr Ile Ser Ser Leu Gln Ser Glu Asp Phe Ala Val Tyr Tyr Cys
225                 230                 235                 240

Gln Gln Tyr Asp Thr Trp Pro Phe Thr Phe Gly Pro Gly Thr Lys Val
                245                 250                 255

Asp Phe Lys Arg Ala Ala Ala Leu Ser Asn Ser Ile Met Tyr Phe Ser
            260                 265                 270

His Phe Val Pro Val Phe Leu Pro Ala Lys Pro Thr Thr Thr Pro Ala
        275                 280                 285

Pro Arg Pro Pro Thr Pro Ala Pro Thr Ile Ala Ser Gln Pro Leu Ser
    290                 295                 300

Leu Arg Pro Glu Ala Cys Arg Pro Ala Ala Gly Gly Ala Val His Thr
305                 310                 315                 320

Arg Gly Leu Asp Phe Ala Cys Asp Ile Tyr Ile Trp Ala Pro Leu Ala
                325                 330                 335

Gly Thr Cys Gly Val Leu Leu Leu Ser Leu Val Ile Thr Leu Tyr Cys
            340                 345                 350

Asn His Arg Asn Arg Ser Lys Arg Ser Arg Leu Leu His Ser Asp Tyr
        355                 360                 365

Met Asn Met Thr Pro Arg Arg Pro Gly Pro Thr Arg Lys His Tyr Gln
    370                 375                 380

Pro Tyr Ala Pro Pro Arg Asp Phe Ala Ala Tyr Arg Ser Arg Val Lys
385                 390                 395                 400

Phe Ser Arg Ser Ala Asp Ala Pro Ala Tyr Gln Gln Gly Gln Asn Gln
                405                 410                 415

Leu Tyr Asn Glu Leu Asn Leu Gly Arg Arg Glu Glu Tyr Asp Val Leu
            420                 425                 430

Asp Lys Arg Arg Gly Arg Asp Pro Glu Met Gly Gly Lys Pro Arg Arg
        435                 440                 445

Lys Asn Pro Gln Glu Gly Leu Tyr Asn Glu Leu Gln Lys Asp Lys Met
    450                 455                 460

Ala Glu Ala Tyr Ser Glu Ile Gly Met Lys Gly Glu Arg Arg Arg Gly
```

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
            485                 490                 495
        500                 505

<210> SEQ ID NO 113
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
caggtgcagt tggttgaatc aggagggggt gtggtgcaac ccggtcggtc actgcgcctc        60
agttgtgctg cttccgggtt tactttcagc tcatatggga tgcactgggt acggcaggct       120
ccaggtaaag gcttggaatg ggtggcggtg atcagctatg acggctctga caaatattat       180
gtggactccg tgaaaggcag attcaccatc agtcgagaca actcaaagaa tagactctac       240
ttgcagatga atagcctccg ggccgaagat actgcagtct attattgcgc ccggagcgc        300
tacagtggaa gagactattg ggggcaagga actcttgtca cagtctcatc tggcggcggc       360
ggcagcggtg gggcggatc tggcgggggc ggcagcgaaa tcgttatgac tcagagtcct       420
gccacactga gcgttagccc tggtgagaga gcaacactta gctgcagagc tagtcagagt       480
gtttccagtc ttttgacatg gtaccaacag aagcccggtc aagctccacg actgctcatc       540
ttcggtgcat ccacccgcgc aaccgggata cccgccggt tttccggttc tggaagtggc        600
acaggattca cgctcaccat ttcttctctg cagtctgaag actttgccgt gtattactgc       660
cagcagtacg ataccgtggcc ctttacctttt ggcccaggta ctaaagtgga ttttaaacga     720
gctgctgcac tttccaatag tattatgtac ttttcacatt ttgtgcccgt gttcctgcct       780
gcgaagccta cgacaacccc agcccctagg ccgcccacac cggccccaac tattgcctcc       840
cagccattgt ctctgagacc cgaagcttgc agacctgctg ctggaggcgc cgttcacacc       900
cgaggattgg atttcgcatg tgacatttac atctgggccc ctttggccgg aacctgcggt       960
gtgctgctgc tgtcactcgt gattacactt tactgcaacc accgaaacag atccaaaaga      1020
agccgcctgc tccatagcga ttacatgaat atgactccac gccgcctgg ccccacaagg       1080
aaacactacc agccttacgc accacctaga gatttcgctg cctatcggag cagggtgaag      1140
ttttccagat ctgcagatgc accagcgtat cagcagggcc agaaccaact gtataacgag      1200
ctcaacctgg gacgcaggga agagtatgac gttttggaca agcgcagagg acgggaccct      1260
gagatgggtg gcaaaccaag acgaaaaaac ccccaggagg gtctctataa tgagctgcag      1320
aaggataaga tggctgaagc ctattctgaa ataggcatga aggagagcg gagaagggga      1380
aaagggcacg acggtttgta ccagggactg agcactgcta cgaaggatac ttatgacgct      1440
ctccacatgc aagccctgcc acctagg                                         1467
```

<210> SEQ ID NO 114
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Val Asp Ser Val
50                  55                  60

Lys Gly Arg Phe Thr Ile Ser Arg Asp Asn Ser Lys Asn Arg Leu Tyr
65                      70                  75                  80

Leu Gln Met Asn Ser Leu Arg Ala Glu Asp Thr Ala Val Tyr Tyr Cys
                85                  90                  95

Ala Arg Glu Arg Tyr Ser Gly Arg Asp Tyr Trp Gly Gln Gly Thr Leu
            100                 105                 110

Val Thr Val Ser Ser Gly Gly Gly Ser Gly Gly Gly Ser Gly
            115                 120                 125

Gly Gly Gly Ser Glu Ile Val Met Thr Gln Ser Pro Ala Thr Leu Ser
130                 135                 140

Val Ser Pro Gly Glu Arg Ala Thr Leu Ser Cys Arg Ala Ser Gln Ser
145                 150                 155                 160

Val Ser Ser Leu Leu Thr Trp Tyr Gln Gln Lys Pro Gly Gln Ala Pro
                165                 170                 175

Arg Leu Leu Ile Phe Gly Ala Ser Thr Arg Ala Thr Gly Ile Pro Ala
            180                 185                 190

Arg Phe Ser Gly Ser Gly Ser Gly Thr Gly Phe Thr Leu Thr Ile Ser
            195                 200                 205

Ser Leu Gln Ser Glu Asp Phe Ala Val Tyr Tyr Cys Gln Gln Tyr Asp
210                 215                 220

Thr Trp Pro Phe Thr Phe Gly Pro Gly Thr Lys Val Asp Phe Lys Arg
225                 230                 235                 240

Ala Ala Ala Leu Ser Asn Ser Ile Met Tyr Phe Ser His Phe Val Pro
            245                 250                 255

Val Phe Leu Pro Ala Lys Pro Thr Thr Thr Pro Ala Pro Arg Pro Pro
            260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Asn His Arg Asn
            325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
            355                 360                 365

Pro Arg Asp Phe Ala Ala Tyr Arg Ser Arg Val Lys Phe Ser Arg Ser
            370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415
```

Gly Arg Asp Pro Glu Met Gly Gly Lys Pro Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 115
<211> LENGTH: 1425
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115

```
atggcactcc ccgtaactgc tctgctgctg ccgttggcat tgctcctgca cgccgcacgc      60
ccggagattg tgatgaccca gtcccctgct accctgtccg tcagtccggg cgagagagcc     120
accttgtcat gccgggccag ccagtccgtc agcagtctcc tgacttggta tcagcaaaaa     180
ccagggcagg caccgcggct tttgattttt ggtgcaagca cacgcgccac tggcattcca     240
gctaggtttt ctggaagtgg atctgggaca ggcttcactc tgacaatcag tagcctgcag     300
agtgaggact ttgctgttta ctactgtcaa cagtacgaca cctggccatt cacattcggg     360
cccggcacca aggtcgactt caagaggggc ggtggaggtt caggtggtgg cgggtcaggc     420
ggcggtgggt ctcaggttca actggtggaa tcaggtggcg gcgttgtcca accggggcga     480
tcacttcgac tttcctgtgc tgcctcaggc tttactttttt catcctatgg gatgcactgg     540
gttcggcagg ctcccggaaa aggactcgag tgggttgcag tgatctctta cgatggctca     600
gacaagtatt atgtggactc agtcaagggg agattcacaa taagccgaga caactccaaa     660
aaccggcttt atctccagat gaacagcctt agagcggaag ataccgcggt atactactgt     720
gcccgcgaga ggtattccgg cagagactac tggggacagg gcacactggt caccgtgagt     780
tctgccgcag cgctcgataa cgaaaagagc aacggaacca ttatccacgt taagggcaag     840
cacctgtgcc ccagtcccct cttcccagga ccatctaaac ccttctgggt tctggtagta     900
gttggagggg tccttgcatg ttactccctt ttggtcaccg tcgccttcat tattttctgg     960
gtgagatcca aaagaagccg cctgctccat agcgattaca tgaatatgac tccacgccgc    1020
cctggcccca aaggaaaaca ctaccagcct tacgcaccac tagagatttt cgctgcctat    1080
cggagcaggg tgaagttttc cagatctgca gatgcaccag cgtatcagca gggccagaac    1140
caactgtata acgagctcaa cctgggacgc agggaagagt atgacgtttt ggacaagcgc    1200
agaggacggg accctgagat gggtggcaaa ccaagacgaa aaaaccccca ggagggtctc    1260
tataatgagc tgcagaagga taagatggct gaagcctatt ctgaaatagg catgaaagga    1320
gagcggagaa ggggaaaagg gcacgacggt ttgtaccagg gactcagcac tgctacgaag    1380
gatacttatg acgctctcca catgcaagcc ctgccaccta ggtaa                    1425
```

<210> SEQ ID NO 116
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Leu Leu Thr Trp Tyr Gln Gln Lys Pro Gly Gln Ala
    50                  55                  60

Pro Arg Leu Leu Ile Phe Gly Ala Ser Thr Arg Ala Thr Gly Ile Pro
65                  70                  75                  80

Ala Arg Phe Ser Gly Ser Gly Ser Gly Thr Gly Phe Thr Leu Thr Ile
                85                  90                  95

Ser Ser Leu Gln Ser Glu Asp Phe Ala Val Tyr Tyr Cys Gln Gln Tyr
            100                 105                 110

Asp Thr Trp Pro Phe Thr Phe Gly Pro Gly Thr Lys Val Asp Phe Lys
        115                 120                 125

Arg Gly Gly Gly Gly Ser Gly Gly Gly Gly Ser Gly Gly Gly Gly Ser
    130                 135                 140

Gln Val Gln Leu Val Glu Ser Gly Gly Gly Val Val Gln Pro Gly Arg
145                 150                 155                 160

Ser Leu Arg Leu Ser Cys Ala Ala Ser Gly Phe Thr Phe Ser Ser Tyr
                165                 170                 175

Gly Met His Trp Val Arg Gln Ala Pro Gly Lys Gly Leu Glu Trp Val
            180                 185                 190

Ala Val Ile Ser Tyr Asp Gly Ser Asp Lys Tyr Tyr Val Asp Ser Val
        195                 200                 205

Lys Gly Arg Phe Thr Ile Ser Arg Asp Asn Ser Lys Asn Arg Leu Tyr
    210                 215                 220

Leu Gln Met Asn Ser Leu Arg Ala Glu Asp Thr Ala Val Tyr Tyr Cys
225                 230                 235                 240

Ala Arg Glu Arg Tyr Ser Gly Arg Asp Tyr Trp Gly Gln Gly Thr Leu
                245                 250                 255

Val Thr Val Ser Ser Ala Ala Ala Leu Asp Asn Glu Lys Ser Asn Gly
            260                 265                 270

Thr Ile Ile His Val Lys Gly Lys His Leu Cys Pro Ser Pro Leu Phe
        275                 280                 285

Pro Gly Pro Ser Lys Pro Phe Trp Val Leu Val Val Val Gly Gly Val
    290                 295                 300

Leu Ala Cys Tyr Ser Leu Leu Val Thr Val Ala Phe Ile Ile Phe Trp
305                 310                 315                 320

Val Arg Ser Lys Arg Ser Arg Leu Leu His Ser Asp Tyr Met Asn Met
                325                 330                 335

Thr Pro Arg Arg Pro Gly Pro Thr Arg Lys His Tyr Gln Pro Tyr Ala
            340                 345                 350

Pro Pro Arg Asp Phe Ala Ala Tyr Arg Ser Arg Val Lys Phe Ser Arg
        355                 360                 365

Ser Ala Asp Ala Pro Ala Tyr Gln Gln Gly Gln Asn Gln Leu Tyr Asn
    370                 375                 380

Glu Leu Asn Leu Gly Arg Arg Glu Glu Tyr Asp Val Leu Asp Lys Arg
```

Arg Gly Arg Asp Pro Glu Met Gly Gly Lys Pro Arg Arg Lys Asn Pro
385             390             395             400
                    405                     410                 415

Gln Glu Gly Leu Tyr Asn Glu Leu Gln Lys Asp Lys Met Ala Glu Ala
                    420                 425                 430

Tyr Ser Glu Ile Gly Met Lys Gly Glu Arg Arg Arg Gly Lys Gly His
            435                 440                 445

Asp Gly Leu Tyr Gln Gly Leu Ser Thr Ala Thr Lys Asp Thr Tyr Asp
        450                 455                 460

Ala Leu His Met Gln Ala Leu Pro Pro Arg
465                 470

<210> SEQ ID NO 117
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 117
gagattgtga tgacccagtc ccctgctacc ctgtccgtca gtccgggcga gagagccacc      60
ttgtcatgcc gggccagcca gtccgtcagc agtctcctga cttggtatca gcaaaaacca     120
gggcaggcac cgcggctttt gattttggt gcaagcacac gcgccactgg cattccagct     180
aggttttctg gaagtggatc tgggacaggc ttcactctga caatcagtag cctgcagagt     240
gaggactttg ctgtttacta ctgtcaacag tacgacacct ggccattcac attcgggccc     300
ggcaccaagg tcgacttcaa gaggggcggt ggaggttcag gtggtggcgg tcaggcggc     360 ggtgggtctc aggttcaact ggtggaatca ggtggcggcg ttgtccaacc ggggcgatca     420
cttcgacttt cctgtgctgc ctcaggcttt acttttcat cctatgggat gcactgggtt     480
cggcaggctc ccggaaaagg actcgagtgg gttgcagtga tctcttacga tggctcagac     540
aagtattatg tggactcagt caaggggaga ttcacaataa gccgagacaa ctccaaaaac     600
cggctttatc tccagatgaa cagccttaga gcggaagata ccgcggtata ctactgtgcc     660
cgcgagaggt attccggcag agactactgg ggacagggca cactggtcac cgtgagttct     720
gccgcagcgc tcgataacga aaagagcaac ggaaccatta tccacgttaa gggcaagcac     780
ctgtgcccca gtcccctctt cccaggacca tctaaaccct ctgggttct ggtagtagtt     840 ggagggtcc ttgcatgtta ctccctttg gtcaccgtcg ccttcattat tttctgggtg     900
agatccaaaa gaagccgcct gctccatagc gattacatga atatgactcc acgccgccct     960
ggccccacaa ggaaacacta ccagccttac gcaccacta gagatttcgc tgcctatcgg    1020
agcagggtga agttttccag atctgcagat gcaccagcgt atcagcaggg ccagaaccaa    1080
ctgtataacg agctcaacct gggacgcagg gaagagtatg acgttttgga caagcgcaga    1140
ggacgggacc ctgagatggg tggcaaacca agacgaaaaa accccagga gggtctctat    1200 aatgagctgc agaaggataa gatggctgaa gcctattctg aaataggcat gaaggagag    1260 cggagaaggg gaaagggca cgacggtttg taccagggac tcagcactgc tacgaaggat    1320
acttatgacg ctctccacat gcaagccctg ccacctagg                         1359

<210> SEQ ID NO 118
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Leu
            20                  25                  30

Leu Thr Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
50                  55                  60

Ser Gly Ser Gly Thr Gly Phe Thr Leu Thr Ile Ser Ser Leu Gln Ser
65                  70                  75                  80

Glu Asp Phe Ala Val Tyr Tyr Cys Gln Gln Tyr Asp Thr Trp Pro Phe
                85                  90                  95

Thr Phe Gly Pro Gly Thr Lys Val Asp Phe Lys Arg Gly Gly Gly Gly
            100                 105                 110

Ser Gly Gly Gly Gly Ser Gly Gly Gly Ser Gln Val Gln Leu Val
            115                 120                 125

Glu Ser Gly Gly Gly Val Val Gln Pro Gly Arg Ser Leu Arg Leu Ser
130                 135                 140

Cys Ala Ala Ser Gly Phe Thr Phe Ser Ser Tyr Gly Met His Trp Val
145                 150                 155                 160

Arg Gln Ala Pro Gly Lys Gly Leu Glu Trp Val Ala Val Ile Ser Tyr
            165                 170                 175

Asp Gly Ser Asp Lys Tyr Tyr Val Asp Ser Val Lys Gly Arg Phe Thr
        180                 185                 190

Ile Ser Arg Asp Asn Ser Lys Asn Arg Leu Tyr Leu Gln Met Asn Ser
    195                 200                 205

Leu Arg Ala Glu Asp Thr Ala Val Tyr Tyr Cys Ala Arg Glu Arg Tyr
210                 215                 220

Ser Gly Arg Asp Tyr Trp Gly Gln Gly Thr Leu Val Thr Val Ser Ser
225                 230                 235                 240

Ala Ala Ala Leu Asp Asn Glu Lys Ser Asn Gly Thr Ile Ile His Val
            245                 250                 255

Lys Gly Lys His Leu Cys Pro Ser Pro Leu Phe Pro Gly Pro Ser Lys
        260                 265                 270

Pro Phe Trp Val Leu Val Val Gly Val Leu Ala Cys Tyr Ser
    275                 280                 285

Leu Leu Val Thr Val Ala Phe Ile Ile Phe Trp Val Arg Ser Lys Arg
290                 295                 300

Ser Arg Leu Leu His Ser Asp Tyr Met Asn Met Thr Pro Arg Arg Pro
305                 310                 315                 320

Gly Pro Thr Arg Lys His Tyr Gln Pro Tyr Ala Pro Pro Arg Asp Phe
            325                 330                 335

Ala Ala Tyr Arg Ser Arg Val Lys Phe Ser Arg Ser Ala Asp Ala Pro
        340                 345                 350

Ala Tyr Gln Gln Gly Gln Asn Gln Leu Tyr Asn Glu Leu Asn Leu Gly
    355                 360                 365

Arg Arg Glu Glu Tyr Asp Val Leu Asp Lys Arg Arg Gly Arg Asp Pro
370                 375                 380

Glu Met Gly Gly Lys Pro Arg Arg Lys Asn Pro Gln Glu Gly Leu Tyr

```
                385                 390                 395                 400
Asn Glu Leu Gln Lys Asp Lys Met Ala Glu Ala Tyr Ser Glu Ile Gly
                405                 410                 415

Met Lys Gly Glu Arg Arg Gly Lys Gly His Asp Gly Leu Tyr Gln
                420                 425                 430

Gly Leu Ser Thr Ala Thr Lys Asp Thr Tyr Asp Ala Leu His Met Gln
                435                 440                 445

Ala Leu Pro Pro Arg
        450
```

<210> SEQ ID NO 119
<211> LENGTH: 1452
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119

| | | | | | |
|---|---|---|---|---|---|
| atggcactcc | ccgtaactgc | tctgctgctg | ccgttggcat | tgctcctgca | cgccgcacgc | 60 |
| ccggagatcg | tcatgacaca | gagtccagct | accctgagcg | tgtccctgg | agagagagcc | 120 |
| accctgtcct | gtagggctag | tcagagtgtg | tccagcctcc | tcacctggta | tcaacagaag | 180 |
| cctggtcaag | ctccccggct | gcttatcttc | ggggccagca | cgcgagccac | aggcatcccg | 240 |
| gccagattct | ctggctctgg | cagtggcacc | gggttcactc | tcacgatctc | atccctgcag | 300 |
| tcagaggatt | tcgctgtgta | ttactgtcag | cagtacgata | catggccctt | caccttcggc | 360 |
| ccgggcacaa | agtagattt | caagcgcggc | ggcggggta | gtggggcgg | gggatcagga | 420 |
| ggaggggct | cccaagtaca | gctggttgag | agcggcggcg | gggtggttca | gcccgggcgc | 480 |
| agcctcaggc | tgagttgcgc | agcatcagga | ttcacattca | gttcttatgg | aatgcattgg | 540 |
| gtcagacagg | ctcccgggaa | gggccttgaa | tgggtggcag | tcattagcta | cgacggaagc | 600 |
| gataagtact | atgtggactc | agttaaaggg | agatttacta | tcagccgcga | caattccaaa | 660 |
| aacagattgt | atttgcagat | gaactccctc | agggcggagg | acactgctgt | atattactgc | 720 |
| gcacgagaga | gatactccgg | ccgagactat | tggggccaag | gaacattggt | aactgtgagc | 780 |
| tccgccgcag | ctattgaggt | catgtacccc | ccaccttatc | tcgataatga | aagagtaat | 840 |
| gggactataa | ttcacgtaaa | gggcaaacac | ctgtgccctt | ccccgctgtt | tccaggtcca | 900 |
| agtaagccgt | tctgggtcct | ggttgtggtg | ggagggtgc | tggcctgcta | ttctctgttg | 960 |
| gttaccgtgg | cctttatcat | tttctgggtg | agatccaaaa | gaagccgcct | gctccatagc | 1020 |
| gattacatga | atatgactcc | acgccgccct | ggccccacaa | ggaaacacta | ccagccttac | 1080 |
| gcaccaccta | gagatttcgc | tgcctatcgg | agcagggtga | agttttccag | atctgcagat | 1140 |
| gcaccagcgt | atcagcaggg | ccagaaccaa | ctgtataacg | agctcaacct | gggacgcagg | 1200 |
| gaagagtatg | acgttttgga | caagcgcaga | ggacgggacc | ctgagatggg | tggcaaacca | 1260 |
| agacgaaaaa | accccagga | gggtctctat | aatgagctgc | agaaggataa | gatggctgaa | 1320 |
| gcctattctg | aaataggcat | gaaggagag | cggagaaggg | gaaaagggca | cgacggtttg | 1380 |
| taccagggac | tcagcactgc | tacgaaggat | acttatgacg | ctctccacat | gcaagccctg | 1440 |
| ccacctaggt | aa | | | | | 1452 |

<210> SEQ ID NO 120
<211> LENGTH: 483
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 120

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Leu Leu Thr Trp Tyr Gln Gln Lys Pro Gly Gln Ala
    50                  55                  60

Pro Arg Leu Leu Ile Phe Gly Ala Ser Thr Arg Ala Thr Gly Ile Pro
65                  70                  75                  80

Ala Arg Phe Ser Gly Ser Gly Ser Gly Thr Gly Phe Thr Leu Thr Ile
                85                  90                  95

Ser Ser Leu Gln Ser Glu Asp Phe Ala Val Tyr Tyr Cys Gln Gln Tyr
            100                 105                 110

Asp Thr Trp Pro Phe Thr Phe Gly Pro Gly Thr Lys Val Asp Phe Lys
        115                 120                 125

Arg Gly Gly Gly Gly Ser Gly Gly Gly Gly Ser Gly Gly Gly Gly Ser
    130                 135                 140

Gln Val Gln Leu Val Glu Ser Gly Gly Val Val Gln Pro Gly Arg
145                 150                 155                 160

Ser Leu Arg Leu Ser Cys Ala Ala Ser Gly Phe Thr Phe Ser Ser Tyr
                165                 170                 175

Gly Met His Trp Val Arg Gln Ala Pro Gly Lys Gly Leu Glu Trp Val
            180                 185                 190

Ala Val Ile Ser Tyr Asp Gly Ser Asp Lys Tyr Tyr Val Asp Ser Val
        195                 200                 205

Lys Gly Arg Phe Thr Ile Ser Arg Asp Asn Ser Lys Asn Arg Leu Tyr
    210                 215                 220

Leu Gln Met Asn Ser Leu Arg Ala Glu Asp Thr Ala Val Tyr Tyr Cys
225                 230                 235                 240

Ala Arg Glu Arg Tyr Ser Gly Arg Asp Tyr Trp Gly Gln Gly Thr Leu
                245                 250                 255

Val Thr Val Ser Ser Ala Ala Ala Ile Glu Val Met Tyr Pro Pro Pro
            260                 265                 270

Tyr Leu Asp Asn Glu Lys Ser Asn Gly Thr Ile Ile His Val Lys Gly
        275                 280                 285

Lys His Leu Cys Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
    370                 375                 380
```

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Gly Arg Asp Pro Glu Met
            405                 410                 415

Gly Gly Lys Pro Arg Arg Lys Asn Pro Gln Glu Gly Leu Tyr Asn Glu
        420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
        450                 455                 460

Ser Thr Ala Thr Lys Asp Thr Tyr Asp Ala Leu His Met Gln Ala Leu
465                 470                 475                 480

Pro Pro Arg

<210> SEQ ID NO 121
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121

| | | | | | |
|---|---|---|---|---|---|
| gagatcgtca | tgacacagag | tccagctacc | ctgagcgtgt | ccctggaga | gagagccacc | 60 |
| ctgtcctgta | gggctagtca | gagtgtgtcc | agcctcctca | cctggtatca | acagaagcct | 120 |
| ggtcaagctc | cccggctgct | tatcttcggg | gccagcacgc | gagccacagg | catcccggcc | 180 |
| agattctctg | gctctggcag | tggcaccggg | ttcactctca | cgatctcatc | cctgcagtca | 240 |
| gaggatttcg | ctgtgtatta | ctgtcagcag | tacgatacat | ggcccttcac | cttcggcccg | 300 |
| ggcacaaaag | tagatttcaa | gcgcggcggc | ggggtagtg | ggggcggggg | atcaggagga | 360 |
| gggggctccc | aagtacagct | ggttgagagc | ggcggcgggg | tggttcagcc | cgggcgcagc | 420 |
| ctcaggctga | gttgcgcagc | atcaggattc | acattcagtt | cttatggaat | gcattgggtc | 480 |
| agacaggctc | ccgggaaggg | ccttgaatgg | gtggcagtca | ttagctacga | cggaagcgat | 540 |
| aagtactatg | tggactcagt | taaagggaga | tttactatca | gccgcgacaa | ttccaaaaac | 600 |
| agattgtatt | tgcagatgaa | ctccctcagg | gcggaggaca | ctgctgtata | ttactgcgca | 660 |
| cgagagagat | actccggccg | agactattgg | ggccaaggaa | cattggtaac | tgtgagctcc | 720 |
| gccgcagcta | ttgaggtcat | gtaccccca | ccttatctcg | ataatgagaa | gagtaatggg | 780 |
| actataattc | acgtaaaggg | caaacacctg | tgcccttccc | cgctgtttcc | aggtccaagt | 840 |
| aagccgttct | gggtcctggt | tgtggtggga | ggggtgctgg | cctgctattc | tctgttggtt | 900 |
| accgtggcct | ttatcatttt | ctgggtgaga | tccaaaagaa | gccgcctgct | ccatagcgat | 960 |
| tacatgaata | tgactccacg | ccgccctggc | ccacaaggaa | acactacca | gccttacgca | 1020 |
| ccacctagag | atttcgctgc | ctatcggagc | agggtgaagt | tttccagatc | tgcagatgca | 1080 |
| ccagcgtatc | agcagggcca | gaaccaactg | tataacgagc | tcaacctggg | acgcagggaa | 1140 |
| gagtatgacg | ttttggacaa | gcgcagagga | cgggaccctg | agatgggtgg | caaaccaaga | 1200 |
| cgaaaaaacc | cccaggaggg | tctctataat | gagctgcaga | aggataagat | ggctgaagcc | 1260 |
| tattctgaaa | taggcatgaa | aggagagcgg | agaaggggaa | aagggcacga | cggtttgtac | 1320 |
| cagggactca | gcactgctac | gaaggatact | tatgacgctc | tccacatgca | agccctgcca | 1380 |
| cctagg | | | | | | 1386 |

<210> SEQ ID NO 122
<211> LENGTH: 462
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Leu
            20                  25                  30

Leu Thr Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
50                  55                  60

Ser Gly Ser Gly Thr Gly Phe Thr Leu Thr Ile Ser Ser Leu Gln Ser
65                  70                  75                  80

Glu Asp Phe Ala Val Tyr Tyr Cys Gln Gln Tyr Asp Thr Trp Pro Phe
                85                  90                  95

Thr Phe Gly Pro Gly Thr Lys Val Asp Phe Lys Arg Gly Gly Gly Gly
            100                 105                 110

Ser Gly Gly Gly Gly Ser Gly Gly Gly Gly Ser Gln Val Gln Leu Val
        115                 120                 125

Glu Ser Gly Gly Gly Val Val Gln Pro Gly Arg Ser Leu Arg Leu Ser
130                 135                 140

Cys Ala Ala Ser Gly Phe Thr Phe Ser Ser Tyr Gly Met His Trp Val
145                 150                 155                 160

Arg Gln Ala Pro Gly Lys Gly Leu Glu Trp Val Ala Val Ile Ser Tyr
                165                 170                 175

Asp Gly Ser Asp Lys Tyr Tyr Val Asp Ser Val Lys Gly Arg Phe Thr
            180                 185                 190

Ile Ser Arg Asp Asn Ser Lys Asn Arg Leu Tyr Leu Gln Met Asn Ser
        195                 200                 205

Leu Arg Ala Glu Asp Thr Ala Val Tyr Tyr Cys Ala Arg Glu Arg Tyr
210                 215                 220

Ser Gly Arg Asp Tyr Trp Gly Gln Gly Thr Leu Val Thr Val Ser Ser
225                 230                 235                 240

Ala Ala Ala Ile Glu Val Met Tyr Pro Pro Pro Tyr Leu Asp Asn Glu
                245                 250                 255

Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Arg Val
            340                 345                 350

Lys Phe Ser Arg Ser Ala Asp Ala Pro Ala Tyr Gln Gln Gly Gln Asn
        355                 360                 365
```

```
Gln Leu Tyr Asn Glu Leu Asn Leu Gly Arg Arg Glu Glu Tyr Asp Val
        370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460

<210> SEQ ID NO 123
<211> LENGTH: 1533
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 123
atggcactcc ccgtaactgc tctgctgctg ccgttggcat tgctcctgca cgccgcacgc      60
ccggaaatag tgatgactca gtccccggcc accctcagcg tgtcccccgg ggagcgagcg     120
accctgtcat gcagggcttc ccagagtgtc agctccctgc tcacttggta tcagcaaaag     180
ccgggggcag ctccccgcct cctcatcttc ggggcatcaa ctagggccac ggcattcct     240 gcaagatttt ccgggtctgg cagcggcacc ggcttcaccc ttaccattag ctctctgcag     300
tctgaggact cgccgtttta ctattgtcag cagtatgata cttggccctt taccttcggt     360
cccggaacta aggtggactt caagcgcggg ggggtggat ctggaggtgg tggctccggg      420
ggcggtggaa gccaggtcca gttggttgag agcggcggcg gagtggtgca gcccgggagg     480
tccttgcggc tgagctgtgc agcctccggt tttacttttt ctagctatgg aatgcattgg     540
gtaagacagg ctcccggaaa aggcctcgag tgggtggcgg tcattagcta tgatggatct     600
gataaatact atgtggactc agttaagggg cgcttcacaa tctcaagaga caatagcaaa     660
aatagactgt acctgcagat gaatagtctg cgcgccgagg acactgccgt gtactactgc     720
gcccgcgaga gatacagcgg acgggattac tggggccagg gtaccctcgt aacggtgtcc     780
tccgctgccg cccttagcaa cagcattatg tacttttctc atttcgtgcc agtctttctc     840
ccagcaaagc ccaccactac cccggcccc aggccgccta ctcctgcccc cactatcgcg      900
tctcagcctc tctccttgcg gcccgaggcc tgccggccag ccgcaggggg cgccgtacat     960
actcggggtt tggatttcgc ttgcgacata tatatttggg cccccctcgc cggcacatgt    1020
ggagtgctgc tcctgagtct cgttataacc ctctattgca accatagaaa cagatccaaa    1080
agaagccgcc tgctccatag cgattacatg aatatgactc cacgccgccc tggccccaca    1140
aggaaacact accagcctta cgcaccacct agagatttcg ctgcctatcg gagcagggtg    1200 aagtttttcca gatctgcaga tgcaccgcg tatcagcagg ccagaaccaa actgtataac     1260
gagctcaacc tgggacgcag ggaagagtat gacgttttgg acaagcgcag aggacgggac    1320
cctgagatgg gtggcaaacc aagacgaaaa aaccccccagg agggtctcta taatgagctg    1380
cagaaggata gatggctga agcctattct gaaataggga tgaaaggaga gcggagaagg    1440
ggaaaagggc acgacggttt gtaccaggga ctcagcactg ctacgaagga tacttatgac    1500
```

```
gctctccaca tgcaagccct gccacctagg taa                                    1533
```

<210> SEQ ID NO 124
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Leu Leu Thr Trp Tyr Gln Gln Lys Pro Gly Gln Ala
    50                  55                  60

Pro Arg Leu Leu Ile Phe Gly Ala Ser Thr Arg Ala Thr Gly Ile Pro
65                  70                  75                  80

Ala Arg Phe Ser Gly Ser Gly Ser Gly Thr Gly Phe Thr Leu Thr Ile
                85                  90                  95

Ser Ser Leu Gln Ser Glu Asp Phe Ala Val Tyr Tyr Cys Gln Gln Tyr
            100                 105                 110

Asp Thr Trp Pro Phe Thr Phe Gly Pro Gly Thr Lys Val Asp Phe Lys
        115                 120                 125

Arg Gly Gly Gly Gly Ser Gly Gly Gly Gly Ser Gly Gly Gly Gly Ser
    130                 135                 140

Gln Val Gln Leu Val Glu Ser Gly Gly Gly Val Val Gln Pro Gly Arg
145                 150                 155                 160

Ser Leu Arg Leu Ser Cys Ala Ala Ser Gly Phe Thr Phe Ser Ser Tyr
                165                 170                 175

Gly Met His Trp Val Arg Gln Ala Pro Gly Lys Gly Leu Glu Trp Val
            180                 185                 190

Ala Val Ile Ser Tyr Asp Gly Ser Asp Lys Tyr Tyr Val Asp Ser Val
        195                 200                 205

Lys Gly Arg Phe Thr Ile Ser Arg Asp Asn Ser Lys Asn Arg Leu Tyr
    210                 215                 220

Leu Gln Met Asn Ser Leu Arg Ala Glu Asp Thr Ala Val Tyr Tyr Cys
225                 230                 235                 240

Ala Arg Glu Arg Tyr Ser Gly Arg Asp Tyr Trp Gly Gln Gly Thr Leu
                245                 250                 255

Val Thr Val Ser Ser Ala Ala Ala Leu Ser Asn Ser Ile Met Tyr Phe
            260                 265                 270

Ser His Phe Val Pro Val Phe Leu Pro Ala Lys Pro Thr Thr Thr Pro
        275                 280                 285

Ala Pro Arg Pro Pro Thr Pro Ala Pro Thr Ile Ala Ser Gln Pro Leu
    290                 295                 300

Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
                325                 330                 335

Ala Gly Thr Cys Gly Val Leu Leu Leu Ser Leu Val Ile Thr Leu Tyr
            340                 345                 350

```
Cys Asn His Arg Asn Arg Ser Lys Arg Ser Arg Leu Leu His Ser Asp
            355                 360                 365

Tyr Met Asn Met Thr Pro Arg Arg Pro Gly Pro Thr Arg Lys His Tyr
    370                 375                 380

Gln Pro Tyr Ala Pro Pro Arg Asp Phe Ala Ala Tyr Arg Ser Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
            450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 125
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125
gaaatagtga tgactcagtc cccggccacc ctcagcgtgt cccccgggga gcgagcgacc      60
ctgtcatgca gggcttccca gagtgtcagc tccctgctca cttggtatca gcaaaagccg     120
gggcaggctc ccgcctcct catcttcggg gcatcaacta gggccaccgg cattcctgca      180
agattttccg gtctggcag cggcaccggc ttcacccctta ccattagctc tctgcagtct     240
gaggacttcg ccgtttacta ttgtcagcag tatgatactt ggcccttac cttcggtccc      300 ggaactaagg tggacttcaa cgcgggggg ggtggatctg gaggtggtgg ctccggggc       360 ggtggaagcc aggtccagtt ggttgagagc ggcggcggag tggtgcagcc gggaggtcc      420 ttgcggctga gctgtgcagc ctccggtttt acttttttcta gctatggaat gcattgggta     480
agacaggctc ccggaaaagg cctcgagtgg gtggcggtca ttagctatga tggatctgat     540
aaatactatg tggactcagt taagggggcgc ttcacaatct caagagacaa tagcaaaaat     600
agactgtacc tgcagatgaa tagtctgcgc gccgaggaca ctgccgtgta ctactgcgcc     660
cgcgagagat acagcggacg ggattactgg ggccagggta ccctcgtaac ggtgtcctcc      720
gctgccgccc ttagcaacag cattatgtac ttttctcatt tcgtgccagt ctttctccca      780
gcaaagccca ccactacccc ggcccccagg ccgcctactc ctgccccac tatcgcgtct      840 cagcctctct ccttgcggcc cgaggcctgc cggccagccg cagggggcgc cgtacatact      900
cggggtttgg attcgcttg cgacatatat atttgggccc ccctcgccgg cacatgtgga      960
gtgctgctcc tgagtctcgt tataaccctc tattgcaacc atagaaacag atccaaaaga    1020
agccgcctgc tccatagcga ttacatgaat atgactccac gccgcctgg ccccacaagg     1080 aaacactacc agccttacgc accacctaga gatttcgctg cctatcggag cagggtgaag    1140
```

```
ttttccagat ctgcagatgc accagcgtat cagcagggcc agaaccaact gtataacgag    1200
ctcaacctgg gacgcaggga gagtatgac gttttggaca gcgcagagg acgggaccct     1260 gagatgggtg gcaaaccaag acgaaaaaac ccccaggagg gtctctataa tgagctgcag    1320
aaggataaga tggctgaagc ctattctgaa ataggcatga aggagagcg gagaagggga    1380 aaagggcacg acggtttgta ccagggactc agcactgcta cgaaggatac ttatgacgct    1440
ctccacatgc aagccctgcc acctagg                                       1467
```

<210> SEQ ID NO 126
<211> LENGTH: 489
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Leu
            20                  25                  30

Leu Thr Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Gly Ser Gly Thr Gly Phe Thr Leu Thr Ile Ser Ser Leu Gln Ser
65                  70                  75                  80

Glu Asp Phe Ala Val Tyr Tyr Cys Gln Gln Tyr Asp Thr Trp Pro Phe
                85                  90                  95

Thr Phe Gly Pro Gly Thr Lys Val Asp Phe Lys Arg Gly Gly Gly Gly
            100                 105                 110

Ser Gly Gly Gly Gly Ser Gly Gly Gly Ser Gln Val Gln Leu Val
        115                 120                 125

Glu Ser Gly Gly Gly Val Val Gln Pro Gly Arg Ser Leu Arg Leu Ser
130                 135                 140

Cys Ala Ala Ser Gly Phe Thr Phe Ser Ser Tyr Gly Met His Trp Val
145                 150                 155                 160

Arg Gln Ala Pro Gly Lys Gly Leu Glu Trp Val Ala Val Ile Ser Tyr
                165                 170                 175

Asp Gly Ser Asp Lys Tyr Tyr Val Asp Ser Val Lys Gly Arg Phe Thr
            180                 185                 190

Ile Ser Arg Asp Asn Ser Lys Asn Arg Leu Tyr Leu Gln Met Asn Ser
        195                 200                 205

Leu Arg Ala Glu Asp Thr Ala Val Tyr Tyr Cys Ala Arg Glu Arg Tyr
    210                 215                 220

Ser Gly Arg Asp Tyr Trp Gly Gln Gly Thr Leu Val Thr Val Ser Ser
225                 230                 235                 240

Ala Ala Ala Leu Ser Asn Ser Ile Met Tyr Phe Ser His Phe Val Pro
                245                 250                 255

Val Phe Leu Pro Ala Lys Pro Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
```

```
                290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Asn His Arg Asn
                325                 330                 335

Arg Ser Lys Arg Ser Arg Leu Leu His Ser Asp Tyr Met Asn Met Thr
                340                 345                 350

Pro Arg Arg Pro Gly Pro Thr Arg Lys His Tyr Gln Pro Tyr Ala Pro
                355                 360                 365

Pro Arg Asp Phe Ala Ala Tyr Arg Ser Arg Val Lys Phe Ser Arg Ser
                370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
                420                 425                 430

Glu Gly Leu Tyr Asn Glu Leu Gln Lys Asp Lys Met Ala Glu Ala Tyr
                435                 440                 445

Ser Glu Ile Gly Met Lys Gly Glu Arg Arg Arg Gly Lys Gly His Asp
450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 127
<211> LENGTH: 63
<212> TYPE: DNA
<213> ORGANISM: Homo sapiens

<400> SEQUENCE: 127
atggcactcc ccgtaactgc tctgctgctg ccgttggcat tgctcctgca cgccgcacgc    60
ccg                                                                  63

<210> SEQ ID NO 128
<211> LENGTH: 21
<212> TYPE: PRT
<213> ORGANISM: Homo sapiens

<400> SEQUENCE: 128

Met Ala Leu Pro Val Thr Ala Leu Leu Leu Pro Leu Ala Leu Leu Leu
1               5                   10                  15

His Ala Ala Arg Pro
            20

<210> SEQ ID NO 129
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ggcggtggag gctccggagg gggggctct ggcggagggg gctcc                      45

<210> SEQ ID NO 130
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Gly Gly Gly Ser Gly Gly Gly Ser Gly Gly Gly Gly Ser
1               5                   10                  15

<210> SEQ ID NO 131
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
gggtctacat ccggctccgg aagcccgga agtggcgaag gtagtacaaa gggg            54

<210> SEQ ID NO 132
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Ser Thr Ser Gly Ser Gly Lys Pro Gly Ser Gly Glu Gly Ser Thr
1               5                   10                  15

Lys Gly

<210> SEQ ID NO 133
<211> LENGTH: 152
<212> TYPE: PRT
<213> ORGANISM: Homo sapiens

<400> SEQUENCE: 133

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro
145                 150
```

```
<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly, Phe or Tyr
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Ile, Phe or Leu
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(7)
<223> OTHER INFORMATION: May or may not be present
<220> FEATURE:
<221> NAME/KEY: MOD_RES
<222> LOCATION: (8)..(8)
<223> OTHER INFORMATION: Glu, Gly or absent
<220> FEATURE:
<221> NAME/KEY: MOD_RES
<222> LOCATION: (9)..(9)
<223> OTHER INFORMATION: Phe, Leu or Tyr

<400> SEQUENCE: 134

Gly Xaa Xaa Xaa Xaa Ser Gly Xaa Xaa
1               5

<210> SEQ ID NO 135
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp, His, Ser or Tyr
<220> FEATURE:
<221> NAME/KEY: MOD_RES
<222> LOCATION: (2)..(2)
<223> OTHER INFORMATION: His, Pro or Tyr
<220> FEATURE:
<221> NAME/KEY: MOD_RES
<222> LOCATION: (3)..(3)
<223> OTHER INFORMATION: Asp, Glu or Ser
<220> FEATURE:
<221> NAME/KEY: MOD_RES
<222> LOCATION: (4)..(4)
<223> OTHER INFORMATION: Asp or Gly
<220> FEATURE:
<221> NAME/KEY: MOD_RES
<222> LOCATION: (5)..(5)
<223> OTHER INFORMATION: Gly or Ser
<220> FEATURE:
<221> NAME/KEY: MOD_RES
<222> LOCATION: (6)..(6)
<223> OTHER INFORMATION: Asp, Glu or absent

<400> SEQUENCE: 135

Xaa Xaa Xaa Xaa Xaa Xaa
1               5
```

```
<210> SEQ ID NO 136
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Leu
<220> FEATURE:
<221> NAME/KEY: MOD_RES
<222> LOCATION: (2)..(2)
<223> OTHER INFORMATION: Arg, Ser or Val
<220> FEATURE:
<221> NAME/KEY: MOD_RES
<222> LOCATION: (3)..(3)
<223> OTHER INFORMATION: Arg or Tyr
<220> FEATURE:
<221> NAME/KEY: MOD_RES
<222> LOCATION: (4)..(4)
<223> OTHER INFORMATION: Cys, Gly or Ser
<220> FEATURE:
<221> NAME/KEY: MOD_RES
<222> LOCATION: (5)..(5)
<223> OTHER INFORMATION: Gly, Ile or absent
<220> FEATURE:
<221> NAME/KEY: MOD_RES
<222> LOCATION: (6)..(8)
<223> OTHER INFORMATION: May or may not be present
<220> FEATURE:
<221> NAME/KEY: MOD_RES
<222> LOCATION: (9)..(9)
<223> OTHER INFORMATION: Trp, Tyr or absent
<220> FEATURE:
<221> NAME/KEY: MOD_RES
<222> LOCATION: (10)..(10)
<223> OTHER INFORMATION: Pro, Ser or absent
<220> FEATURE:
<221> NAME/KEY: MOD_RES
<222> LOCATION: (11)..(11)
<223> OTHER INFORMATION: Gly, Tyr or absent
<220> FEATURE:
<221> NAME/KEY: MOD_RES
<222> LOCATION: (12)..(12)
<223> OTHER INFORMATION: Phe or Arg

<400> SEQUENCE: 136

Xaa Xaa Xaa Xaa Xaa Gly Asp Cys Xaa Xaa Xaa Xaa Asp Tyr
1               5                   10

<210> SEQ ID NO 137
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Arg
<220> FEATURE:
<221> NAME/KEY: MOD_RES
<222> LOCATION: (5)..(5)
<223> OTHER INFORMATION: Asp or Ser
<220> FEATURE:
<221> NAME/KEY: MOD_RES
<222> LOCATION: (6)..(6)
<223> OTHER INFORMATION: Ile or Val
<220> FEATURE:
<221> NAME/KEY: MOD_RES
<222> LOCATION: (7)..(8)
<223> OTHER INFORMATION: Asn or Ser
```

```
<220> FEATURE:
<221> NAME/KEY: MOD_RES
<222> LOCATION: (9)..(9)
<223> OTHER INFORMATION: Phe, Leu or Tyr
<220> FEATURE:
<221> NAME/KEY: MOD_RES
<222> LOCATION: (11)..(11)
<223> OTHER INFORMATION: Asn or Thr

<400> SEQUENCE: 137

Xaa Ala Ser Gln Xaa Xaa Xaa Xaa Xaa Leu Xaa
1               5                   10

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Gly
<220> FEATURE:
<221> NAME/KEY: MOD_RES
<222> LOCATION: (4)..(4)
<223> OTHER INFORMATION: Asn, Ser or Thr
<220> FEATURE:
<221> NAME/KEY: MOD_RES
<222> LOCATION: (5)..(5)
<223> OTHER INFORMATION: Leu or Arg
<220> FEATURE:
<221> NAME/KEY: MOD_RES
<222> LOCATION: (6)..(6)
<223> OTHER INFORMATION: Ala, Glu or Lys
<220> FEATURE:
<221> NAME/KEY: MOD_RES
<222> LOCATION: (7)..(7)
<223> OTHER INFORMATION: Ser or Thr

<400> SEQUENCE: 138

Xaa Ala Ser Xaa Xaa Xaa Xaa
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Tyr
<220> FEATURE:
<221> NAME/KEY: MOD_RES
<222> LOCATION: (4)..(4)
<223> OTHER INFORMATION: Asp, Gly or Tyr
<220> FEATURE:
<221> NAME/KEY: MOD_RES
<222> LOCATION: (5)..(5)
<223> OTHER INFORMATION: Asn, Ser or Thr
<220> FEATURE:
<221> NAME/KEY: MOD_RES
<222> LOCATION: (6)..(6)
<223> OTHER INFORMATION: Leu, Thr or Tyr
<220> FEATURE:
<221> NAME/KEY: MOD_RES
<222> LOCATION: (8)..(8)
<223> OTHER INFORMATION: Phe or Ile

<400> SEQUENCE: 139
```

Gln Gln Xaa Xaa Xaa Pro Xaa Thr
1               5

<210> SEQ ID NO 140
<211> LENGTH: 265
<212> TYPE: PRT
<213> ORGANISM: Homo sapiens

<400> SEQUENCE: 140

Met Ser Glu Glu Val Thr Tyr Ala Asp Leu Gln Phe Gln Asn Ser Ser
1               5                   10                  15

Glu Met Glu Lys Ile Pro Glu Ile Gly Lys Phe Gly Glu Lys Ala Pro
            20                  25                  30

Pro Ala Pro Ser His Val Trp Arg Pro Ala Ala Leu Phe Leu Thr Leu
        35                  40                  45

Leu Cys Leu Leu Leu Leu Ile Gly Leu Gly Val Leu Ala Ser Met Phe
50                  55                  60

His Val Thr Leu Lys Ile Glu Met Lys Lys Met Asn Lys Leu Gln Asn
65                  70                  75                  80

Ile Ser Glu Glu Leu Gln Arg Asn Ile Ser Leu Gln Leu Met Ser Asn
                85                  90                  95

Met Asn Ile Ser Asn Lys Ile Arg Asn Leu Ser Thr Thr Leu Gln Thr
            100                 105                 110

Ile Ala Thr Lys Leu Cys Arg Glu Leu Tyr Ser Lys Glu Gln Glu His
        115                 120                 125

Lys Cys Lys Pro Cys Pro Arg Arg Trp Ile Trp His Lys Asp Ser Cys
130                 135                 140

Tyr Phe Leu Ser Asp Asp Val Gln Thr Trp Gln Glu Ser Lys Met Ala
145                 150                 155                 160

Cys Ala Ala Gln Asn Ala Ser Leu Leu Lys Ile Asn Asn Lys Asn Ala
                165                 170                 175

Leu Glu Phe Ile Lys Ser Gln Ser Arg Ser Tyr Asp Tyr Trp Leu Gly
            180                 185                 190

Leu Ser Pro Glu Glu Asp Ser Thr Arg Gly Met Arg Val Asp Asn Ile
        195                 200                 205

Ile Asn Ser Ser Ala Trp Val Ile Arg Asn Ala Pro Asp Leu Asn Asn
210                 215                 220

Met Tyr Cys Gly Tyr Ile Asn Arg Leu Tyr Val Gln Tyr Tyr His Cys
225                 230                 235                 240

Thr Tyr Lys Lys Arg Met Ile Cys Glu Lys Met Ala Asn Pro Val Gln
                245                 250                 255

Leu Gly Ser Thr Tyr Phe Arg Glu Ala
            260                 265

<210> SEQ ID NO 141
<211> LENGTH: 126
<212> TYPE: DNA
<213> ORGANISM: Homo sapiens

<400> SEQUENCE: 141
aagcgcggca ggaagaagct cctctacatt tttaagcagc cttttatgag gcccgtacag     60
acaacacagg aggaagatgg ctgtagctgc agatttcccg aggaggagga aggtgggtgc    120
gagctg                                                               126

<210> SEQ ID NO 142
<211> LENGTH: 42

```
-continued

<212> TYPE: PRT
<213> ORGANISM: Homo sapiens

<400> SEQUENCE: 142

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 143
<211> LENGTH: 37
<212> TYPE: PRT
<213> ORGANISM: Homo sapiens

<400> SEQUENCE: 143

Arg Arg Asp Gln Arg Leu Pro Pro Asp Ala His Lys Pro Pro Gly Gly
1               5                   10                  15

Gly Ser Phe Arg Thr Pro Ile Gln Glu Gln Ala Asp Ala His Ser
            20                  25                  30

Thr Leu Ala Lys Ile
        35

<210> SEQ ID NO 144
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Met Ala Leu Pro Val Thr Ala Leu Leu Leu Pro Leu Ala Leu Leu Leu
1               5                   10                  15

His Ala Ala Arg Pro
            20

<210> SEQ ID NO 145
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Gly Gly Gly Ser Gly Gly Gly Ser Gly Gly Gly Ser Gly
1               5                   10                  15

Gly Gly Gly Ser
            20

<210> SEQ ID NO 146
<211> LENGTH: 112
<212> TYPE: PRT
<213> ORGANISM: Homo sapiens

<400> SEQUENCE: 146

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30
```

Asp Val Leu Asp Lys Arg Arg Gly Arg Asp Pro Glu Met Gly Gly Lys
         35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
             100                 105                 110

<210> SEQ ID NO 147
<211> LENGTH: 6762
<212> TYPE: DNA
<213> ORGANISM: Lentivirus

<400> SEQUENCE: 147

```
ctgacgcgcc ctgtagcggc gcattaagcg cggcgggtgt ggtggttacg cgcagcgtga      60
ccgctacact tgccagcgcc ctagcgcccg ctcctttcgc tttcttccct tcctttctcg     120
ccacgttcgc cggctttccc cgtcaagctc taaatcgggg ctcccttta  gggttccgat     180
ttagtgcttt acggcacctc gaccccaaaa aacttgatta gggtgatggt tcacgtagtg     240
ggccatcgcc ctgatagacg gtttttcgcc ctttgacgtt ggagtccacg ttctttaata     300
gtggactctt gttccaaact ggaacaacac tcaaccctat ctcggtctat tcttttgatt     360
tataaggat  tttgccgatt tcggcctatt ggttaaaaaa tgagctgatt taacaaaaat     420
ttaacgcgaa ttttaacaaa atattaacgc ttacaatttg ccattcgcca ttcaggctgc     480
gcaactgttg ggaagggcga tcggtgcggg cctcttcgct attacgccag ctggcgaaag     540
ggggatgtgc tgcaaggcga ttaagttggg taacgccagg gttttcccag tcacgacgtt     600
gtaaaacgac ggccagtgaa ttgtaatacg actcactata gggcgacccg ggatggcgc      660
gccagtaatc aattacgggg tcattagttc atagcccata tatggagttc cgcgttacat     720
aacttacggt aaatggcccg cctggctgac cgcccaacga cccccgccca ttgacgtcaa     780
taatgacgta tgttcccata gtaacgccaa tagggacttt ccattgacgt caatgggtgg     840
agtatttacg gtaaactgcc cacttggcag tacatcaagt gtatcatatg ccaagtacgc     900
cccctattga cgtcaatgac ggtaaatggc ccgcctggca ttatgcccag tacatgacct     960
tatgggactt tcctacttgg cagtacatct acgtattagt catcgctatt accatgctga    1020
tgcggttttg gcagtacatc aatgggcgtg atagcggtt  tgactcacgg ggatttccaa    1080
gtctccaccc cattgacgtc aatgggagtt tgttttggca ccaaaatcaa cgggactttc    1140
caaaatgtcg taacaactcc gccccattga cgcaaatggg cggtaggcgt gtacggtggg    1200
aggtctatat aagcagagct ggtttagtga accgggtct  ctctggttag accagatctg    1260
agcctgggag ctctctggct aactagggaa cccactgctt aagcctcaat aaagcttgcc    1320
ttgagtgctt caagtagtgt gtgcccgtct gttgtgtgac tctggtaact agagatccct    1380
cagacccttt tagtcagtgt ggaaaatctc tagcagtggc gcccgaacag ggacttgaaa    1440
gcgaaaggga accagagga  gctctctcga cgcaggactc ggcttgctga agcgcgcacg    1500
gcaagaggcg agggggcggcg actggtgagt acgccaaaaa ttttgactag cggaggctag    1560
aaggagagag atgggtgcga gagcgtcagt attaagcggg ggagaattag atcgcgatgg    1620
gaaaaaattc ggttaaggcc agggggaaag aaaaaatata aattaaaaca tatagtatgg    1680
```

-continued

```
gcaagcaggg agctagaacg attcgcagtt aatcctggcc tgttagaaac atcagaaggc    1740
tgtagacaaa tactgggaca gctacaacca tcccttcaga caggatcaga agaacttaga    1800
tcattatata atacagtagc aaccctctat tgtgtgcatc aaaggataga gataaaagac    1860
accaaggaag ctttagacaa gatagaggaa gagcaaaaca aaagtaagac caccgcacag    1920
caagccgccg ctgatcttca gacctggagg aggagatatg agggacaatt ggagaagtga    1980
attatataaa tataaagtag taaaaattga accattagga gtagcaccca ccaaggcaaa    2040
gagaagagtg gtgcagagag aaaaaagagc agtgggaata ggagctttgt tccttgggtt    2100
cttgggagca gcaggaagca ctatgggcgc agcgtcaatg acgctgacgg tacaggccag    2160
acaattattg tctggtatag tgcagcagca gaacaatttg ctgagggcta ttgaggcgca    2220
acagcatctg ttgcaactca cagtctgggg catcaagcag ctccaggcaa gaatcctggc    2280
tgtggaaaga tacctaaagg atcaacagct cctggggatt tggggttgct ctggaaaact    2340
catttgcacc actgctgtgc cttggaatgc tagttggagt aataaatctc tggaacagat    2400
ttggaatcac acgacctgga tggagtggga cagagaaatt aacaattaca caagcttaat    2460
acactcctta attgaagaat cgcaaaacca gcaagaaaag aatgaacaag aattattgga    2520
attagataaa tgggcaagtt tgtggaattg gtttaacata acaaattggc tgtggtatat    2580
aaaattattc ataatgatag taggaggctt ggtaggttta agaatagttt ttgctgtact    2640
ttctatagtg aatagagtta ggcagggata ttcaccatta tcgtttcaga cccacctccc    2700
aaccccgagg ggacccgaca ggcccgaagg aatagaagaa gaaggtggag agagagacag    2760
agacagatcc attcgattag tgaacggatc tcgacggtat cggttaactt ttaaagaaa    2820
agggggatt gggggtaca gtgcagggga agaatagta gacataatag caacagacat    2880
acaaactaaa gaattacaaa aacaaattac aaaattcaaa attttatcgc gatcgcggaa    2940
tgaaagaccc cacctgtagg tttggcaagc tagcttaagt aacgccattt tgcaaggcat    3000
ggaaaataca taactgagaa tagagaagtt cagatcaagg ttaggaacag agagacagca    3060
gaatatgggc caaacaggat atctgtggta agcagttcct gccccggctc agggccaaga    3120
acagatggtc cccagatgcg gtcccgccct cagcagtttc tagagaacca tcagatgttt    3180
ccagggtgcc ccaaggacct gaaaatgacc ctgtgcctta tttgaactaa ccaatcagtt    3240
cgcttctcgc ttctgttcgc gcgcttctgc tccccgagct caataaaaga gcccacaacc    3300
cctcactcgg cgcgccagtc cttcgaagta gatctttgtc gatcctacca tccactcgac    3360
acaccgccca gcgccgcctg ccaagcttcc gagctctcga attaattcac ggtacccacc    3420
atggcctagg gagactagtc gaatcgatat caacctctgg attacaaaat tgtgaaaga    3480
ttgactggta ttcttaacta tgttgctcct tttacgctat gtggatacgc tgctttaatg    3540
cctttgtatc atgctattgc ttcccgtatg gctttcattt tctcctcctt gtataaatcc    3600
tggttgctgt ctctttatga ggagttgtgg cccgttgtca ggcaacgtgg cgtggtgtgc    3660
actgtgtttg ctgacgcaac ccccactggt tgggcattg ccaccacctg tcagctcctt    3720
tccgggactt tcgctttccc cctccctatt gccacggcgg aactcatcgc cgcctgcctt    3780
gcccgctgct ggacagggc tcggctgttg gcactgaca attccgtggt gttgtcgggg    3840
aagctgacgt ccttttcatg ctgctcgcc tgtgttgcca cctggattct gcgcgggacg    3900
tccttctgct acgtcccttc ggccctcaat ccagcggacc ttccttcccg cggcctgctg    3960
ccggctctgc ggcctcttcc gcgtcttcgc cttcgccctc agacgagtcg gatctccctt    4020
tgggccgcct ccccgcctgg ttaattaaag tacctttaag accaatgact tacaaggcag    4080
```

-continued

```
ctgtagatct tagccacttt ttaaaagaaa agggggggact ggaagggcga attcactccc    4140
aacgaagaca agatctgctt tttgcttgta ctgggtctct ctggttagac cagatctgag    4200
cctgggagct ctctggctaa ctagggaacc cactgcttaa gcctcaataa agcttgcctt    4260
gagtgcttca agtagtgtgt gcccgtctgt tgtgtgactc tggtaactag agatccctca    4320 gacccttttta gtcagtgtgg aaaatctcta gcaggcatgc cagacatgat aagatacatt    4380
gatgagtttg gacaaaccac aactagaatg cagtgaaaaa aatgctttat ttgtgaaatt    4440
tgtgatgcta ttgctttatt tgtaaccatt ataagctgca ataaacaagt taacaacaac    4500
aattgcattc attttatgtt tcaggttcag ggggaggtgt gggaggtttt ttggcgcgcc    4560
atcgtcgagg ttcccttttag tgagggttaa ttgcgagctt ggcgtaatca tggtcatagc    4620
tgtttcctgt gtgaaattgt tatccgctca caattccaca caacatacga gccgaagca    4680 taaagtgtaa agcctggggt gcctaatgag tgagctaact cacattaatt gcgttgcgct    4740
cactgcccgc tttccagtcg ggaaacctgt cgtgccagct gcattaatga atcggccaac    4800
gcgcggggag aggcggtttg cgtattgggc gctcttccgc ttcctcgctc actgactcgc    4860
tgcgctcggt cgttcggctg cggcgagcgg tatcagctca ctcaaaggcg gtaatacggt    4920
tatccacaga atcaggggat aacgcaggaa agaacatgtg agcaaaaggc cagcaaaagg    4980
ccaggaaccg taaaaaggcc gcgttgctgg cgtttttcca taggctccgc cccccctgacg    5040 agcatcacaa aaatcgacgc tcaagtcaga ggtggcgaaa cccgacagga ctataaagat    5100
accaggcgtt tccccctgga agctccctcg tgcgctctcc tgttccgacc ctgccgctta    5160
ccggatacct gtccgccttt ctcccttcgg gaagcgtggc gctttctcat agctcacgct    5220
gtaggtatct cagttcggtg taggtcgttc gctccaagct gggctgtgtg cacgaacccc    5280
ccgttcagcc cgaccgctgc gccttatccg gtaactatcg tcttgagtcc aacccggtaa    5340
gacacgactt atcgccactg gcagcagcca ctggtaacag gattagcaga gcgaggtatg    5400
taggcggtgc tacagagttc ttgaagtggt ggcctaacta cggctacact agaagaacag    5460
tatttggtat ctgcgctctg ctgaagccag ttaccttcgg aaaaagagtt ggtagctctt    5520
gatccggcaa acaaaccacc gctggtagcg gtggtttttt tgtttgcaag cagcagatta    5580
cgcgcagaaa aaaaggatct caagaagatc ctttgatctt ttctacgggg tctgacgctc    5640
agtggaacga aaactcacgt taagggattt tggtcatgag attatcaaaa aggatcttca    5700
cctagatcct tttaaattaa aaatgaagtt ttaaatcaat ctaaagtata tatgagtaaa    5760
cttggtctga cagttaccaa tgcttaatca gtgaggcacc tatctcagcg atctgtctat    5820
ttcgttcatc catagttgcc tgactccccg tcgtgtagat aactacgata cgggagggct    5880
taccatctgg ccccagtgct gcaatgatac cgcgagaccc acgctcaccg gctccagatt    5940
tatcagcaat aaaccagcca gccggaaggg ccgagcgcag aagtggtcct gcaactttat    6000
ccgcctccat ccagtctatt aattgttgcc gggaagctag agtaagtagt tcgccagtta    6060
atagtttgcg caacgttgtt gccattgcta caggcatcgt ggtgtcacgc tcgtcgtttg    6120
gtatggcttc attcagctcc ggttcccaac gatcaaggcg agttacatga tcccccatgt    6180
tgtgcaaaaa agcggttagc tccttcggtc ctccgatcgt tgtcagaagt aagttggccg    6240
cagtgttatc actcatggtt atggcagcac tgcataattc tcttactgtc atgccatccg    6300
taagatgctt ttctgtgact ggtgagtact caaccaagtc attctgagaa tagtgtatgc    6360
ggcgaccgag ttgctcttgc ccggcgtcaa tacgggataa taccgcgcca catagcagaa    6420
```

-continued

```
ctttaaaagt gctcatcatt ggaaaacgtt cttcggggcg aaaactctca aggatcttac    6480
cgctgttgag atccagttcg atgtaaccca ctcgtgcacc caactgatct tcagcatctt    6540
ttactttcac cagcgtttct gggtgagcaa aaacaggaag gcaaaatgcc gcaaaaaagg    6600
gaataagggc gacacggaaa tgttgaatac tcatactctt cctttttcaa tattattgaa    6660
gcatttatca gggttattgt ctcatgagcg gatacatatt tgaatgtatt tagaaaaata    6720
aacaaatagg ggttccgcgc acatttcccc gaaaagtgcc ac                      6762
```

CHIMERIC RECEPTORS AND METHODS OF USE THEREOF

CROSS REFERENCE TO RELATED APPLICATIONS

This application claims the benefit of U.S. Provisional Patent Application No. 62/317,068, filed Apr. 1, 2016, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 9, 2018, is named K-1029_02US SL.txt and is 274,746 bytes in size.

BACKGROUND OF THE INVENTION

C-type lectin-like-1 (CLL-1, also known as CLEC-1, CLEC12A, MICL, Dendritic Cell-Associated Lectin-1 (DCAL-1), and DCAL-2) is a glycoprotein receptor and member of a family of C-type lectin-like receptors involved in the regulation of cell proliferation and immune regulation. CLL-1 is expressed in hematopoietic cells, primarily on innate immune cells including monocytes, granulocytes, dendritic cells, as well as myeloid progenitor cells. Van Rhenen et al., Blood 2007:110(7). CLL-1 has been implicated in the regulation of myeloid cell proliferation and differentiation (Bakker et al., Cancer Res. 64:8443-8450 (2004); Marshall et al., J. Biol. Chem. 279:14792-14802 (2004)), and is present on acute myeloid (myelogenous) leukemia (AML) cells as well as on leukemic stem cells (Zhao et al., Haematologica 2010, 95(1):71-78).

Accordingly, CLL-1 has been implicated in multiple diseases, including but not limited to, acute myeloid (myelogenous) leukemia (AML), chronic myeloid (myelogenous) leukemia (CML), chronic myelomonocytic leukemia (CMML), juvenile myelomonocytic leukemia, atypical chronic myeloid leukemia, acute promyelocytic leukemia (APL), acute monocytic leukemia, acute monoblastic leukemia, acute erythroid leukemia, acute megakaryoblastic leukemia, myelodysplastic syndrome (MDS), myeloproliferative disorder, myeloid neoplasm, myeloid sarcoma), Blastic Plasmacytoid Dendritic Cell Neoplasm (BPDCN), or combinations thereof.

CLL-1 may additionally play a role in inflammatory or autoimmune diseases such as rheumatoid arthritis, psoriasis, allergies, asthma, Crohn's disease, IBD, IBS, fibromyalga, mastocytosis, and Celiac disease.

Human CLL-1 protein comprises a polypeptide of the following amino acid sequence:

```
                                     (SEQ ID NO. 140)
MSEEVTYADLQFQNSSEMEKIPEIGKFGEKAPPAPSHVWRPAALFLTLLC

LLLLIGLGVLASMFHVTLKIEMKKMNKLQNISEELQRNISLQLMSNMNIS

NKIRNLSTTLQTIATKLCRELYSKEQEHKCKPCPRRWIWHKDSCYFLSDD

VQTWQESKMACAAQNASLLKINNKNALEFIKSQSRSYDYWLGLSPEEDST

RGMRVDNIINSSAWVIRNAPDLNNMYCGYINRLYVQYYHCTYKKRMICEK

MANPVQLGSTYFREA.
```

Additional sequence information is contained in the CLL-1 Uniprot listing at: www.uniprot.org/uniprot/ Q5QGZ9, as well as NCBI Reference Sequence NP_612210.4 (www.ncbi.nlm.nih.gov/protein/NP_612210.4).

When referring to CLL-1, it will be appreciated that reference thereto encompasses fragments thereof, as well as related polypeptides, which include, but are not limited to, allelic variants, splice variants, derivative variants, substitution variants, deletion variants, and/or insertion variants including the addition of an N-terminal methionine, fusion polypeptides, and interspecies homologs. In certain embodiments, a CLL-1 polypeptide includes terminal residues, such as, but not limited to, leader sequence residues, targeting residues, amino terminal methionine residues, lysine residues, tag residues and/or fusion protein residues.

Certain antibodies to CLL-1 are described in U.S. Pat. No. 8,536,310 and in U.S. Pat. No. 9,163,090.

Engineered immune cells have been shown to possess desired qualities in therapeutic treatments, particularly in oncology. Two main types of engineered immune cells are those that contain chimeric antigen receptors (termed "CARs" or "CAR-Ts") and T-cell receptors ("TCRs"). These engineered cells are engineered to endow them with antigen specificity while retaining or enhancing their ability to recognize and kill a target cell. Chimeric antigen receptors may comprise, for example, (i) an antigen-specific component ("antigen binding molecule"), (ii) an extracellular domain, (iii) one or more costimulatory domains, and (iv) one or more activating domains. Each domain may be heterogeneous, that is, comprised of sequences derived from (or corresponding to) different protein chains. Chimeric antigen receptor-expressing immune cells (such as T cells) may be used in various therapies, including cancer therapies. It will be appreciated that costimulating domains may be used to enhance the activation of CAR-expressing cells against target antigens, and therefore increase the potency of adoptive immunotherapy.

Certain CARs to CLL-1 have been described in, e.g., U.S. Patent Application 20160051651 (PCT US2015/041337).

T cells can be engineered to possess specificity to one or more desired targets. For example, T cells can be transduced with DNA or other genetic material encoding an antigen binding molecule, such as one or more single chain variable fragment ("scFv") of an antibody, in conjunction with one or more signaling molecules, and/or one or more activating domains, such as CD3 zeta.

In addition to the CAR-T cells' ability to recognize and destroy the targeted cells, successful T cell therapy benefits from the CAR-T cells' ability to persist and maintain the ability to proliferate in response to antigen.

T cell receptors (TCRs) are molecules found on the surface of T cells that are responsible for recognizing antigen fragments as peptides bound to major histocompatibility complex (MHC) molecules. The TCR is comprised of two different protein chains—in approximately 95% of human TCRs, the TCR consists of an alpha (α) and beta (β) chain. In approximately 5% of human T cells the TCR consists of gamma and delta (γ/δ) chains. Each chain is composed of two extracellular domains: a variable (V) region and a constant (C) region, both of the immunoglobulin superfamily. As in other immunoglobulins, the variable domains of the TCR α-chain and β-chain (or gamma and delta (γ/δ) chains) each have three hypervariable or complementarity determining regions (CDRs). When the TCR engages with antigenic peptide and MHC (peptide/MHC), the T cell becomes activated, enabling it to attack and destroy the target cell.

However, current therapies have shown varying levels of effectiveness with undesired side effects. Therefore, a need exists to identify novel and improved therapies for treating CLL-1 related diseases and disorders.

SUMMARY OF THE INVENTION

The invention relates to engineered immune cells (such as CARs or TCRs), antigen binding molecules (including but not limited to, antibodies, scFvs, heavy and/or light chains, and CDRs of these antigen binding molecules) with specificity to CLL-1.

The invention further relates to a novel CD28 extracellular (hinge) sequence useful as costimulatory domains in these cells.

Chimeric antigen receptors of the invention typically comprise: (i) a CLL-1 specific antigen binding molecule, (ii) an extracellular (which may comprise a hinge) domain, (iii) one or more costimulatory domain, and (iv) one or more activating domain. It will be appreciated that each domain may be heterogeneous, thus comprised of sequences derived from (or corresponding to) different protein chains.

In some embodiments, the invention relates to a chimeric antigen receptor comprising an antigen binding molecule that specifically binds to CLL-1, wherein the antigen binding molecule comprises at least one of: a) a variable heavy chain CDR1 comprising an amino acid sequence selected from the group consisting of SEQ ID NOs: 17, 51, 73, and 95, b) a variable heavy chain CDR2 comprising an amino acid sequence selected from the group consisting of SEQ ID NOs. 18, 52, 74, and 96, c) a variable heavy chain CDR3 comprising an amino acid sequence selected from the group consisting of SEQ ID NOs. 19, 53, 75, and 97, d) a variable light chain CDR1 comprising an amino acid sequence selected from the group consisting of SEQ ID NOs: 22, 56, 78, and 100, e) a variable light chain CDR2 comprising an amino acid sequence selected from the group consisting of SEQ ID NOs. 23, 57, 79, and 101, and f) a variable light chain CDR3 comprising an amino acid sequence selected from the group consisting of SEQ ID NOs. 24, 58, 80, and 102. The chimeric antigen receptor can further comprise at least one costimulatory domain. The chimeric antigen receptor according to claim 1 further comprising at least one activating domain.

In certain embodiments, the invention relates to chimeric antigen receptors having at least about 75%, at least about 80%, at least about 85%, at least about 90%, at least about 95%, at least about 96%, at least about 97%, at least about 98%, at least about 99%, or 100% identical to the chimeric antigen receptors set forth herein.

Also encompassed by the invention are chimeric antigen receptors having no more than 8 amino acid substitutions thereto.

In certain embodiments the costimulatory domain comprises a signaling domain (or other suitable portion) of CD28, OX-40, 4-1BB/CD137, CD2, CD7, CD27, CD30, CD40, Programmed Death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

In some embodiments, the costimulatory domain can comprise all or a portion of the 4-1BB nucleic acid sequence set forth in SEQ ID NO. 141, and the corresponding amino acid sequence as set forth in SEQ ID NO. 142. In other embodiments, the costimulatory domain can comprise all or a portion of the amino acid sequence of OX40 as set forth in SEQ ID NO. 143. See also Hombach et al., Oncoimmunology. 2012 Jul. 1; 1(4): 458-466. In still other embodiments, the costimulatory domain can comprise all or a portion of the ICOS molecule as described in Guedan et al., Aug. 14, 2014; Blood: 124 (7) and Shen et al., Journal of Hematology & Oncology (2013) 6:33. In still other embodiments, the costimulatory domain can comprise all or a portion of CD27 as described in Song et al., Oncoimmunology. 2012 Jul. 1; 1(4): 547-549.

Preferred embodiments include incorporation into the CARs of the invention one or more of the following sequences: SEQ ID NO. 2, SEQ ID NO. 4, SEQ ID NO. 6, and SEQ ID NO. 8. Additional preferred embodiments include incorporation into the CARs of the invention the sequence set forth in SEQ ID NO. 14.

In further embodiments, the activating domain comprises CD3, preferably CD3 zeta, more preferably CD3 zeta having the sequence set forth in SEQ ID NO. 10.

In other embodiments, the invention relates to a chimeric antigen receptor comprising an antigen binding molecule further comprising SEQ ID NO. 2 and further comprising SEQ ID NO. 10.

The invention further relates to isolated polynucleotides encoding the chimeric antigen receptors, and vectors comprising the polynucleotides. Any vector known in the art can be suitable for the present invention. In some embodiments, the vector is a viral vector. In some embodiments, the vector is a retroviral vector (such as pMSVG1), a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector (such as pGAR), or any combination thereof. The pGAR sequence is as follows:

(SEQ ID NO: 147)
CTGACGCGCCCTGTAGCGGCGCATTAAGCGCGGCGGGTGTGGTGGTTACG

CGCAGCGTGACCGCTACACTTGCCAGCGCCCTAGCGCCCGCTCCTTTCGC

TTTCTTCCCTTCCTTTCTCGCCACGTTCGCCGGCTTTCCCCGTCAAGCTC

TAAATCGGGGGCTCCCTTTAGGGTTCCGATTTAGTGCTTTACGGCACCTC

GACCCCAAAAAACTTGATTAGGGTGATGGTTCACGTAGTGGGCCATCGCC

```
CTGATAGACGGTTTTTCGCCCTTTGACGTTGGAGTCCACGTTCTTTAATA
GTGGACTCTTGTTCCAAACTGGAACAACACTCAACCCTATCTCGGTCTAT
TCTTTTGATTTATAAGGGATTTTGCCGATTTCGGCCTATTGGTTAAAAAA
TGAGCTGATTTAACAAAAATTTAACGCGAATTTTAACAAAATATTAACGC
TTACAATTTGCCATTCGCCATTCAGGCTGCGCAACTGTTGGGAAGGGCGA
TCGGTGCGGGCCTCTTCGCTATTACGCCAGCTGGCGAAAGGGGGATGTGC
TGCAAGGCGATTAAGTTGGGTAACGCCAGGGTTTTCCCAGTCACGACGTT
GTAAAACGACGGCCAGTGAATTGTAATACGACTCACTATAGGGCGACCCG
GGGATGGCGCGCCAGTAATCAATTACGGGGTCATTAGTTCATAGCCCATA
TATGGAGTTCCGCGTTACATAACTTACGGTAAATGGCCCGCCTGGCTGAC
CGCCCAACGACCCCCGCCCATTGACGTCAATAATGACGTATGTTCCCATA
GTAACGCCAATAGGGACTTTCCATTGACGTCAATGGGTGGAGTATTTACG
GTAAACTGCCCACTTGGCAGTACATCAAGTGTATCATATGCCAAGTACGC
CCCCTATTGACGTCAATGACGGTAAATGGCCCGCCTGGCATTATGCCCAG
TACATGACCTTATGGGACTTTCCTACTTGGCAGTACATCTACGTATTAGT
CATCGCTATTACCATGCTGATGCGGTTTTGGCAGTACATCAATGGGCGTG
GATAGCGGTTTGACTCACGGGGATTTCCAAGTCTCCACCCCATTGACGTC
AATGGGAGTTTGTTTTGGCACCAAAATCAACGGGACTTTCCAAAATGTCG
TAACAACTCCGCCCCATTGACGCAAATGGGCGGTAGGCGTGTACGGTGGG
AGGTCTATATAAGCAGAGCTGGTTTAGTGAACCGGGGTCTCTCTGGTTAG
ACCAGATCTGAGCCTGGGAGCTCTCTGGCTAACTAGGGAACCCACTGCTT
AAGCCTCAATAAAGCTTGCCTTGAGTGCTTCAAGTAGTGTGTGCCCGTCT
GTTGTGTGACTCTGGTAACTAGAGATCCCTCAGACCCTTTTAGTCAGTGT
GGAAAATCTCTAGCAGTGGCGCCCGAACAGGGACTTGAAAGCGAAAGGA
AACCAGAGGAGCTCTCTCGACGCAGGACTCGGCTTGCTGAAGCGCGCACG
GCAAGAGGCGAGGGGCGGCGACTGGTGAGTACGCCAAAAATTTTGACTAG
CGGAGGCTAGAAGGAGAGATGGGTGCGAGAGCGTCAGTATTAAGCGGG
GGAGAATTAGATCGCGATGGGAAAAAATTCGGTTAAGGCCAGGGGAAAG
AAAAAATATAAATTAAAACATATAGTATGGGCAAGCAGGGAGCTAGAACG
ATTCGCAGTTAATCCTGGCCTGTTAGAAACATCAGAAGGCTGTAGACAAA
TACTGGGACAGCTACAACCATCCCTTCAGACAGGATCAGAAGAACTTAGA
TCATTATATAATACAGTAGCAACCCTCTATTGTGTGCATCAAAGGATAGA
GATAAAAGACACCAAGGAAGCTTTAGACAAGATAGAGGAAGAGCAAAACA
AAAGTAAGACCACCGCACAGCAAGCCGCCGCTGATCTTCAGACCTGGAGG
AGGAGATATGAGGGACAATTGGAGAAGTGAATTATATAAATATAAAGTAG
TAAAAATTGAACCATTAGGAGTAGCACCCACCAAGGCAAAGAGAAGAGTG
GTGCAGAGAGAAAAAGAGCAGTGGGAATAGGAGCTTTGTTCCTTGGGTT
CTTGGGAGCAGCAGGAAGCACTATGGGCGCAGCGTCAATGACGCTGACGG
TACAGGCCAGACAATTATTGTCTGGTATAGTGCAGCAGCAGAACAATTTG
CTGAGGGCTATTGAGGCGCAACAGCATCTGTTGCAACTCACAGTCTGGGG
CATCAAGCAGCTCCAGGCAAGAATCCTGGCTGTGGAAAGATACCTAAAGG

ATCAACAGCTCCTGGGGATTTGGGGTTGCTCTGGAAAACTCATTTGCACC
ACTGCTGTGCCTTGGAATGCTAGTTGGAGTAATAAATCTCTGGAACAGAT
TTGGAATCACACGACCTGGATGGAGTGGGACAGAGAAATTAACAATTACA
CAAGCTTAATACACTCCTTAATTGAAGAATCGCAAAACCAGCAAGAAAAG
AATGAACAAGAATTATTGGAATTAGATAAATGGGCAAGTTTGTGGAATTG
GTTTAACATAACAAATTGGCTGTGGTATATAAAATTATTCATAATGATAG
TAGGAGGCTTGGTAGGTTTAAGAATAGTTTTTGCTGTACTTTCTATAGTG
AATAGAGTTAGGCAGGGATATTCACCATTATCGTTTCAGACCCACCTCCC
AACCCCGAGGGGACCCGACAGGCCCGAAGGAATAGAAGAAGAAGGTGGAG
AGAGAGACAGAGACAGATCCATTCGATTAGTGAACGGATCTCGACGGTAT
CGGTTAACTTTTAAAAGAAAGGGGGGATTGGGGGGTACAGTGCAGGGGA
AAGAATAGTAGACATAATAGCAACAGACATACAAACTAAAGAATTACAAA
AACAAATTACAAAAATTCAAAATTTTATCGCGATCGCGGAATGAAAGACCC
CACCTGTAGGTTTGGCAAGCTAGCTTAAGTAACGCCATTTTGCAAGGCAT
GGAAAATACATAACTGAGAATAGAGAAGTTCAGATCAAGGTTAGGAACAG
AGAGACAGCAGAATATGGGCCAAACAGGATATCTGTGGTAAGCAGTTCCT
GCCCCGGCTCAGGGCCAAGAACAGATGGTCCCCAGATGCGGTCCCGCCCT
CAGCAGTTTCTAGAGAACCATCAGATGTTTCCAGGGTGCCCAAGGACCT
GAAAATGACCCTGTGCCTTATTTGAACTAACCAATCAGTTCGCTTCTCGC
TTCTGTTCGCGCGCTTCTGCTCCCCGAGCTCAATAAAAGAGCCCACAACC
CCTCACTCGGCGCGCCAGTCCTTCGAAGTAGATCTTTGTCGATCCTACCA
TCCACTCGACACACCCGCCAGCGCCGCTGCCAAGCTTCCGAGCTCTCGA
ATTAATTCACGGTACCCACCATGGCCTAGGGAGACTAGTCGAATCGATAT
CAACCTCTGGATTACAAAATTTGTGAAAGATTGACTGGTATTCTTAACTA
TGTTGCTCCTTTTACGCTATGTGGATACGCTGCTTTAATGCCTTTGTATC
ATGCTATTGCTTCCCGTATGGCTTTCATTTTCTCCTCCTTGTATAAATCC
TGGTTGCTGTCTCTTTATGAGGAGTTGTGGCCCGTTGTCAGGCAACGTGG
CGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATT
GCCACGGCGGAACTCATCGCCGCCTGCCTTGCCCGCTGCTGGACAGGGGC
TCGGCTGTTGGGCACTGACAATTCCGTGGTGTTGTCGGGGAAGCTGACGT
CCTTTTCATGGCTGCTCGCCTGTGTTGCCACCTGGATTCTGCGCGGGACG
TCCTTCTGCTACGTCCCTTCGGCCCTCAATCCAGCGGACCTTCCTTCCCG
CGGCCTGCTGCCGGCTCTGCGGCCTCTTCCGCGTCTTCGCCTTCGCCCTC
AGACGAGTCGGATCTCCCTTTGGGCCGCCTCCCCGCCTGGTAATTAAAG
TACCTTTAAGACCAATGACTTACAAGGCAGCTGTAGATCTTAGCCACTTT
TTAAAAGAAAGGGGGGACTGGAAGGGCGAATTCACTCCCAACGAAGACA
AGATCTGCTTTTTGCTTGTACTGGGTCTCTCTGGTTAGACCAGATCTGAG
CCTGGGAGCTCTCTGGCTAACTAGGGAACCCACTGCTTAAGCCTCAATAA
AGCTTGCCTTGAGTGCTTCAAGTAGTGTGTGCCCGTCTGTTGTGTGACTC
```

-continued
TGGTAACTAGAGATCCCTCAGACCCTTTTAGTCAGTGTGGAAAATCTCTA

GCAGGCATGCCAGACATGATAAGATACATTGATGAGTTTGGACAAACCAC

AACTAGAATGCAGTGAAAAAAATGCTTTATTTGTGAAATTTGTGATGCTA

TTGCTTTATTTGTAACCATTATAAGCTGCAATAAACAAGTTAACAACAAC

AATTGCATTCATTTTATGTTTCAGGTTCAGGGGGAGGTGTGGGAGGTTTT

TTGGCGCGCCATCGTCGAGGTTCCCTTTAGTGAGGGTTAATTGCGAGCTT

GGCGTAATCATGGTCATAGCTGTTTCCTGTGTGAAATTGTTATCCGCTCA

CAATTCCACACAACATACGAGCCGGAAGCATAAAGTGTAAAGCCTGGGGT

GCCTAATGAGTGAGCTAACTCACATTAATTGCGTTGCGCTCACTGCCCGC

TTTCCAGTCGGGAAACCTGTCGTGCCAGCTGCATTAATGAATCGGCCAAC

GCGCGGGGAGAGGCGGTTTGCGTATTGGGCGCTCTTCCGCTTCCTCGCTC

ACTGACTCGCTGCGCTCGGTCGTTCGGCTGCGGCGAGCGGTATCAGCTCA

CTCAAAGGCGGTAATACGGTTATCCACAGAATCAGGGGATAACGCAGGAA

AGAACATGTGAGCAAAAGGCCAGCAAAAGGCCAGGAACCGTAAAAAGGCC

GCGTTGCTGGCGTTTTTCCATAGGCTCCGCCCCCCTGACGAGCATCACAA

AAATCGACGCTCAAGTCAGAGGTGGCGAAACCCGACAGGACTATAAAGAT

ACCAGGCGTTTCCCCCTGGAAGCTCCCTCGTGCGCTCTCCTGTTCCGACC

CTGCCGCTTACCGGATACCTGTCCGCCTTTCTCCCTTCGGGAAGCGTGGC

GCTTTCTCATAGCTCACGCTGTAGGTATCTCAGTTCGGTGTAGGTCGTTC

GCTCCAAGCTGGGCTGTGTGCACGAACCCCCCGTTCAGCCCGACCGCTGC

GCCTTATCCGGTAACTATCGTCTTGAGTCCAACCCGGTAAGACACGACTT

ATCGCCACTGGCAGCAGCCACTGGTAACAGGATTAGCAGAGCGAGGTATG

TAGGCGGTGCTACAGAGTTCTTGAAGTGGTGGCCTAACTACGGCTACACT

AGAAGAACAGTATTTGGTATCTGCGCTCTGCTGAAGCCAGTTACCTTCGG

AAAAAGAGTTGGTAGCTCTTGATCCGGCAAACAAACCACCGCTGGTAGCG

GTGGTTTTTTTGTTTGCAAGCAGCAGATTACGCGCAGAAAAAAAGGATCT

CAAGAAGATCCTTTGATCTTTTCTACGGGGTCTGACGCTCAGTGGAACGA

AAACTCACGTTAAGGGATTTTGGTCATGAGATTATCAAAAGGATCTTCA

CCTAGATCCTTTTAAATTAAAAATGAAGTTTTAAATCAATCTAAAGTATA

TATGAGTAAACTTGGTCTGACAGTTACCAATGCTTAATCAGTGAGGCACC

TATCTCAGCGATCTGTCTATTTCGTTCATCCATAGTTGCCTGACTCCCCG

TCGTGTAGATAACTACGATACGGGAGGGCTTACCATCTGGCCCCAGTGCT

GCAATGATACCGCGAGACCCACGCTCACCGGCTCCAGATTTATCAGCAAT

AAACCAGCCAGCCGGAAGGGCCGAGCGCAGAAGTGGTCCTGCAACTTTAT

CCGCCTCCATCCAGTCTATTAATTGTTGCCGGGAAGCTAGAGTAAGTAGT

TCGCCAGTTAATAGTTTGCGCAACGTTGTTGCCATTGCTACAGGCATCGT

GGTGTCACGCTCGTCGTTTGGTATGGCTTCATTCAGCTCCGGTTCCCAAC

GATCAAGGCGAGTTACATGATCCCCCATGTTGTGCAAAAAAGCGGTTAGC

TCCTTCGGTCCTCCGATCGTTGTCAGAAGTAAGTTGGCCGCAGTGTTATC

ACTCATGGTTATGGCAGCACTGCATAATTCTCTTACTGTCATGCCATCCG

TAAGATGCTTTTCTGTGACTGGTGAGTACTCAACCAAGTCATTCTGAGAA

-continued
TAGTGTATGCGGCGACCGAGTTGCTCTTGCCCGGCGTCAATACGGGATAA

TACCGCGCCACATAGCAGAACTTTAAAAGTGCTCATCATTGGAAAACGTT

CTTCGGGGCGAAAACTCTCAAGGATCTTACCGCTGTTGAGATCCAGTTCG

ATGTAACCCACTCGTGCACCCAACTGATCTTCAGCATCTTTTACTTTCAC

CAGCGTTTCTGGGTGAGCAAAAACAGGAAGGCAAAATGCCGCAAAAAAGG

GAATAAGGGCGACACGGAAATGTTGAATACTCATACTCTTCCTTTTTCAA

TATTATTGAAGCATTTATCAGGGTTATTGTCTCATGAGCGGATACATATT

TGAATGTATTTAGAAAAATAAACAAATAGGGGTTCCGCGCACATTTCCCC

GAAAAGTGCCAC

The pGAR vector map is set forth in FIG. 11.

Suitable additional exemplary vectors include e.g., pBABE-puro, pBABE-neo largeTcDNA, pBABE-hygro-hTERT, pMKO.1 GFP, MSCV-IRES-GFP, pMSCV PIG (Puro IRES GFP empty plasmid), pMSCV-loxp-dsRed-loxp-eGFP-Puro-WPRE, MSCV IRES Luciferase, pMIG, MDH1-PGK-GFP_2.0, TtRMPVIR, pMSCV-IRES-mCherry FP, pRetroX GFP T2A Cre, pRXTN, pLncEXP, and pLXIN-Luc.

Exemplary immune cells include, but are not limited to T cells, tumor infiltrating lymphocytes (TILs), NK cells, TCR-expressing cells, dendritic cells, or NK-T cells. The T cells can be autologous, allogeneic, or heterologous. In other embodiments, the invention relates to pharmaceutical compositions comprising the immune cells of described herein.

In certain embodiments, the invention relates to antigen binding molecules (and chimeric antigen receptors comprising these molecules) comprising at least one of:
(a) a VH region comprising the amino acid sequence of SEQ ID NO: 16 and a VL region comprising the amino acid sequence of SEQ ID NO: 21;
(b) a VH region comprising the amino acid sequence of SEQ ID NO: 50 and a VL region comprising the amino acid sequence of SEQ ID NO: 55;
(c) a VH region comprising the amino acid sequence of SEQ ID NO: 72 and a VL region comprising the amino acid sequence of SEQ ID NO: 77;
(d) a VH region comprising the amino acid sequence of SEQ ID NO: 94 and a VL region comprising the amino acid sequence of SEQ ID NO: 99;
and wherein the VH and VL region or regions are linked by at least one linker. Also encompassed by the invention are chimeric antigen receptors and/or antigen binding molecules having no more than 8 amino acid substitutions thereto.

The linker may be, e.g., a poly-Gly linker such as GGGGSGGGGSGGGGS (SEQ ID NO. 130) or GGGGSGGGGSGGGGSGGGGS (SEQ ID NO. 145).

In other embodiments, the invention relates to antigen binding molecules (and chimeric antigen receptors comprising these molecules) wherein the linker comprises at least one of SEQ ID NO. 130 and SEQ ID NO. 132.

In certain embodiments, the invention relates to antigen binding molecules and/or chimeric antigen receptors having at least about 75%, at least about 80%, at least about 85%, at least about 90%, at least about 95%, at least about 96%, at least about 97%, at least about 98%, at least about 99%, or 100% identical to the antigen binding molecules and/or chimeric antigen receptors set forth herein.

In other embodiments, the invention relates to isolated polynucleotides comprising at least one of: SEQ ID NO. 27;

SEQ ID NO. 31; SEQ ID NO. 35; SEQ ID NO. 39; SEQ ID NO. 43; SEQ ID NO. 47; SEQ ID NO. 61; SEQ ID NO. 65; SEQ ID NO. 69; SEQ ID NO. 83; SEQ ID NO. 87; SEQ ID NO. 91; SEQ ID NO. 105; SEQ ID NO. 109; SEQ ID NO. 113; SEQ ID NO. 117; SEQ ID NO. 121; and SEQ ID NO. 125.

In certain embodiments, the invention relates to isolated polynucleotides having at least about 75%, at least about 80%, at least about 85%, at least about 90%, at least about 95%, at least about 96%, at least about 97%, at least about 98%, at least about 99%, or 100% identical to the polynucleotides set forth herein.

The invention further relates to vectors comprising these polynucleotides, as well as cells transduced using these vectors.

In further embodiments, the invention relates to isolated polypeptides comprising the amino acid sequence set forth in at least one of: SEQ ID NO. 28; SEQ ID NO. 32; SEQ ID NO. 36; SEQ ID NO. 40; SEQ ID NO. 44; SEQ ID NO. 48; SEQ ID NO. 62; SEQ ID NO. 66; SEQ ID NO. 70; SEQ ID NO. 84; SEQ ID NO. 88; SEQ ID NO. 92; SEQ ID NO. 106; SEQ ID NO. 110; SEQ ID NO. 114; SEQ ID NO. 118; SEQ ID NO. 122; and SEQ ID NO. 126. In other embodiments, the invention relates to vectors encoding these polypeptides, immune cells comprising these polypeptides. Preferred immune cells include T cells, tumor infiltrating lymphocytes (TILs), NK cells, TCR-expressing cells, dendritic cells, or NK-T cells. The T cells may be autologous, allogeneic, or heterologous. Also encompassed by the invention are chimeric antigen receptors having no more than 8 amino acid substitutions thereto.

In other embodiments, the invention relates to isolated polynucleotides encoding a chimeric antigen receptor (CAR) or T cell receptor (TCR) comprising an antigen binding molecule that specifically binds to CLL-1, wherein the antigen binding molecule comprises a variable heavy ($V_H$) chain CDR3 comprising an amino acid sequence selected from the group consisting of SEQ ID NOs: 19, 53, 75, and 97. Also encompassed by the invention are chimeric antigen receptors having no more than 8 amino acid substitutions thereto. The polynucleotides may further comprising an activating domain. In preferred embodiments, the activating domain is CD3, more preferably CD3 zeta, more preferably the amino acid sequence set forth in SEQ ID NO. 9.

In other embodiments, the invention includes a costimulatory domain comprising the signaling domain (or other suitable portion) of CD28, CD28T, OX40, 4-1BB/CD137, CD2, CD3 (alpha, beta, delta, epsilon, gamma, zeta), CD4, CD5, CD7, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CD1 la/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF, TNFr, integrin, signaling lymphocytic activation molecule, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1-1d, ITGAE, CD103, ITGAL, CD1-1a, LFA-1, ITGAM, CD1-1b, ITGAX, CD1-1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD83 ligand, or fragments or combinations thereof. Preferred costimulatory domains are recited hereinbelow.

In further embodiments, the invention relates to isolated polynucleotides encoding a chimeric antigen receptor (CAR) or T cell receptor (TCR), wherein said CAR or TCR comprises an antigen binding molecule that specifically binds to CLL-1, and wherein the antigen binding molecule comprises a variable light ($V_L$) chain CDR3 comprising an amino acid sequence selected from the group consisting of SEQ ID NOs: 24, 58, 80, and 102. The polynucleotide can further comprise an activating domain. The polynucleotide can further comprise a costimulatory domain.

In other embodiments, the invention relates to isolated polynucleotides encoding a chimeric antigen receptor (CAR) or T cell receptor (TCR) comprising an antigen binding molecule that specifically binds to CLL-1, wherein the antigen binding molecule heavy chain comprises CDR1 (SEQ ID NO. 17), CDR2 (SEQ ID NO. 18), and CDR3 (SEQ ID NO. 19) and the antigen binding molecule light chain comprises CDR1 (SEQ ID NO. 22), CDR2 (SEQ ID NO. 23), and CDR3 (SEQ ID NO. 24).

In certain embodiments, the invention relates to isolated polynucleotides having at least about 75%, at least about 80%, at least about 85%, at least about 90%, at least about 95%, at least about 96%, at least about 97%, at least about 98%, at least about 99%, or 100% identical to the above sequences.

In other embodiments, the invention relates to isolated polynucleotides encoding a chimeric antigen receptor (CAR) or T cell receptor (TCR) comprising an antigen binding molecule that specifically binds to CLL-1, wherein the antigen binding molecule heavy chain comprises CDR1 (SEQ ID NO. 51), CDR2 (SEQ ID NO. 52), and CDR3 (SEQ ID NO. 53) and the antigen binding molecule light chain comprises CDR1 (SEQ ID NO. 56), CDR2 (SEQ ID NO. 57), and CDR3 (SEQ ID NO. 58).

In certain embodiments, the invention relates to isolated polynucleotides having at least about 75%, at least about 80%, at least about 85%, at least about 90%, at least about 95%, at least about 96%, at least about 97%, at least about 98%, at least about 99%, or 100% identical to the above sequences.

In other embodiments, the invention relates to isolated polynucleotides encoding a chimeric antigen receptor (CAR) or T cell receptor (TCR) comprising an antigen binding molecule that specifically binds to CLL-1, wherein the antigen binding molecule heavy chain comprises CDR1 (SEQ ID NO. 73), CDR2 (SEQ ID NO. 74), and CDR3 (SEQ ID NO. 75) and the antigen binding molecule light chain comprises CDR1 (SEQ ID NO. 78), CDR2 (SEQ ID NO. 79), and CDR3 (SEQ ID NO. 80).

In certain embodiments, the invention relates to isolated polynucleotides having at least about 75%, at least about 80%, at least about 85%, at least about 90%, at least about 95%, at least about 96%, at least about 97%, at least about 98%, at least about 99%, or 100% identical to the above sequences.

In other embodiments, the invention relates to isolated polynucleotides encoding a chimeric antigen receptor (CAR) or T cell receptor (TCR) comprising an antigen binding molecule that specifically binds to CLL-1, wherein the antigen binding molecule heavy chain comprises CDR1 (SEQ ID NO. 95), CDR2 (SEQ ID NO. 96), and CDR3

(SEQ ID NO. 97) and the antigen binding molecule light chain comprises CDR1 (SEQ ID NO. 100), CDR2 (SEQ ID NO. 101), and CDR3 (SEQ ID NO. 102).

In certain embodiments, the invention relates to isolated polynucleotides having at least about 75%, at least about 80%, at least about 85%, at least about 90%, at least about 95%, at least about 96%, at least about 97%, at least about 98%, at least about 99%, or 100% identical to the above sequences.

In further embodiments, the invention relates to isolated polynucleotides encoding a chimeric antigen receptor (CAR) or T cell receptor (TCR) comprising an antigen binding molecule that specifically binds to CLL-1, and wherein the antigen binding molecule comprises:

(a) a heavy chain variable region (VH) complementarity determining region (CDR) 1 comprising the amino acid sequence $GX_2X_3X_4X_5X_6X_7X_8X_9$ (SEQ ID NO: 134), wherein $X_2$ is G, F, or Y; $X_3$ is S or T; $X_4$ is I, F, or L; $X_5$ is S or T; $X_6$ is not present or S; $X_7$ is not present or G; $X_8$ is not present or E or G; and $X_9$ is F, L, or Y;

(b) a heavy chain variable region (VH) complementarity determining region (CDR) 2 comprising the amino acid sequence $X_1X_2X_3X_4X_5X_6$ (SEQ ID NO: 135), wherein $X_1$ is D, H, S, or Y; $X_2$ is H, P, or Y; $X_3$ is D, E, or S; $X_4$ is D or G; $X_5$ is G or S; and $X_6$ is not present of D or E;

(c) a heavy chain variable region (VH) complementarity determining region (CDR) 3, comprising the amino acid sequence $X_1X_2X_3X_4X_5X_6X_7X_8X_9X_{10}X_{11}X_{12}DY$ (SEQ ID NO: 136), wherein $X_1$ is E or L; $X_2$ is R, S, or V; $X_3$ is R or Y; $X_4$ is C, G, or S; $X_5$ is not present or G or I; $X_6$ is not present or G; $X_7$ is not present or D; $X_8$ is not present or C; $X_9$ is not present or W or Y; $X_{10}$ is not present or P or S; $X_{11}$ is not present or G or Y; and $X_{12}$ is F or R;

(d) a light chain variable region (VL) CDR1 comprising the amino acid sequence $X_1ASQX_5X_6X_7X_8X_9LX_{11}$ (SEQ ID NO: 137), wherein $X_1$ is Q or R; $X_5$ is D or S; $X_6$ is I or V; $X_7$ is N or S; $X_8$ is N or S; $X_9$ is F, L, or Y; and $X_{11}$ is N or T;

(e) a light chain variable region (VL) CDR2 comprising the amino acid sequence $X_1ASX_4X_5X_6X_7$ (SEQ ID NO: 138), wherein $X_1$ is D or G; $X_4$ is N, S, or T; $X_5$ is L or R; $X_6$ is A, E, or K; and $X_7$ is S or T; and/or (f) a light chain variable region (VL) CDR3 comprising the amino acid sequence $QQX_3X_4X_5X_6PX_8T$ (SEQ ID NO: 139), wherein $X_3$ is S or Y; $X_4$ is D, G, or Y; $X_5$ is N, S, or T; $X_6$ is L, T, or Y; and $X_8$ is F or I.

The invention further relates to antigen binding molecules to CLL-1 comprising at least one variable heavy chain CDR3 or variable light chain CDR3 sequence as set forth herein. The invention further relates to antigen binding molecules to CLL-1 comprising at least one variable heavy chain CDR1, CDR2, and CDR3 sequences as described herein. The invention further relates to antigen binding molecules to CLL-1 comprising at least one variable light chain CDR1, CDR2, and CDR3 sequences as described herein. The invention further relates to antigen binding molecules to CLL-1 comprising both variable heavy chain CDR1, CDR2, CDR3, and variable light chain CDR1, CDR2, and CDR3 sequences as described herein.

The invention further relates to methods of treating a disease or disorder in a subject in need thereof comprising administering to the subject the antigen binding molecules, the CARs, TCRs, polynucleotides, vectors, cells, or compositions according to the invention. Suitable diseases for treatment include, but are not limited to, acute myeloid leukemia (AML), chronic myelogenous leukemia (CML), chronic myelomonocytic leukemia (CMML), juvenile myelomonocytic leukemia, atypical chronic myeloid leukemia, acute promyelocytic leukemia (APL), acute monoblastic leukemia, acute erythroid leukemia, acute megakaryoblastic leukemia, myelodysplastic syndrome (MDS), myeloproliferative disorder, myeloid neoplasm, myeloid sarcoma, Blastic Plasmacytoid Dendritic Cell Neoplasm (BPDCN), or combinations thereof. Additional diseases include inflammatory and/or autoimmune diseases such as rheumatoid arthritis, psoriasis, allergies, asthma, Crohn's disease, IBD, IBS, fibromyalga, mastocytosis, and Celiac disease.

BRIEF DESCRIPTION OF THE FIGURES

FIGS. 9A-9D set forth sequence alignments of the CLL-1 antigen binding molecules of the invention. CDRs are notated in boxes.

DETAILED DESCRIPTION OF THE INVENTION

Figure 1:
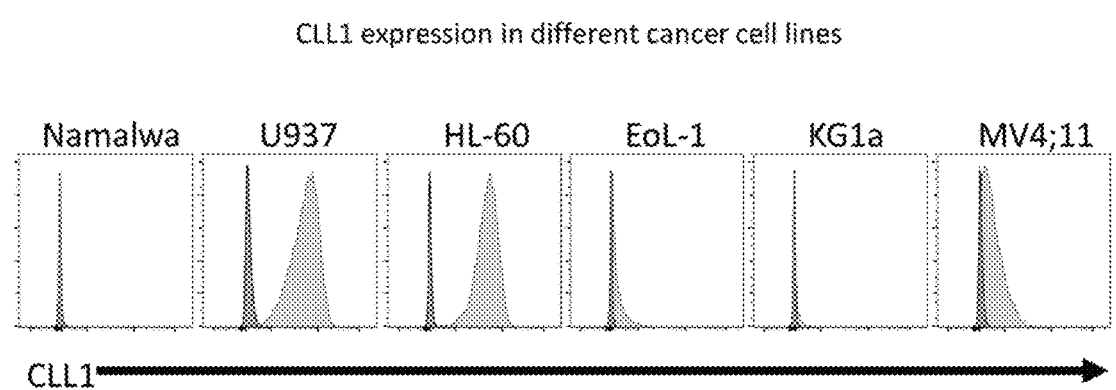
FIG. 1 shows CLL-1 expression in different cancer cell lines.

It will be appreciated that chimeric antigen receptors (CARs or CAR-Ts) and T cell receptors (TCRs) are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell.

CARs can be engineered to bind to an antigen (such as a cell-surface antigen) by incorporating an antigen binding molecule that interacts with that targeted antigen. Preferably, the antigen binding molecule is an antibody fragment thereof, and more preferably one or more single chain antibody fragment ("scFv"). An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45: 131-136. An scFv retains the parent antibody's ability to specifically interact with target antigen. scFvs are preferred for use in chimeric antigen receptors because they can be engineered to be expressed as part of a single chain along with the other CAR components. Id. See also Krause et al., J. Exp. Med., Volume 188, No. 4, 1998 (619-626); Finney et al., *Journal of Immunology*, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the invention, with specificity to more than one target of interest.

Costimulatory Domains.

Chimeric antigen receptors may incorporate costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Annu. Rev. Pharmacol. Toxicol. 56:59-83 (2016). For example, CD28 is a costimulatory protein found naturally on T-cells. A variety of costimulatory molecules are set forth herein, but it will be appreciated that additional costimulatory molecules are also included within the scope of this invention.

The complete native amino acid sequence of CD28 is described in NCBI Reference Sequence: NP_006130.1. The complete native CD28 nucleic acid sequence is described in NCBI Reference Sequence: NM_006139.1.

Certain CD28 domains have been used in chimeric antigen receptors. In accordance with the present invention, it has now been found that a novel CD28 extracellular (hinge) construct, termed "CD28T", unexpectedly provides certain benefits when utilized in a CAR construct. This construct demonstrates the ability to retain (and at times exceed) the properties of CD28-containing CARs, despite truncation (removal) of multiple amino acids from the extracellular CD28 sequence. These benefits include equivalent or superior cytokine production, equivalent or superior cytolytic activity, and/or equivalent or superior CAR expression levels.

The nucleotide sequence of the CD28T molecule, including the extracellular domain, and the CD28 transmembrane and intracellular domains is set forth in SEQ ID NO. 1:

CTTGATAATGAAAAGTCAAACGGAACAATCATTCACGTGAAGGGCAAGCA

CCTCTGTCCGTCACCCTTGTTCCCTGGTCCATCCAAGCCATTCTGGGTGT

TGGTCGTAGTGGGTGGAGTCCTCGCTTGTTACTCTCTGCTCGTCACCGTG

GCTTTTATAATCTTCTGGGTTAGATCCAAAAGAAGCCGCCTGCTCCATAG

CGATTACATGAATATGACTCCACGCCGCCCTGGCCCCACAAGGAAACACT

ACCAGCCTTACGCACCACCTAGAGATTTCGCTGCCTATCGGAGC

The corresponding amino acid sequence is set forth in SEQ ID NO. 2:

LDNEKSNGTI IHVKGKHLCPSPLFPGPSKPFWVLVVVGGVLACYSLLVTV

AFIIFWVRSK RSRLLHSDYM NMTPRRPGPT RKHYQPYAPP

RDFAAYRS

The nucleotide sequence of the extracellular portion of CD28T is set forth in SEQ ID NO. 3:

CTTGATAATGAAAAGTCAAACGGAACAATCATTCACGTGAAGGGCAAGCA

CCTCTGTCCGTCACCCTTGTTCCCTGGTCCATCCAAGCCA

The corresponding amino acid sequence of the CD28T extracellular domain is set forth in SEQ ID NO. 4: LDNEK-SNGTI IHVKGKHLCP SPLFPGPSKP The nucleotide sequence of the CD28 transmembrane domain is set forth in SEQ ID NO. 5):

TTCTGGGTGTTGGTCGTAGTGGGTGGAGTCCTCGCTTGTTACTCTCTGCT

CGTCACCGTGGCTTTTATAATCTTCTGGGTT

The amino acid sequence of the CD28 transmembrane domain is set forth in SEQ ID NO. 6:

FWVLVVVGGV LACYSLLVTV AFIIFWV

The nucleotide sequence of the CD28 intracellular signaling domain is set forth in SEQ ID NO. 7:

AGATCCAAAAGAAGCCGCCTGCTCCATAGCGATTACATGAATATGACTCC

ACGCCGCCCTGGCCCCACAAGGAAACACTACCAGCCTTACGCACCACCTA

GAGATTTCGCTGCCTATCGGAGC

The amino acid sequence of the CD28 intracellular signaling domain is set forth in SEQ ID NO. 8:

RSKRSRLLHSDYMNMTPRRPGPTRKHYQPYAPPRDFAAYRS

Additional CD28 sequences suitable for use in the invention include the CD28 nucleotide sequence set forth in SEQ ID NO. 11:

ATTGAGGTGATGTATCCACCGCCTTACCTGGATAACGAAAAGAGTAACGG

TACCATCATTCACGTGAAAGGTAAACACCTGTGTCCTTCTCCCCTCTTCC

CCGGGCCATCAAAGCCC

The corresponding amino acid sequence is set forth in SEQ ID NO. 12:

IEVMYPPPYLDNEKSNGTIIHVKGKHLCPSPLFPGPSKP

It will be appreciated that the invention relates to antigen binding molecules, CARs, TCRs, and the like comprising at least one isolated nucleic acid sequence of SEQ ID NO. 1 or SEQ ID NO. 3. It will further be appreciated that the invention relates to antigen binding molecules, CARs, TCRs, and the like wherein the extracellular portion consists of at least one isolated nucleic acid sequence of SEQ ID NO. 1 or SEQ ID NO. 3. Additionally, it will be appreciated that the invention relates to antigen binding molecules, CARs, TCRs, and the like wherein the extracellular portion consists essentially of at least one isolated nucleic acid sequence of SEQ ID NO. 1 or SEQ ID NO. 3.

It will be appreciated that the invention relates to antigen binding molecules, CARs, TCRs, and the like comprising at least one amino acid sequence of SEQ ID NO. 2 or SEQ ID NO. 4. It will further be appreciated that the invention relates to antigen binding molecules, CARs, TCRs, and the like wherein the extracellular portion consists of at least one amino acid sequence of SEQ ID NO. 2 or SEQ ID NO. 4. It will also be appreciated that the invention relates to antigen binding molecules, CARs, TCRs, and the like wherein the extracellular portion consists essentially of at least one amino acid sequence of SEQ ID NO. 2 or SEQ ID NO. 4.

Another suitable source of extracellular and/or transmembrane domains can be derived from (or correspond to) some or all of CD8. The nucleotide sequence of a suitable CD8 extracellular and transmembrane domain is set forth in SEQ ID NO. 13:

```
GCTGCAGCATTGAGCAACTCAATAATGTATTTTAGTCACTTTGTACCAGT

GTTCTTGCCGGCTAAGCCTACTACCACACCCGCTCCACGGCCACCTACCC

CAGCTCCTACCATCGCTTCACAGCCTCTGTCCCTGCGCCCAGAGGCTTGC

CGACCGGCCGCAGGGGGCGCTGTTCATACCAGAGGACTGGATTTCGCCTG

CGATATCTATATCTGGGCACCCCTGGCCGGAACCTGCGGCGTACTCCTGC

TGTCCCTGGTCATCACGCTCTATTGTAATCACAGGAAC
```

The corresponding amino acid sequence is set forth in SEQ ID NO. 14:

```
AAALSNSIMYFSHFVPVFLPAKPTTTPAPRPPTPAPTIASQPLSLRPEAC

RPAAGGAVHTRGLDFACDIYIWAPLAGTCGVLLLSLVITLYCNHRN
```

It will be appreciated that suitable costimulatory domains within the scope of the invention can be derived from (or correspond to) for example, CD28, CD28T, OX40, 4-1BB/CD137, CD2, CD3 (alpha, beta, delta, epsilon, gamma, zeta), CD4, CD5, CD7, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CD1 la/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF, TNFr, integrin, signaling lymphocytic activation molecule, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1-1d, ITGAE, CD103, ITGAL, CD1-1a, LFA-1, ITGAM, CD1-1b, ITGAX, CD1-1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD83 ligand, or fragments or combinations thereof. It will be appreciated that additional costimulatory molecules, or fragments thereof, not listed above are within the scope of the invention.

Activating Domains.

CD3 is an element of the T cell receptor on native T cells, and has been shown to be an important intracellular activating element in CARs. In a preferred embodiment, the CD3 is CD3 zeta, the nucleotide sequence of which is set forth in SEQ ID NO. 9:

```
AGGGTGAAGTTTTCCAGATCTGCAGATGCACCAGCGTATCAGCAGGGCCA

GAACCAACTGTATAACGAGCTCAACCTGGGACGCAGGGAAGAGTATGACG

TTTTGGACAAGCGCAGAGGACGGGACCCTGAGATGGGTGGCAAACCAAGA

CGAAAAAACCCCCAGGAGGGTCTCTATAATGAGCTGCAGAAGGATAAGAT

GGCTGAAGCCTATTCTGAAATAGGCATGAAAGGAGAGCGGAGAAGGGGAA

AAGGGCACGACGGTTTGTACCAGGGACTCAGCACTGCTACGAAGGATACT

TATGACGCTCTCCACATGCAAGCCCTGCCACCTAGG
```

The corresponding amino acid of intracellular CD3 zeta is set forth in SEQ ID NO. 10:

```
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR
```

Domain Orientation Relative to the Cell

Structurally, it will appreciated that the domains described herein correspond to locations relative to an immune or other cell. These domains thus can be part of the (i) "hinge" or extracellular (EC) domain, (ii) the transmembrane (TM) domain, and/or (iii) the intracellular/cytoplasmic domain (IC). The intracellular component frequently comprises, in part, an activating domain such as a portion of a member of the CD3 family, preferably CD3 zeta. This domain is capable of activating the T cell upon binding of the antigen binding molecule to its target. It will be appreciated that the intracellular domain typically further comprises one or more costimulatory molecules as described herein.

"Activation" or "Stimulation" as used herein, refers to a primary response induced by binding of an activating molecule with its cognate ligand, wherein the binding mediates a signal transduction event.

An "activating molecule" or "stimulating molecule" refers to a molecule on a T cell, e.g., the TCR/CD3 complex that specifically binds with a cognate stimulatory ligand present on an antigen present cell. Suitable activating molecules are described herein.

A "costimulatory molecule" as used herein refers to a molecule that provides a signal which mediates a T cell response, including, but not limited to, proliferation, activation, differentiation, and the like. Costimulatory molecules can provide a signal in addition to the primary signal provided by an activating molecule as described herein.

Suitable costimulatory molecules include, but are not limited to, all or portions of CD28, CD28T, OX40, 4-1BB/CD137, CD2, CD3 (alpha, beta, delta, epsilon, gamma, zeta), CD4, CD5, CD7, CD9, CD16, CD22, CD27, CD30, CD 33, CD37, CD40, CD 45, CD64, CD80, CD86, CD134, CD137, CD154, PD-1, ICOS, lymphocyte function-associated antigen-1 (LFA-1 (CD1 la/CD18), CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF, TNFr, integrin, signaling lymphocytic activation molecule, BTLA, Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1-1d, ITGAE, CD103, ITGAL, CD1-1a, LFA-1, ITGAM, CD1-1b, ITGAX, CD1-

1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, CD83 ligand, or fragments or combinations thereof. It will be appreciated that the hinge region may contain some or all of a member of the immunoglobulin family such as IgG1, IgG2, IgG3, IgG4, IgA, IgD, IgE, IgM, or fragment thereof.

In some embodiments, the extracellular domain is positioned between the antigen binding molecule and the transmembrane domain.

Exemplary CAR constructs in accordance with the invention are set forth in Table 1.

TABLE 1

| Construct Name | scFv | Hinge Domain | Activating Domain |
| --- | --- | --- | --- |
| 24C1 CD28T | 24C1 | CD28T | CD3 zeta |
| 24C1 CD28 | 24C1 | CD28 | CD3 zeta |
| 24C1 CD8 | 24C1 | CD8 | CD3 zeta |
| 24C8 CD28T | 24C8 | CD28T | CD3 zeta |
| 24C8 CD28 | 24C8 | CD28 | CD3 zeta |
| 24C8 CD8 | 24C8 | CD8 | CD3 zeta |
| 20C5.1 CD28T | 20C5.1 | CD28T | CD3 zeta |
| 20C5.1 CD28 | 20C5.1 | CD28 | CD3 zeta |
| 20C5.1 CD8 | 20C5.1 | CD8 | CD3 zeta |
| 20C5.2 CD28T | 20C5.2 | CD28T | CD3 zeta |
| 20C5.2 CD28 | 20C5.2 | CD28 | CD3 zeta |
| 20C5.2 CD8 | 20C5.2 | CD8 | CD3 zeta |

As noted, the engineered T cells of the invention comprise an antigen binding molecule (such as an scFv), an extracellular domain (which may comprise a "hinge" domain), a transmembrane domain, and an intracellular domain. The intracellular domain can comprise at least in part an activating domain, preferably comprised of a CD3 family member such as CD3 zeta, CD3 epsilon, CD3 gamma, or portions thereof.

It will further be appreciated that the antigen binding molecule (e.g., one or more scFvs) is engineered such that it is located in the extracellular portion of the molecule/construct, such that it is capable of recognizing and binding to its target or targets.

Extracellular Domain.

Extracellular domains of particular use in this invention may be derived from (i.e., comprise) all or some of CD28, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof. The extracellular domain may be derived either from a natural or from a synthetic source.

Extracellular domains often comprise the hinge portion, sometimes referred to as the "spacer" region. A variety of hinges can be employed in accordance with the invention, including portions or derivatives of the molecules described herein.

In certain embodiments, the hinge region comprises an amino acid sequence that is at least about 75%, at least about 80%, at least about 85%, at least about 90%, at least about 95%, at least about 96%, at least about 97%, at least about 98%, at least about 99%, or 100% identical to the extracellular domain amino acid sequences set forth herein.

In certain embodiments, the hinge region comprises an amino acid sequence that is at least about 75%, at least about 80%, at least about 85%, at least about 90%, at least about 95%, at least about 96%, at least about 97%, at least about 98%, at least about 99%, or 100% identical to the extracellular nucleotide amino acid sequences set forth herein.

Transmembrane Domain.

The CAR can be designed with a transmembrane domain that is fused to the extracellular domain of the CAR. It can similarly be fused to the intracellular domain of the CAR. In some instances, the transmembrane domain can be selected or modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein. Transmembrane regions of particular use in this invention may be derived from (comprise, or correspond to) CD28, CD28T, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, ITGA4, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

Optionally, short linkers may form linkages between any or some of the extracellular, transmembrane, and intracellular domains of the CAR.

In other embodiments, the transmembrane domain in the CAR of the invention is a CD8 transmembrane domain. In one embodiment, the CD8 transmembrane domain comprises the transmembrane portion of the nucleic acid sequence of SEQ ID NO: 13. In another embodiment, the CD8 transmembrane domain comprises the nucleic acid sequence that encodes the transmembrane amino acid sequence contained within SEQ ID NO: 14.

In certain embodiments, the transmembrane domain in the CAR of the invention is the CD28 transmembrane domain. In one embodiment, the CD28 transmembrane domain comprises the nucleic acid sequence of SEQ ID NO: 5. In one embodiment, the CD28 transmembrane domain comprises the nucleic acid sequence that encodes the amino acid sequence of SEQ ID NO: 6. In another embodiment, the CD28 transmembrane domain comprises the amino acid sequence of SEQ ID NO: 6.

Intracellular (Cytoplasmic) Domain.

The intracellular (cytoplasmic) domain of the engineered T cells of the invention can provide activation of at least one of the normal effector functions of the immune cell. Effector function of a T cell, for example, may refer to cytolytic activity or helper activity, including the secretion of cytokines.

It will be appreciated that suitable intracellular molecules include (i.e., comprise), but are not limited to signaling domains derived from (or corresponding to) CD28, CD28T, OX-40, 4-1BB/CD137, CD2, CD7, CD27, CD30, CD40, programmed death-1 (PD-1), inducible T cell costimulator (ICOS), lymphocyte function-associated antigen-1 (LFA-1, CD1-1a/CD18), CD3 gamma, CD3 delta, CD3 epsilon, CD247, CD276 (B7-H3), LIGHT, (TNFSF14), NKG2C, Ig alpha (CD79a), DAP-10, Fc gamma receptor, MHC class 1 molecule, TNF receptor proteins, an Immunoglobulin protein, cytokine receptor, integrins, Signaling Lymphocytic Activation Molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL-2R beta, IL-2R gamma, IL-7R alpha, VLA1, CD49a, ITGA4, IA4, CD49D, ITGA6, VLA-6, CD49f, ITGAD, CD1 ld, ITGAE, CD103, ITGAL, CD1 la, LFA-1, ITGAM, CD1 lb, ITGAX, CD1 lc, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof.

In a preferred embodiment, the intracellular/cytoplasmic domain of the CAR can be designed to comprise the CD3 zeta domain by itself or combined with any other desired intracellular domain(s) useful in the context of the CAR of the invention. For example, the intracellular domain of the CAR can comprise a CD3 zeta chain portion and a portion of a costimulatory signaling molecule. The intracellular signaling sequences within the intracellular signaling portion of the CAR of the invention may be linked to each other in a random or specified order.

In another preferred embodiment, the intracellular domain is designed to comprise the activating domain of CD3 zeta and a signaling domain of CD28. In another embodiment, the intracellular domain is designed to comprise the activating domain of CD3 zeta and a signaling domain of 4-1BB. In another embodiment, the intracellular domain in the CAR is designed to comprise a portion of CD28 and CD3 zeta, wherein the intracellular CD28 comprises the nucleic acid sequence set forth in SEQ ID NO: 7 and the amino acid sequence set forth in SEQ ID NO. 8. The CD3 zeta nucleic acid sequence is set forth in SEQ ID NO: 9, and the amino acid sequence is set forth in SEQ ID NO. 8.

It will be appreciated that one preferred orientation of the CARs in accordance with the invention comprises an antigen binding molecule (such as scFv) in tandem with an extracellular and/or hinge domain, a costimulatory domain, and an activating domain. It will be further appreciated that multiple domains can be utilized in tandem.

In some embodiments, isolated nucleic acids are provided comprising a promoter operably linked to a first polynucleotide encoding an antigen binding molecule, at least one costimulatory molecule, and an activating domain. In some embodiments, the nucleic acid construct is contained within a viral vector. In some embodiments, the viral vector is selected from the group consisting of retroviral vectors, murine leukemia virus vectors, SFG vectors, adenoviral vectors, lentiviral vectors, adeno-associated virus (AAV) vectors, Herpes virus vectors, and vaccinia virus vectors. In some embodiments, the nucleic acid is contained within a plasmid.

In some embodiments, the engineered immune cell is a T cell, tumor infiltrating lymphocyte (TIL), NK cell, TCR-expressing cell, dendritic cell, or NK-T cell. In some embodiments, the cell is obtained or prepared from peripheral blood. In some embodiments, the cell is obtained or prepared from peripheral blood mononuclear cells (PBMCs). In some embodiments, the cell is obtained or prepared from bone marrow. In some embodiments, the cell is obtained or prepared from umbilical cord blood. In some embodiments, the cell is a human cell. In some embodiments, the cell is transfected or transduced by the nucleic acid vector using a method selected from the group consisting of electroporation, sonoporation, biolistics (e.g., Gene Gun), lipid transfection, polymer transfection, nanoparticles, or polyplexes.

In some embodiments, chimeric antigen receptors are expressed in the engineered immune cells that comprise the nucleic acids of the present application. These chimeric antigen receptors of the present application may comprise, in some embodiments, (i) an antigen binding molecule (such as an scFv), (ii) a transmembrane region, and (iii) a T cell activation molecule or region.

It is to be further understood that wherever aspects are described herein with the language "comprising," otherwise analogous aspects described in terms of "consisting of" and/or "consisting essentially of" are also provided.

Additionally, the terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% (i.e., ±10%). For example, about 3 mg can include any number between 2.7 mg and 3.3 mg (for 10%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

Antigen Binding Molecules

Antigen binding molecules are within the scope of the invention. An "antigen binding molecule" as used herein means any protein that binds a specified target antigen. In the instant application, the specified target antigen is the CLL-1 protein or fragment thereof. Antigen binding molecules include, but are not limited to antibodies and binding parts thereof, such as immunologically functional fragments. Peptibodies (i.e., Fc fusion molecules comprising peptide binding domains) are another example of suitable antigen binding molecules.

In certain embodiments, the invention is directed to an antigen binding molecule comprising:
- (a) a heavy chain variable region (VH) complementarity determining region (CDR) 1 comprising the amino acid sequence $GX_2X_3X_4X_5X_6X_7X_8X_9$ (SEQ ID NO: 134), wherein $X_2$ is G, F, or Y; $X_3$ is S or T; $X_4$ is I, F, or L; $X_5$ is S or T; $X_6$ is not present or S; $X_7$ is not present or G; $X_8$ is not present or E or G; and $X_9$ is F, L, or Y;
- (b) a heavy chain variable region (VH) complementarity determining region (CDR) 2 comprising the amino acid sequence $X_1X_2X_3X_4X_5X_6$ (SEQ ID NO: 135), wherein $X_1$ is D, H, S, or Y; $X_2$ is H, P, or Y; $X_3$ is D, E, or S; $X_4$ is D or G; $X_5$ is G or S; and $X_6$ is not present of D or E;
- (c) a heavy chain variable region (VH) complementarity determining region (CDR) 3, comprising the amino acid sequence $X_1X_2X_3X_4X_5X_6X_7X_8X_9X_{10}X_{11}X_{12}DY$ (SEQ ID NO: 136), wherein $X_1$ is E or L; $X_2$ is R, S, or V; $X_3$ is R or Y; $X_4$ is C, G, or S; $X_5$ is not present or G or I; $X_6$ is not present or G; $X_7$ is not present or D; $X_8$ is not present or C; $X_9$ is not present or W or Y; $X_{10}$ is not present or P or S; $X_{11}$ is not present or G or Y; and $X_{12}$ is F or R;
- (d) a light chain variable region (VL) CDR1 comprising the amino acid sequence $X_1ASQX_5X_6X_7X_8X_9LX_{11}$ (SEQ ID NO: 137), wherein $X_1$ is Q or R; $X_5$ is D or S; $X_6$ is I or V; $X_7$ is N or S; $X_8$ is N or S; $X_9$ is F, L, or Y; and $X_{11}$ is N or T;
- (e) a light chain variable region (VL) CDR2 comprising the amino acid sequence $X_1ASX_4X_5X_6X_7$ (SEQ ID NO: 138), wherein $X_1$ is D or G; $X_4$ is N, S, or T; $X_5$ is L or R; $X_6$ is A, E, or K; and $X_7$ is S or T; and/or
- (f) a light chain variable region (VL) CDR3 comprising the amino acid sequence $QQX_3X_4X_5X_6PX_8T$ (SEQ ID NO: 139), wherein $X_3$ is S or Y; $X_4$ is D, G, or Y; $X_5$ is N, S, or T; $X_6$ is L, T, or Y; and $X_8$ is F or I.

In some embodiments, the invention relates to antigen binding molecules comprising at least one of: (a) a variable heavy chain CDR1 comprising an amino acid sequence selected from the group consisting of SEQ ID NOs: 17, 51, 73, 95, 5, and 97; (b) a variable heavy chain CDR2 comprising an amino acid sequence selected from the group consisting of SEQ ID NOs 18, 52, 74, 96; (c) a variable heavy chain CDR3 comprising an amino acid sequence selected from the group consisting of SEQ ID NOs SEQ ID NO: 19, 53, 75, and 97; (d) a variable light chain CDR1 comprising an amino acid sequence selected from the group consisting of SEQ ID NOs: 22, 56, 78, and 100; (e) a variable light chain CDR2 comprising an amino acid sequence selected from the group consisting of SEQ ID NOs. 23, 57, 79, and 101; (f) a variable light chain CDR3 comprising an amino acid sequence selected from the group consisting of SEQ ID NOs. 24, 58, 80, and 102.

In other embodiments, the invention relates to antigen binding molecules (and chimeric antigen receptors comprising these molecules) comprising at least one of: (a) a VH region comprising the amino acid sequence of SEQ ID NO: 16 and a VL region comprising the amino acid sequence of SEQ ID NO: 21; (b) a VH region comprising the amino acid sequence of SEQ ID NO: 50 and a VL region comprising the amino acid sequence of SEQ ID NO: 55; (c) a VH region comprising the amino acid sequence of SEQ ID NO: 72 and a VL region comprising the amino acid sequence of SEQ ID NO: 77; (d) a VH region comprising the amino acid sequence of SEQ ID NO: 94 and a VL region comprising the amino acid sequence of SEQ ID NO: 99; and wherein the VH and VL region or regions are linked by at least one linker. In other embodiments, the invention relates to antigen binding molecules (and chimeric antigen receptors comprising these molecules) wherein the linker comprises at least one of SEQ ID NO. 130 and SEQ ID NO. 132.

In further embodiments, the invention relates to antigen binding molecules comprising a variable light ($V_L$) chain CDR3 comprising an amino acid sequence selected from the group consisting of SEQ ID NOs: 24, 58, 80, and 102.

In other embodiments, the invention relates to isolated polynucleotides encoding an antigen binding molecule that specifically binds to CLL-1, wherein the antigen binding molecule heavy chain comprises CDR1 (SEQ ID NO. 17), CDR2 (SEQ ID NO. 18), and CDR3 (SEQ ID NO. 19) and the antigen binding molecule light chain comprises CDR1 (SEQ ID NO. 22), CDR2 (SEQ ID NO. 23), and CDR3 (SEQ ID NO. 24).

In other embodiments, the invention relates to an antigen binding molecule that specifically binds to CLL-1, wherein the antigen binding molecule heavy chain comprises CDR1 (SEQ ID NO. 51), CDR2 (SEQ ID NO. 52), and CDR3 (SEQ ID NO. 53) and the antigen binding molecule light chain comprises CDR1 (SEQ ID NO. 56), CDR2 (SEQ ID NO. 57), and CDR3 (SEQ ID NO. 58).

In other embodiments, the invention relates an antigen binding molecule that specifically binds to CLL-1, wherein the antigen binding molecule heavy chain comprises CDR1 (SEQ ID NO. 73), CDR2 (SEQ ID NO. 74), and CDR3 (SEQ ID NO. 75) and the antigen binding molecule light chain comprises CDR1 (SEQ ID NO. 78), CDR2 (SEQ ID NO. 79), and CDR3 (SEQ ID NO. 80).

In other embodiments, the invention relates to isolated polynucleotides encoding an antigen binding molecule that specifically binds to CLL-1, wherein the antigen binding molecule heavy chain comprises CDR1 (SEQ ID NO. 95), CDR2 (SEQ ID NO. 96), and CDR3 (SEQ ID NO. 97) and the antigen binding molecule light chain comprises CDR1 (SEQ ID NO. 100), CDR2 (SEQ ID NO. 101), and CDR3 (SEQ ID NO. 102).

In certain embodiments, the present invention is directed to an isolated polynucleotide encoding an anti-CLL-1 antigen binding molecule which cross competes with one or more antibodies described herein or an antigen binding molecule thereof encoded by the polynucleotide. In one embodiment, the invention is directed to isolated polynucleotides encoding an anti-CLL-1 antigen binding molecule thereof which binds to the same epitope as one or more of the antigen binding molecules described herein.

In some embodiments, the antigen binding molecule binds to an antigen on a tumor cell. In some embodiments, the antigen binding molecule binds to an antigen on a cell involved in a hyperproliferative disease or to a viral or bacterial antigen. In further embodiments, the antigen binding molecule is an antibody of fragment thereof, including one or more of the complementarity determining regions (CDRs) thereof. In further embodiments, the antigen binding molecule is a single chain variable fragment (scFv).

The term "immunologically functional fragment" (or "fragment") of an antigen binding molecule is a species of antigen binding molecule comprising a portion (regardless of how that portion is obtained or synthesized) of an antibody that lacks at least some of the amino acids present in a full-length chain but which is still capable of specifically binding to an antigen. Such fragments are biologically active in that they bind to the target antigen and can compete with other antigen binding molecules, including intact antibodies, for binding to a given epitope. In some embodiments, the fragments are neutralizing fragments. In some embodiments, the fragments can block or reduce the activity of CLL-1.

In one aspect, such a fragment will retain at least one CDR present in the full-length light or heavy chain, and in some embodiments will comprise a single heavy chain and/or light chain or portion thereof. These fragments can be produced by recombinant DNA techniques, or can be produced by enzymatic or chemical cleavage of antigen binding molecules, including intact antibodies.

Immunologically functional immunoglobulin fragments include, but are not limited to, scFv fragments, Fab fragments (Fab', F(ab')$_2$, and the like), one or more CDR, a diabody (heavy chain variable domain on the same polypeptide as a light chain variable domain, connected via a short peptide linker that is too short to permit pairing between the two domains on the same chain), domain antibodies, and single-chain antibodies. These fragments can be derived from any mammalian source, including but not limited to human, mouse, rat, camelid or rabbit. As will be appreciated by one of skill in the art, an antigen binding molecule can include non-protein components.

Variants of the antigen binding molecules are also within the scope of the invention, e.g., variable light and/or variable heavy chains that each have at least 70-80%, 80-85%, 85-90%, 90-95%, 95-97%, 97-99%, or above 99% identity to the amino acid sequences of the sequences described herein. In some instances, such molecules include at least one heavy chain and one light chain, whereas in other instances the variant forms contain two identical light chains and two identical heavy chains (or subparts thereof). A skilled artisan will be able to determine suitable variants of the antigen binding molecules as set forth herein using well-known techniques. In certain embodiments, one skilled in the art can identify suitable areas of the molecule that may be changed without destroying activity by targeting regions not believed to be important for activity.

In certain embodiments, the polypeptide structure of the antigen binding molecules is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof, respectively. In some embodiments, the antigen binding molecule comprises or consists of avimers.

In some embodiments, an antigen binding molecule to CLL-1 is administered as part of a CAR, TCR, or other immune cell. In such immune cells, the antigen binding molecule to CLL-1 can be under the control of the same promoter region, or a separate promoter. In certain embodiments, the genes encoding protein agents and/or an antigen binding molecule to CLL-1 can be in separate vectors.

The invention further provides for pharmaceutical compositions comprising an antigen binding molecule to CLL-1 together with a pharmaceutically acceptable diluent, carrier, solubilizer, emulsifier, preservative and/or adjuvant. In certain embodiments, pharmaceutical compositions will include more than one different antigen binding molecule to CLL-1. In certain embodiments, pharmaceutical compositions will include more than one antigen binding molecule to CLL-1 wherein the antigen binding molecules to CLL-1 bind more than one epitope. In some embodiments, the various antigen binding molecules will not compete with one another for binding to CLL-1.

In other embodiments, the pharmaceutical composition can be selected for parenteral delivery, for inhalation, or for delivery through the digestive tract, such as orally. The preparation of such pharmaceutically acceptable compositions is within the ability of one skilled in the art. In certain embodiments, buffers are used to maintain the composition at physiological pH or at a slightly lower pH, typically within a pH range of from about 5 to about 8. In certain embodiments, when parenteral administration is contemplated, a therapeutic composition can be in the form of a pyrogen-free, parenterally acceptable aqueous solution comprising a desired antigen binding molecule to CLL-1, with or without additional therapeutic agents, in a pharmaceutically acceptable vehicle. In certain embodiments, a vehicle for parenteral injection is sterile distilled water in which an antigen binding molecule to CLL-1, with or without at least one additional therapeutic agent, is formulated as a sterile, isotonic solution, properly preserved. In certain embodiments, the preparation can involve the formulation of the desired molecule with polymeric compounds (such as polylactic acid or polyglycolic acid), beads or liposomes that can provide for the controlled or sustained release of the product which can then be delivered via a depot injection. In certain embodiments, implantable drug delivery devices can be used to introduce the desired molecule.

In some embodiments, the antigen binding molecule is used as a diagnostic or validation tool. The antigen binding molecule can be used to assay the amount of CLL-1 present in a sample and/or subject. In some embodiments, the diagnostic antigen binding molecule is not neutralizing. In some embodiments, the antigen binding molecules disclosed herein are used or provided in an assay kit and/or method for the detection of CLL-1 in mammalian tissues or cells in order to screen/diagnose for a disease or disorder associated with changes in levels of CLL-1. The kit can comprise an antigen binding molecule that binds CLL-1, along with means for indicating the binding of the antigen binding molecule with CLL-1, if present, and optionally CLL-1 protein levels.

The antigen binding molecules will be further understood in view of the definitions and descriptions below.

An "Fc" region comprises two heavy chain fragments comprising the CH1 and CH2 domains of an antibody. The two heavy chain fragments are held together by two or more disulfide bonds and by hydrophobic interactions of the CH3 domains.

A "Fab fragment" comprises one light chain and the CH1 and variable regions of one heavy chain. The heavy chain of a Fab molecule cannot form a disulfide bond with another heavy chain molecule. A "Fab'" fragment comprises one light chain and a portion of one heavy chain that contains the VH domain and the CH1 domain and also the region between the CH1 and CH2 domains, such that an interchain disulfide bond can be formed between the two heavy chains of two Fab' fragments to form an F(ab')$_2$ molecule. An "F(ab')$_2$ fragment" contains two light chains and two heavy chains containing a portion of the constant region between the CH1 and CH2 domains, such that an interchain disulfide bond is formed between the two heavy chains. An F(ab')$_2$ fragment thus is composed of two Fab' fragments that are held together by a disulfide bond between the two heavy chains.

The "Fv region" comprises the variable regions from both the heavy and light chains, but lacks the constant regions.

"Single chain variable fragment" ("scFv", also termed "single-chain antibody") refers to Fv molecules in which the heavy and light chain variable regions have been connected by a flexible linker to form a single polypeptide chain, which forms an antigen binding region. See PCT application WO88/01649 and U.S. Pat. Nos. 4,946,778 and 5,260,203, the disclosures of which are incorporated by reference in their entirety.

A "bivalent antigen binding molecule" comprises two antigen binding sites. In some instances, the two binding sites have the same antigen specificities. Bivalent antigen binding molecules can be bispecific. A "multispecific antigen binding molecule" is one that targets more than one antigen or epitope. A "bispecific," "dual-specific" or "bifunctional" antigen binding molecule is a hybrid antigen binding molecule or antibody, respectively, having two different antigen binding sites. The two binding sites of a bispecific antigen binding molecule will bind to two different epitopes, which can reside on the same or different protein targets.

An antigen binding molecule is said to "specifically bind" its target antigen when the dissociation constant ($K_d$) is ~$1 \times 10^{-7}$ M. The antigen binding molecule specifically binds antigen with "high affinity" when the $K_d$ is $1$–$5 \times 10^{-9}$ M, and with "very high affinity" when the $K_d$ is $1$–$5 \times 10^{-10}$ M. In one embodiment, the antigen binding molecule has a $K_d$ of $10^{-9}$ M. In one embodiment, the off-rate is <$1 \times 10^{-5}$. In other embodiments, the antigen binding molecules will bind to human CLL-1 with a $K_d$ of between about $10^{-7}$ M and $10^{-13}$ M, and in yet another embodiment the antigen binding molecules will bind with a $K_d$ $1.0$–$5 \times 10^{-10}$.

In some embodiments, the antibody or antigen binding molecules of the present invention specifically bind CLL-1 (e.g., hCLL-1). In certain embodiments, an anti-CLL-1 antibody or antigen binding molecule of the present invention binds human CLL-1 with a $K_D$ of less than $1 \times 10^{-6}$ M, less than $1 \times 10^{-7}$ M, less than $1 \times 10^{-8}$ M, or less than $1 \times 10^{-9}$ M. In one particular embodiment, the anti-CLL-1 antibody or antigen binding molecules binds human CLL-1 with a $K_D$ of less than $1 \times 10^{-7}$ M. In another embodiment, the anti-CLL-1 antibody or antigen binding molecules binds human CLL-1 with a $K_D$ of less than $1 \times 10^{-8}$ M. In some embodiments, the anti-CLL-1 antibody or antigen binding molecules binds human CLL-1 with a $K_D$ of about $1 \times 10^{-7}$ M, about $2 \times 10^{-7}$ M, about $3 \times 10^{-7}$ M, about $4 \times 10^{-7}$ M, about $5 \times 10^{-7}$ M, about $6 \times 10^{-7}$ M, about $7 \times 10^{-7}$ M, about $8 \times 10^{-7}$ M, about $9 \times 10^{-7}$ M, about $1 \times 10^{-8}$ M, about $2 \times 10^{-8}$ M, about $3 \times 10^{-8}$ M, about $4 \times 10^{-8}$ M, about $5 \times 10^{-8}$ M, about $6 \times 10^{-8}$ M, about $7 \times 10^{-8}$ M, about $8 \times 10^{-8}$ M, about $9 \times 10^{-8}$ M, about $1 \times 10^{-9}$ M, about $2 \times 10^{-9}$ M, about $3 \times 10^{-9}$ M, about $4 \times 10^{-9}$ M, about $5 \times 10^{-9}$ M, about $6 \times 10^{-9}$ M, about $7 \times 10^{-9}$ M, about $8 \times 10^{-9}$ M, about $9 \times 10^{-9}$ M, about $1 \times 10^{-10}$ M, or about $5 \times 10^{-10}$ M. In certain embodiments, the $K_D$ is calculated as the quotient of $k_{off}/k_{on}$, and the $K_{on}$ and $k_{off}$ are determined using a monovalent antibody, such as a Fab fragment, as measured by, e.g., BIAcore® surface plasmon resonance technology. In other embodiments, the $K_D$ is calculated as the quotient of $k_{off}/k_{on}$, and the $k_{on}$ and $k_{off}$ are determined using a bivalent antibody, such as a Fab fragment, as measured by, e.g., BIAcore® surface plasmon resonance technology.

In other embodiments, the anti-CLL-1 antibody or antigen binding molecule binds human CLL-1-Fc with a $K_D$ of less than $1 \times 10^{-9}$ M, less than $3 \times 10^{-9}$ M, less than $5 \times 10^{-9}$ M, less than $1 \times 10^{-10}$ M, less than $3 \times 10^{-10}$ M, or less than $5 \times 10^{-10}$ M. In other embodiments, the anti-CLL-1 antibody or antigen binding molecules binds cyno CLL-1-Fc with a $K_D$ of less than $1 \times 10^{-5}$ M, less than $1 \times 10^{-6}$ M, less than $1 \times 10^{-7}$ M, less than $1 \times 10^{-8}$ M, less than $1 \times 10^{-9}$ M, or less than $1 \times 10^{-10}$ M.

In some embodiments, the anti-CLL-1 antibody or antigen binding molecule binds human CLL-1 with an association rate ($k_{on}$) of less than $1 \times 10^{-4}$ M$^{-1}$ s$^{-1}$, less than $2 \times 10^{-4}$ M$^{-1}$ s$^{-1}$, less than $3 \times 10^{-4}$ M$^{-4}$ s$^{-1}$, less than $4 \times 10^{-4}$ M$^{-1}$ s$^{-1}$, less than $5 \times 10^{-4}$ M$^{-1}$ s$^{-1}$, less less than $7 \times 10^{-4}$ M$^{-1}$ s$^{-1}$, less than $8 \times 10^{-4}$ M$^{-1}$ s$^{-1}$, less than $9 \times 10^{-4}$ M$^{-1}$ s$^{-1}$, less than $1 \times 10^{-5}$ M$^{-1}$ s$^{-1}$, less than $2 \times 10^{-5}$ M$^{-1}$ s$^{-1}$, less than $3 \times 10^{-5}$ M$^{-1}$ s$^{-1}$, less than $4 \times 10^{-5}$ M$^{-1}$ s$^{-1}$, less than $5 \times 10^{-5}$ M$^{-1}$ s$^{-1}$, less than $6 \times 10^{-5}$ M$^{-1}$ s$^{-1}$, less than $7 \times 10^{-5}$ M$^{-1}$ s$^{-1}$, less than $8 \times 10^{-5}$ M$^{-1}$ s$^{-1}$, less than $9 \times 10^{-5}$ M$^{-1}$ s$^{-1}$, less than $1 \times 10^{-6}$ M$^{-1}$ s$^{-1}$, less than $2 \times 10^{-6}$ M$^{-1}$ s$^{-1}$, less than $3 \times 10^{-6}$ M$^{-1}$ s$^{-1}$, less than $4 \times 10^{-6}$ M$^{-1}$ s$^{-1}$, less than $5 \times 10^{-6}$ M$^{-1}$ s$^{-1}$, less than $6 \times 10^{-6}$ M$^{-1}$ s$^{-1}$, less than $7 \times 10^{-6}$ M$^{-1}$ s$^{-1}$, less than $8 \times 10^{-6}$ M$^{-1}$ s$^{-1}$, less than $9 \times 10^{-6}$ M$^{-1}$ s$^{-1}$, or less than $1 \times 10^{-7}$ M$^{-1}$ s$^{-1}$. In certain embodiments, the $k_{on}$ is determined using a monovalent antibody, such as a Fab fragment, as measured by, e.g., BIAcore® surface plasmon resonance technology. In other embodiments, the $k_{on}$ is determined using a bivalent antibody as measured by, e.g., BIAcore® surface plasmon resonance technology.

In some embodiments, the anti-CLL-1 antibody or antigen binding molecule binds human CLL-1 with an dissociation rate ($k_{off}$) of less than $1 \times 10^{-2}$ s$^{-1}$, less than $2 \times 10^{-2}$ s$^{-1}$, less than $3 \times 10^{-2}$ s$^{-1}$, less than $4 \times 10^{-2}$ s$^{-1}$, less than $5 \times 10^{-2}$ s$^{-1}$, less than $6 \times 10^{-2}$ s$^{-1}$, less than $7 \times 10^{-2}$ s$^{-1}$, less than $8 \times 10^{-2}$ s$^{-1}$, less than $9 \times 10^{-2}$ s$^{-1}$, less than $1 \times 10^{-3}$ s$^{-1}$, less than $2 \times 10^{-3}$ s$^{-1}$, less than $3 \times 10^{-3}$ s$^{-1}$, less than $4 \times 10^{-3}$ s$^{-1}$, less than $5 \times 10^{-3}$ s$^{-1}$, less than $6 \times 10^{-3}$ s$^{-1}$, less than $7 \times 10^{-3}$ s$^{-1}$, less than $8 \times 10^{-3}$ s$^{-1}$, less than $9 \times 10^{-3}$ s$^{-1}$, less than $1 \times 10^{-4}$ s$^{-1}$, less than $2 \times 10^{-4}$ s$^{-1}$, less than $3 \times 10^{-4}$ s$^{-1}$, less than $4 \times 10^{-4}$ s$^{-1}$, less than $5 \times 10^{-4}$ s$^{-1}$, less than $6 \times 10^{-4}$ s$^{-1}$, less than $7 \times 10^{-4}$ s$^{-1}$, less than $8 \times 10^{-4}$ s$^{-1}$, less than $9 \times 10^{-4}$ s$^{-1}$, less than $1 \times 10^{-4}$ s$^{-1}$, or less than $5 \times 10^{-4}$ s$^{-1}$. In certain embodiments, the $k_{off}$ is determined using a monovalent antibody, such as a Fab fragment, as measured by, e.g., BIAcore® surface plasmon resonance technology. In other embodiments, the $k_{off}$ is determined using a bivalent antibody as measured by, e.g., BIAcore® surface plasmon resonance technology.

An antigen binding molecule is said to be "selective" when it binds to one target more tightly than it binds to a second target.

The term "antibody" refers to an intact immunoglobulin of any isotype, or a fragment thereof that can compete with the intact antibody for specific binding to the target antigen, and includes, for instance, chimeric, humanized, fully human, and bispecific antibodies. An "antibody" is a species of an antigen binding molecule as defined herein. An intact antibody will generally comprise at least two full-length heavy chains and two full-length light chains, but in some instances can include fewer chains such as antibodies naturally occurring in camelids which can comprise only heavy chains. Antibodies can be derived solely from a single source, or can be chimeric, that is, different portions of the antibody can be derived from two different antibodies as described further below. The antigen binding molecules, antibodies, or binding fragments can be produced in hybridomas, by recombinant DNA techniques, or by enzymatic or chemical cleavage of intact antibodies. Unless otherwise indicated, the term "antibody" includes, in addition to antibodies comprising two full-length heavy chains and two full-length light chains, derivatives, variants, fragments, and muteins thereof, examples of which are described below. Furthermore, unless explicitly excluded, antibodies include monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates") and fragments thereof, respectively.

The variable regions typically exhibit the same general structure of relatively conserved framework regions (FR) joined by the 3 hypervariable regions (i.e., "CDRs"). The CDRs from the two chains of each pair typically are aligned by the framework regions, which can enable binding to a specific epitope. From N-terminal to C-terminal, both light and heavy chain variable regions typically comprise the domains FR1, CDR1, FR2, CDR2, FR3, CDR3 and FR4. By convention, CDR regions in the heavy chain are typically referred to as HC CDR1, CDR2, and CDR3. The CDR regions in the light chain are typically referred to as LC CDR1, CDR2, and CDR3. The assignment of amino acids to each domain is typically in accordance with the definitions of Kabat, Chothia, or the AbM definition.

The term "Kabat numbering" and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34).

In a specific embodiment, the CDRs of the antibodies described herein have been determined according to the Chothia numbering scheme.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 2

| | CDR Numbering | | | |
|---|---|---|---|---|
| Loop | Kabat | AbM | Chothia | Contact |
| L1 | L24--L34 | L24--L34 | L24--L34 | L30--L36 |
| L2 | L50--L56 | L50--L56 | L50--L56 | L46--L55 |
| L3 | L89--L97 | L89--L97 | L89--L97 | L89--L96 |
| H1 | H31--H35B (Kabat Numbering) | H26--H35B | H26--H32 . . . 34 | H30--H35B |
| H1 | H31--H35 (Chothia Numbering) | H26--H35 | H26--H32 | H30--H35 |
| H2 | H50--H65 | H50--H58 | H52--H56 | H47--H58 |
| H3 | H95--H102 | H95--H102 | H95--H102 | H93--H101 |

As used herein, the term "heavy chain" when used in reference to an antibody can refer to any distinct type, e.g., alpha (α), delta (δ), epsilon (ε), gamma (γ) and mu (μ), based on the amino acid sequence of the constant domain, which give rise to IgA, IgD, IgE, IgG and IgM classes of antibodies, respectively, including subclasses of IgG, e.g., IgG1, IgG2, IgG3 and IgG4.

As used herein, the term "light chain" when used in reference to an antibody can refer to any distinct type, e.g., kappa (κ) or lambda (λ) based on the amino acid sequence of the constant domains. Light chain amino acid sequences are well known in the art. In specific embodiments, the light chain is a human light chain.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. The variable region of an antibody typically determines specificity of a particular antibody for its target.

Variability is not evenly distributed throughout the variable domains of antibodies or antigen binding molecules; it is concentrated in sub-domains of each of the heavy and light chain variable regions. These subdomains are called "hypervariable regions" or "complementarity determining regions" (CDRs) as further described herein. The more conserved (i.e., non-hypervariable) portions of the variable domains are called the "framework" regions (FRM or FR) and provide a scaffold for the six CDRs in three dimensional space to form an antigen-binding surface. The variable domains of naturally occurring heavy and light chains each comprise four FRM regions (FR1, FR2, FR3, and FR4), largely adopting a (β-sheet configuration, connected by three hypervariable regions, which form loops connecting, and in some cases forming part of, the (β-sheet structure. The hypervariable regions in each chain are held together in close proximity by the FRM and, with the hypervariable regions from the other chain, contribute to the formation of the antigen-binding site (see Kabat et al., described further herein.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol, 1996, 263: 800). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "canonical structure" may also include considerations as to the linear sequence of the antibody, for example, as catalogued by Kabat (Kabat et al., herein). The Kabat numbering scheme (system) is a widely adopted standard for numbering the amino acid residues of an antibody variable domain in a consistent manner and is the preferred scheme applied in the present invention as also mentioned elsewhere herein. Additional structural considerations can also be used to determine the canonical structure of an antibody. For example, those differences not fully reflected by Kabat numbering can be described by the numbering system of Chothia et al. and/or revealed by other techniques, for example, crystallography and two- or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al. (herein) and their implications for construing canonical aspects of antibody structure, are described in the literature. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988.

The CDR3 of the light chain and, particularly, the CDR3 of the heavy chain may constitute the most important determinants in antigen binding within the light and heavy chain variable regions. In some antibody constructs, the heavy chain CDR3 appears to constitute the major area of contact between the antigen and the antibody. In vitro selection schemes in which CDR3 alone is varied can be used to vary the binding properties of an antibody or determine which residues contribute to the binding of an antigen. Hence, CDR3 is typically the greatest source of molecular diversity within the antibody-binding site. H3, for example, can be as short as two amino acid residues or greater than 26 amino acids.

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIAcore® or KinExA.

The term "neutralizing" refers to an antigen binding molecule, scFv, or antibody, respectively, that binds to a ligand and prevents or reduces the biological effect of that ligand. This can be done, for example, by directly blocking a binding site on the ligand or by binding to the ligand and altering the ligand's ability to bind through indirect means (such as structural or energetic alterations in the ligand). In some embodiments, the term can also denote an antigen binding molecule that prevents the protein to which it is bound from performing a biological function.

The term "target" or "antigen" refers to a molecule or a portion of a molecule capable of being bound by an antigen binding molecule. In certain embodiments, a target can have one or more epitopes.

The term "compete" when used in the context of antigen binding molecules that compete for the same epitope means competition between antigen binding molecules as determined by an assay in which the antigen binding molecule (e.g., antibody or immunologically functional fragment thereof) being tested prevents or inhibits (e.g., reduces) specific binding of a reference antigen binding molecule to an antigen. Numerous types of competitive binding assays can be used to determine if one antigen binding molecule competes with another, for example: solid phase direct or indirect radioimmunoassay (RIA), solid phase direct or indirect enzyme immunoassay (EIA), sandwich competition assay (Stahli et al., 1983, Methods in Enzymology 9:242-253); solid phase direct biotin-avidin EIA (Kirkland et al., 1986, J. Immunol. 137:3614-3619), solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

As used herein, the term "epitope" refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R. et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In certain embodiments, the label or marker can also be therapeutic. Various methods of labeling polypeptides and glycoproteins are known in the art and can be used.

Methods of Treatment

Using adoptive immunotherapy, native T cells can be (i) removed from a patient, (ii) genetically engineered to express a chimeric antigen receptor (CAR) that binds to at least one tumor antigen (iii) expanded ex vivo into a larger population of engineered T cells, and (iv) reintroduced into the patient. See e.g., U.S. Pat. Nos. 7,741,465, and 6,319,494, Eshhar et al. (Cancer Immunol, supra); Krause et al. (supra); Finney et al. (supra). After the engineered T cells are reintroduced into the patient, they mediate an immune response against cells expressing the tumor antigen. See e.g., Krause et al., J. Exp. Med., Volume 188, No. 4, 1998 (619-626). This immune response includes secretion of IL-2 and other cytokines by T cells, the clonal expansion of T cells recognizing the tumor antigen, and T cell-mediated specific killing of target-positive cells. See Hombach et al., Journal of Immun. 167: 6123-6131 (2001).

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory $T_{SCM}$ cells, like naive cells, are CD45RO−, CCR7+, CD45RA+, CD62L+(L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory $T_{EM}$ cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising at least one costimulatory domain and at least one activating domain. The costimulatory domain can be derived from (or correspond to), e.g., CD28, and the activating domain can be derived from (or correspond to) e.g., CD3-zeta. In certain embodiments, the CAR is designed to have two, three, four, or more costimulatory domains.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

In some aspects, the invention therefore comprises a method for treating or preventing a condition associated with undesired and/or elevated CLL-1 levels in a patient, comprising administering to a patient in need thereof an effective amount of at least one isolated antigen binding molecule, CAR, or TCR disclosed herein.

Methods are provided for treating diseases or disorders, including cancer. In some embodiments, the invention relates to creating a T cell-mediated immune response in a subject, comprising administering an effective amount of the engineered immune cells of the present application to the subject. In some embodiments, the T cell-mediated immune response is directed against a target cell or cells. In some embodiments, the engineered immune cell comprises a chimeric antigen receptor (CAR), or a T cell receptor (TCR). In some embodiments, the target cell is a tumor cell. In some aspects, the invention comprises a method for treating or preventing a malignancy, said method comprising administering to a subject in need thereof an effective amount of at least one isolated antigen binding molecule described herein. In some aspects, the invention comprises a method for treating or preventing a malignancy, said method comprising administering to a subject in need thereof an effective amount of at least one immune cell, wherein the immune cell comprises at least one chimeric antigen receptor, T cell receptor, and/or isolated antigen binding molecule as described herein.

In some aspects, the invention comprises a pharmaceutical composition comprising at least one antigen binding molecule as described herein and a pharmaceutically acceptable excipient. In some embodiments, the pharmaceutical composition further comprises an additional active agent.

The antigen binding molecules, CARs, TCRs, immune cells, and the like of the invention can be used to treat myeloid diseases including but not limited to acute myeloid leukemia (AML), chronic myelogenous leukemia (CML), chronic myelomonocytic leukemia (CMML), juvenile myelomonocytic leukemia, atypical chronic myeloid leukemia, acute promyelocytic leukemia (APL), acute monoblastic leukemia, acute erythroid leukemia, acute megakaryoblastic leukemia, myelodysplastic syndrome (MDS), myeloproliferative disorder, myeloid neoplasm, myeloid sarcoma), Blastic Plasmacytoid Dendritic Cell Neoplasm (BPDCN), or combinations thereof. Additional diseases include inflammatory and/or autoimmune diseases such as rheumatoid arthritis, psoriasis, allergies, asthma, Crohn's disease, IBD, IBS, fibromyalga, mastocytosis, and Celiac disease.

It will be appreciated that target doses for $CAR^+$/$CAR$-$T^+$/$TCR^+$ cells can range from $1\times10^6$-$2\times10^{10}$ cells/kg, preferably $2\times10^6$ cells/kg, more preferably. It will be appreciated that doses above and below this range may be appropriate for certain subjects, and appropriate dose levels can be determined by the healthcare provider as needed. Additionally, multiple doses of cells can be provided in accordance with the invention.

Also provided are methods for reducing the size of a tumor in a subject, comprising administering to the subject an engineered cell of the present invention to the subject, wherein the cell comprises a chimeric antigen receptor, a T cell receptor, or a T cell receptor based chimeric antigen receptor comprising an antigen binding molecule binds to an antigen on the tumor. In some embodiments, the subject has a solid tumor, or a blood malignancy such as lymphoma or leukemia. In some embodiments, the engineered cell is delivered to a tumor bed. In some embodiments, the cancer is present in the bone marrow of the subject. In some embodiments, the engineered cells are autologous T cells. In some embodiments, the engineered cells are allogeneic T cells. In some embodiments, the engineered cells are heterologous T cells. In some embodiments, the engineered cells of the present application are transfected or transduced in vivo. In other embodiments, the engineered cells are transfected or transduced ex vivo. As used herein, the term "in vitro cell" refers to any cell which is cultured ex vivo. In particular, an in vitro cell can include a T cell.

The methods can further comprise administering one or more chemotherapeutic agent. In certain embodiments, the chemotherapeutic agent is a lymphodepleting (preconditioning) chemotherapeutic. Beneficial preconditioning treatment regimens, along with correlative beneficial biomarkers are described in U.S. Provisional Patent Applications 62/262,143 and 62/167,750 which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). A preferred dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient.

In other embodiments, the antigen binding molecule, transduced (or otherwise engineered) cells (such as CARs or TCRs), and the chemotherapeutic agent are administered each in an amount effective to treat the disease or condition in the subject.

In certain embodiments, compositions comprising CAR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2', 2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RF S2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell, polypeptide, or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell, polypeptide, or nucleic acid. In other embodiments, the chemotherapeutic agent is administered at least 1 month before administering the cell, polypeptide, or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (Opdivo®), pembrolizumab (Keytruda®), pembrolizumab, pidilizumab, and atezolizumab.

Additional therapeutic agents suitable for use in combination with the invention include, but are not limited to, ibrutinib (Imbruvica®), ofatumumab (Arzerra®, rituximab (Rituxan®), bevacizumab (Avastin®), trastuzumab (Herceptin®), trastuzumab emtansine (KADCYLA®, imatinib (Gleevec®), cetuximab (Erbitux®, panitumumab) (Vectibix®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In additional embodiments, the composition comprising CAR-containing immune can be administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In certain embodiments, the compositions described herein are administered in conjunction with a cytokine. "Cytokine" as used herein is meant to refer to proteins released by one cell population that act on another cell as intercellular mediators. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In some aspects, the invention comprises an antigen binding molecule that binds to CLL-1 with a $K_d$ that is smaller than 100 pM. In some embodiments, the antigen binding molecule binds with a $K_d$ that is smaller than 10 pM. In other embodiments, the antigen binding molecule binds with a $K_d$ that is less than 5 pM.

Methods of Making

A variety of known techniques can be utilized in making the polynucleotides, polypeptides, vectors, antigen binding molecules, immune cells, compositions, and the like according to the invention.

Prior to the in vitro manipulation or genetic modification of the immune cells described herein, the cells may be obtained from a subject. In some embodiments, the immune cells comprise T cells. T cells can be obtained from a number of sources, including peripheral blood mononuclear cells (PBMCs), bone marrow, lymph nodes tissue, cord blood, thymus tissue, tissue from a site of infection, ascites, pleural effusion, spleen tissue, and tumors. In certain embodiments, T cells can be obtained from a unit of blood collected from the subject using any number of techniques known to the skilled person, such as FICOLL™ separation. Cells may preferably be obtained from the circulating blood of an individual by apheresis. The apheresis product typically contains lymphocytes, including T cells, monocytes, granulocytes, B cells, other nucleated white blood cells, red blood cells, and platelets. In certain embodiments, the cells collected by apheresis may be washed to remove the plasma fraction, and placed in an appropriate buffer or media for subsequent processing. The cells may be washed with PBS. As will be appreciated, a washing step may be used, such as by using a semiautomated flowthrough centrifuge—for example, the Cobe™ 2991 cell processor, the Baxter CytoMate™, or the like. After washing, the cells may be resuspended in a variety of biocompatible buffers, or other saline solution with or without buffer. In certain embodiments, the undesired components of the apheresis sample may be removed.

In certain embodiments, T cells are isolated from PBMCs by lysing the red blood cells and depleting the monocytes, for example, using centrifugation through a PERCOLL™ gradient. A specific subpopulation of T cells, such as $CD28^+$, $CD4^+$, $CD8^+$, $CD45RA^-$, and $CD45RO^+$ T cells can be further isolated by positive or negative selection techniques known in the art. For example, enrichment of a T cell population by negative selection can be accomplished with a combination of antibodies directed to surface markers unique to the negatively selected cells. One method for use herein is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. Flow cytometry and cell sorting may also be used to isolate cell populations of interest for use in the present invention.

PBMCs may be used directly for genetic modification with the immune cells (such as CARs or TCRs) using methods as described herein. In certain embodiments, after isolating the PBMCs, T lymphocytes can be further isolated and both cytotoxic and helper T lymphocytes can be sorted into naive, memory, and effector T cell subpopulations either before or after genetic modification and/or expansion.

In some embodiments, $CD8^+$ cells are further sorted into naive, central memory, and effector cells by identifying cell surface antigens that are associated with each of these types of $CD8^+$ cells. In some embodiments, the expression of phenotypic markers of central memory T cells include CD45RO, CD62L, CCR7, CD28, CD3, and CD127 and are negative for granzyme B. In some embodiments, central memory T cells are $CD45RO^+$, $CD62L^+$, $CD8^+$ T cells. In some embodiments, effector T cells are negative for CD62L, CCR7, CD28, and CD127, and positive for granzyme B and perforin. In certain embodiments, $CD4^+$ T cells are further sorted into subpopulations. For example, $CD4^+$ T helper cells can be sorted into naive, central memory, and effector cells by identifying cell populations that have cell surface antigens.

The immune cells, such as T cells, can be genetically modified following isolation using known methods, or the immune cells can be activated and expanded (or differentiated in the case of progenitors) in vitro prior to being genetically modified. In another embodiment, the immune cells, such as T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, for example, in U.S. Pat. Nos. 6,905,874; 6,867,041; 6,797,514; and PCT WO2012/079000, the contents of which are hereby incorporated by reference in their entirety. Generally, such methods include contacting PBMC or isolated T cells with a stimulatory molecule and a costimulatory molecule, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells may be activated and stimulated to proliferate with feeder cells and appropriate antibodies and cytokines using methods such as those described in U.S. Pat. Nos. 6,040,177; 5,827,642; and WO2012129514, the contents of which are hereby incorporated by reference in their entirety.

Certain methods for making the constructs and engineered immune cells of the invention are described in PCT application PCT/US15/14520, the contents of which are hereby incorporated by reference in their entirety. Additional methods of making the constructs and cells can be found in U.S. provisional patent application No. 62/244,036 the contents of which are hereby incorporated by reference in their entirety.

It will be appreciated that PBMCs can further include other cytotoxic lymphocytes such as NK cells or NKT cells. An expression vector carrying the coding sequence of a chimeric receptor as disclosed herein can be introduced into a population of human donor T cells, NK cells or NKT cells. Successfully transduced T cells that carry the expression vector can be sorted using flow cytometry to isolate CD3 positive T cells and then further propagated to increase the number of these CAR expressing T cells in addition to cell activation using anti-CD3 antibodies and IL-2 or other methods known in the art as described elsewhere herein. Standard procedures are used for cryopreservation of T cells expressing the CAR for storage and/or preparation for use in a human subject. In one embodiment, the in vitro transduction, culture and/or expansion of T cells are performed in the absence of non-human animal derived products such as fetal calf serum and fetal bovine serum.

For cloning of polynucleotides, the vector may be introduced into a host cell (an isolated host cell) to allow replication of the vector itself and thereby amplify the copies of the polynucleotide contained therein. The cloning vectors may contain sequence components generally include, without limitation, an origin of replication, promoter sequences, transcription initiation sequences, enhancer sequences, and selectable markers. These elements may be selected as appropriate by a person of ordinary skill in the art. For example, the origin of replication may be selected to promote autonomous replication of the vector in the host cell.

In certain embodiments, the present disclosure provides isolated host cells containing the vector provided herein. The host cells containing the vector may be useful in expression or cloning of the polynucleotide contained in the vector. Suitable host cells can include, without limitation, prokaryotic cells, fungal cells, yeast cells, or higher eukaryotic cells such as mammalian cells. Suitable prokaryotic cells for this purpose include, without limitation, eubacteria, such as Gram-negative or Gram-positive organisms, for example, Enterobactehaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis*, *Pseudomonas* such as *P. aeruginosa*, and *Streptomyces*.

The vector can be introduced to the host cell using any suitable methods known in the art, including, without limitation, DEAE-dextran mediated delivery, calcium phosphate precipitate method, cationic lipids mediated delivery, liposome mediated transfection, electroporation, microprojectile bombardment, receptor-mediated gene delivery, delivery mediated by polylysine, histone, chitosan, and peptides. Standard methods for transfection and transformation of cells for expression of a vector of interest are well known in the art. In a further embodiment, a mixture of different expression vectors can be used in genetically modifying a donor population of immune effector cells wherein each vector encodes a different CAR as disclosed herein. The resulting transduced immune effector cells form a mixed population of engineered cells, with a proportion of the engineered cells expressing more than one different CARs.

In one embodiment, the invention provides a method of storing genetically engineered cells expressing CARs or TCRs which target a CLL-1 protein. This involves cryopreserving the immune cells such that the cells remain viable upon thawing. A fraction of the immune cells expressing the CARs can be cryopreserved by methods known in the art to provide a permanent source of such cells for the future treatment of patients afflicted with a malignancy. When needed, the cryopreserved transformed immune cells can be thawed, grown and expanded for more such cells.

As used herein, "cryopreserve" refers to the preservation of cells by cooling to sub-zero temperatures, such as (typically) 77 Kelvin or −196° C. (the boiling point of liquid nitrogen). Cryoprotective agents are often used at sub-zero temperatures to prevent the cells being preserved from damage due to freezing at low temperatures or warming to room temperature. Cryopreservative agents and optimal cooling rates can protect against cell injury. Cryoprotective agents which can be used in accordance with the invention include but are not limited to: dimethyl sulfoxide (DMSO) (Lovelock & Bishop, Nature (1959); 183: 1394-1395; Ashwood-Smith, Nature (1961); 190: 1204-1205), glycerol, polyvinylpyrrolidine (Rinfret, Ann. N.Y. Acad. Sci. (1960); 85: 576), and polyethylene glycol (Sloviter & Ravdin, Nature (1962); 196: 48). The preferred cooling rate is 1°-3° C./minute.

The term, "substantially pure," is used to indicate that a given component is present at a high level. The component is desirably the predominant component present in a composition. Preferably it is present at a level of more than 30%, of more than 50%, of more than 75%, of more than 90%, or even of more than 95%, said level being determined on a dry weight/dry weight basis with respect to the total composition under consideration. At very high levels (e.g. at levels of more than 90%, of more than 95% or of more than 99%) the component can be regarded as being in "pure form." Biologically active substances of the present invention (CARs, TCRs, isolated polypeptides, isolated nucleic acid molecules, antigen binding molecules, moieties) can be provided in a form that is substantially free of one or more contaminants with which the substance might otherwise be associated. When a composition is substantially free of a given contaminant, the contaminant will be at a low level (e.g., at a level of less than 10%, less than 5%, or less than 1% on the dry weight/dry weight basis set out above).

In some embodiments, the cells are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

Desired treatment amounts of cells in the composition is generally at least 2 cells (for example, at least 1 CD8$^+$ central memory T cell and at least 1 CD4$^+$ helper T cell subset) or is more typically greater than $10^2$ cells, and up to $10^6$, up to and including $10^8$ or $10^9$ cells and can be more than $10^{10}$ cells. The number of cells will depend upon the desired use for which the composition is intended, and the type of cells included therein. The density of the desired cells is typically greater than $10^6$ cells/ml and generally is greater than $10^7$ cells/ml, generally $10^8$ cells/ml or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen (CLL-1), lower numbers of cells, in the range of $10^6$/kilogram ($10^6$-$10^{11}$ per patient) may be administered. CAR treatments may be administered multiple times at dosages within these ranges. The cells may be autologous, allogeneic, or heterologous to the patient undergoing therapy.

The CAR expressing cell populations of the present invention may be administered either alone, or as a pharmaceutical composition in combination with diluents and/or with other components such as IL-2 or other cytokines or cell populations. Pharmaceutical compositions of the present invention may comprise a CAR or TCR expressing cell population, such as T cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

The pharmaceutical compositions (solutions, suspensions or the like), may include one or more of the following: sterile diluents such as water for injection, saline solution, preferably physiological saline, Ringer's solution, isotonic sodium chloride, fixed oils such as synthetic mono- or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

It will be appreciated that adverse events may be minimized by transducing the immune cells (containing one or more CARs or TCRs) with a suicide gene. It may also be desired to incorporate an inducible "on" or "accelerator" switch into the immune cells. Suitable techniques include use of inducible caspase-9 (U.S. Appl. 2011/0286980) or a thymidine kinase, before, after or at the same time, as the cells are transduced with the CAR construct of the present invention. Additional methods for introducing suicide genes and/or "on" switches include TALENS, zinc fingers, RNAi, siRNA, shRNA, antisense technology, and other techniques known in the art.

In accordance with the invention, additional on-off or other types of control switch techniques may be incorporated herein. These techniques may employ the use of dimerization domains and optional activators of such domain dimerization. These techniques include, e.g., those described by Wu et al., Science 2014 350 (6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of which are also incorporated by reference herein in their entirety. Additional dimerization pairs may include cyclosporine-A/cyclophilin, receptor, estrogen/estrogen receptor (optionally using tamoxifen), glucocorticoids/glucocorticoid receptor, tetracycline/tetracycline receptor, vitamin D/vitamin D receptor. Further examples of dimerization technology can be found in e.g., WO 2014/127261, WO 2015/090229, US 2014/0286987, US2015/0266973, US2016/0046700, U.S. Pat. No. 8,486,693, US 2014/0171649, and US 2012/0130076, the contents of which are further incorporated by reference herein in their entirety.

It will be understood that descriptions herein are exemplary and explanatory only and are not restrictive of the invention as claimed. In this application, the use of the singular includes the plural unless specifically stated otherwise.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. As utilized in accordance with the present disclosure, the following terms, unless otherwise indicated, shall be understood to have the following meanings:

In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

The term "CLL-1 activity" includes any biological effect of CLL-1. In certain embodiments, CLL-1 activity includes the ability of CLL-1 to interact or bind to a substrate or receptor.

The term "polynucleotide," "nucleotide," or "nucleic acid" includes both single-stranded and double-stranded nucleotide polymers. This preferably includes isolated polynucleotides, nucleotides or nucleic acids as defined herein. The nucleotides comprising the polynucleotide can be ribonucleotides or deoxyribonucleotides or a modified form of either type of nucleotide. Said modifications include base modifications such as bromouridine and inosine derivatives, ribose modifications such as 2', 3'-dideoxyribose, and internucleotide linkage modifications such as phosphorothioate, phosphorodithioate, phosphoroselenoate, phosphoro-diselenoate, phosphoro-anilothioate, phoshoraniladate and phosphoroamidate.

The term "oligonucleotide" refers to a polynucleotide comprising 200 or fewer nucleotides. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences (signal peptides) and/or fusion partner sequences.

In some embodiments, the polynucleotide of the present invention encodes a CAR or a TCR can further comprises a leader sequence or peptide (also referred to herein as a "signal peptide"). In certain embodiments, the leader peptide comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence MALPVTALLLPLALLLHAARP (SEQ ID NO: 144). In some embodiments, the leader peptide comprises the amino acid sequence of SEQ ID NO: 144.

As used herein, "operably linked" means that the components to which the term is applied are in a relationship that allows them to carry out their inherent functions under suitable conditions.

The term "vector" means any molecule or entity (e.g., nucleic acid, plasmid, bacteriophage or virus) used to transfer protein coding information into a host cell. The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto.

The term "host cell" refers to a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The term "transfection" refers to the uptake of foreign or exogenous DNA by a cell. A number of transfection techniques are well known in the art and are disclosed herein. See, e.g., Graham et al., 1973, Virology 52:456; Sambrook et al., 2001, Molecular Cloning: A Laboratory Manual, supra; Davis et al., 1986, Basic Methods in Molecular Biology, Elsevier; Chu et al., 1981, Gene 13:197.

The term "transduction" refers to the process whereby foreign DNA is introduced into a cell via viral vector. See Jones et al., (1998). Genetics: principles and analysis. Boston: Jones & Bartlett Publ.

The terms "polypeptide" or "protein" refer to a macromolecule having the amino acid sequence of a protein, including deletions from, additions to, and/or substitutions of one or more amino acids of the native sequence, and preferably no more than 8 amino acid substitutions therein. Preferably, the polypeptides or proteins are isolated as defined herein. The terms "polypeptide" and "protein" specifically encompass CLL-1 antigen binding molecules, antibodies, or sequences that have deletions from, additions to, and/or substitutions of one or more amino acid of antigen-binding protein, and preferably no more than 8 amino acid substitutions therein. The term "polypeptide fragment" refers to an isolated polypeptide that has an amino-terminal deletion, a carboxyl-terminal deletion, and/or an internal deletion as compared with the full-length native protein. Such fragments can also contain modified amino acids as compared with the native protein. Useful polypeptide fragments include immunologically functional fragments of antigen binding molecules. Useful fragments include but are not limited to one or more CDR regions, variable domains of a heavy and/or light chain, a portion of other portions of an antibody chain, and the like.

The term "isolated" means (i) free of at least some other proteins with which it would normally be found, (ii) is essentially free of other proteins from the same source, e.g., from the same species, (iii) separated from at least about 50 percent of polynucleotides, lipids, carbohydrates, or other materials with which it is associated in nature, (iv) operably associated (by covalent or noncovalent interaction) with a polypeptide with which it is not associated in nature, or (v) does not occur in nature.

A "variant" of a polypeptide (e.g., an antigen binding molecule, or an antibody) comprises an amino acid sequence wherein one or more amino acid residues are inserted into, deleted from and/or substituted into the amino acid sequence relative to another polypeptide sequence. Variants include fusion proteins.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any)

are preferably addressed by a particular mathematical model or computer program (i.e., an "algorithm").

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

As used herein, the twenty conventional (e.g., naturally occurring) amino acids and their abbreviations follow conventional usage. See Immunology—A Synthesis (2nd Edition, Golub and Gren, Eds., Sinauer Assoc., Sunderland, Mass. (1991)), which is incorporated herein by reference for any purpose. Stereoisomers (e.g., D-amino acids) of the twenty conventional amino acids, unnatural amino acids such as alpha-, alpha-disubstituted amino acids, N-alkyl amino acids, lactic acid, and other unconventional amino acids can also be suitable components for polypeptides of the present invention. Examples of unconventional amino acids include: 4-hydroxyproline, .gamma.-carboxyglutamate, epsilon-N,N,N-trimethyllysine, e-N-acetyllysine, 0-phosphoserine, N-acetylserine, N-formylmethionine, 3-methylhi stidine, 5-hydroxylysine, .sigma.-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties. Naturally occurring residues can be divided into classes based on common side chain properties:
a) hydrophobic: norleucine, Met, Ala, Val, Leu, Ile;
b) neutral hydrophilic: Cys, Ser, Thr, Asn, Gln;
c) acidic: Asp, Glu;
d) basic: His, Lys, Arg;
e) residues that influence chain orientation: Gly, Pro; and
f) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule. Exemplary amino acid substitutions are set forth in Table 3.

TABLE 3

| Original Residues | Exemplary Substitutions | Preferred Substitutions |
| --- | --- | --- |
| Ala | Val, Leu, Ile | Val |
| Arg | Lys, Gln, Asn | Lys |

TABLE 3-continued

| Original Residues | Exemplary Substitutions | Preferred Substitutions |
| --- | --- | --- |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding molecule can have a greater circulating half-life than an antigen binding molecule that is not chemically modified. In some embodiments, a derivative antigen binding molecule is covalently modified to include one or more water soluble polymer attachments, including, but not limited to, polyethylene glycol, polyoxyethylene glycol, or polypropylene glycol.

Peptide analogs are commonly used in the pharmaceutical industry as non-peptide drugs with properties analogous to those of the template peptide. These types of non-peptide compound are termed "peptide mimetics" or "peptidomimetics." Fauchere, J., Adv. Drug Res., 15:29 (1986); Veber & Freidinger, TINS, p. 392 (1985); and Evans et al., J. Med. Chem., 30:1229 (1987), which are incorporated herein by reference for any purpose.

A "therapeutically effective amount," "effective dose," "effective amount," or "therapeutically effective dosage" of a therapeutic agent, e.g., engineered CART cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

INCORPORATION BY REFERENCE

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

The foregoing written specification is considered to be sufficient to enable one skilled in the art to practice the invention. The foregoing description and examples detail certain preferred embodiments of the invention and describe the best mode contemplated by the inventors. It will be appreciated, however, that no matter how detailed the foregoing may appear in text, the invention may be practiced in many ways and the invention should be construed in accordance with the appended claims and any equivalents thereof.

The following examples, including the experiments conducted and results achieved, are provided for illustrative purposes only and are not to be construed as limiting the present invention.

EXAMPLE 1

Determining CLL-1 CAR activity by mRNA electroporation in human PBMCs. Plasmids encoding a T7 promoter, CAR construct and a beta globin stabilizing sequence were linearize by overnight digestion of 10 ug of DNA with EcoRI and BamHI (NEB). DNA was then digested for 2 hours at 50° C. with proteinase K (Thermo Fisher™, 600 U/ml) purified with phenol/chloroform and precipitated by adding sodium acetate and two volumes of ethanol. Pellets were then dried, resuspended in RNAse/DNAse free water and quantified. 1 ug of the linear DNA was then use to generate the in vitro transcription using the mMESSAGE mMACHINE T7 Ultra (Thermo Fisher™) following the manufacturer instructions. RNA was further purified using the MEGAClear Kit (Thermo Fisher™) following the manufacturer instructions, and quantified using NanoDrop™. mRNA integrity was assessed by running an agarose gel.

Different cancer cell lines were evaluated for CLL-1 expression. Namalwa (ATCC), U937 (ATCC), HL-60 (ATCC), EoL-1 (Sigma), KG1a (ATCC) and MV4; 11 (ATCC) cells were stained with anti-CLL-1 antibody conjugated to PE (BD Pharmingen™) in stain buffer (BD Pharmingen™) for 30 minutes at 4° C. Cells were then washed and resuspended in stain buffer with propidium iodide (BD Pharmingen™) prior to data acquisition. Samples were then acquired by flow cytometry and data analyzed and plotted in histograms using FlowJo™. Results for the CLL-1 expression can be seen in FIG. 1.

PBMCs were isolated from healthy donor leukopaks (Hemacare™) using ficoll-paque density centrifugation per manufacturer's instructions. PBMCs were stimulated using OKT3 (50 ng/ml, Miltenyi Biotec™) in R10 media+IL-2 (300 IU/ml, Proleukin®, Prometheus® Therapeutics and Diagnostics). Seven days after stimulation, T cells were washed twice in Opti-MEM™ (Thermo Fisher Scientific™) and resuspended at a final concentration of $2.5 \times 10^7$ cells/ml in Opti-MEM. 10 μg of mRNA was used per electroporation. Electroporation of cells was performed using a Gemini X2 system (Harvard Apparatus BTX™) set to deliver a single 400V pulse for 0.5 ms in 2 mm cuvettes (Harvard Apparatus BTX™). Cells were immediately transferred to R10+IL-2 media and allowed to recover. Cells were maintained at $0.5$-$2.0 \times 10^6$ cells/ml prior to use in activity assays.

Figure 2:
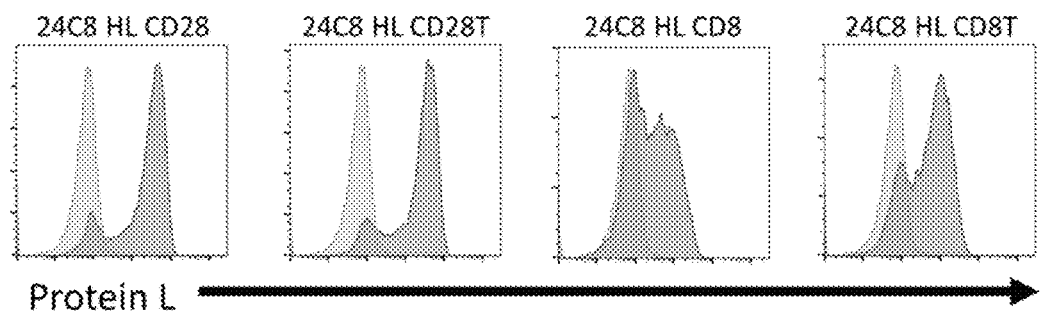
FIG. 2 shows CLL-1 CAR expression determined by protein L 6 hours post mRNA electroporation.

Six hours after mRNA electroporation, T cells were stained with biotinylated Protein L (Thermo Scientific™) in stain buffer (BD Pharmingen™) for 30 minutes at 4° C. Cells were then washed and stained with PE Streptavidin (BD Pharmingen™) in stain buffer for 30 minutes at 4° C. Cells were then washed and resuspended in stain buffer with propidium iodide (BD Pharmingen™) prior to data acquisition. Results for CAR detection are shown in FIG. 2.

Figure 3:
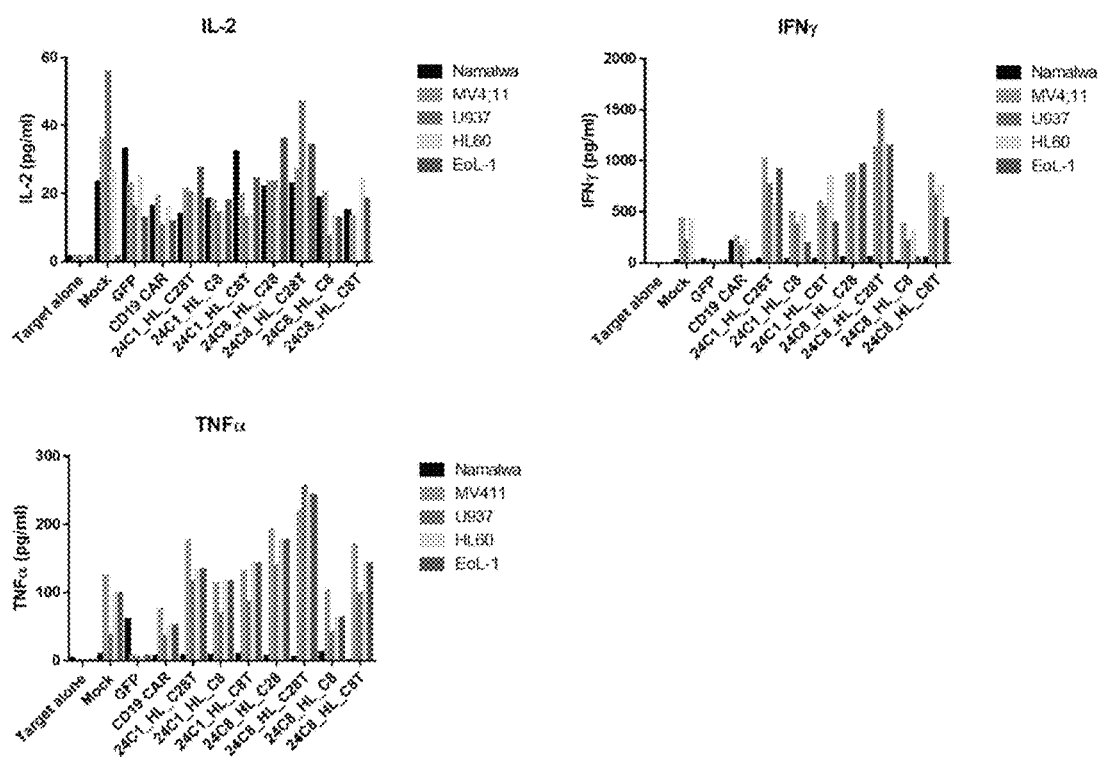
FIG. 3 shows the results from a cytokine release assay from different CLL-1 CAR-T cell constructs 24 hours after mRNA electroporation.
Figure 4:
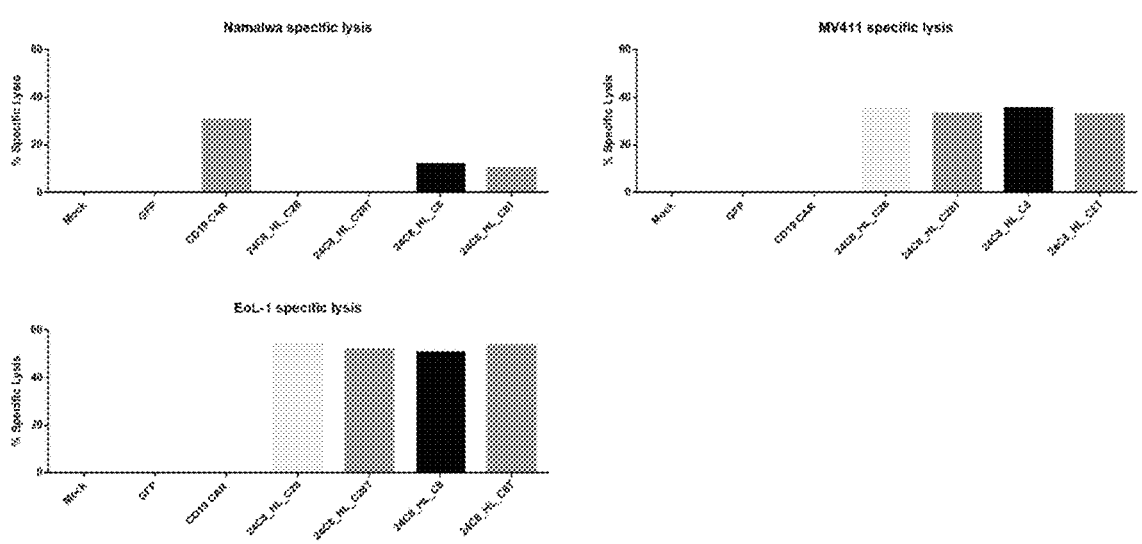
FIG. 4 shows cytolytic activity of different CLL-1 CAR-T cell constructs 24 hours after mRNA electroporation.
Figure 5:
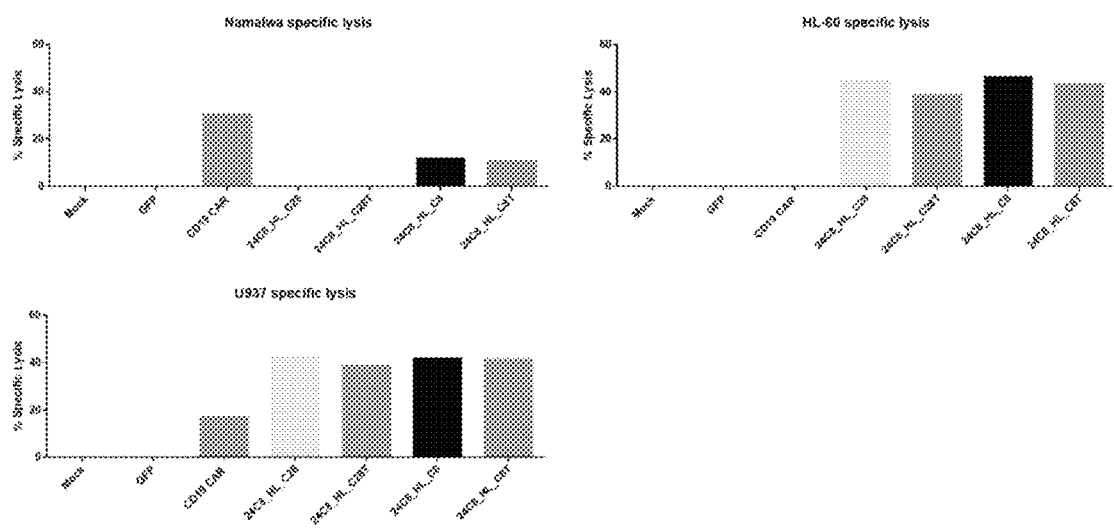
FIG. 5 shows cytolytic activity of different CLL-1 CAR-T cell constructs 24 hours after mRNA electroporation.

Effector cells were cultured with target cells at a 1:1 E:T ratio in R10 media 6 hours after mRNA electroporation. Cell lines tested included Namalwa, U937, HL-60, EoL-1, KG1a and MV4; 11. Sixteen hours post-coculture, supernatants were analyzed by Luminex (EMD Millipore) following manufacturer instructions and target cell viability was assessed by flow cytometric analysis of propidium iodide (PI) uptake. Results corresponding to the cytokine release assay can be found in FIG. 3. Results of the cytolytic activity assay can be found in FIG. 4 and FIG. 5.

EXAMPLE 2

Determining CLL-1 CAR activity by lentiviral transduction of human PBMCs. A third generation lentiviral transfer vector containing the different CLL-1 CAR construct was used along with the ViraPower™ Lentiviral Packaging Mix (Life Technologies™) to generate the lentiviral supernatants. Briefly, a transfection mix was generated by mixing 15 ug of DNA and 22.5 ul of polyethileneimine (Polysciences™, 1 mg/ml) in 600 ul of OptiMEM™ media. The mix was incubated for 5 minutes at room temperature. Simultaneously, 293T cells (ATCC) were trypsinized, counted and a total of $10 \times 10^6$ total cells were plated in a T75 flask along the transfection mix. Three days after the transfection, supernatants were collected and filtered through a 0.45 um filter and stored at −80C until used.

PBMCs were isolated from healthy donor leukopaks (Hemacare™) using ficoll-paque density centrifugation per manufacturer's instructions. PBMCs were stimulated using OKT3 (50 ng/ml, Miltenyi Biotec™) in R10 media+IL-2 (300 IU/ml, Proleukin®, Prometheus® Therapeutics and Diagnostics). Forty eight hours post-stimulation, cells were transduced using lentivirus at a MOI=10. Cells were maintained at 0.5-2.0×10⁶ cells/ml prior to use in activity assays.

Figure 6:
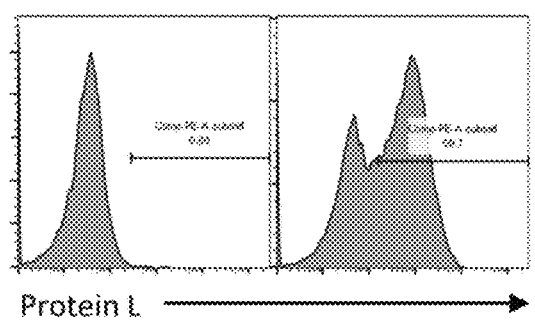
FIG. 6 shows CLL-1 CAR expression determined by protein L at day 12 after transduction.

At day 12 post stimulation, T cells were stained with biotinylated Protein L (Thermo Scientific™) in stain buffer (BD Pharmingen™) for 30 minutes at 4° C. Cells were then washed and stained with PE Streptavidin (BD Pharmingen™) in stain buffer for 30 minutes at 4° C. Cells were then washed and resuspended in stain buffer with propidium iodide (BD Pharmingen™) prior to data acquisition. Results for CAR detection are shown in FIG. 6.

Figure 7:
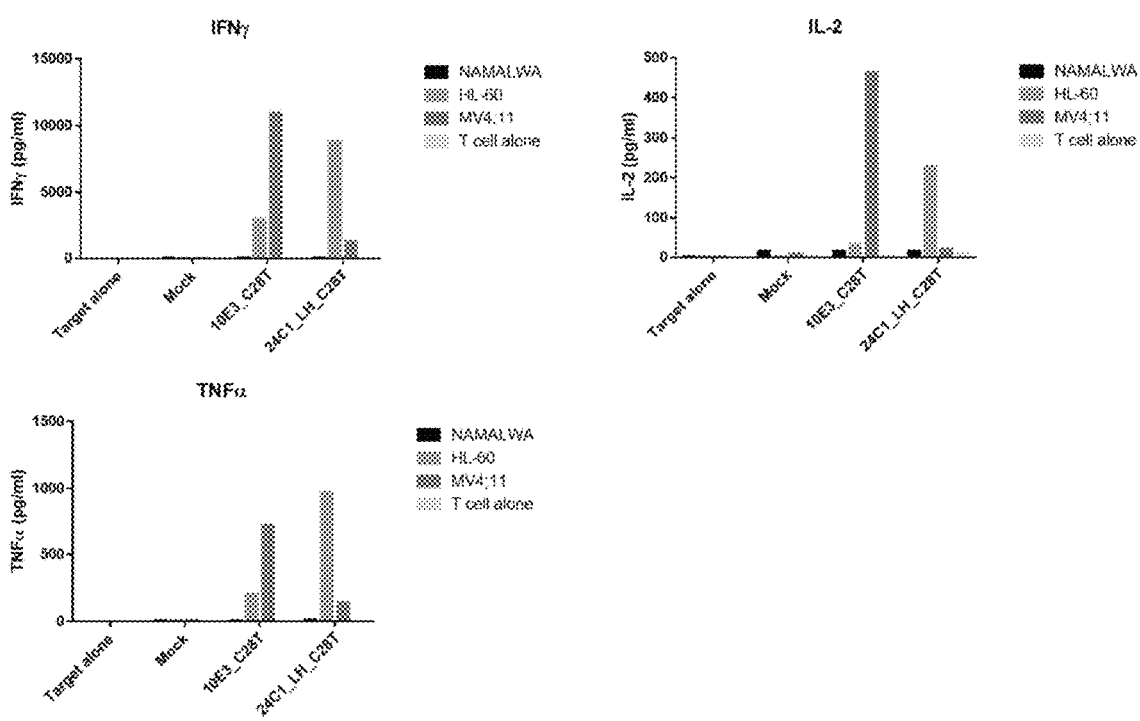
FIG. 7 shows cytokine release assay from CLL-1 CAR-T cells 16 hours after co-culture with different target cell lines.
Figure 8:
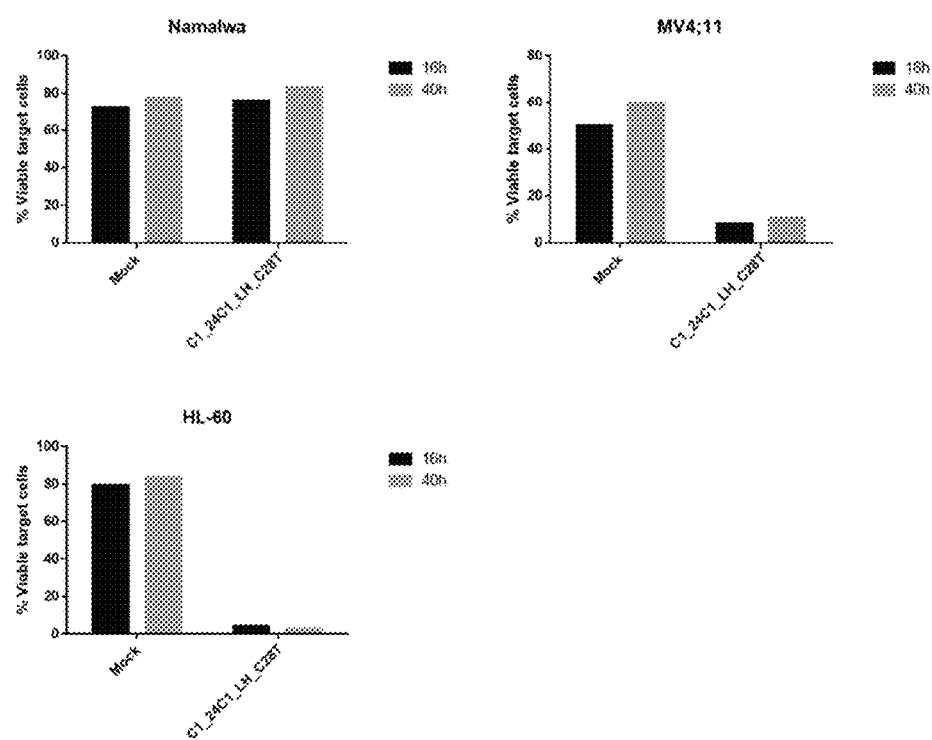
FIG. 8 shows cytolytic activity from CLL-1 CAR-T cells 16 hours and 40 hours after co-culture with different target cell lines.

Effector cells were cultured with target cells at a 1:1 E:T ratio in R10 media 12 days after T cell stimulation. Cell lines tested included Namalwa, U937, HL-60, EoL-1, KG1 a and MV4; 11. 16 hours post-coculture, supernatants were analyzed by Luminex (EMD Millipore™) following manufacturer instructions and target cell viability was assessed by flow cytometric analysis of propidium iodide (PI) uptake. Results corresponding to the cytokine release assay can be found in FIG. 7. Results of the cytolytic activity assay can be found in FIG. 8.

EXAMPLE 3

Female Jackson NSG mice (NOD.Cg-Prkdc$^{scid}$ Il2rg$^{tm1Wjl}$/SzJ) aged 5-6 weeks old were used in this study. The mice were fed an irradiated Harlan 2918.15 Rodent Diet and water ad libitum. The mice were housed in Innovive™ disposable ventilated caging with corn cob bedding inside Biobubble® Clean Rooms that provide H.E.P.A filtered air into the bubble environment at 100 complete air changes per hour. All treatments, body weight determinations, and tumor measurements were carried out in the bubble environment. The environment was controlled to a temperature range of 70°±2° F. and a humidity range of 30-70%. All procedures were conducted in compliance with all the laws, regulations and guidelines of the National Institutes of Health (NIH) and with the approval of Molecular Imaging, Inc.'s Animal Care and Use Committee.

Tumor Cell Preparation

U937-luc cells were obtained in Lifor® Preservation Solution. The cells were centrifuged at 200 rcf for 8 minutes at 4° C., the supernatant was aspirated, and the pellet was re-suspended in cold Dulbecco's Phosphate Buffered Saline (DPBS) by pipetting. An aliquot of the homogeneous cell suspension was diluted in a trypan blue solution and counted using a Luna™ automated cell counter. The cell suspension was centrifuged at 200 rcf for 8 minutes at 4° C. The supernatant was aspirated and the cell pellet was re-suspended in cold serum-free medium to generate the final concentrations of trypan-excluding cells/ml. The cell suspension was maintained on wet ice during implantation. Test animals were implanted with 1.00E+06 cells intravenously via the lateral tail vein on Day 0 in 0.2 ml using a 27-gauge needle and syringe.

CAR T-Cell Preparation

T cells according to the invention were obtained, frozen on dry ice, and stored in liquid nitrogen. On the day of treatment, the provided cryovials were removed from cryostorage and thawed in a 37° C. water bath. For each group, the provided T cells were combined into a single 50 ml conical tube with warm RPMI 1640 supplemented with 10% FBS. The cryovial tubes were rinsed with warm RPMI 1640 with 10% FBS to minimize loss of cells to reach a total volume of 50 ml in each conical tube. Each 50 ml conical tube was centrifuged at 200 rcf for 8 minutes at 4° C. The supernatants were aspirated, and the cell pellets re-suspended in 10 ml of room temperature DPBS. An aliquot of the homogeneous cell suspension was diluted in a trypan blue solution and manually counted using a hemacytometer. The cell suspensions were again centrifuged at 200 rcf for 8 minutes at 4° C. The supernatants were aspirated and the cell pellets were re-suspended in room temperature DPBS to generate the required final concentrations. The cell suspensions were maintained on wet ice during treatment administration.

Bioluminescence Imaging

In vivo bioluminescence imaging (BLI) was performed using an IVIS Spectrum (Perkin Elmer, Hopkinton, Mass.). Animals were imaged up to 5 at a time under ~1-2% isoflurane gas anesthesia. Each mouse was injected IP with 150 mg/kg (15 mg/ml) D-luciferin and imaged in the prone, then supine positions, 10 minutes following injection. Large to small binning of the CCD chip was used, and exposure time adjusted (2 seconds to 2 minutes) to obtain at least several hundred counts per image, and further to avoid saturation of the CCD chip. BLI images were collected on Days 3, 11, 18, and 25. Images were analyzed using the Living Image version 4.5 (Perkin Elmer, Hopkinton, Mass.) software. Whole body fixed-volume ROIs were placed on prone and supine images for each individual animal, and labeled based on animal identification. Total radiance expressed in photon/sec (p/s) was calculated and exported for all ROIs to facilitate analyses between groups. The prone and supine ROIs were summed together to estimate whole body tumor burden.

Treatment

Figure 10:
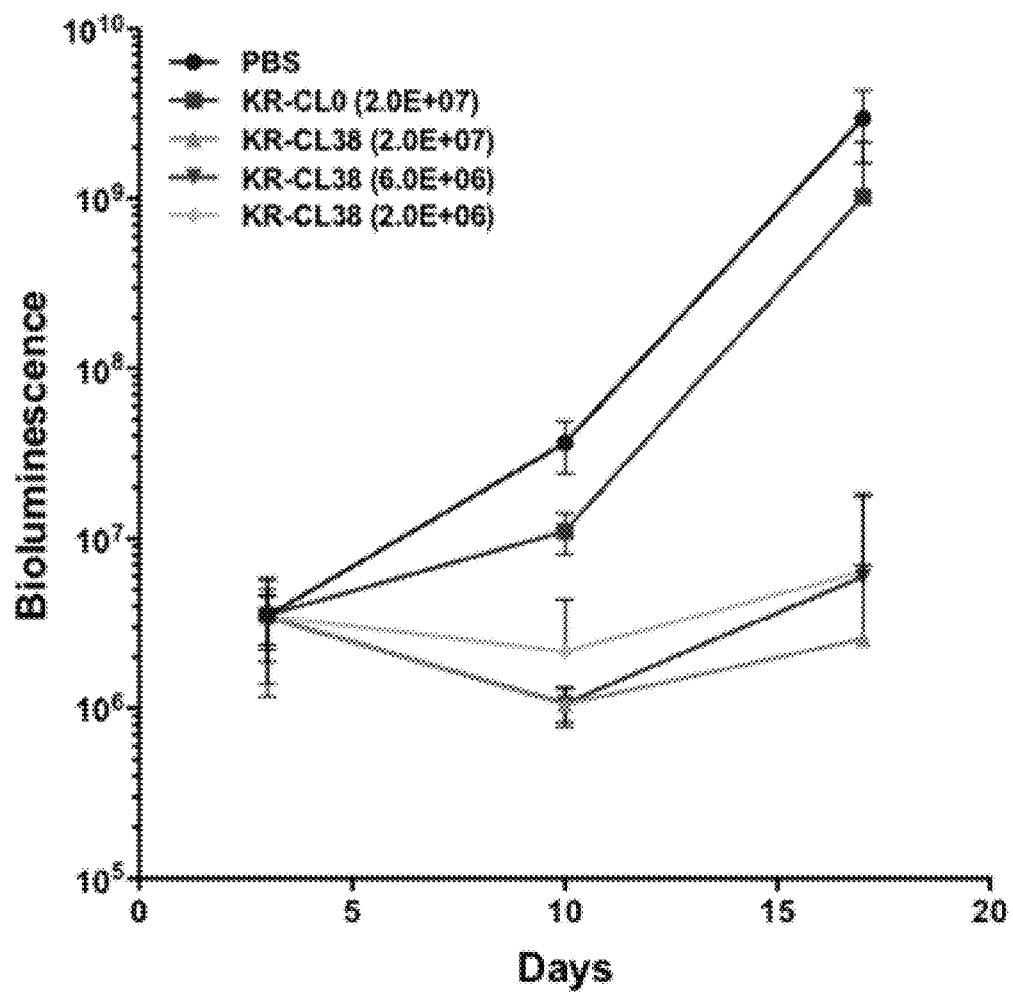
FIG. 10 sets forth bioluminescence results on NSG mice treated with CARs according to the invention.
Figure 11:
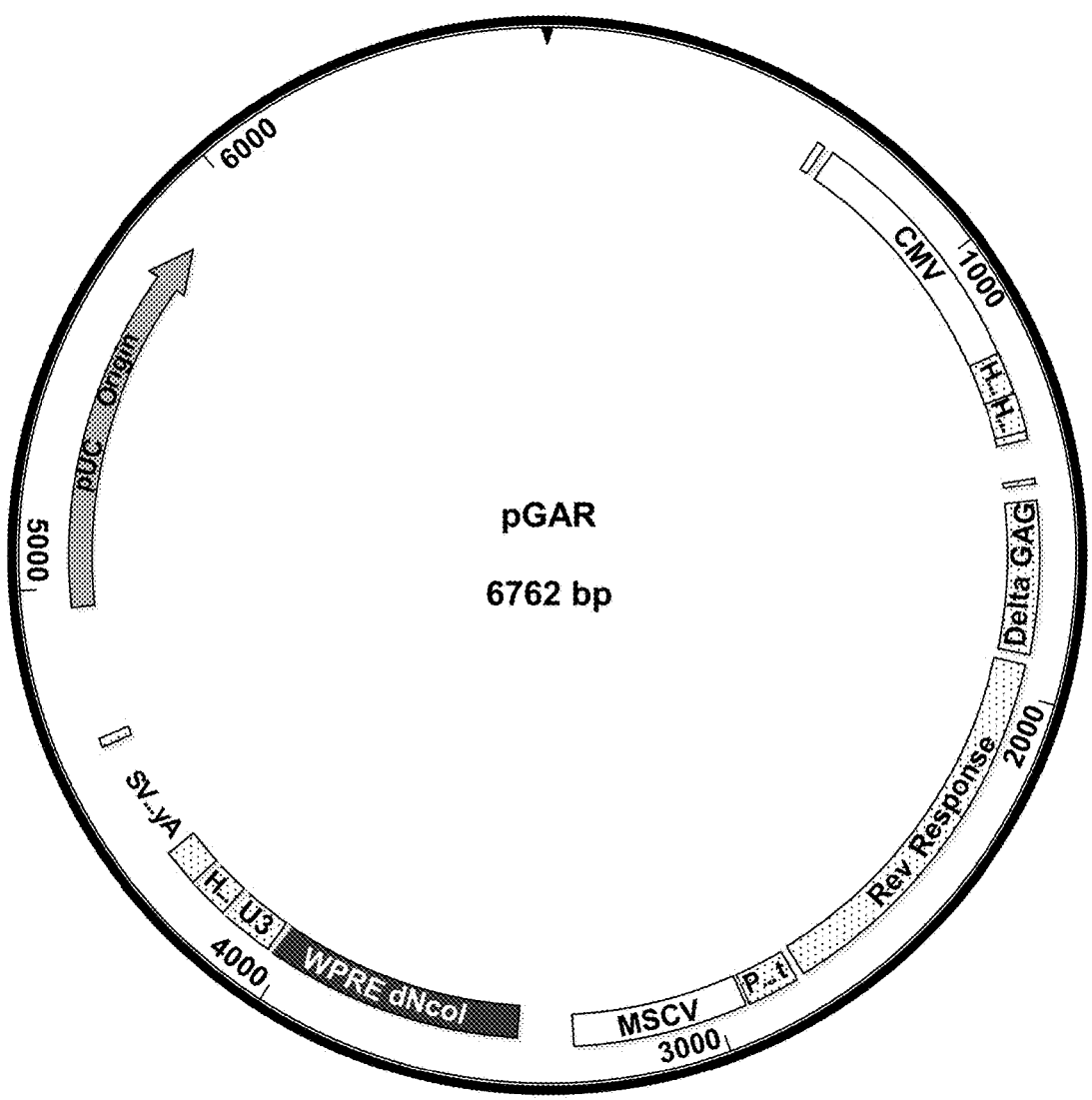
FIG. 11 sets forth the pGAR vector map.

All mice were sorted into study groups based on BLI-derived estimation of whole body tumor burden. The mice were distributed to ensure that the mean tumor burden for all groups was within 10% of the overall mean tumor burden for the study population. Treatment with CAR T cells began on Day 3. All mice were dosed with a fixed volume of 0.2 mL. The results are set forth in FIG. 10.

Assessment of Side Effects

All animals were observed for clinical signs at least once daily. Animals were weighed on each day of treatment. Individual body weights were recorded 3 times weekly.

The following sequences will further exemplify the invention.

```
CD28T DNA Extracellular, transmembrane,
intracellular
                                      (SEQ ID NO. 1)
CTTGATAATGAAAAGTCAAACGGAACAATCATTCACGTGAAGGG

CAAGCACCTCTGTCCGTCACCCTTGTTCCCTGGTCCATCCAAGCCA

TTCTGGGTGTTGGTCGTAGTGGGTGGAGTCCTCGCTTGTTACTCTC

TGCTCGTCACCGTGGCTTTTATAATCTTCTGGGTTAGATCCAAAAG
```

```
AAGCCGCCTGCTCCATAGCGATTACATGAATATGACTCCACGCCG
CCCTGGCCCCACAAGGAAACACTACCAGCCTTACGCACCACCTAG
AGATTTCGCTGCCTATCGGAGC
```

CD28T Extracellular, transmembrane,
intracellular AA
(SEQ ID NO. 2)
```
LDNEKSNGTIIHVKGKHLCPSPLFPGPSKPFWVLVVVGGVLACYSLL
VTVAFIIFWVRSKRSRLLHSDYMNMTPRRPGPTRKHYQPYAPPRDFA
AYRS
```

CD28T DNA - Extracellular
(SEQ ID NO. 3)
```
CTTGATAATGAAAAGTCAAACGGAACAATCATTCACGTGAAGGG
CAAGCACCTCTGTCCGTCACCCTTGTTCCCTGGTCCATCCAAGCCA
```

CD28T AA - Extracellular
(SEQ ID NO. 4)
```
LDNEKSNGTI IHVKGKHLCP SPLFPGPSKP
```

CD28 DNA Transmembrane Domain
(SEQ ID NO. 5)
```
TTCTGGGTGTTGGTCGTAGTGGGTGGAGTCCTCGCTTGTTACTCTC
TGCTCGTCACCGTGGCTTTTATAATCTTCTGGGTT
```

CD28 AA Transmembrane Domain
(SEQ ID NO. 6)
```
FWVLVVVGGV LACYSLLVTV AFIIFWV
```

CD28 DNA Intracellular Domain
(SEQ ID NO. 7)
```
AGATCCAAAAGAAGCCGCCTGCTCCATAGCGATTACATGAATATG
ACTCCACGCCGCCCTGGCCCCACAAGGAAACACTACCAGCCTTAC
GCACCACCTAGAGATTTCGCTGCCTATCGGAGC
```

CD28 AA Intracellular Domain
(SEQ ID NO. 8)
```
RSKRSRLLHSDYMNMTPRRPGPTRKHYQPYAPPRDFAAYRS
```

CD3 zeta DNA
(SEQ ID NO. 9)
```
AGGGTGAAGTTTTCCAGATCTGCAGATGCACCAGCGTATCAGCAG
GGCCAGAACCAACTGTATAACGAGCTCAACCTGGGACGCAGGGA
AGAGTATGACGTTTTGGACAAGCGCAGAGGACGGGACCCTGAGA
TGGGTGGCAAACCAAGACGAAAAAACCCCCAGGAGGGTCTCTAT
AATGAGCTGCAGAAGGATAAGATGGCTGAAGCCTATTCTGAAAT
AGGCATGAAAGGAGAGCGGAGAAGGGGAAAAGGGCACGACGGT
TTGTACCAGGGACTCAGCACTGCTACGAAGGATACTTATGACGCT
CTCCACATGCAAGCCCTGCCACCTAGG
```

CD3 zeta AA
(SEQ ID NO. 10)
```
RVKFSRSADAPAYQQGQNQLYNELNLGRREEYDVLDKRRGRDPEM
GGKPRRKNPQEGLYNELQKDKMAEAYSEIGMKGERRRGKGHDGLY
QGLSTATKDTYDALHMQALPPR
```

CD3 zeta variant AA
(SEQ ID NO. 146)
```
RVKFSRSADAPAYKQGQNQLYNELNLGRREEYDVLDKRRGRDPEM
GGKPRRKNPQEGLYNELQKDKMAEAYSEIGMKGERRRGKGHDGLY
QGLSTATKDTYDALHMQALPPR
```

CD28 DNA
(SEQ ID NO. 11)
```
ATTGAGGTGATGTATCCACCGCCTTACCTGGATAACGAAAAGAGT
AACGGTACCATCATTCACGTGAAAGGTAAACACCTGTGTCCTTCT
CCCCTCTTCCCCGGGCCATCAAAGCCC
```

CD28 AA
(SEQ ID NO. 12)
```
IEVMYPPPYLDNEKSNGTIIHVKGKHLCPSPLFPGPSKP
```

CD8 DNA extracellular & transmembrane domain
(SEQ ID NO. 13)
```
GCTGCAGCATTGAGCAACTCAATAATGTATTTTAGTCACTTTGTAC
CAGTGTTCTTGCCGGCTAAGCCTACTACCACACCCGCTCCACGGC
CACCTACCCCAGCTCCTACCATCGCTTCACAGCCTCTGTCCCTGCG
CCCAGAGGCTTGCCGACCGGCCGCAGGGGGCGCTGTTCATACCAG
AGGACTGGATTTCGCCTGCGATATCTATATCTGGGCACCCCTGGC
CGGAACCTGCGGCGTACTCCTGCTGTCCCTGGTCATCACGCTCTAT
TGTAATCACAGGAAC
```

CD8 AA extracellular & transmembrane Domain
(SEQ ID NO. 14)
```
AAALSNSIMYFSHFVPVFLPAKPTTTPAPRPPTPAPTIASQPLSLRPEA
CRPAAGGAVHTRGLDFACDIYIWAPLAGTCGVLLLSVITLYCNHRN
```

Clone 24C1 HC DNA
(SEQ ID NO. 15)
```
CAGGTGCAGCTGCAGGAATCCGGACCGGGGCTGGTGAAGCCCAG
CGAGACTCTGAGTCTCACGTGTACAGTTTCTGGAGGTAGCATTAG
CTCCTACTATTGGTCATGGATAAGGCAGCCCCCCGGGAAGGGATT
GGAATGGATCGGCTATATTTACTACAGTGGGAGCACCAATTACAA
CCCCTCACTGAAGTCTAGAGTTACAATCAGCGTTGACACCTCAAA
GAATCAGTTCAGTTTGAAATTGTCTAGCGTCACAGCAGCTGATAC
AGCCGTCTATTATTGTGTTTCTCTGGTCTATTGCGGTGGGGATTGT
TACAGTGGCTTTGACTATTGGGGGCAGGGTACTCTGGTTACAGTT
TCTTCC
```

Clone 24C1 HC AA (CDRs Underlined)
(SEQ ID NO. 16)
```
QVQLQESGPGLVKPSETLSLTCTVSGGSISSYYWSWIRQPPGKGLEWIGY
IYYSGSTNYNPSLKSRVTISVDTSKNQFSLKLSSVTAADTAVYYCVSLVY
CGGDCYSGFDYWGQGTLVTVSS
```

Clone 24C1 HC AA CDR1:
(SEQ ID NO. 17)
```
GGSISSY
```

Clone 24C1 HC AA CDR2:
(SEQ ID NO. 18)
```
YYSGS
```

Clone 24C1 HC AA CDR3:
(SEQ ID NO. 19)
```
LVYCGGDCYS GFDY
```

Clone 24C1 LC DNA
(SEQ ID NO. 20)
```
GACATCCAGTTGACACAGAGCCCGAGTTCCTTGTCCGCCTCCGTC
```

```
GGGGATAGAGTGTCATTTACCTGTCAGGCCTCTCAGGATATTAAT

AACTTTCTGAATTGGTATCAGCAAAAGCCCGGAAAGGCACCCAAG

CTGTTGATTTACGACGCCAGTAACCTGGAGACAGGCGTGCCCTCC

CGGTTTAGTGGTAGCGGAAGCGGTACGGATTTTACCTTTACTATC

AGCTCTCTCCAACCCGAAGACATTGCAACCTACTATTGTCAACAA

TATGGAAACCTGCCTTTTACATTTGGCGGCGGCACCAAGGTGGAG

ATTAAGCGG
```

Clone 24C1 LC AA (CDRs Underlined)
(SEQ ID NO. 21)
DIQLTQSPSSLSASVGDRVSFTCQASQDINNFLNWYQQKPGKAPKLLI
YDASNLETGVPSRFSGSGSGTDFTFTISSLQPEDIATYYCQQYGNLPFT
FGGGTKVEIKR Clone 24C1 LC CDR1 AA:
(SEQ ID NO. 22)
QASQDINNFLN Clone 24C1 LC CDR2 AA:
(SEQ ID NO. 23)
DASNLET Clone 24C1 LC CDR3 AA:
(SEQ ID NO. 24)
QQYGNLPFT Clone 24C1 CD28T CD3 zeta CAR DNA Heavy &
Light Chains
(SEQ ID NO. 25)
```
ATGGCACTCCCCGTAACTGCTCTGCTGCTGCCGTTGGCATTGCTCC

TGCACGCCGCACGCCCGCAGGTCCAACTGCAAGAAAGCGGACCC

GGACTGGTGAAGCCTTCTGAGACACTTAGTCTGACGTGCACGGTC

AGTGGCGGCTCCATCTCCTCCTATTATTGGTCATGGATACGACAA

CCCCCAGGTAAGGGCCTGGAATGGATTGGCTATATCTACTATTCA

GGAAGCACGAACTACAATCCCAGCCTGAAGTCCCGAGTGACAATT

TCAGTAGATACCAGTAAAAACCAGTTCAGTCTTAAACTGTCAAGC

GTGACAGCTGCCGACACCGCTGTGTATTACTGCGTCTCACTGGTG

TATTGTGGAGGGGATTGTTATAGCGGGTTCGATTATTGGGGACAG

GGAACCCTGGTGACTGTATCTTCCGGCGGCGGCGGCTCAGGGGGT

GGCGGTAGTGGCGGTGGGGGTTCCGATATTCAACTGACACAATCC

CCCAGCTCACTCAGCGCCAGCGTGGGGACAGGGTTAGCTTTACC

TGTCAAGCCTCTCAGGATATAAATAACTTTCTGAACTGGTATCAA

CAGAAGCCTGGGAAGGCGCCCAAACTCCTGATCTATGATGCGTCC

AACCTGGAAACTGGCGTGCCTTCACGCTTTAGCGGCTCTGGCAGT

GGTACAGACTTCACTTTTACCATCTCTTCACTTCAGCCGGAGGACA

TCGCCACATATTACTGTCAACAGTACGGAAACTTGCCCTTTACTTT

TGGAGGCGGCACCAAAGTTGAAATCAAAAGGGCCGCTGCCCTGG

ATAACGAAAAGAGCAATGGGACTATAATACATGTTAAAGGAAAA

CACCTGTGTCCATCTCCCCTGTTCCCTGGACCGTCAAAGCCATTTT

GGGTGCTCGTGGTTGTCGGTGGCGTTCTCGCCTGTTATAGCTTGCT

GGTGACAGTAGCCTTCATTATCTTTTGGGTGAGATCCAAAAGAAG
```

```
CCGCCTGCTCCATAGCGATTACATGAATATGACTCCACGCCGCCC

TGGCCCCACAAGGAAACACTACCAGCCTTACGCACCACCTAGAGA

TTTCGCTGCCTATCGGAGCAGGGTGAAGTTTTCCAGATCTGCAGA

TGCACCAGCGTATCAGCAGGGCCAGAACCAACTGTATAACGAGCT

CAACCTGGGACGCAGGGAAGAGTATGACGTTTTGGACAAGCGCA

GAGGACGGGACCCTGAGATGGGTGGCAAACCAAGACGAAAAAAC

CCCCAGGAGGGTCTCTATAATGAGCTGCAGAAGGATAAGATGGCT

GAAGCCTATTCTGAAATAGGCATGAAAGGAGAGCGGAGAAGGGG

AAAAGGGCACGACGGTTTGTACCAGGGACTCAGCACTGCTACGA

AGGATACTTATGACGCTCTCCACATGCAAGCCCTGCCACCTAGGT

AA
```

Clone 24C1 CD28T CD3 zeta CAR AA Heavy &
Light Chains
(Signal Peptide in bold)
(SEQ ID NO. 26)
MALPVTALLLPLALLLHAARPQVQLQESGPGLVKPSETLSLTCTVS
GGSISSYYWSWIRQPPGKGLEWIGYIYYSGSTNYNPSLKSRVTISVDT
SKNQFSLKLSSVTAADTAVYYCVSLVYCGGDCYSGFDYWGQGTLV
TVSSGGGGSGGGGSGGGGSDIQLTQSPSSLSASVGDRVSFTCQASQDI
NNFLNWYQQKPGKAPKLLIYDASNLETGVPSRFSGSGSGTDFTFTISS
LQPEDIATYYCQQYGNLPFTFGGGTKVEIKRAAALDNEKSNGTIIHV
KGKHLCPSPLFPGPSKPFWVLVVVGGVLACYSLLVTVAFIIFWVRSK
RSRLLHSDYMNMTPRRPGPTRKHYQPYAPPRDFAAYRSRVKFSRSA
DAPAYQQGQNQLYNELNLGRREEYDVLDKRRGRDPEMGGKPRRKN
PQEGLYNELQKDKMAEAYSEIGMKGERRRGKGHDGLYQGLSTATK
DTYDA LHMQALPPR Clone 24C1 CD28T CD3 zeta CAR DNA Heavy &
Light Chains
(SEQ ID NO. 27)
```
CAGGTCCAACTGCAAGAAAGCGGACCCGGACTGGTGAAGCCTTCT

GAGACACTTAGTCTGACGTGCACGGTCAGTGGCGGCTCCATCTCC

TCCTATTATTGGTCATGGATACGACAACCCCCAGGTAAGGGCCTG

GAATGGATTGGCTATATCTACTATTCAGGAAGCACGAACTACAAT

CCCAGCCTGAAGTCCCGAGTGACAATTTCAGTAGATACCAGTAAA

AACCAGTTCAGTCTTAAACTGTCAAGCGTGACAGCTGCCGACACC

GCTGTGTATTACTGCGTCTCACTGGTGTATTGTGGAGGGGATTGTT

ATAGCGGGTTCGATTATTGGGGACAGGGAACCCTGGTGACTGTAT

CTTCCGGCGGCGGCGGCTCAGGGGGTGGCGGTAGTGGCGGTGGG

GGTTCCGATATTCAACTGACACAATCCCCCAGCTCACTCAGCGCC

AGCGTGGGGACAGGGTTAGCTTTACCTGTCAAGCCTCTCAGGAT

ATAAATAACTTTCTGAACTGGTATCAACAGAAGCCTGGGAAGGCG

CCCAAACTCCTGATCTATGATGCGTCCAACCTGGAAACTGGCGTG

CCTTCACGCTTTAGCGGCTCTGGCAGTGGTACAGACTTCACTTTTA

CCATCTCTTCACTTCAGCCGGAGGACATCGCCACATATTACTGTCA
```

```
ACAGTACGGAAACTTGCCCTTTACTTTTGGAGGCGGCACCAAAGT
TGAAATCAAAAGGGCCGCTGCCCTGGATAACGAAAAGAGCAATG
GGACTATAATACATGTTAAAGGAAAACACCTGTGTCCATCTCCCC
TGTTCCCTGGACCGTCAAAGCCATTTTGGGTGCTCGTGGTTGTCGG
TGGCGTTCTCGCCTGTTATAGCTTGCTGGTGACAGTAGCCTTCATT
ATCTTTTGGGTGAGATCCAAAAGAAGCCGCCTGCTCCATAGCGAT
TACATGAATATGACTCCACGCCGCCCTGGCCCCACAAGGAAACAC
TACCAGCCTTACGCACCACCTAGAGATTTCGCTGCCTATCGGAGC
AGGGTGAAGTTTTCCAGATCTGCAGATGCACCAGCGTATCAGCAG
GGCCAGAACCAACTGTATAACGAGCTCAACCTGGGACGCAGGGA
AGAGTATGACGTTTTGGACAAGCGCAGAGGACGGGACCCTGAGA
TGGGTGGCAAACCAAGACGAAAAAACCCCCAGGAGGGTCTCTAT
AATGAGCTGCAGAAGGATAAGATGGCTGAAGCCTATTCTGAAAT
AGGCATGAAAGGAGAGCGGAGAAGGGGAAAAGGGCACGACGGT
TTGTACCAGGGACTCAGCACTGCTACGAAGGATACTTATGACGCT
CTCCACATGCAAGCCCTGCCACCTAGG
```

Clone 24C1 CD28T CD3 zeta CAR AA Heavy &
Light Chains
(SEQ ID NO. 28)
QVQLQESGPGLVKPSETLSLTCTVSGGSISSYYWSWIRQPPGKGLEWI
GYIYYSGSTNYNPSLKSRVTISVDTSKNQFSLKLSSVTAADTAVYYC
VSLVYCGGDCYSGFDYWGQGTLVTVSSGGGGSGGGGSGGGGSDIQ
LTQSPSSLSASVGDRVSFTCQASQDINNFLNWYQQKPGKAPKLLIYD
ASNLETGVPSRFSGSGSGTDFTFTISSLQPEDIATYYCQQYGNLPFTFG
GGTKVEIKRAAALDNEKSNGTIIHVKGKHLCPSPLFPGPSKPFWVLV
VVGGVLACYSLLVTVAFIIFWVRSKRSRLLHSDYMNMTPRRPGPTRK
HYQPYAPPRDFAAYRSRVKFSRSADAPAYQQGQNQLYNELNLGRRE
EYDVLDKRRGRDPEMGGKPRRKNPQEGLYNELQKDKMAEAYSEIG
MKGERRRGKGHDGLYQGLSTATKDTYDALHMQALPPR Clone 24C1 CD28 CD3 zeta CAR DNA Heavy &
Light Chains
(SEQ ID NO. 29)
```
ATGGCACTCCCCGTAACTGCTCTGCTGCTGCCGTTGGCATTGCTCC
TGCACGCCGCACGCCCGCAGGTGCAGCTGCAGGAATCCGGACCG
GGGCTGGTGAAGCCCAGCGAGACTCTGAGTCTCACGTGTACAGTT
TCTGGAGGTAGCATTAGCTCCTACTATTGGTCATGGATAAGGCAG
CCCCCCGGGAAGGGATTGGAATGGATCGGCTATATTTACTACAGT
GGGAGCACCAATTACAACCCCTCACTGAAGTCTAGAGTTACAATC
AGCGTTGACACCTCAAAGAATCAGTTCAGTTTGAAATTGTCTAGC
GTCACAGCAGCTGATACAGCCGTCTATTATTGTGTTTCTCTGGTCT
ATTGCGGTGGGGATTGTTACAGTGGCTTTGACTATTGGGGGCAGG
GTACTCTGGTTACAGTTTCTTCCGGGGGGGGAGGCTCTGGGGGCG
GAGGCTCAGGTGGTGGAGGCAGCGACATCCAGTTGACACAGAGC
CCGAGTTCCTTGTCCGCCTCCGTCGGGGATAGAGTGTCATTTACCT
```

```
GTCAGGCCTCTCAGGATATTAATAACTTTCTGAATTGGTATCAGC
AAAAGCCCGGAAAGGCACCCAAGCTGTTGATTTACGACGCCAGT
AACCTGGAGACAGGCGTGCCCTCCCGGTTTAGTGGTAGCGGAAGC
GGTACGGATTTTACCTTTACTATCAGCTCTCTCCAACCCGAAGACA
TTGCAACCTACTATTGTCAACAATATGGAAACCTGCCTTTTACATT
TGGCGGCGGCACCAAGGTGGAGATTAAGCGGGCGGCAGCTATTG
AGGTGATGTATCCACCGCCTTACCTGGATAACGAAAAGAGTAACG
GTACCATCATTCACGTGAAAGGTAAACACCTGTGTCCTTCTCCCCT
CTTCCCCGGGCCATCAAAGCCCTTCTGGGTTCTTGTGGTCGTGGGA
GGCGTGCTTGCTTGTTATTCTCTGCTCGTTACCGTGGCGTTTATCA
TTTTTTGGGTTAGATCCAAAAGAAGCCGCCTGCTCCATAGCGATT
ACATGAATATGACTCCACGCCGCCCTGGCCCCACAAGGAAACACT
ACCAGCCTTACGCACCACCTAGAGATTTCGCTGCCTATCGGAGCA
GGGTGAAGTTTTCCAGATCTGCAGATGCACCAGCGTATCAGCAGG
GCCAGAACCAACTGTATAACGAGCTCAACCTGGGACGCAGGGAA
GAGTATGACGTTTTGGACAAGCGCAGAGGACGGGACCCTGAGAT
GGGTGGCAAACCAAGACGAAAAAACCCCCAGGAGGGTCTCTATA
ATGAGCTGCAGAAGGATAAGATGGCTGAAGCCTATTCTGAAATA
GGCATGAAAGGAGAGCGGAGAAGGGGAAAAGGGCACGACGGTT
TGTACCAGGGACTCAGCACTGCTACGAAGGATACTTATGACGCTC
TCCACATGCAAGCCCTGCCACCTAGGTAA
```

Clone 24C1 CD28 CD3 zeta CAR AA Heavy &
Light Chains
(Signal Peptide in Bold)
(SEQ ID NO. 30)
MALPVTALLLPLALLLHAARPQVQLQESGPGLVKPSETLSLTCTVS
GGSISSYYWSWIRQPPGKGLEWIGYIYYSGSTNYNPSLKSRVTISVDT
SKNQFSLKLSSVTAADTAVYYCVSLVYCGGDCYSGFDYWGQGTLV
TVSSGGGGSGGGGSGGGGSDIQLTQSPSSLSASVGDRVSFTCQASQDI
NNFLNWYQQKPGKAPKLLIYDASNLETGVPSRFSGSGSGTDFTFTISS
LQPEDIATYYCQQYGNLPFTFGGGTKVEIKRAAAIEVMYPPPYLDNE
KSNGTIIHVKGKHLCPSPLFPGPSKPFWVLVVVGGVLACYSLLVTVA
FIIFWVRSKRSRLLHSDYMNMTPRRPGPTRKHYQPYAPPRDFAAYRS
RVKFSRSADAPAYQQGQNQLYNELNLGRREEYDVLDKRRGRDPEM
GGKPRRKNPQEGLYNELQKDKMAEAYSEIGMKGERRRGKGHDGLY
QGLSTATKDTYDALHMQALPPR Clone 24C1 CD28 CD3 zeta CAR DNA Heavy &
Light Chains
(SEQ ID NO. 31)
```
CAGGTGCAGCTGCAGGAATCCGGACCGGGGCTGGTGAAGCCCAG
CGAGACTCTGAGTCTCACGTGTACAGTTTCTGGAGGTAGCATTAG
CTCCTACTATTGGTCATGGATAAGGCAGCCCCCCGGGAAGGGATT
GGAATGGATCGGCTATATTTACTACAGTGGGAGCACCAATTACAA
CCCCTCACTGAAGTCTAGAGTTACAATCAGCGTTGACACCTCAAA
```

```
GAATCAGTTCAGTTTGAAATTGTCTAGCGTCACAGCAGCTGATAC
AGCCGTCTATTATTGTGTTTCTCTGGTCTATTGCGGTGGGGATTGT
TACAGTGGCTTTGACTATTGGGGGCAGGGTACTCTGGTTACAGTT
TCTTCCGGGGGGGAGGCTCTGGGGGCGGAGGCTCAGGTGGTGG
AGGCAGCGACATCCAGTTGACACAGAGCCCGAGTTCCTTGTCCGC
CTCCGTCGGGGATAGAGTGTCATTTACCTGTCAGGCCTCTCAGGA
TATTAATAACTTTCTGAATTGGTATCAGCAAAAGCCCGGAAAGGC
ACCCAAGCTGTTGATTTACGACGCCAGTAACCTGGAGACAGGCGT
GCCCTCCCGGTTTAGTGGTAGCGGAAGCGGTACGGATTTTACCTT
TACTATCAGCTCTCTCCAACCCGAAGACATTGCAACCTACTATTGT
CAACAATATGGAAACCTGCCTTTTACATTTGGCGGCGGCACCAAG
GTGGAGATTAAGCGGGCGGCAGCTATTGAGGTGATGTATCCACCG
CCTTACCTGGATAACGAAAGAGTAACGGTACCATCATTCACGTG
AAAGGTAAACACCTGTGTCCTTCTCCCCTCTTCCCCGGGCCATCAA
AGCCCTTCTGGGTTCTTGTGGTCGTGGGAGGCGTGCTTGCTTGTTA
TTCTCTGCTCGTTACCGTGGCGTTTATCATTTTTTGGGTTAGATCC
AAAAGAAGCCGCCTGCTCCATAGCGATTACATGAATATGACTCCA
CGCCGCCCTGGCCCCACAAGGAAACACTACCAGCCTTACGCACCA
CCTAGAGATTTCGCTGCCTATCGGAGCAGGGTGAAGTTTTCCAGA
TCTGCAGATGCACCAGCGTATCAGCAGGGCCAGAACCAACTGTAT
AACGAGCTCAACCTGGGACGCAGGGAAGAGTATGACGTTTTGGA
CAAGCGCAGAGGACGGGACCCTGAGATGGGTGGCAAACCAAGAC
GAAAAAACCCCCAGGAGGGTCTCTATAATGAGCTGCAGAAGGAT
AAGATGGCTGAAGCCTATTCTGAAATAGGCATGAAAGGAGAGCG
GAGAAGGGGAAAAGGGCACGACGGTTTGTACCAGGGACTCAGCA
CTGCTACGAAGGATACTTATGACGCTCTCCACATGCAAGCCCTGC
CACCTAGG

Clone 24C1 CD28 CD3 zeta CAR AA Heavy &
Light Chains
                                    (SEQ ID NO. 32)
QVQLQESGPGLVKPSETLSLTCTVSGGSISSYYWSWIRQPPGKGLEWI
GYIYYSGSTNYNPSLKSRVTISVDTSKNQFSLKLSSVTAADTAVYYC
VSLVYCGGDCYSGFDYWGQGTLVTVSSGGGGSGGGGSGGGGSDIQ
LTQSPSSLSASVGDRVSFTCQASQDINNFLNWYQQKPGKAPKLLIYD
ASNLETGVPSRFSGSGSGTDFTFTISSLQPEDIATYYCQQYGNLPFTFG
GGTKVEIKRAAAIEVMYPPPYLDNEKSNGTIIHVKGKHLCPSPLFPGP
SKPFWVLVVVGGVLACYSLLVTVAFIIFWVRSKRSRLLHSDYMNMT
PRRPGPTRKHYQPYAPPRDFAAYRSRVKFSRSADAPAYQQGQNQLY
NELNLGRREEYDVLDKRRGRDPEMGGKPRRKNPQEGLYNELQKDK
MAEAYSEIGMKGERRRGKGHDGLYQGLST
ATKDTYDALHMQALPPR Clone 24C1 CD8 CD3 zeta CAR DNA Heavy &
Light Chains
                                    (SEQ ID NO. 33)
ATGGCACTCCCCGTAACTGCTCTGCTGCTGCCGTTGGCATTGCTCC
TGCACGCCGCACGCCCGCAGGTGCAATTGCAAGAGTCCGGCCCCG
GACTCGTTAAACCCAGTGAGACGCTTAGCCTGACCTGTACCGTCT
CAGGGGGCAGCATCTCCTCTTATTACTGGAGCTGGATCAGGCAGC
CTCCAGGAAAAGGCCTTGAATGGATTGGGTACATCTACTACTCTG
GCTCAACAAATTATAATCCATCCCTGAAGTCCCGCGTGACTATCT
CTGTGGACACCAGCAAGAATCAGTTTTCACTGAAGTTGTCTAGTG
TTACCGCGGCCGACACCGCCGTATACTACTGTGTGTCTCTTGTGTA
CTGTGGCGGCGACTGCTATTCCGGGTTCGACTACTGGGGCCAAGG
GACTCTGGTAACCGTGTCCTCAGGCGGCGGCGGGTCAGGAGGAG
GCGGCAGTGGAGGTGGCGGCTCCGACATCCAGCTGACACAATCA
CCATCTTCCCTTTCAGCTTCAGTCGGGGACAGAGTGTCCTTCACAT
GCCAGGCCAGCCAGGATATCAATAACTTCCTGAACTGGTACCAAC
AGAAACCCGGAAAGGCTCCAAAGCTCCTGATCTATGATGCTTCCA
ACCTGGAGACCGGCGTGCCCTCCAGGTTCAGTGGTTCAGGATCAG
GCACTGACTTTACGTTCACCATATCCAGTCTTCAGCCCGAAGACA
TTGCAACCTATTACTGCCAACAATACGGGAACCTTCCCTTTACATT
CGGAGGCGGCACCAAGGTGGAAATCAAAAGGGCTGCAGCATTGA
GCAACTCAATAATGTATTTTAGTCACTTTGTACCAGTGTTCTTGCC
GGCTAAGCCTACTACCACACCCGCTCCACGGCCACCTACCCCAGC
TCCTACCATCGCTTCACAGCCTCTGTCCCTGCGCCCAGAGGCTTGC
CGACCGGCCGCAGGGGCGCTGTTCATACCAGAGGACTGGATTTC
GCCTGCGATATCTATATCTGGGCACCCCTGGCCGGAACCTGCGGC
GTACTCCTGCTGTCCCTGGTCATCACGCTCTATTGTAATCACAGGA
ACAGATCCAAAAGAAGCCGCCTGCTCCATAGCGATTACATGAATA
TGACTCCACGCCGCCCTGGCCCCACAAGGAAACACTACCAGCCTT
ACGCACCACCTAGAGATTTCGCTGCCTATCGGAGCAGGGTGAAGT
TTTCCAGATCTGCAGATGCACCAGCGTATCAGCAGGGCCAGAACC
AACTGTATAACGAGCTCAACCTGGGACGCAGGGAAGAGTATGAC
GTTTTGGACAAGCGCAGAGGACGGGACCCTGAGATGGGTGGCAA
ACCAAGACGAAAAAACCCCCAGGAGGGTCTCTATAATGAGCTGC
AGAAGGATAAGATGGCTGAAGCCTATTCTGAAATAGGCATGAAA
GGAGAGCGGAGAAGGGGAAAAGGGCACGACGGTTTGTACCAGGG
ACTCAGCACTGCTACGAAGGATACTTATGACGCTCTCCACATGCA
AGCCCTGCCACCTAGGTAA Clone 24C1 CD8 CD3 zeta CAR AA Heavy &
Light Chains
(Signal peptide in bold)
                                    (SEQ ID NO. 34)
MALPVTALLLPLALLLHAARPQVQLQESGPGLVKPSETLSLTCTVS
GGSISSYYWSWIRQPPGKGLEWIGYIYYSGSTNYNPSLKSRVTISVDT
```

SKNQFSLKLSSVTAADTAVYYCVSLVYCGGDCYSGFDYWGQGTLV

TVSSGGGGSGGGGSGGGGSDIQLTQSPSSLSASVGDRVSFTCQASQDI

NNFLNWYQQKPGKAPKLLIYDASNLETGVPSRFSGSGSGTDFTFTISS

LQPEDIATYYCQQYGNLPFTFGGGTKVEIKRAAALSNSIMYFSHFVPV

FLPAKPTTTPAPRPPTPAPTIASQPLSLRPEACRPAAGGAVHTRGLDFA

CDIYIWAPLAGTCGVLLLSLVITLYCNHRNRSKRSRLLHSDYMNMTP

RRPGPTRKHYQPYAPPRDFAAYRSRVKFSRSADAPAYQQGQNQLYN

ELNLGRREEYDVLDKRRGRDPEMGGKPRRKNPQEGLYNELQKDKM

AEAYSEIGMKGERRRGKGHDGLYQGLSTATKDTYDALHMQALPPR

Clone 24C1 CD8 CD3 zeta CAR DNA Heavy &
Light Chains
(SEQ ID NO. 35)
CAGGTGCAATTGCAAGAGTCCGGCCCCGGACTCGTTAAACCCAGT

GAGACGCTTAGCCTGACCTGTACCGTCTCAGGGGGCAGCATCTCC

TCTTATTACTGGAGCTGGATCAGGCAGCCTCCAGGAAAAGGCCTT

GAATGGATTGGGTACATCTACTACTCTGGCTCAACAAATTATAAT

CCATCCCTGAAGTCCCGCGTGACTATCTCTGTGGACACCAGCAAG

AATCAGTTTTCACTGAAGTTGTCTAGTGTTACCGCGGCCGACACC

GCCGTATACTACTGTGTGTCTCTTGTGTACTGTGGCGGCGACTGCT

ATTCCGGGTTCGACTACTGGGGCCAAGGGACTCTGGTAACCGTGT

CCTCAGGCGGCGGCGGGTCAGGAGGAGGCGGCAGTGGAGGTGGC

GGCTCCGACATCCAGCTGACACAATCACCATCTTCCCTTTCAGCTT

CAGTCGGGGACAGAGTGTCCTTCACATGCCAGGCCAGCCAGGATA

TCAATAACTTCCTGAACTGGTACCAACAGAAACCCGGAAAGGCTC

CAAAGCTCCTGATCTATGATGCTTCCAACCTGGAGACCGGCGTGC

CCTCCAGGTTCAGTGGTTCAGGATCAGGCACTGACTTTACGTTCA

CCATATCCAGTCTTCAGCCCGAAGACATTGCAACCTATTACTGCC

AACAATACGGGAACCTTCCCTTTACATTCGGAGGCGGCACCAAGG

TGGAAATCAAAAGGGCTGCAGCATTGAGCAACTCAATAATGTATT

TTAGTCACTTTGTACCAGTGTTCTTGCCGGCTAAGCCTACTACCAC

ACCCGCTCCACGGCCACCTACCCCAGCTCCTACCATCGCTTCACA

GCCTCTGTCCCTGCGCCCAGAGGCTTGCCGACCGGCCGCAGGGGG

CGCTGTTCATACCAGAGGACTGGATTTCGCCTGCGATATCTATATC

TGGGCACCCCTGGCCGGAACCTGCGGCGTACTCCTGCTGTCCCTG

GTCATCACGCTCTATTGTAATCACAGGAACAGATCCAAAAGAAGC

CGCCTGCTCCATAGCGATTACATGAATATGACTCCACGCCGCCCT

GGCCCCACAAGGAAACACTACCAGCCTTACGCACCACCTAGAGAT

TTCGCTGCCTATCGGAGCAGGGTGAAGTTTTCCAGATCTGCAGAT

GCACCAGCGTATCAGCAGGGCCAGAACCAACTGTATAACGAGCT

CAACCTGGGACGCAGGGAAGAGTATGACGTTTTGGACAAGCGCA

GAGGACGGGACCCTGAGATGGGTGGCAAACCAAGACGAAAAAAC

CCCCAGGAGGGTCTCTATAATGAGCTGCAGAAGGATAAGATGGCT

GAAGCCTATTCTGAAATAGGCATGAAAGGAGAGCGGAGAAGGGG

AAAAGGGCACGACGGTTTGTACCAGGGACTCAGCACTGCTACGA

AGGATACTTATGACGCTCTCCACATGCAAGCCCTGCCACCTAGG

Clone 24C1 CD8 CD3 zeta CAR AA Heavy &
Light Chains
(SEQ ID NO. 36)
QVQLQESGPGLVKPSETLSLTCTVSGGSISSYYWSWIRQPPGKGLEWI

GYIYYSGSTNYNPSLKSRVTISVDTSKNQFSLKLSSVTAADTAVYYC

VSLVYCGGDCYSGFDYWGQGTLVTVSSGGGGSGGGGSGGGGSDIQ

LTQSPSSLSASVGDRVSFTCQASQDINNFLNWYQQKPGKAPKLLIYD

ASNLETGVPSRFSGSGSGTDFTFTISSLQPEDIATYYCQQYGNLPFTFG

GGTKVEIKRAAALSNSIMYFSHFVPVFLPAKPTTTPAPRPPTPAPTIAS

QPLSLRPEACRPAAGGAVHTRGLDFACDIYIWAPLAGTCGVLLLSLVI

TLYCNHRNRSKRSRLLHSDYMNMTPRRPGPTRKHYQPYAPPRDFAA

YRSRVKFSRSADAPAYQQGQNQLYNELNLGRREEYDVLDKRRGRDP

EMGGKPRRKNPQEGLYNELQKDKMAEAYSEIGMKGERRRGKGHDG

LYQGLSTATK DTYDALHMQALPPR

Clone 24C1 CD28T CD3 zeta CAR DNA Heavy &
Light Chains
(SEQ ID NO. 37)
ATGGCACTCCCCGTAACTGCTCTGCTGCTGCCGTTGGCATTGCTCC

TGCACGCCGCACGCCCGGATATCCAGCTCACGCAATCCCCCTCAA

GCTTGAGTGCCTCCGTGGGCGACCGGGTGTCCTTCACATGTCAGG

CAAGCCAAGACATAAATAATTTCCTGAATTGGTACCAACAAAAAC

CCGGCAAGGCTCCCAAACTCCTGATTTATGATGCCTCCAATCTGG

AGACCGGGGTCCCTTCTAGATTCAGCGGAAGTGGCAGCGGCACA

GACTTTACATTTACTATCTCTTCTGCAACCAGAGGACATCGCCA

CATACTATTGCCAGCAATACGGCAATCTGCCCTTCACCTTCGGAG

GCGGAACCAAGGTAGAAATTAAAAGGGGCGGTGGAGGCTCCGGA

GGGGGGGGCTCTGGCGGAGGGGGCTCCCAAGTACAATTGCAGGA

GTCAGGGCCTGGACTCGTGAAGCCTTCAGAAACTTTGTCACTGAC

ATGTACAGTGTCCGGCGGAAGCATTTCCAGTTACTATTGGTCCTG

GATTAGACAGCCACCCGGCAAGGACTGGAATGGATTGGATATA

TCTACTACTCTGGATCTACAAACTATAATCCCAGCCTCAAATCCA

GGGTCACTATTAGTGTGGATACATCAAAGAATCAGTTCTCCTTGA

AGCTGAGCTCAGTCACTGCTGCCGACACCGCAGTGTACTATTGTG

TGAGCCTGGTCTACTGCGGCGGAGATTGCTACAGCGGTTTCGATT

ACTGGGGCCAGGGCACCCTGGTTACCGTTAGTTCCGCGGCTGCTC

TTGATAACGAGAAGTCCAACGGTACGATTATCCACGTTAAGGGTA

AGCACCTTTGCCCTAGCCCGCTGTTCCCAGGCCCCAGTAAGCCCTT

TTGGGTCCTCGTTGTGGTAGGTGGGGTACTCGCCTGCTACTCCCTG

CTCGTCACTGTCGCATTCATCATCTTCTGGGTCAGATCCAAAGA

AGCCGCCTGCTCCATAGCGATTACATGAATATGACTCCACGCCGC

CCTGGCCCCACAAGGAAACACTACCAGCCTTACGCACCACCTAGA

GATTTCGCTGCCTATCGGAGCAGGGTGAAGTTTTCCAGATCTGCA

GATGCACCAGCGTATCAGCAGGGCCAGAACCAACTGTATAACGA

GCTCAACCTGGGACGCAGGGAAGAGTATGACGTTTTGGACAAGC

GCAGAGGACGGGACCCTGAGATGGGTGGCAAACCAAGACGAAAA

AACCCCCAGGAGGGTCTCTATAATGAGCTGCAGAAGGATAAGAT

GGCTGAAGCCTATTCTGAAATAGGCATGAAAGGAGAGCGGAGAA

GGGGAAAAGGGCACGACGGTTTGTACCAGGGACTCAGCACTGCT

ACGAAGGATACTTATGACGCTCTCCACATGCAAGCCCTGCCACCT

AGGTAA

Clone 24C1 CD28T CD3 zeta CAR AA Heavy &
Light Chains
(Signal Peptide in Bold)
(SEQ ID NO. 38)
MALPVTALLLPLALLLHAARPDIQLTQSPSSLSASVGDRVSFTCQAS

QDINNFLNWYQQKPGKAPKLLIYDASNLETGVPSRFSGSGSTDFTF

TISSLQPEDIATYYCQQYGNLPFTFGGGTKVEIKRGGGGSGGGGSGG

GGSQVQLQESGPGLVKPSETLSLTCTVSGGSISSYYWSWIRQPPGKGL

EWIGYIYYSGSTNYNPSLKSRVTISVDTSKNQFSLKLSSVTAADTAVY

YCVSLVYCGGDCYSGFDYWGQGTLVTVSSAAALDNEKSNGTIIHVK

GKHLCPSPLFPGPSKPFWVLVVVGGVLACYSLLVTVAFIIFWVRSKRS

RLLHSDYMNMTPRRPGPTRKHYQPYAPPRDFAAYRSRVKFSRSADA

PAYQQGQNQLYNELNLGRREEYDVLDKRRGRDPEMGGKPRRKNPQ

EGLYNELQKDKMAEAYSEIGMKGERRRGKGHDGLYQGLSTATKDT

YDA LHMQALPPR

Clone 24C1 CD28T CD3 zeta CAR DNA Heavy &
Light Chains
(SEQ ID NO. 39)
GATATCCAGCTCACGCAATCCCCCTCAAGCTTGAGTGCCTCCGTG

GGCGACCGGGTGTCCTTCACATGTCAGGCAAGCCAAGACATAAAT

AATTTCCTGAATTGGTACCAACAAAAACCCGGCAAGGCTCCCAAA

CTCCTGATTTATGATGCCTCCAATCTGGAGACCGGGGTCCCTTCTA

GATTCAGCGGAAGTGGCAGCGGCACAGACTTTACATTTACTATCT

CTTCTCTGCAACCAGAGGACATCGCCACATACTATTGCCAGCAAT

ACGGCAATCTGCCCTTCACCTTCGGAGGCGGAACCAAGGTAGAAA

TTAAAAGGGGCGGTGGAGGCTCCGGAGGGGGGGGCTCTGGCGGA

GGGGGCTCCCAAGTACAATTGCAGGAGTCAGGGCCTGGACTCGTG

AAGCCTTCAGAAACTTTGTCACTGACATGTACAGTGTCCGGCGGA

AGCATTTCCAGTTACTATTGGTCCTGGATTAGACAGCCACCCGGC

AAAGGACTGGAATGGATTGGATATATCTACTACTCTGGATCTACA

AACTATAATCCCAGCCTCAAATCCAGGGTCACTATTAGTGTGGAT

ACATCAAAGAATCAGTTCTCCTTGAAGCTGAGTCAGTCACTGCT

GCCGACACCGCAGTGTACTATTGTGTGAGCCTGGTCTACTGCGGC

GGAGATTGCTACAGCGGTTTCGATTACTGGGGCCAGGGCACCCTG

GTTACCGTTAGTTCCGCGGCTGCTCTTGATAACGAGAAGTCCAAC

GGTACGATTATCCACGTTAAGGGTAAGCACCTTTGCCCTAGCCCG

CTGTTCCCAGGCCCCAGTAAGCCCTTTTGGGTCCTCGTTGTGGTAG

GTGGGGTACTCGCCTGCTACTCCCTGCTCGTCACTGTCGCATTCAT

CATCTTCTGGGTCAGATCCAAAAGAAGCCGCCTGCTCCATAGCGA

TTACATGAATATGACTCCACGCCGCCCTGGCCCCACAAGGAAACA

CTACCAGCCTTACGCACCACCTAGAGATTTCGCTGCCTATCGGAG

CAGGGTGAAGTTTTCCAGATCTGCAGATGCACCAGCGTATCAGCA

GGGCCAGAACCAACTGTATAACGAGCTCAACCTGGGACGCAGGG

AAGAGTATGACGTTTTGGACAAGCGCAGAGGACGGGACCCTGAG

ATGGGTGGCAAACCAAGACGAAAAAACCCCCAGGAGGGTCTCTA

TAATGAGCTGCAGAAGGATAAGATGGCTGAAGCCTATTCTGAAAT

AGGCATGAAAGGAGAGCGGAGAAGGGGAAAAGGGCACGACGGT

TTGTACCAGGGACTCAGCACTGCTACGAAGGATACTTATGACGCT

CTCCACATGCAAGCCCTGCCACCTAGG

Clone 24C1 CD28T CD3 zeta CAR AA Heavy &
Light Chains
(SEQ ID NO. 40)
DIQLTQSPSSLSASVGDRVSFTCQASQDINNFLNWYQQKPGKAPKLLI

YDASNLETGVPSRFSGSGSTDFTFTISSLQPEDIATYYCQQYGNLPFT

FGGGTKVEIKRGGGGSGGGGSGGGGSQVQLQESGPGLVKPSETLSLT

CTVSGGSISSYYWSWIRQPPGKGLEWIGYIYYSGSTNYNPSLKSRVTI

SVDTSKNQFSLKLSSVTAADTAVYYCVSLVYCGGDCYSGFDYWGQ

GTLVTVSSAAALDNEKSNGTIIHVKGKHLCPSPLFPGPSKPFWVLVV

VGGVLACYSLLVTVAFIIFWVRSKRSRLLHSDYMNMTPRRPGPTRKH

YQPYAPPRDFAAYRSRVKFSRSADAPAYQQGQNQLYNELNLGRREE

YDVLDKRRGRDPEMGGKPRRKNPQEGLYNELQKDKMAEAYSEIGM

KGERRRGKGHDGLYQGLSTATKDTYDALHMQALPPR

Clone 24C1 CD28 CD3 zeta CAR DNA AA Heavy &
Light Chains
(SEQ ID NO. 41)
ATGGCACTCCCCGTAACTGCTCTGCTGCTGCCGTTGGCATTGCTCC

TGCACGCCGCACGCCCGGATATCCAGCTGACCCAGTCTCCATCCT

CTTTGAGTGCCTCCGTGGGTGACCGCGTCTCTTTCACTTGCCAAGC

CAGCCAAGACATCAACAACTTTCTGAATTGGTACCAGCAGAAACC

AGGCAAAGCACCAAAGCTCCTCATCTACGACGCCTCCAACCTGGA

AACCGGGGTGCCCAGCAGGTTTAGCGGGAGCGGTTCTGGCACGG

ATTTTACGTTCACCATCTCCTCTCTGCAGCCCGAGGATATAGCTAC

TTATTACTGTCAGCAGTACGGGAATCTGCCATTTACTTTTGGGGGT

GGAACTAAGGTGGAAATCAAAAGGGGCGGCGGGGGAAGCGGGG

GCGGGGGCTCAGGTGGCGGAGGGAGCCAGGTGCAACTCCAGGAA

AGTGGCCCAGGATTGGTGAAGCCCAGCGAGACCCTTTCCCTTACT

TGTACTGTTAGCGGAGGCAGCATAAGCAGCTACTATTGGTCCTGG

ATCAGACAGCCACCAGGGAAAGGGCTTGAATGGATTGGCTACATT

-continued

TACTATTCCGGGTCCACCAACTACAACCCATCCCTCAAGTCCCGC

GTGACAATTTCCGTCGACACAAGCAAGAACCAGTTCTCCCTGAAA

CTTAGTAGCGTCACTGCTGCAGATACAGCAGTGTACTATTGTGTC

AGCCTTGTCTACTGTGGCGGCGACTGCTACAGTGGCTTTGATTACT

GGGGACAGGGCACGCTCGTGACAGTGTCCAGCGCTGCGGCTATCG

AGGTAATGTATCCGCCACCGTATCTGGACAACGAGAAGTCTAATG

GGACAATCATTCACGTGAAGGGGAAGCACCTGTGTCCATCCCCCC

TGTTTCCGGGTCCCAGTAAACCCTTCTGGGTGCTTGTTGTCGTTGG

CGGGGTGCTGGCCTGCTATTCCCTGCTGGTGACCGTCGCGTTTATT

ATTTTCTGGGTTAGATCCAAAAGAAGCCGCCTGCTCCATAGCGAT

TACATGAATATGACTCCACGCCGCCCTGGCCCCACAAGGAAACAC

TACCAGCCTTACGCACCACCTAGAGATTTCGCTGCCTATCGGAGC

AGGGTGAAGTTTTCCAGATCTGCAGATGCACCAGCGTATCAGCAG

GGCCAGAACCAACTGTATAACGAGCTCAACCTGGGACGCAGGGA

AGAGTATGACGTTTTGGACAAGCGCAGAGGACGGGACCCTGAGA

TGGGTGGCAAACCAAGACGAAAAAACCCCCAGGAGGGTCTCTAT

AATGAGCTGCAGAAGGATAAGATGGCTGAAGCCTATTCTGAAAT

AGGCATGAAAGGAGAGCGGAGAAGGGGAAAAGGGCACGACGGT

TTGTACCAGGGACTCAGCACTGCTACGAAGGATACTTATGACGCT

CTCCACATGCAAGCCCTGCCACCTAGGTAA

Clone 24C1 CD28 CD3 zeta CAR AA Heavy &
Light Chains (Signal Peptide in Bold)
                                       (SEQ ID NO. 42)
MALPVTALLLPLALLLHAARPDIQLTQSPSSLSASVGDRVSFTCQAS

QDINNFLNWYQQKPGKAPKLLIYDASNLETGVPSRFSGSGSGTDFTF

TISSLQPEDIATYYCQQYGNLPFTFGGGTKVEIKRGGGGSGGGGSGG

GGSQVQLQESGPGLVKPSETLSLTCTVSGGSISSYYWSWIRQPPGKGL

EWIGYIYYSGSTNYNPSLKSRVTISVDTSKNQFSLKLSSVTAADTAVY

YCVSLVYCGGDCYSGFDYWGQGTLVTVSSAAAIEVMYPPPYLDNEK

SNGTIIHVKGKHLCPSPLFPGPSKPFWVLVVVGGVLACYSLLVTVAFI

IFWVRSKRSRLLHSDYMNMTPRRPGPTRKHYQPYAPPRDFAAYRSR

VKFSRSADAPAYQQGQNQLYNELNLGRREEYDVLDKRRGRDPEMG

GKPRRKNPQEGLYNELQKDKMAEAYSEIGMKGERRRGKGHDGLYQ

GLSTATKDTYDALHMQALPPR

Clone 24C1 CD28 CD3 zeta CAR DNA Heavy &
Light Chains
                                       (SEQ ID NO. 43)
GATATCCAGCTGACCCAGTCTCCATCCTCTTTGAGTGCCTCCGTGG

GTGACCGCGTCTCTTTCACTTGCCAAGCCAGCCAAGACATCAACA

ACTTTCTGAATTGGTACCAGCAGAAACCAGGCAAAGCACCAAAG

CTCCTCATCTACGACGCCTCCAACCTGGAAACCGGGGTGCCCAGC

AGGTTTAGCGGGAGCGGTTCTGGCACGGATTTTACGTTCACCATC

TCCTCTCTGCAGCCCGAGGATATAGCTACTTATTACTGTCAGCAGT

ACGGGAATCTGCCATTTACTTTTGGGGGTGGAACTAAGGTGGAAA

TCAAAGGGGCGGCGGGGAAGCGGGGCGGGGCTCAGGTGGC

GGAGGGAGCCAGGTGCAACTCCAGGAAAGTGGCCCAGGATTGGT

GAAGCCCAGCGAGACCCTTTCCCTTACTTGTACTGTTAGCGGAGG

CAGCATAAGCAGCTACTATTGGTCCTGGATCAGACAGCCACCAGG

GAAAGGGCTTGAATGGATTGGCTACATTTACTATTCCGGGTCCAC

CAACTACAACCCATCCCTCAAGTCCCGCGTGACAATTTCCGTCGA

CACAAGCAAGAACCAGTTCTCCCTGAAACTTAGTAGCGTCACTGC

TGCAGATACAGCAGTGTACTATTGTGTCAGCCTTGTCTACTGTGGC

GGCGACTGCTACAGTGGCTTTGATTACTGGGGACAGGGCACGCTC

GTGACAGTGTCCAGCGCTGCGGCTATCGAGGTAATGTATCCGCCA

CCGTATCTGGACAACGAGAAGTCTAATGGGACAATCATTCACGTG

AAGGGGAAGCACCTGTGTCCATCCCCCCTGTTTCCGGGTCCCAGT

AAACCCTTCTGGGTGCTTGTTGTCGTTGGCGGGGTGCTGGCCTGCT

ATTCCCTGCTGGTGACCGTCGCGTTTATTATTTTCTGGGTTAGATC

CAAAAGAAGCCGCCTGCTCCATAGCGATTACATGAATATGACTCC

ACGCCGCCCTGGCCCCACAAGGAAACACTACCAGCCTTACGCACC

ACCTAGAGATTTCGCTGCCTATCGGAGCAGGGTGAAGTTTTCCAG

ATCTGCAGATGCACCAGCGTATCAGCAGGGCCAGAACCAACTGTA

TAACGAGCTCAACCTGGGACGCAGGGAAGAGTATGACGTTTTGG

ACAAGCGCAGAGGACGGGACCCTGAGATGGGTGGCAAACCAAGA

CGAAAAAACCCCCAGGAGGGTCTCTATAATGAGCTGCAGAAGGA

TAAGATGGCTGAAGCCTATTCTGAAATAGGCATGAAAGGAGAGC

GGAGAAGGGGAAAAGGGCACGACGGTTTGTACCAGGGACTCAGC

ACTGCTACGAAGGATACTTATGACGCTCTCCACATGCAAGCCCTG

CCACCTAGG

Clone 24C1 CD28 CD3 zeta CAR AA Heavy &
Light Chains
                                       (SEQ ID NO. 44)
DIQLTQSPSSLSASVGDRVSFTCQASQDINNFLNWYQQKPGKAPKLLI

YDASNLETGVPSRFSGSGSGTDFTFTISSLQPEDIATYYCQQYGNLPFT

FGGGTKVEIKRGGGGSGGGGSGGGGSQVQLQESGPGLVKPSETLSLT

CTVSGGSISSYYWSWIRQPPGKGLEWIGYIYYSGSTNYNPSLKSRVTI

SVDTSKNQFSLKLSSVTAADTAVYYCVSLVYCGGDCYSGFDYWGQ

GTLVTVSSAAAIEVMYPPPYLDNEKSNGTIIHVKGKHLCPSPLFPGPS

KPFWVLVVVGGVLACYSLLVTVAFIIFWVRSKRSRLLHSDYMNMTP

RRPGPTRKHYQPYAPPRDFAAYRSRVKFSRSADAPAYQQGQNQLYN

ELNLGRREEYDVLDKRRGRDPEMGGKPRRKNPQEGLYNELQKDKM

AEAYSEIGMKGERRRGKGHDGLYQGLSTATKDTYDALHMQALPPR

Clone 24C1 CD8 CD3 zeta CAR DNA Heavy &
Light Chains
                                       (SEQ ID NO. 45)
ATGGCACTCCCCGTAACTGCTCTGCTGCTGCCGTTGGCATTGCTCC

TGCACGCCGCACGCCCGGACATTCAATTGACCCAGTCCCCTAGCA

GTCTCTCAGCAAGTGTGGGAGATAGGGTGTCATTCACCTGTCAGG

CTTCACAGGACATCAACAACTTCCTCAATTGGTATCAGCAGAAGC

CAGGGAAGGCACCAAAGCTGCTCATATATGACGCTTCAAACCTTG

AAACCGGAGTACCTAGCCGCTTCAGCGGAAGCGGATCAGGGACT

GACTTCACTTTTACCATCTCTTCACTGCAGCCCGAAGACATCGCCA

CATACTACTGCCAGCAGTACGGAAACTTGCCTTTTACATTTGGGG

GCGGCACCAAAGTGGAGATTAAGCGAGGGGGAGGCGGCTCAGGA

GGCGGTGGCTCCGGAGGCGGGGGTTCCCAGGTCCAGCTCCAGGA

ATCCGGCCCAGGTCTGGTTAAGCCCAGTGAAACTTTGTCCCTCAC

GTGTACTGTGAGCGGTGGTTCAATCTCCTCATACTATTGGTCTTGG

ATACGGCAACCTCCTGGAAAGGGCCTCGAGTGGATCGGCTATATC

TACTATAGTGGCTCCACTAATTACAACCCTTCCCTCAAGTCCAGA

GTCACCATTTCCGTGGACACATCTAAGAACCAGTTCAGTCTGAAG

TTGTCCAGCGTTACAGCCGCAGACACAGCCGTTTATTACTGTGTGT

CTCTTGTTTACTGCGGGGGAGACTGTTATAGCGGCTTCGATTACTG

GGGCCAGGGCACCTTGGTCACAGTCTCTTCCGCGGCCGCCCTCTC

TAACAGTATTATGTACTTTTCTCATTTTGTACCCGTGTTCCTTCCCG

CTAAGCCAACTACTACCCCGGCCCCACGGCCGCCTACCCCTGCAC

CCACAATAGCCAGTCAGCCTTTGAGCCTGAGACCTGAGGCTTGTC

GGCCGGCTGCTGGGGGTGCAGTGCACACACGAGGTCTTGATTTTG

CTTGCGACATATACATCTGGGCCCCTCTGGCCGGGACCTGTGGGG

TGCTGCTTCTGAGCTTGGTCATCACGCTCTATTGCAACCATCGCAA

CAGATCCAAAAGAAGCCGCCTGCTCCATAGCGATTACATGAATAT

GACTCCACGCCGCCCTGGCCCCACAAGGAAACACTACCAGCCTTA

CGCACCACCTAGAGATTTCGCTGCCTATCGGAGCAGGGTGAAGTT

TTCCAGATCTGCAGATGCACCAGCGTATCAGCAGGGCCAGAACCA

ACTGTATAACGAGCTCAACCTGGGACGCAGGGAAGAGTATGACG

TTTTGGACAAGCGCAGAGGACGGGACCCTGAGATGGGTGGCAAA

CCAAGACGAAAAAACCCCCAGGAGGGTCTCTATAATGAGCTGCA

GAAGGATAAGATGGCTGAAGCCTATTCTGAAATAGGCATGAAAG

GAGAGCGGAGAAGGGGAAAAGGGCACGACGGTTTGTACCAGGGA

CTCAGCACTGCTACGAAGGATACTTATGACGCTCTCCACATGCAA

GCCCTGCCACCTAGGTAA

Clone 24C1 CD8 CD3 zeta CAR AA Heavy &
Light Chains (Signal Peptide in Bold)

(SEQ ID NO. 46)

MALPVTALLLPLALLLHAARPDIQLTQSPSSLSASVGDRVSFTCQAS

QDINNFLNWYQQKPGKAPKLLIYDASNLETGVPSRFSGSGSGTDFTF

TISSLQPEDIATYYCQQYGNLPFTFGGGTKVEIKRGGGGSGGGGSGG

GGSQVQLQESGPGLVKPSETLSLTCTVSGGSISSYYWSWIRQPPGKGL

EWIGYIYYSGSTNYNPSLKSRVTISVDTSKNQFSLKLSSVTAADTAVY

YCVSLVYCGGDCYSGFDYWGQGTLVTVSSAAALSNSIMYFSHFVPV

FLPAKPTTTPAPRPPTPAPTIASQPLSLRPEACRPAAGGAVHTRGLDFA

CDIYIWAPLAGTCGVLLLSLVITLYCNHRNRSKRSRLLHSDYMNMTP

RRPGPTRKHYQPYAPPRDFAAYRSRVKFSRSADAPAYQQGQNQLYN

ELNLGRREEYDVLDKRRGRDPEMGGKPRRKNPQEGLYNELQKDKM

AEAYSEIGMKGERRRGKGHDGLYQGLSTATKDTYDALHMQALPPR

Clone 24C1 CD8 CD3 zeta CAR DNA Heavy &
Light Chains (SEQ ID NO. 47)

GACATTCAATTGACCCAGTCCCCTAGCAGTCTCTCAGCAAGTGTG

GGAGATAGGGTGTCATTCACCTGTCAGGCTTCACAGGACATCAAC

AACTTCCTCAATTGGTATCAGCAGAAGCCAGGGAAGGCACCAAA

GCTGCTCATATATGACGCTTCAAACCTTGAAACCGGAGTACCTAG

CCGCTTCAGCGGAAGCGGATCAGGGACTGACTTCACTTTTACCAT

CTCTTCACTGCAGCCCGAAGACATCGCCACATACTACTGCCAGCA

GTACGGAAACTTGCCTTTTACATTTGGGGGCGGCACCAAAGTGGA

GATTAAGCGAGGGGGAGGCGGCTCAGGAGGCGGTGGCTCCGGAG

GCGGGGGTTCCCAGGTCCAGCTCCAGGAATCCGGCCCAGGTCTGG

TTAAGCCCAGTGAAACTTTGTCCCTCACGTGTACTGTGAGCGGTG

GTTCAATCTCCTCATACTATTGGTCTTGGATACGGCAACCTCCTGG

AAAGGGCCTCGAGTGGATCGGCTATATCTACTATAGTGGCTCCAC

TAATTACAACCCTTCCCTCAAGTCCAGAGTCACCATTTCCGTGGAC

ACATCTAAGAACCAGTTCAGTCTGAAGTTGTCCAGCGTTACAGCC

GCAGACACAGCCGTTTATTACTGTGTGTCTCTTGTTTACTGCGGGG

GAGACTGTTATAGCGGCTTCGATTACTGGGGCCAGGGCACCTTGG

TCACAGTCTCTTCCGCGGCCGCCCTCTCTAACAGTATTATGTACTT

TTCTCATTTTGTACCCGTGTTCCTTCCCGCTAAGCCAACTACTACC

CCGGCCCCACGGCCGCCTACCCCTGCACCCACAATAGCCAGTCAG

CCTTTGAGCCTGAGACCTGAGGCTTGTCGGCCGGCTGCTGGGGGT

GCAGTGCACACACGAGGTCTTGATTTTGCTTGCGACATATACATC

TGGGCCCCTCTGGCCGGGACCTGTGGGGTGCTGCTTCTGAGCTTG

GTCATCACGCTCTATTGCAACCATCGCAACAGATCCAAAAGAAGC

CGCCTGCTCCATAGCGATTACATGAATATGACTCCACGCCGCCCT

GGCCCCACAAGGAAACACTACCAGCCTTACGCACCACCTAGAGAT

TTCGCTGCCTATCGGAGCAGGGTGAAGTTTTCCAGATCTGCAGAT

GCACCAGCGTATCAGCAGGGCCAGAACCAACTGTATAACGAGCT

CAACCTGGGACGCAGGGAAGAGTATGACGTTTTGGACAAGCGCA

GAGGACGGGACCCTGAGATGGGTGGCAAACCAAGACGAAAAAAC

CCCCAGGAGGGTCTCTATAATGAGCTGCAGAAGGATAAGATGGCT

GAAGCCTATTCTGAAATAGGCATGAAAGGAGAGCGGAGAAGGGG

AAAAGGGCACGACGGTTTGTACCAGGGACTCAGCACTGCTACGA

AGGATACTTATGACGCTCTCCACATGCAAGCCCTGCCACCTAGG

```
Clone 24C1 CD8 CD3 zeta CAR AA Heavy &
Light Chains
                                    (SEQ ID NO. 48)
DIQLTQSPSSLSASVGDRVSFTCQASQDINNFLNWYQQKPGKAPKLLI

YDASNLETGVPSRFSGSGSGTDFTFTISSLQPEDIATYYCQQYGNLPFT

FGGGTKVEIKRGGGGSGGGGSGGGGSQVQLQESGPGLVKPSETLSLT

CTVSGGSISSYYWSWIRQPPGKGLEWIGYIYYSGSTNYNPSLKSRVTI

SVDTSKNQFSLKLSSVTADTAVYYCVSLVYCGGDCYSGFDYWGQGT

LVTVSSAAALSNSIMYFSHFVPVFLPAKPTTTPAPRPPTPAPTIASQPLS

LRPEACRPAAGGAVHTRGLDFACDIYIWAPLAGTCGVLLLSLVITLY

CNHRNRSKRSRLLHSDYMNMTPRRPGPTRKHYQPYAPPRDFAAYRS

RVKFSRSADAPAYQQGQNQLYNELNLGREEYDVLDKRRGRDPEMG

GKPRRKNPQEGLYNELQKDKMAEAYSEIGMKGERRRGKGHDGLYQ

GLSTATK DTYDALHMQA LPPR

Clone 24C8 Heavy Chain (HC) DNA
                                    (SEQ ID NO. 48)
CAGGTACAGCTGCAGGAATCTGGGCCCGGACTTGTCAAGCCAAGT

CAGACACTTTCTCTTACATGTACCGTGAGCGGCGGAAGTATAAGC

AGTGGAGGCTTTTACTGGTCTTGGATACGGCAGCACCCAGGCAAA

GGCTTGGAGTGGATTGGATACATTCATCATTCAGGATCTACACAC

TATAATCCATCCCTTAAGTCCCGGGTCACCATTAGCATTGATACGT

CTAAGAATCTGTTCAGTCTCAGGCTGTCCTCCGTCACTGCTGCCGA

CACAGCCGTGTACTACTGCGCCTCCTTGGTTTACTGCGGAGGCGA

CTGTTATAGCGGCTTTGATTATTGGGGCAGGGGACCCTCGTAAC

CGTGAGCTCT

Clone 24C8 AA HC (CDRs in Underline)
                                    (SEQ ID NO. 50)
QVQLQESGPGLVKPSQTLSLTCTVSGGSISSGGFYWSWIRQHPGKGL

EWIGYIHHSGSTHYNPSLKSRVTISIDTSKNLFSLRLSSVTAADTAVYY

CASLVYCGGDCYSGFDYWGQGTLVTVSS

Clone 24C8 HC CDR1 AA:
                                    (SEQ ID NO. 51)
GGSISSGGF Clone 24C8 HC CDR2 AA:
                                    (SEQ ID NO. 52)
HHSGS Clone 24C8 HC CDR3 AA:
                                    (SEQ ID NO. 53)
LVYCGGDCYS GFDY Clone 24C8 Light Chain (LC) DNA
                                    (SEQ ID NO. 54)
GATATCCAGCTCACTCAAAGCCCCTCTAGTCTCTCTGCCTCAGTGG

GGGATCGGGTCAGTTTTACTTGTCAAGCTTCACAGGATATCAACA

ACTTCCTTAATTGGTATCAGCAGAAGCCAGGAAAAGCACCCAAGC

TGCTCATCTATGATGCCTCAAATTTGGAGACGGGTGTTCCCAGTC

GATTCTCTGGGTCAGGGTCCGGGACCGACTTTACGTTTACGATCTC

CTCTCTGCAGCCCGAAGACATCGCCACATACTATTGTCAACAGTA

CGGCAACTTGCCTTTCACATTTGGGGCGGGACTAAGGTTGAAAT

CAAGAGG

Clone 24C8 LC AA (CDRs in Underline)
                                    (SEQ ID NO. 55)
DIQLTQSPSSLSASVGDRVSFTCQASQDINNFLNWYQQKPGKAPKLLI

YDASNLETGVPSRFSGSGSGTDFTFTISSLQPEDIATYYCQQYGNLPFT

FGGGTKVEIKR

Clone 24C8 LC CDR1 AA:
                                    (SEQ ID NO. 56)
QASQDINNFLN Clone 24C8 LC CDR2 AA:
                                    (SEQ ID NO. 57)
DASNLET Clone 24C8 LC CDR3 AA:
                                    (SEQ ID NO. 58)
QQYGNLPFT Clone 24C8 CD28T CD3 zeta CAR DNA Heavy &
Light Chains
                                    (SEQ ID NO. 59)
ATGGCACTCCCCGTAACTGCTCTGCTGCTGCCGTTGGCATTGCTCC

TGCACGCCGCACGCCCGCAGGTACAGCTGCAGGAATCTGGGCCCG

GACTTGTCAAGCCAAGTCAGACACTTTCTCTTACATGTACCGTGA

GCGGCGGAAGTATAAGCAGTGGAGGCTTTTACTGGTCTTGGATAC

GGCAGCACCCAGGCAAAGGCTTGGAGTGGATTGGATACATTCATC

ATTCAGGATCTACACACTATAATCCATCCCTTAAGTCCCGGGTCA

CCATTAGCATTGATACGTCTAAGAATCTGTTCAGTCTCAGGCTGTC

CTCCGTCACTGCTGCCGACACAGCCGTGTACTACTGCGCCTCCTTG

GTTTACTGCGGAGGCGACTGTTATAGCGGCTTTGATTATTGGGGG

CAGGGGACCCTCGTAACCGTGAGCTCTGGAGGGGGTGGGAGCGG

GGGAGGAGGTTCAGGGGGGGCGGCTCCGATATCCAGCTCACTC

AAAGCCCCTCTAGTCTCTCTGCCTCAGTGGGGGATCGGGTCAGTT

TTACTTGTCAAGCTTCACAGGATATCAACAACTTCCTTAATTGGTA

TCAGCAGAAGCCAGGAAAAGCACCCAAGCTGCTCATCTATGATGC

CTCAAATTTGGAGACGGGTGTTCCCAGTCGATTCTCTGGGTCAGG

GTCCGGGACCGACTTTACGTTTACGATCTCCTCTCTGCAGCCCGAA

GACATCGCCACATACTATTGTCAACAGTACGGCAACTTGCCTTTC

ACATTTGGGGCGGGACTAAGGTTGAAATCAAGAGGGCCGCTGC

ACTGGACAATGAGAAGTCCAACGGCACCATCATCCACGTGAAGG

GCAAGCACCTGTGCCCTAGTCCTCTGTTCCCAGGCCCATCCAAAC

CTTTTTGGGTTCTTGTTGTGGTCGGGGGGTGCTGGCCTGCTATTC

TCTGCTGGTCACGGTGGCCTTCATAATTTTCTGGGTTAGATCCAAA

AGAAGCCGCCTGCTCCATAGCGATTACATGAATATGACTCCACGC

CGCCCTGGCCCCACAAGGAAACACTACCAGCCTTACGCACCACCT

AGAGATTTCGCTGCCTATCGGAGCAGGGTGAAGTTTTCCAGATCT

GCAGATGCACCAGCGTATCAGCAGGGCCAGAACCAACTGTATAA

CGAGCTCAACCTGGGACGCAGGGAAGAGTATGACGTTTTGGACA
```

-continued

AGCGCAGAGGACGGGACCCTGAGATGGGTGGCAAACCAAGACGA

AAAAACCCCCAGGAGGGTCTCTATAATGAGCTGCAGAAGGATAA

GATGGCTGAAGCCTATTCTGAAATAGGCATGAAAGGAGAGCGGA

GAAGGGGAAAAGGGCACGACGTTTGTACCAGGGACTCAGCACT

GCTACGAAGGATACTTATGACGCTCTCCACATGCAAGCCCTGCCA

CCTAGGTAA

Clone 24C8 CD28T CD3 zeta CAR AA Heavy &
Light Chains (Signal Peptide in Bold)
(SEQ ID NO. 60)
MALPVTALLLPLALLLHAARPQVQLQESGPGLVKPSQTLSLTCTVS

GGSISSGGFYWSWIRQHPGKGLEWIGYIHHSGSTHYNPSLKSRVTISI

DTSKNLFSLRLSSVTAADTAVYYCASLVYCGGDCYSGFDYWGQGTL

VTVSSGGGGSGGGGSGGGGSDIQLTQSPSSLSASVGDRVSFTCQASQ

DINNFLNWYQQKPGKAPKLLIYDASNLETGVPSRFSGSGSGTDFTFTI

SSLQPEDIATYYCQQYGNLPFTFGGGTKVEIKRAAALDNEKSNGTIIH

VKGKHLCPSPLFPGPSKPFWVLVVVGGVLACYSLLVTVAFIIFWVRS

KRSRLLHSDYMNMTPRRPGPTRKHYQPYAPPRDFAAYRSRVKFSRS

ADAPAYQQGQNQLYNELNLGRREEYDVLDKRRGRDPEMGGKPRRK

NPQEGLYNELQKDKMAEAYSEIGMKGERRRGKGHDGLYQGLSTAT

KDTYDALHMQALPPR

Clone 24C8 CD28T CD3 zeta CAR DNA Heavy &
Light Chains
(SEQ ID NO. 61)
CAGGTACAGCTGCAGGAATCTGGGCCCGGACTTGTCAAGCCAAGT

CAGACACTTTCTCTTACATGTACCGTGAGCGGCGGAAGTATAAGC

AGTGGAGGCTTTTACTGGTCTTGGATACGGCAGCACCCAGGCAAA

GGCTTGGAGTGGATTGGATACATTCATCATTCAGGATCTACACAC

TATAATCCATCCCTTAAGTCCCGGGTCACCATTAGCATTGATACGT

CTAAGAATCTGTTCAGTCTCAGGCTGTCCTCCGTCACTGCTGCCGA

CACAGCCGTGTACTACTGCGCCTCCTTGGTTTACTGCGGAGGCGA

CTGTTATAGCGGCTTTGATTATTGGGGCAGGGGACCCTCGTAAC

CGTGAGCTCGGAGGGGTGGGAGCGGGGAGGAGGTTCAGGGG

GGGGCGGCTCCGATATCCAGCTCACTCAAAGCCCCTCTAGTCTCT

CTGCCCTCAGTGGGGATCGGGTCAGTTTTACTTGTCAAGCTTCAC

AGGATATCAACAACTTCCTTAATTGGTATCAGCAGAAGCCAGGAA

AAGCACCCAAGCTGCTCATCTATGATGCCTCAAATTTGGAGACGG

GTGTTCCCAGTCGATTCTCTGGGTCAGGGTCCGGGACCGACTTTA

CGTTTACGATCTCCTCTCTGCAGCCCGAAGACATCGCCACATACT

ATTGTCAACAGTACGGCAACTTGCCTTTCACATTTGGGGCGGGA

CTAAGGTTGAAATCAAGAGGGCCGCTGCACTGGACAATGAGAAG

TCCAACGGCACCATCATCCACGTGAAGGGCAAGCACCTGTGCCCT

AGTCCTCTGTTCCCAGGCCCATCCAAACCTTTTTGGGTTCTTGTTG

TGGTCGGGGGGTGCTGGCCTGCTATTCTCTGCTGGTCACGGTGG

-continued

CCTTCATAATTTTCTGGGTTAGATCCAAAAGAAGCCGCCTGCTCC

ATAGCGATTACATGAATATGACTCCACGCCGCCCTGGCCCCACAA

GGAAACACTACCAGCCTTACGCACCACCTAGAGATTTCGCTGCCT

ATCGGAGCAGGGTGAAGTTTTCCAGATCTGCAGATGCACCAGCGT

ATCAGCAGGGCCAGAACCAACTGTATAACGAGCTCAACCTGGGA

CGCAGGGAAGAGTATGACGTTTTGGACAAGCGCAGAGGACGGGA

CCCTGAGATGGGTGGCAAACCAAGACGAAAAAACCCCCAGGAGG

GTCTCTATAATGAGCTGCAGAAGGATAAGATGGCTGAAGCCTATT

CTGAAATAGGCATGAAAGGAGAGCGGAGAAGGGGAAAAGGGCA

CGACGTTTGTACCAGGGACTCAGCACTGCTACGAAGGATACTTA

TGACGCTCTCCACATGCAAGCCCTGCCACCTAGG

Clone 24C8 CD28T CD3 zeta CAR AA Heavy &
Light Chains
(SEQ ID NO. 62)
QVQLQESGPGLVKPSQTLSLTCTVSGGSISSGGFYWSWIRQHPGKGL

EWIGYIHHSGSTHYNPSLKSRVTISIDTSKNLFSLRLSSVTAADTAVYY

CASLVYCGGDCYSGFDYWGQGTLVTVSSGGGGSGGGGSGGGGSDI

QLTQSPSSLSASVGDRVSFTCQASQDINNFLNWYQQKPGKAPKLLIY

DASNLETGVPSRFSGSGSGTDFTFTISSLQPEDIATYYCQQYGNLPFTF

GGGTKVEIKRAAALDNEKSNGTIIHVKGKHLCPSPLFPGPSKPFWVL

VVVGGVLACYSLLVTVAFIIFWVRSKRSRLLHSDYMNMTPRRPGPTR

KHYQPYAPPRDFAAYRSRVKFSRSADAPAYQQGQNQLYNELNLGRR

EEYDVLDKRRGRDPEMGGKPRRKNPQEGLYNELQKDKMAEAYSEI

GMKGERRRGKGHDGLYQGLSTATKDTYDALHMQALPPR

Clone 24C8 CD28 CD3 zeta CAR DNA Heavy &
Light Chains
(SEQ ID NO. 63)
ATGGCACTCCCCGTAACTGCTCTGCTGCTGCCGTTGGCATTGCTCC

TGCACGCCGCACGCCCGCAGGTGCAGCTGCAGGAAAGCGGTCCG

GGACTTGTCAAGCCGTCCCAAACGCTGAGTCTGACGTGTACTGTC

TCTGGTGGCTCTATTTCTTCCGGGGCTTTTATTGGTCTTGGATCA

GACAACACCCTGGCAAAGGGCTGGAGTGGATAGGGTATATTCAC

CACTCTGGGTCCACTCACTACAACCCATCATTGAAATCCAGAGTG

ACTATCTCAATCGACACATCCAAGAACCTTTTCAGCCTGAGGTTG

TCATCAGTTACCGCCGCTGACACCGCGGTGTATTATTGCGCCTCTC

TCGTGTACTGCGGTGGCGATTGTTATAGTGGCTTTGACTACTGGG

GCAGGGGACATTGGTTACCGTTTCAAGTGGAGGCGGTGGGTCTG

GCGGGGGCGGTAGCGGAGGTGGGGGGAGCGACATACAGCTTACG

CAGAGCCCCTCCAGCCTTTCAGCCTCCGTGGGGGATAGGGTGTCC

TTTACCTGCCAGGCTTCCCAGGACATAAACAACTTCCTCAATTGGT

ATCAGCAAAGCCCGGGAAAGCACCAAAGCTGCTCATCTACGAT

GCCAGCAACCTGGAAACCGGAGTGCCGTCTCGCTTCTCTGGAAGT

GGCAGTGGGACCGATTTCACTTTTACAATCTCAAGTTTGCAGCCA

GAAGACATTGCAACATACTACTGTCAACAGTACGGCAATCTCCCC

```
TTTACATTTGGGGGGGGAACTAAAGTGGAGATTAAGCGCGCTGCA

GCCATTGAAGTTATGTATCCGCCCCCGTATCTGGATAACGAGAAA

TCTAATGGTACCATAATACATGTGAAGGGAAGCACCTCTGTCCA

TCACCGCTGTTCCCCGGCCCTTCAAAACCTTTCTGGGTACTCGTTG

TCGTGGGTGGAGTTCTGGCCTGCTATAGTCTGCTGGTGACCGTGG

CGTTTATCATCTTCTGGGTAAGATCCAAAAGAAGCCGCCTGCTCC

ATAGCGATTACATGAATATGACTCCACGCCGCCCTGGCCCCACAA

GGAAACACTACCAGCCTTACGCACCACCTAGAGATTTCGCTGCCT

ATCGGAGCAGGGTGAAGTTTTCCAGATCTGCAGATGCACCAGCGT

ATCAGCAGGGCCAGAACCAACTGTATAACGAGCTCAACCTGGGA

CGCAGGGAAGAGTATGACGTTTTGGACAAGCGCAGAGGACGGGA

CCCTGAGATGGGTGGCAAACCAAGACGAAAAAACCCCCAGGAGG

GTCTCTATAATGAGCTGCAGAAGGATAAGATGGCTGAAGCCTATT

CTGAAATAGGCATGAAAGGAGAGCGGAGAAGGGGAAAAGGGCA

CGACGGTTTGTACCAGGGACTCAGCACTGCTACGAAGGATACTTA

TGACGCTCTCCACATGCAAGCCCTGCCACCTAGGTAA
```

Clone 24C8 CD28 CD3 zeta CAR AA Heavy &
Light Chains (Signal Peptide in Bold)
(SEQ ID NO. 64)

MALPVTALLLPLALLLHAARPQVQLQESGPGLVKPSQTLSLTCTVS
GGSISSGGFYWSWIRQHPGKGLEWIGYIHHSGSTHYNPSLKSRVTISI
DTSKNLFSLRLSSVTAADTAVYYCASLVYCGGDCYSGFDYWGQTL
VTVSSGGGGSGGGGSGGGGSDIQLTQSPSSLSASVGDRVSFTCQASQ
DINNFLNWYQQKPGKAPKLLIYDASNLETGVPSRFSGSGSGTDFTFTI
SSLQPEDIATYYCQQYGNLPFTFGGGTKVEIKRAAAIEVMYPPPYLD
NEKSNGTIIHVKGKHLCPSPLFPGPSKPFWVLVVVGGVLACYSLLVT
VAFIIFWVRSKRSRLLHSDYMNMTPRRPGPTRKHYQPYAPPRDFAAY
RSRVKFSRSADAPAYQQGQNQLYNELNLGRREEYDVLDKRRGRDPE
MGGKPRRKNPQEGLYNELQKDMAEAYSEIGMKGERRRGKGHDGL
YQGLSTATKDTYDALHMQALPPR

Clone 24C8 CD28 CD3 zeta CAR DNA Heavy &
Light Chains
(SEQ ID NO. 65)

```
CAGGTGCAGCTGCAGGAAAGCGGTCCGGGACTTGTCAAGCCGTCC

CAAACGCTGAGTCTGACGTGTACTGTCTCTGGTGGCTCTATTTCTT

CCGGGGGCTTTTATTGGTCTTGGATCAGACAACACCCTGGCAAAG

GGCTGGAGTGGATAGGGTATATTCACCACTCTGGGTCCACTCACT

ACAACCCATCATTGAAATCCAGAGTGACTATCTCAATCGACACAT

CCAAGAACCTTTTCAGCCTGAGGTTGTCATCAGTTACCGCCGCTG

ACACCGCGGTGTATTATTGCGCCTCTCTCGTGTACTGCGGTGGCG

ATTGTTATAGTGGCTTTGACTACTGGGGGCAGGGGACATTGGTTA

CCGTTTCAAGTGGAGGCGGTGGGTCTGGCGGGGGCGGTAGCGGA

GGTGGGGGGAGCGACATACAGCTTACGCAGAGCCCCTCCAGCCTT
```

```
TCAGCCTCCGTGGGGGATAGGGTGTCCTTTACCTGCCAGGCTTCC

CAGGACATAAACAACTTCCTCAATTGGTATCAGCAAAAGCCCGGG

AAAGCACCAAAGCTGCTCATCTACGATGCCAGCAACCTGGAAACC

GGAGTGCCGTCTCGCTTCTCTGGAAGTGGCAGTGGGACCGATTTC

ACTTTTACAATCTCAAGTTTGCAGCCAGAAGACATTGCAACATAC

TACTGTCAACAGTACGGCAATCTCCCCTTTACATTTGGGGGGGA

ACTAAAGTGGAGATTAAGCGCGCTGCAGCCATTGAAGTTATGTAT

CCGCCCCCGTATCTGGATAACGAGAAATCTAATGGTACCATAATA

CATGTGAAGGGAAGCACCTCTGTCCATCACCGCTGTTCCCCGGC

CCTTCAAAACCTTTCTGGGTACTCGTTGTCGTGGGTGGAGTTCTGG

CCTGCTATAGTCTGCTGGTGACCGTGGCGTTTATCATCTTCTGGGT

AAGATCCAAAAGAAGCCGCCTGCTCCATAGCGATTACATGAATAT

GACTCCACGCCGCCCTGGCCCCACAAGGAAACACTACCAGCCTTA

CGCACCACCTAGAGATTTCGCTGCCTATCGGAGCAGGGTGAAGTT

TTCCAGATCTGCAGATGCACCAGCGTATCAGCAGGGCCAGAACCA

ACTGTATAACGAGCTCAACCTGGGACGCAGGGAAGAGTATGACG

TTTTGGACAAGCGCAGAGGACGGGACCCTGAGATGGGTGGCAAA

CCAAGACGAAAAAACCCCCAGGAGGGTCTCTATAATGAGCTGCA

GAAGGATAAGATGGCTGAAGCCTATTCTGAAATAGGCATGAAAG

GAGAGCGGAGAAGGGGAAAAGGGCACGACGGTTTGTACCAGGGA

CTCAGCACTGCTACGAAGGATACTTATGACGCTCTCCACATGCAA

GCCCTGCCACCTAGG
```

Clone 24C8 CD28 CD3 zeta CAR AA Heavy &
Light Chains
(SEQ ID NO. 66)

QVQLQESGPGLVKPSQTLSLTCTVSGGSISSGGFYWSWIRQHPGKGL
EWIGYIHHSGSTHYNPSLKSRVTISIDTSKNLFSLRLSSVTAADTAVYY
CASLVYCGGDCYSGFDYWGQGTLVTVSSGGGGSGGGGSGGGGSDI
QLTQSPSSLSASVGDRVSFTCQASQDINNFLNWYQQKPGKAPKLLIY
DASNLETGVPSRFSGSGSGTDFTFTISSLQPEDIATYYCQQYGNLPFTF
GGGTKVEIKRAAAIEVMYPPPYLDNEKSNGTIIHVKGKHLCPSPLFPG
PSKPFWVLVVVGGVLACYSLLVTVAFIIFWVRSKRSRLLHSDYMNM
TPRRPGPTRKHYQPYAPPRDFAAYRSRVKFSRSADAPAYQQGQNQL
YNELNLGRREEYDVLDKRRGRDPEMGGKPRRKNPQEGLYNELQKD
KMAEAYSEIGMKGERRRGKGHDGLYQGLSTATKDTYDALHMQALP
PR

Clone 24C8 CD8 CD3 zeta CAR DNA Heavy &
Light Chains
(SEQ ID NO. 67)

ATGGCACTCCCCGTAACTGCTCTGCTGCTGCCGTTGGCATTGCTCC
TGCACGCCGCACGCCCGCAGGTGCAGTTGCAGGAAAGCGGGCCT
GGCCTTGTGAAACCAAGCCAGACACTGAGCCTGACATGCACTGTG
TCCGGCGGGTCCATATCTTCCGGGGGTTTTTATTGGTCCTGGATAC
GCCAGCATCCCGGGAAAGGACTTGAATGGATTGGATATATCCACC

ATTCCGGAAGCACCCACTACAATCCAAGCCTTAAATCCCGGGTGA
CAATCTCCATCGACACCTCAAAGAATCTTTTTTCCCTGCGGTTGTC
TTCAGTAACTGCCGCCGATACCGCTGTGTACTACTGTGCCAGCCTC
GTCTATTGCGGCGGAGATTGTTATTCTGGGTTCGATTATTGGGTC
AAGGCACACTGGTAACTGTCAGCAGCGGAGGCGGCGGTTCCGGG
GGCGGGGGCAGTGGAGGGGGCGGATCTGACATTCAGCTTACGCA
GTCCCCATCTTCACTTAGCGCCAGCGTTGGCGATCGGGTCAGCTTC
ACGTGTCAAGCAAGTCAGGATATCAACAACTTTCTTAACTGGTAC
CAGCAGAAGCCAGGCAAGGCACCCAAGTTGCTGATTTACGATGCT
TCTAACCTCGAGACGGGAGTGCCTAGCCGCTTCTCCGGGAGCGGC
AGCGGCACAGACTTTACCTTTACGATTTCCAGTCTGCAGCCAGAG
GATATAGCAACTTATTACTGTCAGCAGTATGGCAACCTCCCTTTTA
CCTTCGGTGGTGGCACAAAGGTCGAGATTAAAAGAGCCGCAGCG
TTGTCCAACTCCATAATGTATTTTTCTCATTTTGTGCCCGTCTTTCT
GCCTGCCAAACCTACCACCACCCCCGCCCCACGACCACCTACTCC
AGCCCCCACCATCGCCTCCCAGCCCCTCAGCCTGAGGCCAGAGGC
TTGTCGCCCTGCTGCGGGGGCGCTGTCCATACCAGAGGACTCGA
CTTCGCCTGCGATATTTATATATGGGCCCCCTCGCCGGCACCTGC
GGAGTCTTGCTCCTGAGCCTTGTGATCACGCTTTATTGTAACCATC
GGAATAGATCCAAAAGAAGCCGCCTGCTCCATAGCGATTACATGA
ATATGACTCCACGCCGCCCTGGCCCCACAAGGAAACACTACCAGC
CTTACGCACCACCTAGAGATTTCGCTGCCTATCGGAGCAGGGTGA
AGTTTTCCAGATCTGCAGATGCACCAGCGTATCAGCAGGGCCAGA
ACCAACTGTATAACGAGCTCAACCTGGGACGCAGGGAAGAGTAT
GACGTTTTGGACAAGCGCAGAGGACGGGACCCTGAGATGGGTGG
CAAACCAAGACGAAAAAACCCCCAGGAGGGTCTCTATAATGAGC
TGCAGAAGGATAAGATGGCTGAAGCCTATTCTGAAATAGGCATG
AAAGGAGAGCGGAGAAGGGGAAAAGGGCACGACGGTTTGTACCA
GGGACTCAGCACTGCTACGAAGGATACTTATGACGCTCTCCACAT
GCAAGCCCTGCCACCTAGGTAA

Clone 24C8 CD8 CD3 zeta CAR AA Heavy &
Light Chains (Signal Peptide in Bold)
(SEQ ID NO. 68)
MALPVTALLLPLALLLHAARPQVQLQESGPGLVKPSQTLSLTCTVS
GGSISSGGFYWSWIRQHPGKGLEWIGYIHHSGSTHYNPSLKSRVTISI
DTSKNLFSLRLSSVTAADTAVYYCASLVYCGGDCYSGFDYWGQGTL
VTVSSGGGGSGGGGSGGGGSDIQLTQSPSSLSASVGDRVSFTCQASQ
DINNFLNWYQQKPGKAPKLLIYDASNLETGVPRFSGSGSGTDFTFTIS
SLQPEDIATYYCQYGNLPFTFGGGTKVEIKRAAALSNSIMYFSHFVPV
FLPAKPTTTPAPRPPTPAPTIASQPLSLRPEACRPAAGGAVHTRGLDFA
CDIYIWAPLAGTCGVLLLSLVITLYCNHRNRSKRSRLLHSDYMNMTP
RRPGPTRKHYQPYAPPRDFAAYRSRVKFSRSADAPAYQQGQNQLYN ELNLGRREEYDVLDKRRGRDPEMGGKPRRKNPQEGLYNELQKDKM
AEAYSEIGMKGERRRGKGHDGLYQGLSTATKDTYDALHMQALPPR Clone 24C8 CD8 CD3 zeta CAR DNA Heavy &
Light Chains
(SEQ ID NO. 69)
CAGGTGCAGTTGCAGGAAAGCGGGCCTGGCCTTGTGAAACCAAG
CCAGACACTGAGCCTGACATGCACTGTGTCCGGCGGGTCCATATC
TTCCGGGGGTTTTTATTGGTCCTGGATACGCCAGCATCCCGGGAA
AGGACTTGAATGGATTGGATATATCCACCATTCCGGAAGCACCCA
CTACAATCCAAGCCTTAAATCCCGGGTGACAATCTCCATCGACAC
CTCAAAGAATCTTTTTTCCCTGCGGTTGTCTTCAGTAACTGCCGCC
GATACCGCTGTGTACTACTGTGCCAGCCTCGTCTATTGCGGCGGA
GATTGTTATTCTGGGTTCGATTATTGGGGTCAAGGCACACTGGTA
ACTGTCAGCAGCGGAGGCGGCGGTTCCGGGGGCGGGGGCAGTGG
AGGGGGCGGATCTGACATTCAGCTTACGCAGTCCCCATCTTCACT
TAGCGCCAGCGTTGGCGATCGGGTCAGCTTCACGTGTCAAGCAAG
TCAGGATATCAACAACTTTCTTAACTGGTACCAGCAGAAGCCAGG
CAAGGCACCCAAGTTGCTGATTTACGATGCTTCTAACCTCGAGAC
GGGAGTGCCTAGCCGCTTCTCCGGGAGCGGCAGCGGCACAGACTT
TACCTTTACGATTTCCAGTCTGCAGCCAGAGGATATAGCAACTTA
TTACTGTCAGCAGTATGGCAACCTCCCTTTTACCTTCGGTGGTGGC
ACAAAGGTCGAGATTAAAAGAGCCGCAGCGTTGTCCAACTCCATA
ATGTATTTTTCTCATTTTGTGCCCGTCTTTCTGCCTGCCAAACCTAC
CACCACCCCCGCCCCACGACCACCTACTCCAGCCCCCACCATCGC
CTCCCAGCCCCTCAGCCTGAGGCCAGAGGCTTGTCGCCCTGCTGC
GGGGGCGCTGTCCATACCAGAGGACTCGACTTCGCCTGCGATAT
TTATATATGGGCCCCCTCGCCGGCACCTGCGGAGTCTTGCTCCTG
AGCCTTGTGATCACGCTTTATTGTAACCATCGGAATAGATCCAAA
AGAAGCCGCCTGCTCCATAGCGATTACATGAATATGACTCCACGC
CGCCCTGGCCCCACAAGGAAACACTACCAGCCTTACGCACCACCT
AGAGATTTCGCTGCCTATCGGAGCAGGGTGAAGTTTTCCAGATCT
GCAGATGCACCAGCGTATCAGCAGGGCCAGAACCAACTGTATAA
CGAGCTCAACCTGGGACGCAGGGAAGAGTATGACGTTTTGGACA
AGCGCAGAGGACGGGACCCTGAGATGGGTGGCAAACCAAGACGA
AAAAACCCCCAGGAGGGTCTCTATAATGAGCTGCAGAAGGATAA
GATGGCTGAAGCCTATTCTGAAATAGGCATGAAAGGAGAGCGGA
GAAGGGGAAAAGGGCACGACGGTTTGTACCAGGGACTCAGCACT
GCTACGAAGGATACTTATGACGCTCTCCACATGCAAGCCCTGCCA
CCTAGG Clone 24C8 CD8 CD3 zeta CAR AA Heavy &
Light Chains
(SEQ ID NO. 70)
QVQLQESGPGLVKPSQTLSLTCTVSGGSISSGGFYWSWIRQHPGKGL

EWIGYIHHSGSTHYNPSLKSRVTISIDTSKNLFSLRLSSVTAADTAVYY

CASLVYCGGDCYSGFDYWGQGTLVTVSSGGGGSGGGGSGGGGSDI

QLTQSPSSLSASVGDRVSFTCQASQDINNFLNWYQQKPGKAPKLLIY

DASNLETGVPSRFSGSGSGTDFTFTISSLQPEDIATYYCQQYGNLPFTF

GGGTKVEIKRAAALSNSIMYFSHFVPVFLPAKPTTTPAPRPPTPAPTIA

SQPLSLRPEACRPAAGGAVHTRGLDFACDIYIWAPLAGTCGVLLLSL

VITLYCNHRNRSKRSRLLHSDYMNMTPRRPGPTRKHYQPYAPPRDF

AAYRSRVKFSRSADAPAYQQGQNQLYNELNLGRREEYDVLDKRRG

RDPEMGGKPRRKNPQEGLYNELQKDKMAEAYSEIGMKGERRRGKG

HDGLYQGLSTA TKDTYDALHM QALPPR

Clone 20C5.1 HC DNA
(SEQ ID NO. 71)
CAGGTCCAACTGGTGCAGTCCGGAGCCGAAGTCAAGAAACCAGG

TGCCTCCGTTAAAGTGAGTTGCAAAGTCTCTGGATACACTCTGAC

CGAGCTCTCTATGCACTGGGTCCGGCAGGCCCCCGGCAAGGGATT

GGAATGGATGGGCGGGTTCGATCCTGAGGACGGAGAGACTATCT

ACGCTCAAAAATTCCAGGGACGAGTGACTGTGACCGAAGACACT

AGTACCGACACTGCCTACATGGAACTTTCCTCTCTGCGATCAGAA

GATACCGCAGTGTACTACTGTGCTACTGAATCTAGGGGCATTGGA

TGGCCCTACTTCGATTACTGGGGTCAGGGAACTCTGGTGACTGTC

TCCAGC

Clone 20C5.1 AA HC (CDRs in Underline)
(SEQ ID NO. 72)
QVQLVQSGAEVKKPGASVKVSCKVS<u>GYTLTEL</u>SMHWVRQAPGKGL EWMGGF<u>DPEDGET</u>IYAQKFQGRVTVTEDTSTDTAYMELSSLRSEDT AVYYCAT<u>ESRGIGWPYFDY</u>WGQGTLVTVSS Clone 20C5.1 HC AA CDR1:
(SEQ ID NO. 73)
GYTLTEL Clone 20C5.1 HC AA CDR2:
(SEQ ID NO. 74)
DPEDGE Clone 20C5.1 HC AA CDR3:
(SEQ ID NO. 75)
ESRGIGWPYFDY Clone 20C5.1 LC DNA
(SEQ ID NO. 76)
GATATTCAGATGACTCAATCTCCTTCTTCTCTGTCCGCTTCCGTGG

GCGATAGAGTGACCATTACTTGTAGGGCGTCCCAGTCAATCTCCA

GTTATTTGAATTGGTATCAGCAGAAGCCCGGGAAAGCACCTAAGC

TGTTGATCAGCGGGGCTTCTAGCCTGAAGAGTGGGGTACCTTCAC

GGTTCAGCGGAAGCGGAAGCGGAACCGATTTCACCCTGACTATCA

GCAGCCTGCCACCTGAGGACTTTGCAACTTACTACTGCCAACAGT

CATACAGCACTCCGATCACTTTCGGCCAGGGCACCCGGCTCGAAA

TCAAGCGC

Clone 20C5.1 AA LC (CDRs in Underline)
(SEQ ID NO. 77)
DIQMTQSPSSLSASVGDRVTITC<u>RASQSISSYLN</u>WYQQKPGKAPKLLI SG<u>ASSLKS</u>GVPSRFSGSGSGTDFTLTISSLPPEDFATYYC<u>QQSYSTPIT</u>F

GQGTRLEIKR

Clone 20C5.1 AA LC CDR1:
(SEQ ID NO. 78)
RASQSISSYLN

Clone 20C5.1 AA LC CDR2:
(SEQ ID NO. 79)
GASSLKS

Clone 20C5.1 AA LC CDR3:
(SEQ ID NO. 80)
QQSYSTPIT

Clone 20C5.1 CD28T CD3 zeta CAR DNA Heavy &
Light Chains
(SEQ ID NO. 81)
ATGGCACTCCCCGTAACTGCTCTGCTGCTGCCGTTGGCATTGCTCC

TGCACGCCGCACGCCCGCAGGTCCAACTGGTGCAGTCCGGAGCCG

AAGTCAAGAAACCAGGTGCCTCCGTTAAAGTGAGTTGCAAAGTCT

CTGGATACACTCTGACCGAGCTCTCTATGCACTGGGTCCGGCAGG

CCCCCGGCAAGGGATTGGAATGGATGGGCGGGTTCGATCCTGAG

GACGGAGAGACTATCTACGCTCAAAAATTCCAGGGACGAGTGAC

TGTGACCGAAGACACTAGTACCGACACTGCCTACATGGAACTTTC

CTCTCTGCGATCAGAAGATACCGCAGTGTACTACTGTGCTACTGA

ATCTAGGGGCATTGGATGGCCCTACTTCGATTACTGGGGTCAGGG

AACTCTGGTGACTGTCTCCAGCGGTGGAGGTGGCAGCGGTGGTGG

CGGAAGCGGGGGGGCGGCTCTGATATTCAGATGACTCAATCTCC

TTCTTCTCTGTCCGCTTCCGTGGGCGATAGAGTGACCATTACTTGT

AGGGCGTCCCAGTCAATCTCCAGTTATTTGAATTGGTATCAGCAG

AAGCCCGGGAAAGCACCTAAGCTGTTGATCAGCGGGGCTTCTAGC

CTGAAGAGTGGGGTACCTTCACGGTTCAGCGGAAGCGGAAGCGG

AACCGATTTCACCCTGACTATCAGCAGCCTGCCACCTGAGGACTT

TGCAACTTACTACTGCCAACAGTCATACAGCACTCCGATCACTTTC

GGCCAGGGCACCCGGCTCGAAATCAAGCGCGCTGCTGCTTTGGAC

AATGAGAAGTCAAACGGCACCATCATACATGTTAAAGGTAAACA

TCTGTGTCCCTCCCCGCTGTTCCCCGGCCCTTCCAAACCGTTCTGG

GTTCTGGTGGTGGTCGGAGGCGTACTCGCTTGCTATAGTCTGCTG

GTAACTGTCGCCTTCATCATCTTTTGGGTGAGATCCAAAAGAAGC

CGCCTGCTCCATAGCGATTACATGAATATGACTCCACGCCGCCCT

GGCCCCACAAGGAAACACTACCAGCCTTACGCACCACCTAGAGAT

TTCGCTGCCTATCGGAGCAGGGTGAAGTTTCCAGATCTGCAGAT

GCACCAGCTATCAGCAGGGCCAGAACCAACTGTATAACGAGCT

CAACCTGGGACGCAGGGAAGAGTATGACGTTTTGGACAAGCGCA

GAGGACGGGACCCTGAGATGGGTGGCAAACCAAGACGAAAAAAC

CCCCAGGAGGGTCTCTATAATGAGCTGCAGAAGGATAAGATGGCT

GAAGCCTATTCTGAAATAGGCATGAAAGGAGAGCGGAGAAGGGG

AAAAGGGCACGACGGTTTGTACCAGGGACTCAGCACTGCTACGA

Clone 20C5.1 CD28T CD3 zeta CAR AA Heavy &
Light Chains (Signal Peptide in Bold)
(SEQ ID NO. 82)
MALPVTALLLPLALLLHAARPQVQLVQSGAEVKKPGASVKVSCKV

SGYTLTELSMHWVRQAPGKGLEWMGGFDPEDGETIYAQKFQGRVT

VTEDTSTDTAYMELSSLRSEDTAVYYCATESRGIGWPYFDYWGQGT

LVTVSSGGGGSGGGGSGGGGSDIQMTQSPSSLSASVGDRVTITCRAS

QSISSYLNWYQQKPGKAPKLLISGASSLKSGVPSRFSGSGSGTDFTLTI

SSLPPEDFATYYCQQSYSTPITFGQGTRLEIKRAAALDNEKSNGTIIHV

KGKHLCPSPLFPGPSKPFWVLVVVGGVLACYSLLVTVAFIIFWVRSK

RSRLLHSDYMNMTPRRPGPTRKHYQPYAPPRDFAAYRSRVKFSRSA

DAPAYQQGQNQLYNELNLGRREEYDVLDKRRGRDPEMGGKPRRKN

PQEGLYNELQKDKMAEAYSEIGMKGERRRGKGHDGLYQGLSTATK

DTYDALHMQALPPR

Clone 20C5.1 CD28T CD3 zeta CAR DNA Heavy &
Light Chains
(SEQ ID NO. 83)
CAGGTCCAACTGGTGCAGTCCGGAGCCGAAGTCAAGAAACCAGG

TGCCTCCGTTAAAGTGAGTTGCAAAGTCTCTGGATACACTCTGAC

CGAGCTCTCTATGCACTGGGTCCGGCAGGCCCCCGGCAAGGGATT

GGAATGGATGGGCGGGTTCGATCCTGAGGACGGAGAGACTATCT

ACGCTCAAAAATTCCAGGGACGAGTGACTGTGACCGAAGACACT

AGTACCGACACTGCCTACATGGAACTTTCCTCTCTGCGATCAGAA

GATACCGCAGTGTACTACTGTGCTACTGAATCTAGGGGCATTGGA

TGGCCCTACTTCGATTACTGGGGTCAGGGAACTCTGGTGACTGTC

TCCAGCGGTGGAGGTGGCAGCGGTGGTGGCGGAAGCGGGGGGGG

CGGCTCTGATATTCAGATGACTCAATCTCCTTCTTCTCTGTCCGCT

TCCGTGGGCGATAGAGTGACCATTACTTGTAGGGCGTCCCAGTCA

ATCTCCAGTTATTTGAATTGGTATCAGCAGAAGCCCGGGAAAGCA

CCTAAGCTGTTGATCAGCGGGGCTTCTAGCCTGAAGAGTGGGGTA

CCTTCACGGTTCAGCGGAAGCGGAAGCGGAACCGATTTCACCCTG

ACTATCAGCAGCCTGCCACCTGAGGACTTTGCAACTTACTACTGC

CAACAGTCATACAGCACTCCGATCACTTTCGGCCAGGGCACCCGG

CTCGAAATCAAGCGCGCTGCTGCTTTGGACAATGAGAAGTCAAAC

GGCACCATCATACATGTTAAAGGTAAACATCTGTGTCCCTCCCCG

CTGTTCCCCGGCCCTTCCAAACCGTTCTGGGTTCTGGTGGTGGTCG

GAGGCGTACTCGCTTGCTATAGTCTGCTGGTAACTGTCGCCTTCAT

CATCTTTTGGGTGAGATCCAAAAGAAGCCGCCTGCTCCATAGCGA

TTACATGAATATGACTCCACGCCGCCCTGGCCCCACAAGGAAACA

CTACCAGCCTTACGCACCACCTAGAGATTTCGCTGCCTATCGGAG

CAGGGTGAAGTTTTCCAGATCTGCAGATGCACCAGCGTATCAGCA

GGGCCAGAACCAACTGTATAACGAGCTCAACCTGGGACGCAGGG

AAGAGTATGACGTTTTGGACAAGCGCAGAGGACGGGACCCTGAG

ATGGGTGGCAAACCAAGACGAAAAAACCCCCAGGAGGGTCTCTA

TAATGAGCTGCAGAAGGATAAGATGGCTGAAGCCTATTCTGAAAT

AGGCATGAAAGGAGAGCGGAGAAGGGGAAAAGGGCACGACGGT

TTGTACCAGGGACTCAGCACTGCTACGAAGGATACTTATGACGCT

CTCCACATGCAAGCCCTGCCACCTAGG

Clone 20C5.1 CD28T CD3 zeta CAR AA Heavy &
Light Chains
(SEQ ID NO. 84)
QVQLVQSGAEVKKPGASVKVSCKVSGYTLTELSMHWVRQAPGKGL

EWMGGFDPEDGETIYAQKFQGRVTVTEDTSTDTAYMELSSLRSEDT

AVYYCATESRGIGWPYFDYWGQGTLVTVSSGGGGSGGGGSGGGGS

DIQMTQSPSSLSASVGDRVTITCRASQSISSYLNWYQQKPGKAPKLLI

SGASSLKSGVPSRFSGSGSGTDFTLTISSLPPEDFATYYCQQSYSTPITF

GQGTRLEIKRAAALDNEKSNGTIIHVKGKHLCPSPLFPGPSKPFWVLV

VVGGVLACYSLLVTVAFIIFWVRSKRSRLLHSDYMNMTPRRPGPTRK

HYQPYAPPRDFAAYRSRVKFSRSADAPAYQQGQNQLYNELNLGRRE

EYDVLDKRRGRDPEMGGKPRRKNPQEGLYNELQKDKMAEAYSEIG

MKGERRRGKGHDGLYQGLSTATKDTYDALHMQALPPR

Clone 20C5.1 CD28 CD3 zeta CAR DNA Heavy &
Light Chains
(SEQ ID NO. 85)
ATGGCACTCCCCGTAACTGCTCTGCTGCTGCCGTTGGCATTGCTCC

TGCACGCCGCACGCCCGCAGGTGCAGCTTGTGCAGAGCGGGGCC

GAGGTGAAGAAGCCCGGGGCCAGCGTCAAAGTGTCCTGTAAGGT

CAGCGGTTACACCCTCACCGAGCTGAGCATGCACTGGGTACGGCA

GGCTCCCGGCAAAGGTCTTGAGTGGATGGGTGGATTTGATCCAGA

AGATGGAGAGACTATCTACGCCCAGAAGTTCCAGGGCCGGGTCA

CCGTAACGAAGACACCTCAACTGACACCGCTTACATGGAGCTGA

GTTCACTGCGGTCCGAGGACACGGCCGTGTATTATTGTGCCACCG

AGAGCCGCGGAATCGGATGGCCTTACTTCGACTACTGGGGACAGG

GTACACTTGTTACAGTATCATCCGGGGTGGCGGCTCTGGTGGGG

GCGGCTCCGGAGGGGGTGGATCAGATATCCAAATGACTCAAAGT

CCAAGTTCCCTGTCTGCCTCAGTCGGAGATAGAGTCACCATAACC

TGCAGGGCAAGTCAGTCCATCTCCTCCTATCTGAACTGGTACCAA

CAGAAACCTGGAAAGGCGCCTAAGCTCCTGATCTCCGGAGCCTCA

TCTTTGAAATCCGGTGTCCCATCTCGCTTCAGTGGCTCTGGAAGCG

GTACAGATTTACTTTGACCATTAGCAGCCTCCCACCGGAAGACT

TTGCTACATATTACTGCCAGCAGTCTTACTCAACCCCAATCACCTT

CGGGCAAGGCACCAGACTCGAAATAAAAAGAGCAGCTGCTATCG

AGGTTATGTACCCACCGCCGTACTTGGATAACGAAAAAAGCAATG

GGACCATCATTCATGTGAAGGGTAAGCACCTTTGCCCTAGCCCAC

TGTTTCCTGGCCCCGAGTAAACCCTTTTGGGTACTTGTGGTCGTCGG

-continued

CGGCGTGCTGGCCTGCTACTCACTCCTGGTTACCGTCGCATTCATC

ATCTTTTGGGTGAGATCCAAAAGAAGCCGCCTGCTCCATAGCGAT

TACATGAATATGACTCCACGCCGCCCTGGCCCCACAAGGAAACAC

TACCAGCCTTACGCACCACCTAGAGATTTCGCTGCCTATCGGAGC

AGGGTGAAGTTTTCCAGATCTGCAGATGCACCAGCGTATCAGCAG

GGCCAGAACCAACTGTATAACGAGCTCAACCTGGGACGCAGGGA

AGAGTATGACGTTTTGGACAAGCGCAGAGGACGGGACCCTGAGA

TGGGTGGCAAACCAAGACGAAAAAACCCCCAGGAGGGTCTCTAT

AATGAGCTGCAGAAGGATAAGATGGCTGAAGCCTATTCTGAAAT

AGGCATGAAAGGAGAGCGGAGAAGGGGAAAAGGGCACGACGGT

TTGTACCAGGGACTCAGCACTGCTACGAAGGATACTTATGACGCT

CTCCACATGCAAGCCCTGCCACCTAGGTAA

Clone 20C5.1 CD28 CD3 zeta CAR AA Heavy &
Light Chains (Signal Peptide in Bold)
(SEQ ID NO. 86)
MALPVTALLLPLALLLHAARPQVQLVQSGAEVKKPGASVKVSCKV

SGYTLTELSMHWVRQAPGKGLEWMGGFDPEDGETIYAQKFQGRVT

VTEDTSTDTAYMELSSLRSEDTAVYYCATESRGIGWPYFDYWGQGT

LVTVSSGGGGSGGGGSGGGGSDIQMTQSPSSLSASVGDRVTITCRAS

QSISSYLNWYQQKPGKAPKLLISGASSLKSGVPSRFSGSGSGTDFTLTI

SSLPPEDFATYYCQQSYSTPITFGQGTRLEIKRAAAIEVMYPPPYLDNE

KSNGTIIHVKGKHLCPSPLFPGPSKPFWVLVVVGGVLACYSLLVTVA

FIIFWVRSKRSRLLHSDYMNMTPRRPGPTRKHYQPYAPPRDFAAYRS

RVKFSRSADAPAYQQGQNQLYNELNLGRREEYDVLDKRRGRDPEM

GGKPRRKNPQEGLYNELQKDKMAEAYSEIGMKGERRRGKGHDGLY

QGLSTATKDTYDALHMQALPPR

Clone 20C5.1 CD28 CD3 zeta CAR DNA Heavy &
Light Chains
(SEQ ID NO. 87)
CAGGTGCAGCTTGTGCAGAGCGGGGCCGAGGTGAAGAAGCCCGG

GGCCAGCGTCAAAGTGTCCTGTAAGGTCAGCGGTTACACCCTCAC

CGAGCTGAGCATGCACTGGGTACGGCAGGCTCCCGGCAAAGGTCT

TGAGTGGATGGGTGGATTTGATCCAGAAGATGGAGAGACTATCTA

CGCCCAGAAGTTCCAGGGCCGGGTCACCGTAACAGAAGACACCT

CAACTGACACCGCTTACATGGAGCTGAGTTCACTGCGGTCCGAGG

ACACGGCCGTGTATTATTGTGCCACCGAGAGCCGCGGAATCGGAT

GGCCTTACTTCGACTACTGGGGACAGGGTACACTTGTTACAGTAT

CATCCGGGGTGGCGGCTCTGGTGGGGCGGCTCCGGAGGGGGT

GGATCAGATATCCAAATGACTCAAAGTCCAAGTTCCCTGTCTGCC

TCAGTCGGAGATAGAGTCACCATAACCTGCAGGGCAAGTCAGTCC

ATCTCCTCCTATCTGAACTGGTACCAACAGAAACCTGGAAAGGCG

CCTAAGCTCCTGATCTCCGGAGCCTCATCTTTGAAATCCGGTGTCC

CATCTCGCTTCAGTGGCTCTGGAAGCGGTACAGATTTTACTTTGAC

CATTAGCAGCCTCCCACCGGAAGACTTTGCTACATATTACTGCCA

GCAGTCTTACTCAACCCCAATCACCTTCGGGCAAGGCACCAGACT

CGAAATAAAAGAGCAGCTGCTATCGAGGTTATGTACCCACCGCC

GTACTTGGATAACGAAAAAAGCAATGGGACCATCATTCATGTGAA

GGGTAAGCACCTTTGCCCTAGCCCACTGTTTCCTGGCCCGAGTAA

ACCCTTTTGGGTACTTGTGGTCGTCGGCGGCGTGCTGGCCTGCTAC

TCACTCCTGGTTACCGTCGCATTCATCATCTTTTGGGTGAGATCCA

AAAGAAGCCGCCTGCTCCATAGCGATTACATGAATATGACTCCAC

GCCGCCCTGGCCCCACAAGGAAACACTACCAGCCTTACGCACCAC

CTAGAGATTTCGCTGCCTATCGGAGCAGGGTGAAGTTTTCCAGAT

CTGCAGATGCACCAGCGTATCAGCAGGGCCAGAACCAACTGTATA

ACGAGCTCAACCTGGGACGCAGGGAAGAGTATGACGTTTTGGAC

AAGCGCAGAGGACGGGACCCTGAGATGGGTGGCAAACCAAGACG

AAAAAACCCCCAGGAGGGTCTCTATAATGAGCTGCAGAAGGATA

AGATGGCTGAAGCCTATTCTGAAATAGGCATGAAAGGAGAGCGG

AGAAGGGGAAAAGGGCACGACGGTTTGTACCAGGGACTCAGCAC

TGCTACGAAGGATACTTATGACGCTCTCCACATGCAAGCCCTGCC

ACCTAGG

Clone 20C5.1 CD28 CD3 zeta CAR AA Heavy &
Light Chains
(SEQ ID NO. 88)
QVQLVQSGAEVKKPGASVKVSCKVSGYTLTELSMHWVRQAPGKGL

EWMGGFDPEDGETIYAQKFQGRVTVTEDTSTDTAYMELSSLRSEDT

AVYYCATESRGIGWPYFDYWGQGTLVTVSSGGGGSGGGGSGGGGS

DIQMTQSPSSLSASVGDRVTITCRASQSISSYLNWYQQKPGKAPKLLI

SGASSLKSGVPSRFSGSGSGTDFTLTISSLPPEDFATYYCQQSYSTPITF

GQGTRLEIKRAAAIEVMYPPPYLDNEKSNGTIIHVKGKHLCPSPLFPG

PSKPFWVLVVVGGVLACYSLLVTVAFIIFWVRSKRSRLLHSDYMNM

TPRRPGPTRKHYQPYAPPRDFAAYRSRVKFSRSADAPAYQQGQNQL

YNELNLGRREEYDVLDKRRGRDPEMGGKPRRKNPQEGLYNELQKD

KMAEAYSEIGMKGERRRGKGHDGLYQGLSTATKDTYDALHM

QALPPR

Clone 20C5.1 CD8 CD3 zeta CAR DNA Heavy &
Light Chains
(SEQ ID NO. 89)
ATGGCACTCCCCGTAACTGCTCTGCTGCTGCCGTTGGCATTGCTCC

TGCACGCCGCACGCCCGCAGGTGCAGTTGGTGCAAAGCGGCGCA

GAAGTTAAGAAACCTGGGGCGTCAGTTAAGGTGTCTTGCAAAGTA

TCTGGCTATACCCTCACTGAGCTGTCCATGCATTGGGTAAGGCAG

GCTCCTGGAAAGGGGCTCGAATGGATGGGAGGATTTGACCCTGA

AGACGGAGAGACCATCTACGCCCAGAAATTCCAGGGTAGAGTAA

CAGTGACTGAGGACACTAGCACTGACACAGCGTACATGGAGCTG

AGTTCTCTGAGAAGTGAGGACACAGCCGTTTACTACTGCGCTACC

GAGTCCAGAGGTATTGGCTGGCCATACTTCGACTATTGGGGTCAG

```
GGCACCCTGGTTACAGTGAGTTCAGGAGGCGGGGGCTCTGGGGG

GGGCGGTTCCGGAGGGGGGGGCTCAGATATACAGATGACGCAGA

GTCCATCAAGTCTCTCAGCCAGCGTGGGAGATCGCGTGACTATTA

CTTGCCGCGCCAGCCAGAGTATTAGCTCCTATCTGAATTGGTACC

AGCAAAAGCCCGGGAAGGCCCCTAAGCTTCTGATTTCTGGCGCCT

CCTCTTTGAAGTCAGGTGTGCCAAGCAGATTTAGCGGGTCTGGAA

GTGGCACTGACTTTACACTTACTATCTCCAGCCTGCCCCAGAGG

ATTTTGCCACATATTACTGTCAGCAAAGCTACTCTACTCCAATCAC

TTTCGGCCAGGGCACAAGATTGGAGATTAAGAGGGCTGCCGCACT

TTCAAATTCCATCATGTATTTCAGCCATTTTGTGCCTGTTTTTCTTC

CGGCCAAACCTACAACCACTCCCGCCCCACGCCCACCTACTCCCG

CCCCTACCATTGCCTCCCAGCCTCTGTCTCTTAGACCTGAGGCTTG

TAGACCTGCTGCCGGCGGAGCCGTGCACACTCGCGGTCTGGACTT

CGCCTGCGACATCTATATCTGGGCCCCTCTGGCCGGCACCTGCGG

CGTTCTCCTTCTCTCACTCGTAATCACACTCTATTGCAATCACAGG

AACAGATCCAAAAGAAGCCGCCTGCTCCATAGCGATTACATGAAT

ATGACTCCACGCCGCCCTGGCCCCACAAGGAAACACTACCAGCCT

TACGCACCACCTAGAGATTTCGCTGCCTATCGGAGCAGGGTGAAG

TTTTCCAGATCTGCAGATGCACCAGCGTATCAGCAGGGCCAGAAC

CAACTGTATAACGAGCTCAACCTGGGACGCAGGGAAGAGTATGA

CGTTTTGGACAAGCGCAGAGGACGGGACCCTGAGATGGGTGGCA

AACCAAGACGAAAAAACCCCCAGGAGGGTCTCTATAATGAGCTG

CAGAAGGATAAGATGGCTGAAGCCTATTCTGAAATAGGCATGAA

AGGAGAGCGGAGAAGGGGAAAAGGGCACGACGGTTTGTACCAGG

GACTCAGCACTGCTACGAAGGATACTTATGACGCTCTCCACATGC

AAGCCCTGCCACCTAGGTAA

Clone 20C5.1 CD8 CD3 zeta CAR AA Heavy &
Light Chains (Signal Peptide in Bold)
                                  (SEQ ID NO. 90)
MALPVTALLLPLALLLHAARPQVQLVQSGAEVKKPGASVKVSCKV

SGYTLTELSMHWVRQAPGKGLEWMGGFDPEDGETIYAQKFQGRVT

VTEDTSTDTAYMELSSLRSEDTAVYYCATESRGIGWPYFDYWGQGT

LVTVSSGGGGSGGGGSGGGGSDIQMTQSPSSLSASVGDRVTITCRAS

QSISSYLNWYQQKPGKAPKLLISGASSLKSGVPSRFSGSGSGTDFTLTI

SSLPPEDFATYYCQQSYSTPITFGQGTRLEIKRAAALSNSIMYFSHFVP

VFLPAKPTTTPAPRPPTPAPTIASQPLSLRPEACRPAAGGAVHTRGLDF

ACDIYIWAPLAGTCGVLLLSLVITLYCNHRNSKRSRLLHSDYMNMT

PRRPGPTRKHYQPYAPPRDFAAYRSRVKFSRSADAPAYQQGQNQLY

NELNLGRREEYDVLDKRRGRDPEMGGKPRRKNPQEGLYNELQKDK

MAEAYSEIGMKGERRRGKGHDGLYQGLSTATKDTYDALHMQALPP

R

Clone 20C5.1 CD8 CD3 zeta CAR DNA Heavy &
Light Chains
                                  (SEQ ID NO. 91)
CAGGTGCAGTTGGTGCAAAGCGGCGCAGAAGTTAAGAAACCTGG

GGCGTCAGTTAAGGTGTCTTGCAAAGTATCTGGCTATACCCTCAC

TGAGCTGTCCATGCATTGGGTAAGGCAGGCTCCTGGAAAGGGGCT

CGAATGGATGGGAGGATTTGACCCTGAAGACGGAGAGACCATCT

ACGCCCAGAAATTCCAGGGTAGAGTAACAGTGACTGAGGACACT

AGCACTGACACAGCGTACATGGAGCTGAGTTCTCTGAGAAGTGAG

GACACAGCCGTTTACTACTGCGCTACCGAGTCCAGAGGTATTGGC

TGGCCATACTTCGACTATTGGGGTCAGGGCACCCTGGTTACAGTG

AGTTCAGGAGGCGGGGGCTCTGGGGGGGGCGGTTCCGGAGGGGG

GGGCTCAGATATACAGATGACGCAGAGTCCATCAAGTCTCTCAGC

CAGCGTGGGAGATCGCGTGACTATTACTTGCCGCGCCAGCCAGAG

TATTAGCTCCTATCTGAATTGGTACCAGCAAAAGCCCGGGAAGGC

CCCTAAGCTTCTGATTTCTGGCGCCTCCTCTTTGAAGTCAGGTGTG

CCAAGCAGATTTAGCGGGTCTGGAAGTGGCACTGACTTTACACTT

ACTATCTCCAGCCTGCCCCAGAGGATTTTGCCACATATTACTGTC

AGCAAAGCTACTCTACTCCAATCACTTTCGGCCAGGGCACAAGAT

TGGAGATTAAGAGGGCTGCCGCACTTTCAAATTCCATCATGTATT

TCAGCCATTTTGTGCCTGTTTTTCTTCCGGCCAAACCTACAACCAC

TCCCGCCCCACGCCCACCTACTCCCGCCCCTACCATTGCCTCCCAG

CCTCTGTCTCTTAGACCTGAGGCTTGTAGACCTGCTGCCGGCGGA

GCCGTGCACACTCGCGGTCTGGACTTCGCCTGCGACATCTATATCT

GGGCCCCTCTGGCCGGCACCTGCGGCGTTCTCCTTCTCTCACTCGT

AATCACACTCTATTGCAATCACAGGAACAGATCCAAAAGAAGCC

GCCTGCTCCATAGCGATTACATGAATATGACTCCACGCCGCCCTG

GCCCCACAAGGAAACACTACCAGCCTTACGCACCACCTAGAGATT

TCGCTGCCTATCGGAGCAGGGTGAAGTTTTCCAGATCTGCAGATG

CACCAGCGTATCAGCAGGGCCAGAACCAACTGTATAACGAGCTC

AACCTGGGACGCAGGGAAGAGTATGACGTTTTGGACAAGCGCAG

AGGACGGGACCCTGAGATGGGTGGCAAACCAAGACGAAAAAACC

CCCAGGAGGGTCTCTATAATGAGCTGCAGAAGGATAAGATGGCT

GAAGCCTATTCTGAAATAGGCATGAAAGGAGAGCGGAGAAGGGG

AAAAGGGCACGACGGTTTGTACCAGGGACTCAGCACTGCTACGA

AGGATACTTATGACGCTCTCCACATGCAAGCCCTGCCACCTAGG

Clone 20C5.1 CD8 CD3 zeta CAR AA Heavy &
Light Chains
                                  (SEQ ID NO. 92)
QVQLVQSGAEVKKPGASVKVSCKVSGYTLTELSMHWVRQAPGKGL

EWMGGFDPEDGETIYAQKFQGRVTVTEDTSTDTAYMELSSLRSEDT

AVYYCATESRGIGWPYFDYWGQGTLVTVSSGGGGSGGGGSGGGGS

DIQMTQSPSSLSASVGDRVTITCRASQSISSYLNWYQQKPGKAPKLLI
```

```
SGASSLKSGVPSRFSGSGSGTDFTLTISSLPPEDFATYYCQQSYSTPITF

GQGTRLEIKRAAALSNSIMYFSHFVPVFLPAKPTTTPAPRPPTPAPTIA

SQPLSLRPEACRPAAGGAVHTRGLDFACDIYIWAPLAGTCGVLLLSL

VITLYCNHRNRSKRSRLLHSDYMNMTPRRPGPTRKHYQPYAPPRDF

AAYRSRVKFSRSADAPAYQQGQNQLYNELNLGRREEYDVLDKRRG

RDPEMGGKPRRKNPQEGLYNELQKDKMAEAYSEIGMKGERRRGKG

HDGLYQGLSTATKDTYDALHMQALPPR
```

Clone 20C5.2 HC DNA
(SEQ ID NO. 93)
```
CAGGTCCAGTTGGTCGAAAGTGGCGGTGGTGTAGTGCAGCCGGGC

CGCAGTTTGAGGCTTTCCTGTGCGGCTTCAGGCTTTACTTTTTCCA

GCTATGGAATGCACTGGGTGCGGCAGGCCCCCGGCAAAGGACTT

GAGTGGGTGGCCGTCATTTCTTATGACGGATCAGATAAGTACTAC

GTGGACAGCGTCAAGGGCAGATTCACCATCTCTAGGGACAACAGT

AAAAATAGACTCTACCTCCAGATGAATAGCCTCAGAGCTGAAGAC

ACGGCCGTCTACTATTGTGCTCGGGAGCGGTATAGTGGCAGAGAC

TACTGGGGGCAGGGCACACTCGTTACAGTGAGTAGC
```

Clone 20C5.2 AA HC (CDRs in Underline)
(SEQ ID NO. 94)
QVQLVESGGGVVQPGRSLRLSCAAS<u>GFTFSSY</u>GMHWVRQAPGKGLE
WVAV<u>ISYDGSD</u>KYYVDSVKGRFTISRDNSKNRLYLQMNSLRAEDTA
VYYCAR<u>ERYSGRDY</u>WGQGTLVTVSS Clone 20C5.2 HC AA CDR1:
(SEQ ID NO. 95)
GFTFSSY Clone 20C5.2 HC AA CDR2:
(SEQ ID NO. 96)
SYDGSD Clone 20C5.2 HC AA CDR3:
(SEQ ID NO. 97)
ERYSGRDY Clone 20C5.2 LC DNA
(SEQ ID NO. 98)
```
GAGATTGTTATGACCCAGAGTCCTGCGACCCTCTCAGTCAGCCCC

GGGGAGCGCGCAACTTTGTCTTGCAGAGCTAGTCAGTCCGTGTCC

TCTCTTCTGACATGGTACCAGCAAAAGCCCGGCAGGCTCCGCGC

CTTTTGATCTTTGGGGCTTCAACAAGAGCCACTGGGATTCCCGCA

CGATTCTCTGGCTCCGGGAGCGGTACTGGTTTCACCCTGACGATT

AGCAGTCTCCAGAGCGAGGACTTCGCCGTATACTACTGCCAGCAG

TACGATACGTGGCCATTCACTTTTGGACCAGGGACTAAAGTGGAT

TTTAAGCGC
```

Clone 20C5.2 AA LC (CDRs in Underline)
(SEQ ID NO. 99)
EIVMTQSPATLSVSPGERATLSC<u>RASQSVSSLLT</u>WYQQKPGQAPRLLI
F<u>GASTRAT</u>GIPARFSGSGSGTGFTLTISSLQSEDFAVYYC<u>QQYDTWPF</u>
<u>T</u>FGPGTKVDFKR Clone 20C5.2 AA LC CDR1:
(SEQ ID NO. 100)
RASQSVSSLLT Clone 20C5.2 AA LC CDR2:
(SEQ ID NO. 101)
GASTRAT Clone 20C5.2 AA LC CDR3:
(SEQ ID NO. 102)
QQYDTWPFT Clone 20C5.2 CD28T CD3 zeta CAR DNA Heavy & Light Chains
(SEQ ID NO. 103)
```
ATGGCACTCCCCGTAACTGCTCTGCTGCTGCCGTTGGCATTGCTCC

TGCACGCCGCACGCCCGCAGGTCCAGTTGGTCGAAAGTGGCGGTG

GTGTAGTGCAGCCGGGCCGCAGTTTGAGGCTTTCCTGTGCGGCTT

CAGGCTTTACTTTTTCCAGCTATGGAATGCACTGGGTGCGGCAGG

CCCCCGGCAAAGGACTTGAGTGGGTGGCCGTCATTTCTTATGACG

GATCAGATAAGTACTACGTGGACAGCGTCAAGGGCAGATTCACC

ATCTCTAGGGACAACAGTAAAAATAGACTCTACCTCCAGATGAAT

AGCCTCAGAGCTGAAGACACGGCCGTCTACTATTGTGCTCGGGAG

CGGTATAGTGGCAGAGACTACTGGGGGCAGGGCACACTCGTTAC

AGTGAGTAGCGGCGGAGGAGGGAGTGGGGCGGTGGCTCCGGTG

GAGGAGGTTCTGAGATTGTTATGACCCAGAGTCCTGCGACCCTCT

CAGTCAGCCCCGGGGAGCGCGCAACTTTGTCTTGCAGAGCTAGTC

AGTCCGTGTCCTCTCTTCTGACATGGTACCAGCAAAAGCCCGGGC

AGGCTCCGCGCCTTTTGATCTTTGGGGCTTCAACAAGAGCCACTG

GGATTCCCGCACGATTCTCTGGCTCCGGGAGCGGTACTGGTTTCA

CCCTGACGATTAGCAGTCTCCAGAGCGAGGACTTCGCCGTATACT

ACTGCCAGCAGTACGATACGTGGCCATTCACTTTTGGACCAGGGA

CTAAAGTGGATTTTAAGCGCGCCGCCGCTCTCGATAACGAAAAGT

CAAATGGCACCATAATCCACGTCAAAGGCAAGCACCTGTGCCCTT

CCCCGCTCTTCCCCGGACCCAGTAAACCATTTTGGGTGCTGGTTGT

TGTGGGGGCGTGCTGGCCTGCTATAGCCTTTTGGTCACTGTAGC

CTTCATTATTTTTTGGGTCAGATCCAAAAGAAGCCGCCTGCTCCAT

AGCGATTACATGAATATGACTCCACGCCGCCCTGGCCCCACAAGG

AAACACTACCAGCCTTACGCACCACCTAGAGATTTCGCTGCCTAT

CGGAGCAGGGTGAAGTTTTCCAGATCTGCAGATGCACCAGCGTAT

CAGCAGGGCCAGAACCAACTGTATAACGAGCTCAACCTGGGACG

CAGGGAAGAGTATGACGTTTTGGACAAGCGCAGAGGACGGGACC

CTGAGATGGGTGGCAAACCAAGACGAAAAAACCCCCAGGAGGGT

CTCTATAATGAGCTGCAGAAGGATAAGATGGCTGAAGCCTATTCT

GAAATAGGCATGAAAGGAGAGCGGAGAAGGGGAAAAGGGCACG

ACGGTTTGTACCAGGGACTCAGCACTGCTACGAAGGATACTTATG

ACGCTCTCCACATGCAAGCCCTGCCACCTAGGTAA
```

Clone 20C5.2 CD28T CD3 zeta CAR AA Heavy & Light Chains (Signal Peptide in Bold)
(SEQ ID NO. 104)
MALPVTALLLPLALLLHAARPQVQLVESGGGVVQPGRSLRLSCAA -continued
SGFTFSSYGMHWVRQAPGKGLEWVAVISYDGSDKYYVDSVKGRFTI

SRDNSKNRLYLQMNSLRAEDTAVYYCARERYSGRDYWGQGTLVTV

SSGGGGSGGGGSGGGGSEIVMTQSPATLSVSPGERATLSCRASQSVSS

LLTWYQQKPGQAPRLLIFGASTRATGIPARFSGSGSGTGFTLTISSLQS

EDFAVYYCQQYDTWPFTFGPGTKVDFKRAAALDNEKSNGTIIHVKG

KHLCPSPLFPGPSKPFWVLVVVGGVLACYSLLVTVAFIIFWVRSKRSR

LLHSDYMNMTPRRPGPTRKHYQPYAPPRDFAAYRSRVKFSRSADAP

AYQQGQNQLYNELNLGRREEYDVLDKRRGRDPEMGGKPRRKNPQE

GLYNELQKDKMAEAYSEIGMKGERRRGKGHDGLYQGLSTATK

DTYDALHMQALPPR

Clone 20C5.2 CD28T CD3 zeta CAR DNA Heavy &
Light Chains
(SEQ ID NO. 105)
CAGGTCCAGTTGGTCGAAAGTGGCGGTGGTGTAGTGCAGCCGGGC

CGCAGTTTGAGGCTTTCCTGTGCGGCTTCAGGCTTTACTTTTTCCA

GCTATGGAATGCACTGGGTGCGGCAGGCCCCCGGCAAGGACTT

GAGTGGGTGGCCGTCATTTCTTATGACGGATCAGATAAGTACTAC

GTGGACAGCGTCAAGGGCAGATTCACCATCTCTAGGGACAACAGT

AAAAATAGACTCTACCTCCAGATGAATAGCCTCAGAGCTGAAGAC

ACGGCCGTCTACTATTGTGCTCGGGAGCGGTATAGTGGCAGAGAC

TACTGGGGCAGGGCACACTCGTTACAGTGAGTAGCGGCGGAGG

AGGGAGTGGGGCGGTGGCTCCGGTGGAGGAGGTTCTGAGATTG

TTATGACCCAGAGTCCTGCGACCCTCTCAGTCAGCCCCGGGGAGC

GCGCAACTTTGTCTTGCAGAGCTAGTCAGTCCGTGTCCTCTCTTCT

GACATGGTACCAGCAAAAGCCCGGCAGGCTCCGCGCCTTTTGAT

CTTTGGGGCTTCAACAAGAGCCACTGGGATTCCCGCACGATTCTC

TGGCTCCGGGAGCGGTACTGGTTTCACCCTGACGATTAGCAGTCT

CCAGAGCGAGGACTTCGCCGTATACTACTGCCAGCAGTACGATAC

GTGGCCATTCACTTTTGGACCAGGGACTAAAGTGGATTTTAAGCG

CGCCGCCGCTCTCGATAACGAAAAGTCAAATGGCACCATAATCCA

CGTCAAAGGCAAGCACCTGTGCCCTTCCCCGCTCTTCCCCGGACC

CAGTAAACCATTTTGGGTGCTGGTTGTTGTGGGGGGCGTGCTGGC

CTGCTATAGCCTTTTGGTCACTGTAGCCTTCATTATTTTTTGGGTC

AGATCCAAAAGAAGCCGCCTGCTCCATAGCGATTACATGAATATG

ACTCCACGCCGCCCTGGCCCCACAAGGAAACACTACCAGCCTTAC

GCACCACCTAGAGATTTCGCTGCCTATCGGAGCAGGGTGAAGTTT

TCCAGATCTGCAGATGCACCAGCGTATCAGCAGGGCCAGAACCA

ACTGTATAACGAGCTCAACCTGGGACGCAGGGAAGAGTATGACG

TTTTGGACAAGCGCAGAGGACGGGACCCTGAGATGGGTGGCAAA

CCAAGACGAAAAACCCCCAGGAGGGTCTCTATAATGAGCTGCA

GAAGGATAAGATGGCTGAAGCCTATTCTGAAATAGGCATGAAAG

GAGAGCGGAGAAGGGGAAAAGGGCACGACGGTTTGTACCAGGGA

-continued
CTCAGCACTGCTACGAAGGATACTTATGACGCTCTCCACATGCAA

GCCCTGCCACCTAGG

Clone 20C5.2 CD28T CD3 zeta CAR AA Heavy &
Light Chains
(SEQ ID NO. 106)
QVQLVESGGGVVQPGRSLRLSCAASGFTFSSYGMHWVRQAPGKGLE

WVAVISYDGSDKYYVDSVKGRFTISRDNSKNRLYLQMNSLRAEDTA

VYYCARERYSGRDYWGQGTLVTVSSGGGGSGGGGSGGGGSEIVMT

QSPATLSVSPGERATLSCRASQSVSSLLTWYQQKPGQAPRLLIFGAST

RATGIPARFSGSGSGTGFTLTISSLQSEDFAVYYCQQYDTWPFTFGPG

TKVDFKRAAALDNEKSNGTIIHVKGKHLCPSPLFPGPSKPFWVLVVV

GGVLACYSLLVTVAFIIFWVRSKRSRLLHSDYMNMTPRRPGPTRKHY

QPYAPPRDFAAYRSRVKFSRSADAPAYQQGQNQLYNELNLGRREEY

DVLDKRRGRDPEMGGKPRRKNPQEGLYNELQKDKMAEAYSEIGMK

GERRRGKGHDGLYQGLSTATKDTYDALHMQALPPR

Clone 20C5.2 CD28 CD3 zeta CAR DNA Heavy &
Light Chains
(SEQ ID NO. 107)
ATGGCACTCCCCGTAACTGCTCTGCTGCTGCCGTTGGCATTGCTCC

TGCACGCCGCACGCCCGCAGGTGCAGCTCGTGGAGTCTGGCGGCG

GCGTGGTCCAGCCCGGCCGGTCCCTGCGCCTGTCCTGCGCCGCCA

GCGGGTTTACTTTTTCCTCCTACGGCATGCACTGGGTGCGCCAGGC

TCCCGGCAAGGGCCTCGAGTGGGTCGCCGTGATCTCATACGATGG

GTCAGACAAATACTATGTCGATTCTGTTAAAGGGCGGTTTACCAT

TTCAAGAGATAACTCTAAGAATAGGCTGTATTTGCAGATGAACAG

CCTGAGGGCTGAAGATACCGCAGTGTACTATTGCGCTAGGGAGCG

GTATAGTGGCCGCGATTACTGGGGACAGGGTACACTGGTGACCGT

GAGCTCTGGGGGTGGCGGAAGCGGGGTGGCGGAAGCGGCGGAG

GGGGTAGTGAAATTGTGATGACCCAGTCTCCGGCTACACTTTCAG

TCTCCCCTGGGGAGAGAGCTACACTGTCATGCAGAGCGTCCCAGT

CCGTCTCTTCTCTCCTTACCTGGTATCAGCAGAAGCCCGGCCAGGC

TCCTCGACTGCTGATCTTCGGTGCCTCCACAAGGGCGACCGGGAT

TCCAGCCCGCTTCTCAGGTTCTGGGAGCGGAACTGGTTTCACTTTG

ACAATCAGTTCACTGCAGTCAGAGGATTTCGCCGTGTACTACTGC

CAGCAATACGACACATGGCCATTCACTTTCGGACCCGGTACCAAA

GTCGATTTCAAGAGAGCCGCGGCCATCGAGGTTATGTACCCACCA

CCATATCTGGACAATGAAAAAGCAATGGAACCATTATCCATGTG

AAGGGTAAACACCTCTGCCCTAGCCCACTTTTCCCTGGCCCATCA

AAGCCCTTCTGGGTCTTGGTGGTCGTGGGGGGTGTGCTGGCCTGT

TACAGCCTTCTGGTGACGGTTGCTTTCATTATCTTCTGGGTTAGAT

CCAAAAGAAGCCGCCTGCTCCATAGCGATTACATGAATATGACTC

CACGCCGCCCTGGCCCCACAAGGAAACACTACCAGCCTTACGCAC

CACCTAGAGATTTCGCTGCCTATCGGAGCAGGGTGAAGTTTTCCA

GATCTGCAGATGCACCAGCGTATCAGCAGGGCCAGAACCAACTGT

-continued
ATAACGAGCTCAACCTGGGACGCAGGGAAGAGTATGACGTTTTG

GACAAGCGCAGAGGACGGGACCCTGAGATGGGTGGCAAACCAAG

ACGAAAAAACCCCCAGGAGGGTCTCTATAATGAGCTGCAGAAGG

ATAAGATGGCTGAAGCCTATTCTGAAATAGGCATGAAAGGAGAG

CGGAGAAGGGGAAAAGGGCACGACGGTTTGTACCAGGGACTCAG

CACTGCTACGAAGGATACTTATGACGCTCTCCACATGCAAGCCCT

GCCACCTAGGTAA

Clone 20C5.2 CD28 CD3 zeta CAR AA Heavy &
Light Chains (Signal Peptide in Bold)
(SEQ ID NO. 108)
MALPVTALLLPLALLLHAARPQVQLVESGGGVVQPGRSLRLSCAA

SGFTFSSYGMHWVRQAPGKGLEWVAVISYDGSDKYYVDSVKGRFTI

SRDNSKNRLYLQMNSLRAEDTAVYYCARERYSGRDYWGQGTLVTV

SSGGGGSGGGGSGGGGSEIVMTQSPATLSVSPGERATLSCRASQSVSS

LLTWYQQKPGQAPRLLIFGASTRATGIPARFSGSGSGTGFTLTISSLQS

EDFAVYYCQQYDTWPFTFGPGTKVDFKRAAAIEVMYPPPYLDNEKS

NGTIIHVKGKHLCPSPLFPGPSKPFWVLVVVGGVLACYSLLVTVAFII

FWVRSKRSRLLHSDYMNMTPRRPGPTRKHYQPYAPPRDFAAYRSRV

KFSRSADAPAYQQGQNQLYNELNLGRREEYDVLDKRRGRDPEMGG

KPRRKNPQEGLYNELQKDKMAEAYSEIGMKGERRRGKGHDGLYQG

LSTATKDTYDALHMQALPPR

Clone 20C5.2 CD28 CD3 zeta CAR DNA Heavy &
Light Chains
(SEQ ID NO. 109)
CAGGTGCAGCTCGTGGAGTCTGGCGGCGGCGTGGTCCAGCCCGGC

CGGTCCCTGCGCCTGTCCTGCGCCGCCAGCGGGTTTACTTTTTCCT

CCTACGGCATGCACTGGGTGCGCCAGGCTCCCGGCAAGGGCCTCG

AGTGGGTCGCCGTGATCTCATACGATGGGTCAGACAAATACTATG

TCGATTCTGTTAAAGGGCGGTTTACCATTTCAAGAGATAACTCTA

AGAATAGGCTGTATTTGCAGATGAACAGCCTGAGGGCTGAAGAT

ACCGCAGTGTACTATTGCGCTAGGGAGCGGTATAGTGGCCGCGAT

TACTGGGGACAGGGTACACTGGTGACCGTGAGCTCTGGGGGTGGC

GGAAGCGGGGGTGGCGGAAGCGGCGGAGGGGGTAGTGAAATTGT

GATGACCCAGTCTCCGGCTACACTTTCAGTCTCCCCTGGGGAGAG

AGCTACACTGTCATGCAGAGCGTCCCAGTCCGTCTCTTCTCTCCTT

ACCTGGTATCAGCAGAAGCCCGGCCAGGCTCCTCGACTGCTGATC

TTCGGTGCCTCCACAAGGGCGACCGGGATTCCAGCCCGCTTCTCA

GGTTCTGGGAGCGGAACTGGTTTCACTTTGACAATCAGTTCACTG

CAGTCAGAGGATTTCGCCGTGTACTACTGCCAGCAATACGACACA

TGGCCATTCACTTTCGGACCCGGTACCAAAGTCGATTTCAAGAGA

GCCGCGGCCATCGAGGTTATGTACCCACCACCATATCTGGACAAT

GAAAAAAGCAATGGAACCATTATCCATGTGAAGGGTAAACACCT

CTGCCCTAGCCCACTTTTTCCCTGGCCCATCAAAGCCCTTCTGGGTC

TTGGTGGTCGTGGGGGGTGTGCTGGCCTGTTACAGCCTTCTGGTG

ACGGTTGCTTTCATTATCTTCTGGGTTAGATCCAAAAGAAGCCGC

CTGCTCCATAGCGATTACATGAATATGACTCCACGCCGCCCTGGC

CCCACAAGGAAACACTACCAGCCTTACGCACCACCTAGAGATTTC

GCTGCCTATCGGAGCAGGGTGAAGTTTTCCAGATCTGCAGATGCA

CCAGCGTATCAGCAGGGCCAGAACCAACTGTATAACGAGCTCAA

CCTGGGACGCAGGGAAGAGTATGACGTTTTGGACAAGCGCAGAG

GACGGGACCCTGAGATGGGTGGCAAACCAAGACGAAAAAACCCC

CAGGAGGGTCTCTATAATGAGCTGCAGAAGGATAAGATGGCTGA

AGCCTATTCTGAAATAGGCATGAAAGGAGAGCGGAGAAGGGGAA

AAGGGCACGACGGTTTGTACCAGGGACTCAGCACTGCTACGAAG

GATACTTATGACGCTCTCCACATGCAAGCCCTGCCACCTAGG

Clone 20C5.2 CD28 CD3 zeta CAR AA Heavy &
Light Chains
(SEQ ID NO. 110)
QVQLVESGGGVVQPGRSLRLSCAASGFTFSSYGMHWVRQAPGKGLE

WVAVISYDGSDKYYVDSVKGRFTISRDNSKNRLYLQMNSLRAEDTA

VYYCARERYSGRDYWGQGTLVTVSSGGGGSGGGGSGGGGSEIVMT

QSPATLSVSPGERATLSCRASQSVSSLLTWYQQKPGQAPRLLIFGAST

RATGIPARFSGSGSGTGFTLTISSLQSEDFAVYYCQQYDTWPFTFGPG

TKVDFKRAAAIEVMYPPPYLDNEKSNGTIIHVKGKHLCPSPLFPGPSK

PFWVLVVVGGVLACYSLLVTVAFIIFWVRSKRSRLLHSDYMNMTPR

RPGPTRKHYQPYAPPRDFAAYRSRVKFSRSADAPAYQQGQNQLYNE

LNLGRREEYDVLDKRRGRDPEMGGKPRRKNPQEGLYNELQKDKMA

EAYSEIGMKGERRRGKGHDGLYQGLSTATKDTYDALHMQALPPR

Clone 20C5.2 CD8 CD3 zeta CAR DNA Heavy &
Light Chains
(SEQ ID NO. 111)
ATGGCACTCCCCGTAACTGCTCTGCTGCTGCCGTTGGCATTGCTCC

TGCACGCCGCACGCCCGCAGGTGCAGTTGGTTGAATCAGGAGGG

GGTGTGGTGCAACCCGGTCGGTCACTGCGCCTCAGTTGTGCTGCT

TCCGGGTTTACTTTCAGCTCATATGGGATGCACTGGGTACGGCAG

GCTCCAGGTAAAGGCTTGGAATGGGTGGCGGTGATCAGCTATGAC

GGCTCTGACAAATATTATGTGGACTCCGTGAAAGGCAGATTCACC

ATCAGTCGAGACAACTCAAAGAATAGACTCTACTTGCAGATGAAT

AGCCTCCGGGCCGAAGATACTGCAGTCTATTATTGCGCCCGGGAG

CGCTACAGTGGAAGAGACTATTGGGGCAAGGAACTCTTGTCACA

GTCTCATCTGGCGGCGGCGGCAGCGGTGGGGGCGGATCTGGCGG

GGGCGGCAGCGAAATCGTTATGACTCAGAGTCCTGCCACACTGAG

CGTTAGCCCTGGTGAGAGAGCAACACTTAGCTGCAGAGCTAGTCA

GAGTGTTTCCAGTCTTTTGACATGGTACCAACAGAAGCCCGGTCA

AGCTCCACGACTGCTCATCTTCGGTGCATCCACCCGCGCAACCGG

GATACCCGCCGGTTTTCCGGTTCTGGAAGTGGCACAGGATTCAC

GCTCACCATTTCTTCTCTGCAGTCTGAAGACTTTGCCGTGTATTAC

```
TGCCAGCAGTACGATACCTGGCCCTTTACCTTTGGCCCAGGTACT

AAAGTGGATTTTAAACGAGCTGCTGCACTTTCCAATAGTATTATG

TACTTTTCACATTTTGTGCCCGTGTTCCTGCCTGCGAAGCCTACGA

CAACCCCAGCCCCTAGGCCGCCCACACCGGCCCCAACTATTGCCT

CCCAGCCATTGTCTCTGAGACCCGAAGCTTGCAGACCTGCTGCTG

GAGGCGCCGTTCACACCCGAGGATTGGATTTCGCATGTGACATTT

ACATCTGGGCCCCTTTGGCCGGAACCTGCGGTGTGCTGCTGCTGT

CACTCGTGATTACACTTTACTGCAACCACCGAAACAGATCCAAAA

GAAGCCGCCTGCTCCATAGCGATTACATGAATATGACTCCACGCC

GCCCTGGCCCCACAAGGAAACACTACCAGCCTTACGCACCACCTA

GAGATTTCGCTGCCTATCGGAGCAGGGTGAAGTTTTCCAGATCTG

CAGATGCACCAGCGTATCAGCAGGGCCAGAACCAACTGTATAAC

GAGCTCAACCTGGGACGCAGGGAAGAGTATGACGTTTTGGACAA

GCGCAGAGGACGGGACCCTGAGATGGGTGGCAAACCAAGACGAA

AAAACCCCCAGGAGGGTCTCTATAATGAGCTGCAGAAGGATAAG

ATGGCTGAAGCCTATTCTGAAATAGGCATGAAAGGAGAGCGGAG

AAGGGGAAAAGGGCACGACGGTTTGTACCAGGGACTCAGCACTG

CTACGAAGGATACTTATGACGCTCTCCACATGCAAGCCCTGCCAC

CTAGGTAA
```

Clone 20C5.2 CD8 CD3 zeta CAR AA Heavy &
Light Chains
(Signal peptide in Bold)
(SEQ ID NO. 112)
MALPVTALLLPLALLLHAARPQVQLVESGGGVVQPGRSLRLSCAA

SGFTFSSYGMHWVRQAPGKGLEWVAVISYDGSDKYYVDSVKGRFTI

SRDNSKNRLYLQMNSLRAEDTAVYYCARERYSGRDYWGGTLVTVS

SGGGGSGGGGSGGGGSEIVMTQSPATLSVSPGERATLSCRASQSVSS

LLTWYQQKPGQAPRLLIFGASTRATGIPARFSGSGSGTGFTLTISSLQS

EDFAVYYCQQYDTWPFTFGPGTKVDFKRAAALSNSIMYFSHFVPVFL

PAKPTTTPAPRPPTPAPTIASQPLSLRPEACRPAAGGAVHTRGLDFAC

DIYIWAPLAGTCGVLLLSLVITLYCNHRNRSKRSRLLHSDYMNMTPR

RPGPTRKHYQPYAPPRDFAAYRSRVKFSRSADAPAYQQGQNQLYNE

LNLGRREEYDVLDKRRGRDPEMGGKPRRKNPQEGLYNELQKDKMA

EAYSEIGMKGERRRGKGHDGLYQGLSTATKDTYDALHMQALPPR

Clone 20C5.2 CD8 CD3 zeta CAR DNA Heavy &
Light Chains
(SEQ ID NO. 113)
```
CAGGTGCAGTTGGTTGAATCAGGAGGGGGTGTGGTGCAACCCGGT

CGGTCACTGCGCCTCAGTTGTGCTGCTTCCGGGTTTACTTTCAGCT

CATATGGGATGCACTGGGTACGGCAGGCTCCAGGTAAAGGCTTGG

AATGGGTGGCGGTGATCAGCTATGACGGCTCTGACAAATATTATG

TGGACTCCGTGAAAGGCAGATTCACCATCAGTCGAGACAACTCAA

AGAATAGACTCTACTTGCAGATGAATAGCCTCCGGGCCGAAGATA

CTGCAGTCTATTATTGCGCCCGGGAGCGCTACAGTGGAAGAGACT
```

```
ATTGGGGGCAAGGAACTCTTGTCACAGTCTCATCTGGCGGCGGCG

GCAGCGGTGGGGCGGATCTGGCGGGGGCGGCAGCGAAATCGTT

ATGACTCAGAGTCCTGCCACACTGAGCGTTAGCCCTGGTGAGAGA

GCAACACTTAGCTGCAGAGCTAGTCAGAGTGTTTCCAGTCTTTTG

ACATGGTACCAACAGAAGCCCGGTCAAGCTCCACGACTGCTCATC

TTCGGTGCATCCACCCGCGCAACCGGGATACCCGCCCGGTTTTCC

GGTTCTGGAAGTGGCACAGGATTCACGCTCACCATTTCTTCTCTGC

AGTCTGAAGACTTTGCCGTGTATTACTGCCAGCAGTACGATACCT

GGCCCTTTACCTTTGGCCCAGGTACTAAAGTGGATTTTAAACGAG

CTGCTGCACTTTCCAATAGTATTATGTACTTTTCACATTTTGTGCC

CGTGTTCCTGCCTGCGAAGCCTACGACAACCCCAGCCCCTAGGCC

GCCCACACCGGCCCCAACTATTGCCTCCCAGCCATTGTCTCTGAG

ACCCGAAGCTTGCAGACCTGCTGCTGGAGGCGCCGTTCACACCCG

AGGATTGGATTTCGCATGTGACATTTACATCTGGGCCCCTTTGGCC

GGAACCTGCGGTGTGCTGCTGCTGTCACTCGTGATTACACTTTACT

GCAACCACCGAAACAGATCCAAAAGAAGCCGCCTGCTCCATAGC

GATTACATGAATATGACTCCACGCCGCCCTGGCCCCACAAGGAAA

CACTACCAGCCTTACGCACCACCTAGAGATTTCGCTGCCTATCGG

AGCAGGGTGAAGTTTTCCAGATCTGCAGATGCACCAGCGTATCAG

CAGGGCCAGAACCAACTGTATAACGAGCTCAACCTGGGACGCAG

GGAAGAGTATGACGTTTTGGACAAGCGCAGAGGACGGGACCCTG

AGATGGGTGGCAAACCAAGACGAAAAAACCCCCAGGAGGGTCTC

TATAATGAGCTGCAGAAGGATAAGATGGCTGAAGCCTATTCTGAA

ATAGGCATGAAAGGAGAGCGGAGAAGGGGAAAAGGGCACGACG

GTTTGTACCAGGGACTCAGCACTGCTACGAAGGATACTTATGACG

CTCTCCACATGCAAGCCCTGCCACCTAGG
```

Clone 20C5.2 CD8 CD3 zeta CAR AA Heavy &
Light Chains
(SEQ ID NO. 114)
QVQLVESGGGVVQPGRSLRLSCAASGFTFSSYGMHWVRQAPGKGLE

WVAVISYDGSDKYYVDSVKGRFTISRDNSKNRLYLQMNSLRAEDTA

VYYCARERYSGRDYWGQGTLVTVSSGGGGSGGGGSGGGGSEIVMT

QSPATLSVSPGERATLSCRASQSVSSLLTWYQQKPGQAPRLLIFGAST

RATGIPARFSGSGSGTGFTLTISSLQSEDFAVYYCQQYDTWPFTFGPG

TKVDFKRAAALSNSIMYFSHFVPVFLPAKPTTTPAPRPPTPAPTIASQP

LSLRPEACRPAAGGAVHTRGLDFACDIYIWAPLAGTCGVLLLSLVITL

YCNHRNRSKRSRLLHSDYMNMTPRRPGPTRKHYQPYAPPRDFAAYR

SRVKFSRSADAPAYQQGQNQLYNELNLGRREEYDVLDKRRGRDPE

MGGKPRRKNPQEGLYNELQKDKMAEAYSEIGMKGERRRGKGHDGL

YQGLSTATKDTYDALHMQALPPR

Clone 20C5.2 CD28T CD3 zeta CAR DNA Heavy &
Light Chains
(SEQ ID NO. 115)
ATGGCACTCCCCGTAACTGCTCTGCTGCTGCCGTTGGCATTGCTCC

TGCACGCCGCACGCCCGGAGATTGTGATGACCCAGTCCCCTGCTA

CCCTGTCCGTCAGTCCGGGCGAGAGAGCCACCTTGTCATGCCGGG

CCAGCCAGTCCGTCAGCAGTCTCCTGACTTGGTATCAGCAAAAAC

CAGGGCAGGCACCGCGGCTTTTGATTTTGGTGCAAGCACACGCG

CCACTGGCATTCCAGCTAGGTTTTCTGGAAGTGGATCTGGGACAG

GCTTCACTCTGACAATCAGTAGCCTGCAGAGTGAGGACTTTGCTG

TTTACTACTGTCAACAGTACGACACCTGGCCATTCACATTCGGGC

CCGGCACCAAGGTCGACTTCAAGAGGGGCGGTGGAGGTTCAGGT

GGTGGCGGGTCAGGCGGCGGTGGGTCTCAGGTTCAACTGGTGGA

ATCAGGTGGCGGCGTTGTCCAACCGGGGCGATCACTTCGACTTTC

CTGTGCTGCCTCAGGCTTTACTTTTTCATCCTATGGGATGCACTGG

GTTCGGCAGGCTCCCGGAAAAGGACTCGAGTGGGTTGCAGTGATC

TCTTACGATGGCTCAGACAAGTATTATGTGGACTCAGTCAAGGGG

AGATTCACAATAAGCCGAGACAACTCCAAAAACCGGCTTTATCTC

CAGATGAACAGCCTTAGAGCGGAAGATACCGCGGTATACTACTGT

GCCCGCGAGAGGTATTCCGGCAGAGACTACTGGGGACAGGGCAC

ACTGGTCACCGTGAGTTCTGCCGCAGCGCTCGATAACGAAAAGAG

CAACGGAACCATTATCCACGTTAAGGGCAAGCACCTGTGCCCCAG

TCCCCTCTTCCCAGGACCATCTAAACCCTTCTGGGTTCTGGTAGTA

GTTGGAGGGGTCCTTGCATGTTACTCCCTTTTGGTCACCGTCGCCT

TCATTATTTTCTGGGTGAGATCCAAAAGAAGCCGCCTGCTCCATA

GCGATTACATGAATATGACTCCACGCCGCCCTGGCCCCACAAGGA

AACACTACCAGCCTTACGCACCACCTAGAGATTTCGCTGCCTATC

GGAGCAGGGTGAAGTTTTCCAGATCTGCAGATGCACCAGCGTATC

AGCAGGGCCAGAACCAACTGTATAACGAGCTCAACCTGGGACGC

AGGGAAGAGTATGACGTTTTGGACAAGCGCAGAGGACGGGACCC

TGAGATGGGTGGCAAACCAAGACGAAAAAACCCCCAGGAGGGTC

TCTATAATGAGCTGCAGAAGGATAAGATGGCTGAAGCCTATTCTG

AAATAGGCATGAAAGGAGAGCGGAGAAGGGGAAAAGGGCACGA

CGGTTTGTACCAGGGACTCAGCACTGCTACGAAGGATACTTATGA

CGCTCTCCACATGCAAGCCCTGCCACCTAGGTAA

Clone 20C5.2 CD28T CD3 zeta CAR AA Heavy &
Light Chains (Signal Peptide in Bold)
(SEQ ID NO. 116)
MALPVTALLLPLALLLHAARPEIVMTQSPATLSVSPGERATLSCRA

SQSVSSLLTWYQQKPGQAPRLLIFGASTRATGIPARFSGSGSGTGFTL

TISSLQSEDFAVYYCQQYDTWPFTFGPGTKVDFKRGGGGSGGGGSG

GGGSQVQLVESGGGVVQPGRSLRLSCAASGFTFSSYGMHWVRQAPG

KGLEWVAVISYDGSDKYYVDSVKGRFTISRDNSKNRLYLQMNSLRA

EDTAVYYCARERYSGRDYWGQGTLVTVSSAAALDNEKSNGTIIHVK

GKHLCPSPLFPGPSKPFWVLVVVGGVLACYSLLVTVAFIIFWVRSKRS

RLLHSDYMNMTPRRPGPTRKHYQPYAPPRDFAAYRSVKFSRSADA

PAYQQGQNQLYNELNLGRREEYDVLDKRRGRDPEMGGKPRRKNPQ

EGLYNELQKDKMAEAYSEIGMKGERRRGKGHDGLYQGLSTATKDT

YDALHMQALPPR

Clone 20C5.2 CD28T CD3 zeta CAR DNA Heavy &
Light Chains
(SEQ ID NO. 117)
GAGATTGTGATGACCCAGTCCCCTGCTACCCTGTCCGTCAGTCCG

GGCGAGAGAGCCACCTTGTCATGCCGGGCCAGCCAGTCCGTCAGC

AGTCTCCTGACTTGGTATCAGCAAAAACCAGGGCAGGCACCGCGG

CTTTTGATTTTGGTGCAAGCACACGCGCCACTGGCATTCCAGCTA

GGTTTTCTGGAAGTGGATCTGGGACAGGCTTCACTCTGACAATCA

GTAGCCTGCAGAGTGAGGACTTTGCTGTTTACTACTGTCAACAGT

ACGACACCTGGCCATTCACATTCGGGCCCGGCACCAAGGTCGACT

TCAAGAGGGGCGGTGGAGGTTCAGGTGGTGGCGGGTCAGGCGGC

GGTGGGTCTCAGGTTCAACTGGTGGAATCAGGTGGCGGCGTTGTC

CAACCGGGGCGATCACTTCGACTTTCCTGTGCTGCCTCAGGCTTTA

CTTTTTCATCCTATGGGATGCACTGGGTTCGGCAGGCTCCCGGAA

AAGGACTCGAGTGGGTTGCAGTGATCTCTTACGATGGCTCAGACA

AGTATTATGTGGACTCAGTCAAGGGGAGATTCACAATAAGCCGAG

ACAACTCCAAAAACCGGCTTTATCTCCAGATGAACAGCCTTAGAG

CGGAAGATACCGCGGTATACTACTGTGCCCGCGAGAGGTATTCCG

GCAGAGACTACTGGGGACAGGGCACACTGGTCACCGTGAGTTCTG

CCGCAGCGCTCGATAACGAAAAGAGCAACGGAACCATTATCCAC

GTTAAGGGCAAGCACCTGTGCCCCAGTCCCCTCTTCCCAGGACCA

TCTAAACCCTTCTGGGTTCTGGTAGTAGTTGGAGGGGTCCTTGCAT

GTTACTCCCTTTTGGTCACCGTCGCCTTCATTATTTTCTGGGTGAG

ATCCAAAAGAAGCCGCCTGCTCCATAGCGATTACATGAATATGAC

TCCACGCCGCCCTGGCCCCACAAGGAAACACTACCAGCCTTACGC

ACCACCTAGAGATTTCGCTGCCTATCGGAGCAGGGTGAAGTTTTC

CAGATCTGCAGATGCACCAGCGTATCAGCAGGGCCAGAACCAAC

TGTATAACGAGCTCAACCTGGGACGCAGGGAAGAGTATGACGTTT

TGGACAAGCGCAGAGGACGGGACCCTGAGATGGGTGGCAAACCA

AGACGAAAAAACCCCCAGGAGGGTCTCTATAATGAGCTGCAGAA

GGATAAGATGGCTGAAGCCTATTCTGAAATAGGCATGAAAGGAG

AGCGGAGAAGGGGAAAAGGGCACGACGGTTTGTACCAGGGACTC

AGCACTGCTACGAAGGATACTTATGACGCTCTCCACATGCAAGCC

CTGCCACCTAGG

Clone 20C5.2 CD28T CD3 zeta CAR AA Heavy &
Light Chains
(SEQ ID NO. 118)
EIVMTQSPATLSVSPGERATLSCRASQSVSSLLTWYQQKPGQAPRLLI

FGASTRATGIPARFSGSGSGTGFTLTISSLQSEDFAVYYCQQYDTWPF

TFGPGTKVDFKRGGGGSGGGGSGGGGSQVQLVESGGGVVQPGRSLR

LSCAASGFTFSSYGMHWVRQAPGKGLEWVAVISYDGSDKYYVDSV

KGRFTISRDNSKNRLYLQMNSLRAEDTAVYYCARERYSGRDYWGQ

GTLVTVSSAAALDNEKSNGTIIHVKGKHLCPSPLFPGPSKPFWVLVV

VGGVLACYSLLVTVAFIIFWVRSKRSRLLHSDYMNMTPRRPGPTRKH

YQPYAPPRDFAAYRSRVKFSRSADAPAYQQGQNQLYNELNLGRREE

YDVLDKRRGRDPEMGGKPRRKNPQEGLYNELQKDKMAEAYSEIGM

KGERRRGKGHDGLYQGLSTATKDTYDALHMQALPPR

Clone 20C5.2 CD28 CD3 zeta CAR DNA Heavy &
Light Chains
(SEQ ID NO. 119)
ATGGCACTCCCCGTAACTGCTCTGCTGCTGCCGTTGGCATTGCTCC

TGCACGCCGCACGCCCGGAGATCGTCATGACACAGAGTCCAGCTA

CCCTGAGCGTGTCCCCTGGAGAGAGAGCCACCCTGTCCTGTAGGG

CTAGTCAGAGTGTGTCCAGCCTCCTCACCTGGTATCAACAGAAGC

CTGGTCAAGCTCCCCGGCTGCTTATCTTCGGGGCCAGCACGCGAG

CCACAGGCATCCCGGCCAGATTCTCTGGCTCTGGCAGTGGCACCG

GGTTCACTCTCACGATCTCATCCCTGCAGTCAGAGGATTTCGCTGT

GTATTACTGTCAGCAGTACGATACATGGCCCTTCACCTTCGGCCC

GGGCACAAAAGTAGATTTCAAGCGCGGCGGCGGGGGTAGTGGGG

GCGGGGGATCAGGAGGAGGGGGCTCCCAAGTACAGCTGGTTGAG

AGCGGCGGCGGGGTGGTTCAGCCCGGGCGCAGCCTCAGGCTGAG

TTGCGCAGCATCAGGATTCACATTCAGTTCTTATGGAATGCATTG

GGTCAGACAGGCTCCCGGGAAGGGCCTTGAATGGGTGGCAGTCA

TTAGCTACGACGGAAGCGATAAGTACTATGTGGACTCAGTTAAAG

GGAGATTTACTATCAGCCGCGACAATTCCAAAAACAGATTGTATT

TGCAGATGAACTCCCTCAGGGCGGAGGACACTGCTGTATATTACT

GCGCACGAGAGAGATACTCCGGCCGAGACTATTGGGGCCAAGGA

ACATTGGTAACTGTGAGCTCCGCCGCAGCTATTGAGGTCATGTAC

CCCCCACCTTATCTCGATAATGAGAAGAGTAATGGGACTATAATT

CACGTAAAGGGCAAACACCTGTGCCCTTCCCCGCTGTTTCCAGGT

CCAAGTAAGCCGTTCTGGGTCCTGGTTGTGGTGGGAGGGGTGCTG

GCCTGCTATTCTCTGTTGGTTACCGTGGCCTTTATCATTTTCTGGGT

GAGATCCAAAAGAAGCCGCCTGCTCCATAGCGATTACATGAATAT

GACTCCACGCCGCCCTGGCCCCACAAGGAAACACTACCAGCCTTA

CGCACCACCTAGAGATTTCGCTGCCTATCGGAGCAGGGTGAAGTT

TTCCAGATCTGCAGATGCACCAGCGTATCAGCAGGGCCAGAACCA

ACTGTATAACGAGCTCAACCTGGGACGCAGGGAAGAGTATGACG

TTTTGGACAAGCGCAGAGGACGGGACCCTGAGATGGGTGGCAAA

CCAAGACGAAAAAACCCCCAGGAGGGTCTCTATAATGAGCTGCA

GAAGGATAAGATGGCTGAAGCCTATTCTGAAATAGGCATGAAAG

GAGAGCGGAGAAGGGGAAAAGGGCACGACGGTTTGTACCAGGGA

CTCAGCACTGCTACGAAGGATACTTATGACGCTCTCCACATGCAA

GCCCTGCCACCTAGGTAA

Clone 20C5.2 CD28 CD3 zeta CAR AA Heavy &
Light Chains (Signal Peptide in Bold)
(SEQ ID NO. 120)
MALPVTALLLPLALLLHAARPEIVMTQSPATLSVSPGERATLSCRA

SQSVSSLLTWYQQKPGQAPRLLIFGASTRATGIPARFSGSGSGTGFTL

TISSLQSEDFAVYYCQQYDTWPFTFGPGTKVDFKRGGGGSGGGGSG

GGGSQVQLVESGGGVVQPGRSLRLSCAASGFTFSSYGMHWVRQAPG

KGLEWVAVISYDGSDKYYVDSVKGRFTISRDNSKNRLYLQMNSLRA

EDTAVYYCARERYSGRDYWGQGTLVTVSSAAAIEVMYPPPYLDNEK

SNGTIIHVKGKHLCPSPLFPGPSKPFWVLVVVGGVLACYSLLVTVAFI

IFWVRSKRSRLLHSDYMNMTPRRPGPTRKHYQPYAPPRDFAAYRSR

VKFSRSADAPAYQQGQNQLYNELNLGRREEYDVLDKRRGRDPEMG

GKPRRKNPQEGLYNELQKDKMAEAYSEIGMKGERRRGKGHDGLYQ

GLSTATKD TYDALHMQALPPR

Clone 20C5.2 CD28 CD3 zeta CAR DNA Heavy &
Light Chains
(SEQ ID NO. 121)
GAGATCGTCATGACACAGAGTCCAGCTACCCTGAGCGTGTCCCCT

GGAGAGAGAGCCACCCTGTCCTGTAGGGCTAGTCAGAGTGTGTCC

AGCCTCCTCACCTGGTATCAACAGAAGCCTGGTCAAGCTCCCCGG

CTGCTTATCTTCGGGGCCAGCACGCGAGCCACAGGCATCCCGGCC

AGATTCTCTGGCTCTGGCAGTGGCACCGGGTTCACTCTCACGATCT

CATCCCTGCAGTCAGAGGATTTCGCTGTGTATTACTGTCAGCAGT

ACGATACATGGCCCTTCACCTTCGGCCCGGGCACAAAAGTAGATT

TCAAGCGCGGCGGCGGGGGTAGTGGGGGCGGGGGATCAGGAGGA

GGGGGCTCCCAAGTACAGCTGGTTGAGAGCGGCGGCGGGGTGGT

TCAGCCCGGGCGCAGCCTCAGGCTGAGTTGCGCAGCATCAGGATT

CACATTCAGTTCTTATGGAATGCATTGGGTCAGACAGGCTCCCGG

GAAGGGCCTTGAATGGGTGGCAGTCATTAGCTACGACGGAAGCG

ATAAGTACTATGTGGACTCAGTTAAAGGGAGATTTACTATCAGCC

GCGACAATTCCAAAAACAGATTGTATTTGCAGATGAACTCCCTCA

GGGCGGAGGACACTGCTGTATATTACTGCGCACGAGAGAGATACT

CCGGCCGAGACTATTGGGGCCAAGGAACATTGGTAACTGTGAGCT

CCGCCGCAGCTATTGAGGTCATGTACCCCCCACCTTATCTCGATA

ATGAGAAGAGTAATGGGACTATAATTCACGTAAAGGGCAAACAC

CTGTGCCCTTCCCCGCTGTTTCCAGGTCCAAGTAAGCCGTTCTGGG

TCCTGGTTGTGGTGGGAGGGGTGCTGGCCTGCTATTCTCTGTTGGT

TACCGTGGCCTTTATCATTTTCTGGGTGAGATCCAAAAGAAGCCG

CCTGCTCCATAGCGATTACATGAATATGACTCCACGCCGCCCTGG

CCCCACAAGGAAACACTACCAGCCTTACGCACCACCTAGAGATTT

-continued
CGCTGCCTATCGGAGCAGGGTGAAGTTTTCCAGATCTGCAGATGC

ACCAGCGTATCAGCAGGGCCAGAACCAACTGTATAACGAGCTCA

ACCTGGGACGCAGGGAAGAGTATGACGTTTTGGACAAGCGCAGA

GGACGGGACCCTGAGATGGGTGGCAAACCAAGACGAAAAACCC

CCAGGAGGGTCTCTATAATGAGCTGCAGAAGGATAAGATGGCTG

AAGCCTATTCTGAAATAGGCATGAAAGGAGAGCGGAGAAGGGGA

AAAGGGCACGACGGTTTGTACCAGGGACTCAGCACTGCTACGAA

GGATACTTATGACGCTCTCCACATGCAAGCCCTGCCACCTAGG

Clone 20C5.2 CD28 CD3 zeta CAR AA Heavy &
Light Chains
(SEQ ID NO. 122)
EIVMTQSPATLSVSPGERATLSCRASQSVSSLLTWYQQKPGQAPRLLI

FGASTRATGIPARFSGSGSGTGFTLTISSLQSEDFAVYYCQQYDTWPF

TFGPGTKVDFKRGGGGSGGGGSGGGGSQVQLVESGGGVVQPGRSLR

LSCAASGFTFSSYGMHWVRQAPGKGLEWVAVISYDGSDKYYVDSV

KGRFTISRDNSKNRLYLQMNSLRAEDTAVYYCARERYSGRDYWGQ

GTLVTVSSAAAIEVMYPPPYLDNEKSNGTIIHVKGKHLCPSPLFPGPS

KPFWVLVVVGGVLACYSLLVTVAFIIFWVRSKRSRLLHSDYMNMTP

RRPGPTRKHYQPYAPPRDFAAYRSRVKFSRSADAPAYQQGQNQLYN

ELNLGRREEYDVLDKRRGRDPEMGGKPRRKNPQEGLYNELQKDKM

AEAYSEIGMKGERRRGKGHDGLYQGLSTATKDTYDALHMQALPPR

Clone 20C5.2 CD8 CD3 zeta CAR DNA Heavy &
Light Chains
(SEQ ID NO. 123)
ATGGCACTCCCCGTAACTGCTCTGCTGCTGCCGTTGGCATTGCTCC

TGCACGCCGCACGCCCGGAAATAGTGATGACTCAGTCCCCGGCCA

CCCTCAGCGTGTCCCCCGGGGAGCGAGCGACCCTGTCATGCAGGG

CTTCCCAGAGTGTCAGCTCCCTGCTCACTTGGTATCAGCAAAAGC

CGGGGCAGGCTCCCCGCCTCCTCATCTTCGGGGCATCAACTAGGG

CCACCGGCATTCCTGCAAGATTTTCCGGGTCTGGCAGCGGCACCG

GCTTCACCCTTACCATTAGCTCTCTGCAGTCTGAGGACTTCGCCGT

TTACTATTGTCAGCAGTATGATACTTGGCCCTTTACCTTCGGTCCC

GGAACTAAGGTGGACTTCAAGCGCGGGGGGGGTGGATCTGGAGG

TGGTGGCTCCGGGGCGGTGGAAGCCAGGTCCAGTTGGTTGAGA

GCGGCGGCGGAGTGGTGCAGCCCGGGAGGTCCTTGCGGCTGAGC

TGTGCAGCCTCCGGTTTTACTTTTTCTAGCTATGGAATGCATTGGG

TAAGACAGGCTCCCGGAAAAGGCCTCGAGTGGGTGGCGGTCATT

AGCTATGATGGATCTGATAAATACTATGTGGACTCAGTTAAGGGG

CGCTTCACAATCTCAAGAGACAATAGCAAAAATAGACTGTACCTG

CAGATGAATAGTCTGCGCGCCGAGGACACTGCCGTGTACTACTGC

GCCCGCGAGAGATACAGCGGACGGGATTACTGGGGCCAGGGTAC

CCTCGTAACGGTGTCCTCCGCTGCCGCCCTTAGCAACAGCATTAT

GTACTTTTCTCATTTCGTGCCAGTCTTTCTCCCAGCAAAGCCCACC

ACTACCCCGGCCCCCAGGCCGCCTACTCCTGCCCCCACTATCGCG

-continued
TCTCAGCCTCTCTCCTTGCGGCCCGAGGCCTGCCGGCCAGCCGCA

GGGGGCGCCGTACATACTCGGGGTTTGGATTTCGCTTGCGACATA

TATATTTGGGCCCCCCTCGCCGGCACATGTGGAGTGCTGCTCCTG

AGTCTCGTTATAACCCTCTATTGCAACCATAGAAACAGATCCAAA

AGAAGCCGCCTGCTCCATAGCGATTACATGAATATGACTCCACGC

CGCCCTGGCCCCACAAGGAAACACTACCAGCCTTACGCACCACCT

AGAGATTTCGCTGCCTATCGGAGCAGGGTGAAGTTTTCCAGATCT

GCAGATGCACCAGCGTATCAGCAGGGCCAGAACCAACTGTATAA

CGAGCTCAACCTGGGACGCAGGGAAGAGTATGACGTTTTGGACA

AGCGCAGAGGACGGGACCCTGAGATGGGTGGCAAACCAAGACGA

AAAAACCCCCAGGAGGGTCTCTATAATGAGCTGCAGAAGGATAA

GATGGCTGAAGCCTATTCTGAAATAGGCATGAAAGGAGAGCGGA

GAAGGGGAAAAGGGCACGACGGTTTGTACCAGGGACTCAGCACT

GCTACGAAGGATACTTATGACGCTCTCCACATGCAAGCCCTGCCA

CCTAGGTAA

Clone 20C5.2 CD8 CD3 zeta CAR AA Heavy &
Light Chains (Signal Peptide in Bold)
(SEQ ID NO. 124)
MALPVTALLLPLALLLHAARPEIVMTQSPATLSVSPGERATLSCRA

SQSVSSLLTWYQQKPGQAPRLLIFGASTRATGIPARFSGSGSGTGFTL

TISSLQSEDFAVYYCQQYDTWPFTFGPGTKVDFKRGGGGSGGGGSG

GGGSQVQLVESGGGVVQPGRSLRLSCAASGFTFSSYGMHWVRQAPG

KGLEWVAVISYDGSDKYYVDSVKGRFTISRDNSKNRLYLQMNSLRA

EDTAVYYCARERYSGRDYWGQGTLVTVSSAAALSNSIMYFSHFVPV

FLPAKPTTTPAPRPPTPAPTIASQPLSLRPEACRPAAGGAVHTRGLDFA

CDIYIWAPLAGTCGVLLLSLVITLYCNHRNRSKRSRLLHSDYMNMTP

RRPGPTRKHYQPYAPPRDFAAYRSRVKFSRSADAPAYQQGQNQLYN

ELNLGRREEYDVLDKRRGRDPEMGGKPRRKNPQEGLYNELQKDKM

AEAYSEIGMKGERRRGKGHDGLYQGLSTATKDTYDALHMQALPPR

Clone 20C5.2 CD8 CD3 zeta CAR DNA Heavy &
Light Chains
(SEQ ID NO. 125)
GAAATAGTGATGACTCAGTCCCCGGCCACCCTCAGCGTGTCCCCC

GGGGAGCGAGCGACCCTGTCATGCAGGGCTTCCCAGAGTGTCAGC

TCCCTGCTCACTTGGTATCAGCAAAAGCCGGGGCAGGCTCCCCGC

CTCCTCATCTTCGGGGCATCAACTAGGGCCACCGGCATTCCTGCA

AGATTTTCCGGGTCTGGCAGCGGCACCGGCTTCACCCTTACCATT

AGCTCTCTGCAGTCTGAGGACTTCGCCGTTTACTATTGTCAGCAGT

ATGATACTTGGCCCTTTACCTTCGGTCCCGGAACTAAGGTGGACTT

CAAGCGCGGGGGGTGGATCTGGAGGTGGTGGCTCCGGGGCG

GTGGAAGCCAGGTCCAGTTGGTTGAGAGCGGCGGCGGAGTGGTG

CAGCCCGGGAGGTCCTTGCGGCTGAGCTGTGCAGCCTCCGGTTTT

ACTTTTTCTAGCTATGGAATGCATTGGGTAAGACAGGCTCCCGGA

```
AAAGGCCTCGAGTGGGTGGCGGTCATTAGCTATGATGGATCTGAT

AAATACTATGTGGACTCAGTTAAGGGGCGCTTCACAATCTCAAGA

GACAATAGCAAAAATAGACTGTACCTGCAGATGAATAGTCTGCGC

GCCGAGGACACTGCCGTGTACTACTGCGCCCGCGAGAGATACAGC

GGACGGGATTACTGGGGCCAGGGTACCCTCGTAACGGTGTCCTCC

GCTGCCGCCCTTAGCAACAGCATTATGTACTTTTCTCATTTCGTGC

CAGTCTTTCTCCCAGCAAAGCCCACCACTACCCCGGCCCCCAGGC

CGCCTACTCCTGCCCCCACTATCGCGTCTCAGCCTCTCTCCTTGCG

GCCCGAGGCCTGCCGGCCAGCCGCAGGGGCGCCGTACATACTC

GGGGTTTGGATTTCGCTTGCGACATATATATTTGGGCCCCCCTCGC

CGGCACATGTGGAGTGCTGCTCCTGAGTCTCGTTATAACCCTCTAT

TGCAACCATAGAAACAGATCCAAAAGAAGCCGCCTGCTCCATAG

CGATTACATGAATATGACTCCACGCCGCCCTGGCCCCACAAGGAA

ACACTACCAGCCTTACGCACCACCTAGAGATTTCGCTGCCTATCG

GAGCAGGGTGAAGTTTTCCAGATCTGCAGATGCACCAGCGTATCA

GCAGGGCCAGAACCAACTGTATAACGAGCTCAACCTGGGACGCA

GGGAAGAGTATGACGTTTTGGACAAGCGCAGAGGACGGGACCCT

GAGATGGGTGGCAAACCAAGACGAAAAAACCCCCAGGAGGGTCT

CTATAATGAGCTGCAGAAGGATAAGATGGCTGAAGCCTATTCTGA

AATAGGCATGAAAGGAGAGCGGAGAAGGGGAAAAGGGCACGAC

GGTTTGTACCAGGGACTCAGCACTGCTACGAAGGATACTTATGAC

GCTCTCCACATGCAAGCCCTGCCACCTAGG

Clone 20C5.2 CD8 CD3 zeta CAR AA Heavy &
Light Chains
                                  (SEQ ID NO. 126)
EIVMTQSPATLSVSPGERATLSCRASQSVSSLLTWYQQKPGQAPRLLI

FGASTRATGIPARFSGSGSGTGFTLTISSLQSEDFAVYYCQQYDTWPF

TFGPGTKVDFKRGGGGSGGGGSGGGGSQVQLVESGGGVVQPGRSLR

LSCAASGFTFSSYGMHWVRQAPGKGLEWVAVISYDGSDKYYVDSV

KGRFTISRDNSKNRLYLQMNSLRAEDTAVYYCARERYSGRDYWGQ

GTLVTVSSAAALSNSIMYFSHFVPVFLPAKPTTTPAPRPPTPAPTIASQ

PLSLRPEACRPAAGGAVHTRGLDFACDIYIWAPLAGTCGVLLLSLVIT

LYCNHRNRSKRSRLLHSDYMNMTPRRPGPTRKHYQPYAPPRDFAAY

RSRVKFSRSADAPAYQQGQNQLYNELNLGRREEYDVLDKRRGRDPE

MGGKPRRKNPQEGLYNELQKDKMAEAYSEIGMKGERRRGKGHDGL

YQGLSTATKDTYDALHMQALPPR

CAR Signal Peptide DNA
                                  (SEQ ID NO. 127)
ATGGCACTCCCCGTAACTGCTCTGCTGCTGCCGTTGGCATTGCTCC

TGCACGCCGCACGCCCG

CAR Signal Peptide:
                                  (SEQ ID NO. 128)
MALPVTALLLPLALLLHAARP scFv G4S linker DNA
                                  (SEQ ID NO. 129)
GGCGGTGGAGGCTCCGGAGGGGGGGGCTCTGGCGGAGGGGGCTCC scFv G4s linker:
                                  (SEQ ID NO. 130)
GGGGSGGGGSGGGGS Additional G4S linker:
                                  (SEQ ID NO. 145)
GGGGSGGGGSGGGGSGGGGS scFv Whitlow linker DNA
                                  (SEQ ID NO. 131)
GGGTCTACATCCGGCTCCGGGAAGCCCGGAAGTGGCGAAGGTAG

TACAAAGGGG scFv Whitlow linker:
                                  (SEQ ID NO. 132)
GSTSGSGKPGSGEGSTKG CD28 AA Extracellular Domain
                                  (SEQ ID NO. 133)
MLRLLLALNLFPSIQVTGNKILVKQSPMLVAYDNAVNLSCKYSYNLF

SREFRASLHKGLDSAVEVCVVYGNYSQQLQVYSKTGFNCDGKLGNE

SVTFYLQNLYVNQTDIYFCKIEVMYPPPYLDNEKSNGTIIHVKGKHLC

PSPLFPGPSKP (SEQ ID NO: 134)
$GX_2X_3X_4X_5X_6X_7X_8X_9$ (SEQ ID NO: 135)
$X_1X_2X_3X_4X_5X_6$ (SEQ ID NO: 136)
$X_1X_2X_3X_4X_5X_6X_7X_8X_9X_{10}X_{11}X_{12}DY$ (SEQ ID NO: 137)
$X_1ASQX_5X_6X_7X_8X_9LX_{11}$ (SEQ ID NO: 138)
$X_1ASX_4X_5X_6X_7$ (SEQ ID NO: 139)
$QQX_3X_4X_5X_6PX_8T$

CLL-1 AA (a.k.a., CLEC12A)
                                  (SEQ ID NO. 140)
MSEEVTYADLQFQNSSEMEKIPEIGKFGEKAPPAPSHVWRPAALFLT

LLCLLLLIGLGVLASMFHVTLKIEMKKMNKLQNISEELQRNISLQLMS

NMNISNKIRNLSTTLQTIATKLCRELYSKEQEHKCKPCPRRWIWHKD

SCYFLSDDVQTWQESKMACAAQNASLLKINNKNALEFIKSQSRSYD

YWLGLSPEEDSTRGMRVDNIINSSAWVIRNAPDLNNMYCGYINRLY

VQYYHCTYKKRMICEKMANPVQLGSTYFREA 4-1BB Nucleic Acid Sequence (intracellular domain)
                                  (SEQ ID NO. 141)
AAGCGCGGCAGGAAGAAGCTCCTCTACATTTTTAAGCAGCCTTTT

ATGAGGCCCGTACAGACAACACAGGAGGAAGATGGCTGTAGCTG

CAGATTTCCCGAGGAGGAGGAAGGTGGGTGCGAGCTG
```

4-1BB AA (intracellular domain)

(SEQ ID NO. 142)
KRGRKKLLYIFKQPFMRPVQTTQEEDGCSCRFPEEEEGGCEL

OX40 AA (SEQ ID NO. 143)
RRDQRLPPDAHKPPGGGSFRTPIQEEQADAHSTLAKI

Leader Sequence AA (SEQ ID NO: 144)
MALPVTALLLPLALLLHAARP

What is claimed:

1. A chimeric antigen receptor that binds to C-type lectin-like-1 ("CLL-1"), wherein the chimeric antigen receptor is a polypeptide comprising a single chain Fv (scFv) that binds CLL-1, a transmembrane domain, and an intracellular activating domain that is a signaling domain of CD3 zeta, and wherein the scFv comprises a heavy chain variable region (VH) and light chain variable region (VL) pair that is selected from the group consisting of:
   (a) a VH region comprising complementarity determining regions ("CDRs") 1, 2, and 3 with amino acid sequences SEQ ID NO: 17, SEQ ID NO: 18, and SEQ ID NO: 19, respectively, and a VL region comprising CDRs 1, 2, and 3 with amino acid sequences SEQ ID NO: 22, SEQ ID NO: 23, and SEQ ID NO: 24, respectively;
   (b) a VH region comprising CDRs 1, 2, and 3 with amino acid sequences SEQ ID NO: 51, SEQ ID NO: 52, and SEQ ID NO: 53, respectively, and a VL region comprising CDRs 1, 2, and 3 with amino acid sequences SEQ ID NO: 56, SEQ ID NO: 57, and SEQ ID NO: 58, respectively;
   (c) a VH region comprising CDRs 1, 2, and 3 with amino acid sequences SEQ ID NO: 73, SEQ ID NO: 74, and SEQ ID NO: 75, respectively, and a VL region comprising CDRs 1, 2, and 3 with amino acid sequences SEQ ID NO: 78, SEQ ID NO: 79, and SEQ ID NO: 80, respectively; and
   (d) a VH region comprising CDRs 1, 2, and 3 with amino acid sequences SEQ ID NO: 95, SEQ ID NO: 96, and SEQ ID NO: 97, respectively, and a VL region comprising CDRs 1, 2, and 3 with amino acid sequences SEQ ID NO: 100, SEQ ID NO: 101, and SEQ ID NO: 102, respectively.

2. The chimeric antigen receptor according to claim 1, wherein the signaling domain of CD3 zeta comprises the amino acid sequence set forth in SEQ ID NO: 10.

3. The chimeric antigen receptor according to claim 1 further comprising at least one costimulatory domain signaling region.

4. The chimeric antigen receptor according to claim 3, wherein the costimulatory domain signaling region is a signaling region of CD28, OX-40, 4-1BB/CD137, CD27, or ICOS.

5. The chimeric antigen receptor according to claim 4, wherein the costimulatory domain signaling region comprises SEQ ID NO: 8.

6. The chimeric antigen receptor according to claim 5, wherein the chimeric antigen receptor comprises SEQ ID NO: 2.

7. The chimeric antigen receptor according to claim 1, wherein the transmembrane domain is a CD28 or a CD8 transmembrane domain.

8. The chimeric antigen receptor according to claim 7, wherein the transmembrane domain is a CD28 transmembrane domain that comprises SEQ ID NO: 6.

9. The chimeric antigen receptor according to claim 1, wherein the chimeric antigen receptor comprises (a) an extracellular and transmembrane domain of CD28 as set forth in SEQ ID NO: 2 or (b) an extracellular and transmembrane domain of CD8 as set forth in SEQ ID NO: 14.

10. The chimeric antigen receptor according to claim 1, wherein the linker of the scFv comprises at least one of SEQ ID NO: 130 or SEQ ID NO: 132.

11. The chimeric antigen receptor of claim 1, wherein the scFv comprises:
   (a) a VH region comprising the amino acid sequence of SEQ ID NO: 16 and a VL region comprising the amino acid sequence of SEQ ID NO: 21;
   (b) a VH region comprising the amino acid sequence of SEQ ID NO: 50 and a VL region comprising the amino acid sequence of SEQ ID NO: 55;
   (c) a VH region comprising the amino acid sequence of SEQ ID NO: 72 and a VL region comprising the amino acid sequence of SEQ ID NO: 77; or
   (d) a VH region comprising the amino acid sequence of SEQ ID NO: 94 and a VL region comprising the amino acid sequence of SEQ ID NO: 99.

12. A chimeric antigen receptor that binds to C-type lectin-like-1 ("CLL-1"), wherein the chimeric antigen receptor is a polypeptide comprising a single chain Fv ("scFv") that binds CLL-1, a transmembrane domain, and an intracellular activating domain that is a signaling domain of CD3 zeta, and wherein the scFv comprises a heavy chain variable region (VH) and light chain variable region (VL) pair that is selected from the group consisting of:
   (a) a VH region comprising the amino acid sequence of SEQ ID NO: 16 and a VL region comprising the amino acid sequence of SEQ ID NO: 21;
   (b) a VH region comprising the amino acid sequence of SEQ ID NO: 50 and a VL region comprising the amino acid sequence of SEQ ID NO: 55;
   (c) a VH region comprising the amino acid sequence of SEQ ID NO: 72 and a VL region comprising the amino acid sequence of SEQ ID NO: 77; and
   (d) a VH region comprising the amino acid sequence of SEQ ID NO: 94 and a VL region comprising the amino acid sequence of SEQ ID NO: 99.

13. An isolated polynucleotide encoding a chimeric antigen receptor of claim 1 or 12.

14. A vector comprising a polynucleotide of claim 13.

15. The vector according to claim 14 which is a retroviral vector, a DNA vector, a plasmid, a RNA vector, an adenoviral vector, an adenovirus associated vector, or a lentiviral vector.

16. An immune cell comprising the vector of claim 14.

17. The immune cell according to claim 16, wherein the immune cell is a T cell, a tumor infiltrating lymphocyte (TIL), an NK cell, or an NK-T cell.

18. The immune cell according to claim 17, wherein the cell is an autologous T cell.

19. The immune cell according to claim 17, wherein the cell is an allogeneic T cell.

20. A pharmaceutical composition comprising the T cell of claim 18 and a pharmaceutically acceptable carrier.

21. A chimeric antigen receptor polypeptide comprising an amino acid sequence as set forth in SEQ ID NO: 28; SEQ ID NO: 32; SEQ ID NO: 36; SEQ ID NO: 40; SEQ ID NO: 44; SEQ ID NO: 48; SEQ ID NO: 62; SEQ ID NO: 66; SEQ ID NO: 70; SEQ ID NO: 84; SEQ ID NO: 88; SEQ ID NO: 92; SEQ ID NO: 106; SEQ ID NO: 110; SEQ ID NO: 114; SEQ ID NO: 118; SEQ ID NO: 122; or SEQ ID NO: 126.

22. An isolated polynucleotide comprising a nucleic acid sequence as set forth in SEQ ID NO: 27; SEQ ID NO: 31; SEQ ID NO: 35; SEQ ID NO: 39; SEQ ID NO: 43; SEQ ID NO: 47; SEQ ID NO: 61; SEQ ID NO: 65; SEQ ID NO: 69; SEQ ID NO: 83; SEQ ID NO: 87; SEQ ID NO: 91; SEQ ID NO: 105; SEQ ID NO: 109; SEQ ID NO: 113; SEQ ID NO: 117; SEQ ID NO: 121; or SEQ ID NO: 125.

23. A vector comprising a polynucleotide of claim 22.

24. The vector according to claim 23 which is a retroviral vector, a DNA vector, a plasmid, a RNA vector, an adenoviral vector, an adenovirus associated vector, or a lentiviral vector.

25. An immune cell comprising the vector of claim 23.

26. The immune cell according to claim 25, wherein the immune cell is a T cell, a tumor infiltrating lymphocyte (TIL), an NK cell, or an NK-T cell.

27. The immune cell according to claim 26, wherein the cell is an autologous T cell.

28. The immune cell according to claim 26, wherein the cell is an allogeneic T cell.

29. A pharmaceutical composition comprising T cells according to claim 27 or 28 and a pharmaceutically acceptable carrier.

30. A method of treating a tumor or malignancy that expresses C-type lectin-like-1 ("CLL-1"), the method comprising administering the pharmaceutical composition of claim 29 to a human with a tumor or malignancy that expresses CLL-1.

31. An antigen-binding molecule that comprises a heavy chain variable region (VH) and a light chain variable region (VL) pair that binds C-type lectin-like-1 ("CLL-1"), wherein the VH and VL pair is selected from the group consisting of:
  (a) a VH region comprising complementarity determining regions ("CDRs") 1, 2, and 3 with amino acid sequences SEQ ID NO: 17, SEQ ID NO: 18, and SEQ ID NO: 19, respectively, and a VL region comprising CDRs 1, 2, and 3 with amino acid sequences SEQ ID NO: 22, SEQ ID NO: 23, and SEQ ID NO: 24, respectively;
  (b) a VH region comprising CDRs 1, 2, and 3 with amino acid sequences SEQ ID NO: 51, SEQ ID NO: 52, and SEQ ID NO: 53, respectively, and a VL region comprising CDRs 1, 2, and 3 with amino acid sequences SEQ ID NO: 56, SEQ ID NO: 57, and SEQ ID NO: 58, respectively;
  (c) a VH region comprising CDRs 1, 2, and 3 with amino acid sequences SEQ ID NO: 73, SEQ ID NO: 74, and SEQ ID NO: 75, respectively, and a VL region comprising CDRs 1, 2, and 3 with amino acid sequences SEQ ID NO: 78, SEQ ID NO: 79, and SEQ ID NO: 80, respectively; and
  (d) a VH region comprising CDRs 1, 2, and 3 with amino acid sequences SEQ ID NO: 95, SEQ ID NO: 96, and SEQ ID NO: 97, respectively, and a VL region comprising CDRs 1, 2, and 3 with amino acid sequences SEQ ID NO: 100, SEQ ID NO: 101, and SEQ ID NO: 102, respectively.

32. The antigen-binding molecule according to claim 31, wherein the VH and VL pair is selected from the group consisting of:
  (a) a VH region comprising the amino acid sequence of SEQ ID NO: 16 and a VL region comprising the amino acid sequence of SEQ ID NO: 21;
  (b) a VH region comprising the amino acid sequence of SEQ ID NO: 50 and a VL region comprising the amino acid sequence of SEQ ID NO: 55;
  (c) a VH region comprising the amino acid sequence of SEQ ID NO: 72 and a VL region comprising the amino acid sequence of SEQ ID NO: 77; and
  (d) a VH region comprising the amino acid sequence of SEQ ID NO: 94 and a VL region comprising the amino acid sequence of SEQ ID NO: 99.

33. The antigen binding molecule according to claim 31, wherein the VH and VL pair comprises a VH region comprising complementarity determining regions ("CDRs") 1, 2, and 3 with amino acid sequences SEQ ID NO: 17, SEQ ID NO: 18, and SEQ ID NO: 19, respectively, and a VL region comprising CDRs 1, 2, and 3 with amino acid sequences SEQ ID NO: 22, SEQ ID NO: 23, and SEQ ID NO: 24, respectively.

34. The antigen binding molecule according to claim 31, wherein the VH and VL pair comprises a VH region comprising CDRs 1, 2, and 3 with amino acid sequences SEQ ID NO: 51, SEQ ID NO: 52, and SEQ ID NO: 53, respectively, and a VL region comprising CDRs 1, 2, and 3 with amino acid sequences SEQ ID NO: 56, SEQ ID NO: 57, and SEQ ID NO: 58, respectively.

35. The antigen binding molecule according to claim 31, wherein the VH and VL pair comprises a VH region comprising CDRs 1, 2, and 3 with amino acid sequences SEQ ID NO: 73, SEQ ID NO: 74, and SEQ ID NO: 75, respectively, and a VL region comprising CDRs 1, 2, and 3 with amino acid sequences SEQ ID NO: 78, SEQ ID NO: 79, and SEQ ID NO: 80, respectively.

36. The antigen binding molecule according to claim 31, wherein the VH and VL pair comprises a VH region comprising CDRs 1, 2, and 3 with amino acid sequences SEQ ID NO: 95, SEQ ID NO: 96, and SEQ ID NO: 97, respectively, and a VL region comprising CDRs 1, 2, and 3 with amino acid sequences SEQ ID NO: 100, SEQ ID NO: 101, and SEQ ID NO: 102, respectively.

37. The antigen binding molecule according to claim 31, wherein the antigen binding molecule is an antibody, or an immunologically functional fragment thereof.

38. The antigen binding molecule according to claim 37, wherein the antigen binding molecule is a scFv fragment, a peptibody, an Fab fragment, a monoclonal antibody, a bispecific antibody, a minibody, a domain antibody, a synthetic anti body, a chimeric antibody, a humanized antibody, a human antibody, or an anti body fusion protein.

39. An isolated polynucleotide encoding an antigen binding molecule, or an immunologically functional fragment thereof, according to claim 31.

40. A vector comprising a polynucleotide of claim 39.

41. The vector according to claim 40 which is a retroviral vector, a DNA vector, a plasmid, a RNA vector, an adenoviral vector, an adenovirus associated vector, or a lentiviral vector.

42. A cell comprising the vector of claim 40.

43. The cell according to claim 42, wherein the cell is a T cell, a malignancy infiltrating lymphocyte (TIL), an NK cell, or an NK-T cell.

44. A pharmaceutical composition comprising an antigen binding molecule, or an immunologically functional fragment thereof, of claim 31, or the cell of claim 42, and a pharmaceutically acceptable carrier.

45. A method of treating a tumor or malignancy that expresses CLL-1, the method comprising administering the pharmaceutical composition of claim 44 to a human with a tumor or malignancy that expresses CLL-1.

46. A pharmaceutical composition comprising the T cell of claim 19 and a pharmaceutically acceptable carrier.

* * * * *

UNITED STATES PATENT AND TRADEMARK OFFICE
CERTIFICATE OF CORRECTION

Page 1 of 2

PATENT NO. : 10,597,456 B2
APPLICATION NO. : 15/476699
DATED : March 24, 2020
INVENTOR(S) : Jed Wiltzius et al.

It is certified that error appears in the above-identified patent and that said Letters Patent is hereby corrected as shown below:

In the Claims

In Column 296, Line 26, Claim 33, delete "antigen binding" and insert -- antigen-binding --.

In Column 296, Line 35 (approx.), Claim 34, delete "antigen binding" and insert
-- antigen-binding --.

In Column 296, Line 42, Claim 35, delete "antigen binding" and insert -- antigen-binding --.

In Column 296, Line 49, Claim 36, delete "antigen binding" and insert -- antigen-binding --.

In Column 296, Line 56, Claim 37, delete "antigen binding" and insert -- antigen-binding --.

In Column 296, Line 57, Claim 37, delete "antigen binding" and insert -- antigen-binding --.

In Column 296, Line 59, Claim 38, delete "antigen binding" and insert -- antigen-binding --.

In Column 296, Line 60, Claim 38, delete "antigen binding" and insert -- antigen-binding --.

In Column 296, Line 61, Claim 38, delete "an Fab" and insert -- a Fab --.

In Column 296, Line 63, Claim 38, delete "anti body," and insert -- antibody, --.

In Column 296, Line 64, Claim 38, delete "anti body" and insert -- antibody --.

In Column 296, Lines 65-66, Claim 39, delete "antigen binding" and insert -- antigen-binding --.

Signed and Sealed this
Eighteenth Day of August, 2020

Andrei Iancu
*Director of the United States Patent and Trademark Office*

In Column 297, Line 8, Claim 43, delete "malignancy infiltrating lymphocyte" and insert -- tumor infiltrating lymphocyte --.

In Column 297, Lines 10-11, Claim 44, delete "antigen binding" and insert -- antigen-binding --.